United States Patent [19]
Okayama et al.

[11] Patent Number: 5,998,130
[45] Date of Patent: Dec. 7, 1999

[54] NON-A, NON-B HEPATITIS VIRUS GENOMIC CDNA AND ANTIGEN POLYPEPTIDE

[75] Inventors: Hiroto Okayama, Minoo; Isao Fuke, Takamatsu; Chisato Mori, Kanonji; Akihisa Takamizawa, Kanonji; Iwao Yoshida, Kanonji, all of Japan

[73] Assignee: The Research Foundation for Microbial Diseases of Osaka University, Suita, Japan

[21] Appl. No.: 08/904,686

[22] Filed: Aug. 1, 1997

Related U.S. Application Data

[62] Division of application No. 08/324,977, Oct. 18, 1994, which is a continuation of application No. 08/099,706, Jul. 30, 1993, abandoned, which is a division of application No. 07/769,996, Oct. 2, 1991, which is a continuation-in-part of application No. 07/635,451, Dec. 28, 1990, abandoned.

[30] Foreign Application Priority Data

| Jun. 25, 1990 | [JP] | Japan | 2-167466 |
| Aug. 31, 1990 | [JP] | Japan | 2-230921 |
| Nov. 9, 1990 | [JP] | Japan | 2-305605 |

[51] Int. Cl.⁶ ........................ C12Q 1/70
[52] U.S. Cl. .............. 435/5; 530/324; 530/350
[58] Field of Search ........ 536/23.72; 424/186.1; 530/324, 350, 826; 435/5; 436/820

[56] References Cited

U.S. PATENT DOCUMENTS

| 4,464,474 | 8/1984 | Coursaget et al. |
| 4,542,016 | 9/1985 | Trepo. |
| 4,673,634 | 6/1987 | Seto et al. |
| 4,808,519 | 2/1989 | Hartley et al. |
| 5,350,671 | 9/1994 | Houghton et al. |

FOREIGN PATENT DOCUMENTS

| 0 293 274 | 11/1988 | European Pat. Off. |
| 0 318 216 | 5/1989 | European Pat. Off. |
| 0 335 135 | 10/1989 | European Pat. Off. |
| 0 363 025 | 4/1990 | European Pat. Off. |
| 0 377 303 | 7/1990 | European Pat. Off. |
| 0 388 232 | 9/1990 | European Pat. Off. |
| 0 398 748 | 11/1990 | European Pat. Off. |
| 0 414 475 | 2/1991 | European Pat. Off. |
| 0 416 725 | 3/1991 | European Pat. Off. |
| 0 419 182 | 3/1991 | European Pat. Off. |
| WO90/00597 | 1/1990 | WIPO. |
| WO90/02206 | 3/1990 | WIPO. |
| WO90/10060 | 9/1990 | WIPO. |

OTHER PUBLICATIONS

Kato et al., "Molecular cloning of the human hepatitis C virus genome from Japanese patients with non–A, non–B hepatitis", *Proc. Natl. Acad. Sci. 87*, 9524–9528, 1990.

Pharmacia P–L, Biochemicals Product Reference Guide 1984, Pharmacia P–L Biochemicals, Inc., Piscataway NJ, pp. 54, 58, 60.

Farci et al., "Lack of protective immunity against reinfection with hepatitis C virus", *Science,*, vol. 258, pp. 135–140, Oct. 1992.

*Primary Examiner*—Donna C. Wortman
*Assistant Examiner*—Brenda G. Brumback
*Attorney, Agent, or Firm*—Armstrong, Westerman, Hattori, McLeland & Naughton

[57] ABSTRACT

Disclosed is an isolated non-A, non-B hepatitis virus genomic cDNA covering the entire region of the virus gene nucleotide sequence from the 1st to 9416th nucleotides shown in FIG. 2(1) through FIG. 2(16) hereof, wherein the coding region is from the 333rd to 9362nd nucleotides, and the 5'- and 3'- noncoding sequences contain 332 nucleotides and 54 nucleotides, respectively. Part of the cDNA and an antigen polypeptide as an expression product thereof are useful as a diagnostic reagent for non-A, non-B hepatitis. The antigen polypeptide is also useful as an active ingredient for a non-A, non-B hepatitis virus vaccine.

2 Claims, 18 Drawing Sheets

FIG. 2(1)

```
1    CGATTGGGGCGACACTCCACCATAGATCACTCCCCTGTGAGGAACTACTGTCTTCACGCAGAAGGTCTAGCCATGGCGTTAGTATGAGTGTGTGCAGCCTCCAGGACCCCCCTCC
     GCTAACCCCGCTGTGAGGTGGTATCTAGTGAGGGACACTCCTTGATGACAGAAGTGGTCTTTGCAGATGGTACCCAATCATACTCACGCACGTCGGAGGTCCTGGGGGGAGG

121  CGGGAGAGCCATAGTGGTCTGCGGAACCGGTGAGTACACCGGAATTGCCAGGAGACGACCGGTCCTTTCTTGGATCAACCGCTCAATGCCTGGAGATTTGGCGTGCCCCGCGAGACTG
     GCCCTCTCGGTATCACCAGACGCTTGGCCACTCATGTGCCTTAACGTCTCCTGCCCCAGGAAGAACCTAGTTGGCGAGTTACGGACCTCTAAACCGCACGGGGGCTCTGAC

MetSerThrAsnProLysProGlnArgLys
241  CTAGCCGAGTAGTGTTGGGTCTGCCAAAGGCCTTGTGTACTGCCTGATAGGGCTGCCCCGGAGGTCTCCGTAGACCGTGCACCATGAGCACGAATCCTAAACCTCAAAGAA
     GATCGGCTCATCACAACCCAGCGCTTCCGAACACCAGCGCTTCCGGAACACGCTCACGGGCCTCCAGAGCATCTGGCACGTGGTACTCGTGCTTAGGATTTGGAGTTTCTT

ThrLysArgAsnThrAsnArgProGlnAspValLysPheProGlyGlyGlnIleValGlyGlyValTyrLeuLeuProArgArgLeuGlyValArgAlaProArg
361  AAACCAAACGTAACACCAACCGCCGCCACAGAGACGTCAAGTTCCCGGCGGTGGTCAGATCGTTGGTGAGTTTACCTGTTGCGCGCAGGGCCCCAGTTGGGTGCGGCGCCCA
     TTTGGTTTGCATTGTGTTGGCGGCGGGTGTCTCTGCAGTTCAAGGGCCGCCACCAGTCTAGCTACAGAACGGCGGGGTCCCGGGGGTCCAACCCACGCCGCGCGGGGT

LysThrSerGluArgSerGlnProArgGlyArgArgGlnProIleProLysAlaArgArgProGluGlyArgThrTrpAlaGlnProGlyTyrProLeuTyrGlyGluGly
481  GAAGACTTCCGAGCGGTCGCAACCTGTGAAGGCGACAACCTATCCCCAAGGCTGCGCGGCCGAGGCTGGCTCAGGACTGGGCTCAGCCGGTACCCTTGGCCTCTCTATGCAATGAGG
     CCTTCTGAAGGCTGCCAGGTTCGAGCCACTTCGCTGTTGGATAGGGGTTCCGAGGGCCGGGCTCCGGTCCTGGACCCTGAGTCGGCCATGGAACCGGAGAAGCGGAGAGATACGTTACTCC
```

FIG. 2(2)

```
                 LeuGlyTrpAlaGlyTrpLeuLeuSerProArgGlySerArgProSerTrpGlyProThrAspProArgArgArgSerArgAsnLeuGlyLysValIleAspThrLeuThrCysGlyPhe
 601 GCTTAGGGTGGCCAGGATGGCTCCTGTCCTCACCCGAGCGGCTCCCGGCCTAGTTGGGGCCCCACGGACCCCGGCTAGTTGCGTAAGTTGGTAAGTTCATGGATACCCTCACATGCGGCT
     CGAATCCCACCCGTCCTCCAGGACAGTGGGCGCCGAGGGCCGGATCAACCCCGGCGGCGCCGCATCCAGCGCATTAACCCATTCCAGTAGCTATGGGAGTGTACGCCGA

AlaAspLeuMetGlyTyrIleProLeuValGlyAlaProLeuGlyGlyValAlaArgValLeuArgValAlaLeuAlaHisGlyValAlaThrGlyAsnLeuPro
 721 TCGCCGATCTCATGGGTACATTCCGCTCGTCGGGGCGCCCCCCTGGGGGCTGCCAGGGCCTGCACATGGTCCGGTTCTGGAGGACGGCGTGAACTATGCAACAGGAATCTGC
     AGCGGCTAGAGTACCCCATGTAAGGGGAGCAGCCGGGGGGAGACCCCGGGACGGTCCCGGACGTGTACCACAGGCCAAGACCTCTGCCGACCTTGATACGTTGTCCCTTAGACG

GlyCysSerPheSerIlePheLeuLeuAlaLeuLeuSerCysLeuThrThrProAlaSerAlaTyrGluValHisAsnValSerGlyIleTyrHisValThrAsnAspCysSerAsnAla
 841 CCGGTTGCTCTTTTTCTATCTTCCTCTTGGCTCTGCTGTCCTGCCTGACCACCCCAGCTTCCGCTTACGAAGTGCACAAGTGTCCGGATATATCATGTCACGAAGACTGCTCAACG
     GGCCAACGAGAAAAGATAGAAGGAGAACCGAGACGACAGGAGGACGGACTGGTGGGGTCGAAGGGAATGCTTCACGTGTTGCACAGGCCCTATATAGTACAGTTGCTGCTGACGAGGTTGC

SerIleValTyrGluAlaAlaAspLeuIleMetHisThrProGlyCysValProCysTrpValAlaLeuThrProThrLeuAlaAlaArgAsn
 961 CAAGCCATTGTGTATGAGGCAGCGGACTTGATCATGCATACTCCTGGGTGCGTGCCCTGCTGGGTAGCGTCACTCCCCAGCTGCAGCCAGGA
     GTTCGTAACACATACTCCGTCGCCTGAACTAGTAGTACGTATGAGGACCCACCCACGCAAGCCCTTCGTTGAGGAGGGACACCCATCGCAGTGAGGGTGGAGCGTCGGTCCT

ValThrIleProThrThrIleArgArgHisValAspLeuLeuValGlyAlaAlaAlaPheCysSerAlaMetTyrValGlyAspLeuCysGlySerValPheLeuValSerGlnLeu
1081 AGGTCACCATCCCCACCACGATAGAGCGCACGTGCGATCTGCTCGTTGGGGCGGCTGCTTTCTGTTCCGCTATGTAGTGGGGAGACCTCGCGATCTGTTTCCTCGTCTCAGC
     TGCAGTGGTAGGGGTGGTGCTGCTATGCCTGCGGTGCACTAGAGCAGAAAGACAAGGCGATACATGCACCCCTGGAGACCCTAGACAGGCCTAGACAAAGGAGCAGAGAGTCG
```

FIG. 2(3)

```
     PheThrPheSerProArgArgIleValThrLeuGlnAspCysAsnCysSerIleTyrProGlyHisValSerGlyHisArgMetAlaTrpAspMetMetMetAsnTrpSerProThrThr
1201 TGTTCACCTTCTCCGCCTCGCCTGGCGCATGTGACATTGACATTACAGGACTGTAACTGCTCAATTTATCCCGGCCATGTGTGGGTCACCGTATGGCTTGGGACATGATGATGAACTGGTCGCCCACAA
     ACAAGTGGAAGAGCGGAGCGGCCCGTACCACTGTAATGTCCTGACATTGACGCAGTTAAATAGGCCGGCCATACCGAACCCTGTACTACTACTGACCAGCGAGGTGTT

AlaLeuValValSerGlnLeuLeuArgIleProGlnAlaValValAspMetValAlaGlyMetValAlaGlyAlaIleIleTrpGlyValLeuAlaGlyLeuAlaTyrTyrSerMetAlaGlyAsnTrpAlaLys
1321 CAGCCCTAGTGGTGTCGCAGTTACTCCGGATCCCACAAGCCGTCGTGGACATGGTTGCGGGGCCACTGGGGAGTCCTCTGGGGCCTTGCCTACTATTCCATGGCGGGAACTGGGCTA
     GTCGGATCACCACAGGTCAATGAGGCCTAGGGTGTTCGGCAGCACCTGTACCACCGCCCCCGGTGACCCCTCAGGACGCCCGGAACGGATGATAAGGTACCGCCCCTGACCCGAT

ValLeuIleValMetLeuLeuPheAlaGlyValAspThrHisValThrGlyGlyAlaGlnAlaLysThrThrAsnArgLeuValSerMetPheAlaSerGlyProSerGlnLys
1441 AGGTTCTGATTGTGATGCTACTTTTTGCTGGGGATACCCACGTGACGGGGATACCCAGTGACAGGGGGGCGCAAGCCAAAACACCAACAGGCTCGTGTCCATGTTCGCAAGTGGGCGTCTCAGA
     TCCAAGACTAACACTACGATGAAAAAGACCGCAACTGCCCTATGGGTGCACTGTCCCCGGGTTGGTTTGTCGAGCACAGGTACAAGCGTTCACCCGGCAGAGTCT

IleGlnLeuIleAsnThrAsnGlySerTrpHisIleAsnArgThrAlaLeuAsnCysAsnAspSerLeuGlnThrGlyPheLeuAlaAlaLeuPheTyrThrHisSerPheAsnSerSer
1561 AATCCAGCTTATAAACACCAATGGGAGTTGGCACATCAACAGGACTGCCCTGAACTGCAATGACTCTCTCCAGACTGGGTTTCTTGCGGCGCTGTTCTACACACATAGTTTCAACTCGT
     TTTAGGTCGAATATTTGTGGTTACCCTCAACGTGTAGTTGTCCTGACGGGACTTACTGAGAGAGTTCTGACCGCAAAGAACGGCGCGACAAGATGTGTGTATCAAAGTTGAGCA

GlyCysProGluArgMetAlaGlnCysArgThrIleAspLysPheAspGlnGlyTrpGlyProIleThrTyrAlaGluSerSerArgSerAspGlnArgProTyrCysTrpHisTyrPro
1681 CGGGGTGCCCAGAGCGCATGGCCCAGTGCCGGCGCACCATTGACAAGTTCGACCAGGGATGGGGTCCCATTACTTATGCTGAGTCTAGCAGATCAGACCAGAGGCCATATTGCTGGCACTACC
     GGCCCACGGGTCTCGGGTACGGGCTCACGGGCCGTCGCGTGGTAACTGTTCAAGCTGGTCCCTACCCCAGGTAATGAATACGACTCAGATCGTCTAGTCTGGTCTCCGGTATAACGACCGTGATGG
```

FIG. 2(4)

```
     ProProGlnCysThrIleValProAlaSerGluValCysGlyProValTyrCysPheThrProSerProValValValGlyThrThrAspArgPheGlyValProThrTyrArgTrpGly
1801 CACCTCCACAATGTACCATGTACTTGTGCTTGGAGGTGTGCGCCCAGTTGTGGGACCCTGTGTGTGGGAGACCGATGTTTCGGTGTCCTAGTATAGATGGG
     GTGGAGGTGTTACATGGTAGCATGGACGCAGCCTCCACACGCCCGGGTTCGGACAGCAGCAGCCTCGCTGGCTAGCAAAGCCACCAGGGATGCATATCTACCC

GluAsnGluThrAspValLeuLeuAsnThrArgProProGlnGlyAsnTrpPheGlyCysThrTrpMetAsnSerThrGlyPheThrLysThrCysGlyGlyProProCysAsn
1921 GGGAACGAGACTGACGTGCTGCTCAACAACAGGCCGCCCCAAGGCAACTGGTTCGGCTGCACATGGATGAATAGCACCGGGTTCACCAAGACATGTGGGGGCCCCGTGTA
     CCCTCTTGCTCGACTGACACGAGTTGTTGTTGTCGGCGGGGGTTCCGTTGACCAAGCCGACGTGTACCTACTTATCGTGCCCAAGTGGTTCTGTACACCCCCGGGGCACAT

IleGlyGlyValGlyAsnThrLeuThrCysProThrAspCysPheArgLysHisProGluAlaThrThrLysCysGlySerGlyLeuTrpLeuThrProArgCysMetValAsp
2041 ACATGGGGGGTCGGCAACAACACCCTGACCTGCCCCACGGACTGCTTCCGGAAGCACCCGGAGGCTACCACCAAAATGTGGTTCGGGGCCTTGGCTGACACCTAGGTGCATGGTTG
     TGTAGCCCCCCAGCCGTTGTTGTGGGACTGGACGGGGTGCCTGAGGAGGCCTTCGTGGGCTCGAATGATGGTTTTACACCAAGCCCGGAACCACTGTGGATCACGTACCAAC

TyrProTyrArgLeuTrpHisTyrProCysThrValAsnPheThrIlePheLysValArgMetTyrValGlyValGluHisArgLeuAsnAlaAlaCysAsnTrpThrArgGlyGlu
2161 ACTATCCATACAGGCTCTGGCATTACCCCTGCACTGTTAACTTTACCATCTTCAAGGTTAGGATGTATGTGGGGGGGTGGAGCACAGGCTCAATGCTGCATGCAGTTGGACCGAGGAG
     TGATAGGTATGTCCGAGACCGTAATGGGGACGTGACAATTGAAATGGTAGAAGTTCCAATCCTACATACACCCCCCACCTCGTCCGAGTTACGACTACGTTAACCTGGGCTCCTC

ArgCysAspLeuGluAspArgAspArgProGluLeuSerProLeuLeuLeuSerThrThrLeuProAlaLeuSerPheThrThrLeuProCysSerPheThrThrLeuProAlaLeuSerThrGlyLeuIle
2281 AGCGTTGTGACTTGGAGGACAGGACATAGGCCGGAGCTCAGCCCGTCCAGCGAGCTGCTGCTCTACAACAGAGTGGCAGGTACTGCCCTGTTCCTTCACCACCCTACCAGCTCTGTCCACTGGCTTGA
     TGGCAACACTGAACCTCCTGTCCTATCCGGCCTGAGTCGGGGACGACGAGCAGACAGATGTTGTCTCACCGTCCATGACGGACAAGGAAGTGGTGGATGGTCGAGACAGGTGACGGAACT
```

FIG. 2(5)

```
           HisLeuHisGlnAsnIleValAspValGlnTyrLeuTyrGlyIleGlySerAlaValValSerPheAlaIleLysTrpGluTyrValLeuLeuLeuPheLeuLeuLeuAlaAspAlaArg
2401  TTCACCTCCATCAGAACATCGTGGACGTGCAATACCTATACGGTATAGGGTCAGCGGTTGTCTCTTTGCAATCAAATGGAGTATGTCCTGTTGCTTTCCTTCTCTCCTAGCGGACGCAC
           AAGTGGAGGTAGTCTTGTAGCACCTGCACCTGCACCATCCCACTGCCAACAGAGGAAAGTTAGTTTACCCTCATACAGGACAACGAAAGGAAGAAGGAATGCCTGGGTG

ValCysAlaCysLeuTrpMetMetLeuLeuIlePheAlaGlnAlaGluAlaAlaAlaLeuValLeuAsnLeuValAlaSerValAlaGlyAlaHisGlyIleLeuSerPheLeuVal
2521  GTGTCTGTGCCTGCTTGTGATGATGCTGCTGATAGCCTGACAGCCGAGGCCGCAGCCCTTGGAGAACCTGGTGCTCAATTCGGCGTCTGCGGGCCACATGGCATCCTCTCCTTCCTTG
           CACACAGACACGGACGAACACCTACTACGACTACGGGCCTCCGGTCCGGCGGAACCTCTTGGACCACCAGGAGTTAAGCCCAGACACGGCGGTGTACCGTAGGAGAGGAAGGAAC

PhePheCysAlaAlaTrpTyrTyrIleLysGlyArgLeuValProGlyAlaThrTyrAlaLeuTyrGlyValTrpProLeuLeuLeuAlaLeuProProArgAlaTyrAlaMet
2641  TGTTCTTCTGTGCCGCTCGGTACATCAAAGGCAGGCTGGTCCCTGGGGCGACATATGCTCTTATGCGTGTGCCGTGCTCCTGCTCTTGCTGGCATTACCACCCGGAGCTTACGCCA
           ACAAGAAGACACGGCGGACCAGTAGTTTCCGTCCGACCAGGAGACCCGGTGTATACGAGAAATACCGCACACGGCGAGCAGACGACCTAATGGTGGCCTCGAATGCGT

AspArgGluMetAlaAlaSerCysGlyGlyAlaValPheValGlyLeuValLeuLeuThrLeuSerProTyrTyrLysValPheLeuAlaArgLeuIleTrpTrpLeuGlnTyrPheThr
2761  TGGACCGGGAGATGGCTGCATCGTGCGGAGCCGGGTTTTGTGGGTCTGGTACTCCTGACTTTGTCACCATACTACAAGGTTTCCTGCTAGGCTCATATGTGTTACAATATTTTA
           ACCTGGCCCTCTACGACGTAGCACGCCTCCGCGCCAAAAACACCCAGACCATGAGGACTGAAACAGTGTATGATGTTCCAAGGAGCGATCCGAGTATACCACCAATGTTATAAAAT

ThrArgAlaGluAlaAspLeuHisValTrpIleProProLeuAsnAlaArgGlyGlyArgAspAlaIleLeuLeuMetCysAlaValHisProGluLeuIlePheAspIleThrLys
2881  CCACCAGAGCCAGGGGACTTACATGTGGATCCCCCCCTCAAGCTCGGGAGGCCGGATGCCATCATCCTCCTCATGCCAGTCCATCCAGAGCTAATCTTTGACATCACCA
           GGTGGTCTCGGCTCCGCTCCAATGTACACACCTAGGGGGGGGAGTTGCGAGCCCCTCCGGGCGCTAGGTAGTAGGAGGAGTACACGGTACAGCGGTCAGGTAGGTCTCGAATTAGAAACTGTAGTGGT
```

FIG. 2(6)

```
            LeuLeuIleAlaIleLeuGlyProLeuMetValLeuGlnAlaGlyIleThrArgValProTyrPheValArgAlaGlnGlyLeuLeuIleHisAlaCysMetLeuValArgLysValAlaGly
3001  AACTTCTAATTGCCATACTGGTCCCGCTCATGGTGCTCCAAGCTGGCATAACCAGAGTGCCGTACTTCGTGCGGGCTCAAGGGCTCATTCATGCATGCATGTTAGTGGGAAGGTGCTG
      TTGAAGATTAACGGTATGAGCCAGGCGAGTACCAGGAGTTGACCGATCCACGGACATGAAGCACGGCGAGTCCCGAGTAAGTACGTACGTACAATCACGCCTTCCAGCGAC

GlyHisTyrValGlnMetAlaPheMetLysGlyAlaLeuThrGlyThrTyrIleTyrAsnHisLeuThrProLeuArgAspTrpProArgAlaGlyLeuArgAspLeuAlaValAla
3121  GGGGTCATTATTGCCAAATGGCCTTCATGAAGGGCCTGACAGGCACTACATTTACCTACACCATCTACCGCTACGGATTGGCCAGGCGCGGGCCTACGAGACCTTGGGTGG
      CCCCAGTAATAACAGGTTTACCGGAAGTACTTGACCGTGATGTCTCCGTGCATGTAAATGTTGTAGAATGGGATGCCTAACCGTGCGCGCCGATGCTCTGGAACGCCACC

ValGluProValValPheSerAspMetGluThrLysIleIleThrTrpGlyAlaAspIleIleLeuGlyLysGlyLeuProValSerAlaArgArgGlyLysGlyIleIle
3241  CAGTGGAGCCCGTGCTCTTCCGACATGGAGACCAAGATCATCACCTGGGGAGCAGACAGACACCGGGCTGTGGGACATCATCTTGGGTCTGCCCGTTCTCGCCCGAAGGGGAAAGGAGA
      GTCACCTGGGCAGCAGAGAAGAGGCTGTACCTCTGGTTCTAGTAGTGGACCCCTCGTCTGTCGCCGACACCCTGTAGTAGAACCAGAGGGGCAGAGGGCGGGCTTCCCCTTCCTCT

LeuLeuGlyProAlaAspSerLeuGluGlyArgGlyLeuLeuArgLeuLeuAlaProIleThrAlaTyrSerGlnThrArgGlyLeuLeuGlyCysIleIleThrSerLeuThrGlyArg
3361  TACTCCTGGGCCCGGCCGATAGTCTTGAAGGGCGGGGGGTTGGACTCCTGCGACTCCTCGCGCCATCACGGCCTACTCCCAACAGACGCGGGCCTACTTGGTTGCATCATCACTAGCCTTACAGGCC
      ATGAGGACCCGGGCGGCCGGCTATCAGAACTTCCCGCCCCCAACGCTAGTGCCCGATGAGGTGTCTGCGCCCGGATGAACCAACGTAGTAGTGATGGAATGTCCGG

AspLysAsnGlnValGlyGluValGlnValSerThrAlaThrGlnSerPheLeuAlaThrCysValCysTrpThrValTyrHisGlyAlaGlySerLysThrLeu
3481  GGGACAAGAACCAGGTCGAGGGAGAGGTTCAGGTGGTTTCCACCGCAACACAATCCTTCCTGGGACCTGGCTCAACGGGCTGTGTTGGACCGTTTACCATGGTGCTGCTCAAAGACCT
      CCCTGTTCTTGGTCCAGCTCCCTCTCCAAGTCCACCAAGGTGGGCGTTGTGTTAGGAAGGACCCTGACGCAGTTGCCCACACAACCTGGCAATGCCAATGGTACCACGACCGAGTTTCTGGA
```

FIG. 2(7)

```
     AlaAlaProLysGlyProIleThrGlnMetTyrThrAsnValAspLeuValGlyTrpProLysProProGlyAlaArgSerLeuThrProCysThrGlySerSerAspLeu
3601 TAGCCGCGCCAAAGGGCCAATCACCCAGATGTACACTAATGTGGACCAGGACCTCGTCGGCTGGCCCAAGCCCCCGGGGGCGGTTCCTTGACACCATGTGGCAGCTCAGACC
     ATGGGCGGGTTTCCCCGGTTAGTGGGTCTACATGTGATTACACCTGGTCCTGGAGCAGCGACCCGGTTCGGGGGGCCCCGGCAAGGAACTGTGGTACGTGGACACCGTGAGTCTGG

TyrLeuValThrArgHisAlaAspValIleProValArgArgArgGlyAspSerArgGlySerLeuLeuSerProArgProValSerTyrLeuLysGlySerGlyProLeuLeu
3721 TTTACTTGGTCACGAGACATGCTGACGTCATTCCGGTGCCGCGGCGGGGACAGTAGGGGGCAGCCTGCTCTCCCCAGCCTGTCCTACTTGAAGGGCTCTTGGGTGTCCACTGC
     AAATGAACCAGTGCTCTGTACGACTGCAGTAAGGCCACGGCGGCGCCGCCCCCCGCGTCATCCCCCTCGGACGAGAGGGGTCCGGACAGGATGAACTTCCGAGAAGCCCACCAGGTGACG

CysProPheGlyHisAlaValGlyIlePheArgAlaAlaAlaValCysThrArgGlyValAlaLysAlaValAspPheValProValGluSerMetGluThrThrMetArgSerProValPhe
3841 TCTGCCCTTTGGGCACGCTGTGGGCATCTTCCGGGCTGCATGCACCCGGGGGTGCGAAGGCGGTGGACTTTGTGCCGGTAGAGTCCATGGAAACTACTATGCGGTCTCCGGTCT
     AGACGGGGAAGCCGTGCGACACCGTAGAAGGCCGACGGCATAGCGTGGGCCCCCACGTTCGCGACCTGAAACACGGGCATCAGGTACCTTTGATGATACGCCAGAGGCCAGA

ThrAspAsnSerSerProAlaValProGlnSerPheGlnValAlaHisLeuHisAlaProThrGlySerGlyLysSerThrLysValProAlaAlaTyrAlaAlaGlnGlyTyrLys
3961 TCACGGACAACTCATCCCCCCGGCCGTACCGCAGTCATTTCAAGTGGCCCACCTACACGTCCCACTGCAGCGGCAAGAGTACTAAAGTGCCGGCTGCATATGCAGCCCAAGGGTACA
     AGTGCCTGTTGAGTAGGGGGCGGCCGGCATGGGCCGGCATGGCCGTCAGTAAAGTTCACGGGTGACCGGTTCTCATGATTTCACGGCCGACGTATACGTCGGGTTCCCATGT

ValLeuValLeuAsnProSerValAlaAlaAlaThrLeuGlyPheGlyAlaThrTyrMetSerLysAlaHisGlyIleAspProAsnIleArgThrGlyValArgThrIleThrGlyAlaPro
4081 AGGTGCTCGTCCTCAATCCGTCCGTTGCGTACGCTCACCTTAGGGTTTGGGGTTTGGGGGTATATGTCTAAGGCACACGGTATTGACCCAACATCAGAAACTGGGTAAGGACCATTACCACAGGCCCC
     TCCACGAGCAGGAGTTAGGCAGGCAACGGCGATGGAATCCCAAACCCGCATAACTGGGTTGTACTCTTGACCCATTCCTGGTAATGGTGTCCGGGG
```

FIG. 2(8)

```
                ValThrTyrSerThrTyrGlyLysPheLeuAlaAspGlyGlyCysSerGlyGlyAlaTyrAspIleIleIleCysAspGluCysIleSerThrThrIleLeuGlyIleGly
4201   CGGTCACATACTTACTTATGGCAAGTTTCTTGCCGATGGCTGTTCTGGGGGCGTATGACATCATAATATGTGACATCGACTGACTGACTACAATCTTGGGCATCG
       GGCAGTGTTATGAGATGGATACCGTTCAAAGAACGGCTACCACCAAACGAGACCCCCGAATACTGTAGTATTATACACTACTCACGGTAAGTTGACTGAGCTGAGTTAGAACCCGTAGC

ThrValLeuAspGlnAlaGluThrAlaGlyGlyAlaArgLeuValValAlaThrProGlySerValThrProHisProAsnIleGluGluValProValAlaLeuSerAsnThr
4321   GCACAGTCCTGGACCAAGCGGAGACGGCTGGAGCGGGGCTTGTGTGTCGCCACCCGTCGGATGGTCACGTGCCACACCCAAACATCGAGGAGGTGGCCCTGTCTAATA
       CGTGTCAGGACCTGGTTCGCCTCTGCGAGACCTGGCGCCGACCTCGCGCCGAACAGCAGGGTGGCGAGCCCTAGCGCAGTGTGGTTTGTAGCTCCTCCACCGGACAGATTAT

GlyGluIleProPheTyrGlyLysAlaIleProIleGluAlaIleArgGlyAlaAlaIleProIleProIleArgGlyArgHisLeuIlePheCysHisSerLysLysLysCysAspGluAlaAlaLysSerGlyLeu
4441   CTGGAGAGATCCCCTTCTATGGCAAAGCCATTGAAGCCATCCAGGGGGGAAGGCATCTCATTTCTGTCATTCCAAGAAGAAGTGCGACGAGCTCCGCAAAGTGTCAGGCC
       GACCTCTCTAGGGGAAGATACCGTTCGGTAGGGTAACCTCGGTAGTCCCCCCTTCGGTAGTAAAAGACAGTAAGTTCTTCTTCACGCTGCTCGAGCGCGTTTCGACAGTCGG

GlyIleAsnAlaValAlaAlaTyrTyrArgGlyLeuAspValSerValIleProThrIleGlyAspValValAlaValAlaThrAspAlaLeuMetThrGlyTyrThrGlyAspPheAspSer
4561   TCGGAATCAACGCTGTGGCTATTACCGGGGGCTCGATGTCCGTCATACCAACTATCGGAGAGTCGTTGTCGTGGCAACAGACGCTCTGATGACGGCTATACGGGCGACTTTGACT
       AGCCTTAGTTGCGACACCGATAATGGCCCCCGAGCTACACAGGCAGTATGGTTGATAGCCTCTGCAGCAACAGCACCGTTGTCTGCAGAGACTACTGCCGATATGCCCGCTGAAACTGA

ValIleAspCysAsnThrCysValThrGlnThrValAspPheSerLeuAspProThrPheThrIleGluThrThrValProGlnAspAlaValSerArgSerGlnArgArgGlyArg
4681   CAGTGATCGACTGTAACACATGTGTCACCCAGACAGTCGACTTCAGCTTGGATCCCACCTTCACCATTGAGACGACGGTGCCTCAAGACGCAGTGTCGCGCTCGCAGGCGGGGGTA
       GTCACTAGCTGACACTGATGTACACAGTGGGTCTGTCAGCTGAAGTCGAACCTAGGGTGGAAGTGGTAACTCTGCTGCCACGAGTTCTGGTCACAGCGCGAGCGTCGCCGCCCAT
```

FIG. 2(9)

```
         ThrGlyArgGlyArgArgGlyIleTyrArgPheValThrProGlyGluArgProSerGlyMetPheAspSerSerValLeuCysGluCysTyrAspAlaGlyCysAlaTrpTyrGluLeu
4801 GGACTGGCAGGGGTAGGAGAGGCATCTACAGGTTTGTGACTCCGGGAGAACGGCCCTCGGGCATGTTCGATTCCTCGGTCCTGTGAGTGTATGAGGGGCTGTGCTTGCTACGAGC
     CCTGACCGTCCCCATCCTCCGTAGATGTCCAAACACTGAGGCCCTTCGCCGGAGCCGTACAGTCAAGTAAGGACCAGGACACACTCAGATACTGCGGCCGACACGAACCATGCTCG

ThrProAlaGluThrSerValArgLeuArgAlaAlaTyrLeuAsnThrProGlyLeuProValCysGlnAspHisLeuGluPheTrpGluSerValPheThrGlyLeuThrHisIleAspAla
4921 TCACCCGGCCGAGACCTCGGTTAGGTTGGGGCCTACCTGAACACACCAGGGTTGCCCGTTTGCCAGGACCACCTGAGTTCTGGGAGAGTGTCTTCACAGGCCTCACCCATAGATG
     AGTGGGGCCGGTCTGAGCCAATCCAACGCCCGATGGACTTGTGTGGTCCCAACGGCAAACGGTCCTGGTGACCCTCAAGAGAGTGTCGGAGTGGGTATATCTAC

HisPheLeuSerGlnThrLysGlnAlaGlyAspAsnPheProTyrLeuValAlaThrValCysAlaArgAlaAlaProProSerTrpAspGlnMetTrpLysCys
5041 CACACTTCTTGTCCCAGACCAAGCAGGCAGGAGACAACTTCCCCTACCTGGTAGCATACCAAGGCCACGGTGCGCAGGCTCAGGCCCCCACCTCCATCATGGGATCAAATGGAAGT
     GTGTGAAGAACAGGGTCTCGGTTCGTCCGTCCTCTCGTTGAAGGGGATGGACCATCGTATGGTTCGGTGCCACACGCGGTCCCGAGTCCGGGTCGGAGTAGTACCCTAGTTTACACCTTCA

LeuIleArgLeuLysProThrLeuHisGlyProThrProLeuLeuTyrArgLeuLeuAlaValGlnAsnGluValThrLeuThrProIleThrLysTyrIleMetAlaCysMetSer
5161 GTCTCATAGGCTGAAACTGCACGCTGCACGGCCAACCTGCGTACAGGCTGGGAGCCGTCCAGATGAGGTCACCCTCACCCATAACCAAATACATCATGGCATGCATGT
     CAGAGTATGCCGACTTTGGATGCGAGGTGCCGGTTGTGGGAACGACATGTCCGCAGGTCTTACTCCAGTGGGTATTGGTTTATGTAGTACCGTAGTACA

AlaAspLeuGluValValThrSerThrTrpValLeuValGlyGlyValLeuAlaAlaAlaTyrCysLeuThrThrGlySerValValIleValGlyArgIleIleLeuSerGly
5281 CGGCTGACCTGGAGGTCGTCACTAGCACCTGGGTGCTGGTGGGGGAGTCCTTGCCAGCTCTTGGCCGGTATTGCCTGACAACAGGCAGTGTGGTCATTGTGGTAGGATTATCTTGTCCG
     GCCGACTGGACCTCCAGCAGTGATCGTGGACCCAGACCACCGCCTCAGGAACCGGCATAACGGACTGTTGTCCGTCACCAGTAACACCCATCCTAATAGAACAGGC
```

FIG. 2(10)

```
     ArgProAlaIleValProAspArgGluLeuLeuTyrGlnGluPheAspGluMetGluGlnGlyMetGlnLeuAlaGluGlnPheLysGln
5401 GGAGGCCGGCCATTGTTCCGACAGGAGTTCTCTACCAGGAGTTCGATGAAATGGAGCAGGGAATGCAGCTCGCCGAGCAATTCAAGC
     LeuTyrIleGluGlnGlyMetGlnLeuAlaSerHisLeuProTyrIleGluGlnGlyMetGlnLeuAlaGluGlnPheLysGln
     AGGAGGCCGGCCATTGTTCCGACAGGAGTTCTCTACCAGGAGTTCGATGAAATGGAGCAGGGAATGCAGCTCGCCGAGCAATTCAAGC
     CCTCCGGCCGGTAACAAGGGCTGTCCCTCGAAGCTACTTACCTTCTCAAGCTACTTACCTTCTCACGCGAGGCGTGAGGGAATGTAGCTGTCCCTTAGTCGAGCGGCTGGTTAGTTCG

LysAlaLeuGlyLeuLeuGlnThrAlaThrLysGlnAlaAlaAlaAlaProValValGluSerLysTrpArgAlaLeuGluThrPheTrpAlaLysHisMetTrpAsnPheIleSer
5521 AGAAAGCGCTCGGGTTACTGCAAACAGCCACCAAACAGCGAGGCTGCTGCTCCCGTGGTGAGTCCAAGTGGCGAGCCCTTGAGACATTCTGGGCGAAGCACATGTGGAATTTCATCA
     TCTTTCGCGAGCCCAATGACGTTTGTCGGTGTGTTGTTGCCTCGCAGAGCGCACCACCTCAGGTTCACGCTCGGAACTCTGTAAGACCGCTTGTGTACACCTTAAAGTAGT

GlyIleGlnTyrLeuAlaGlyLeuSerThrLeuProGlyAsnProAlaIleAlaSerLeuMetAlaPheThrAlaSerIleThrSerProLeuThrThrGlnSerThrLeuPheAsn
5641 GCGGGATACAGTACTTAGCAGGCTTATCCACTCTGCCTGGGAACCCCGCAATGGCATCACTGATGGCATTCACAGCCTCTATCACCACGCCGCTCACCACCCAAAGTACCCTCCTGTTTA
     CGCCCTATGTCATGAATCGTCCGAATAGGTGAGACGGACCCTTGGGGCGTTATCGTAGTAACTACCGTAAGTGTCGGAGATAGTGGTCGGGGAGTGGTGGGTTTCATGGAGGACAAAT

IleLeuGlyGlyTrpValAlaAlaGlnLeuAlaAlaProSerAlaAlaSerAlaAlaPheValGlyAlaAlaGlyIleAlaGlySerIleGlyLeuGlyLeuGlyLysValLeuValAsp
5761 ACATTCTTGGGGGGGTGGGTTGCCGCCCAACTGCCGCCCCCCCCAGCGCCCTTGGCTTTCGTGGGGCCGCCCATCGCGGTCGCGCGTGTTGCAGCATAGCCTTGGGAAGGTGCTTGTGG
     TGTAGAACCCCCCCACCCAGACGGTTGAGCGGCGGGGGTCGGCGGAAGCGAAGGCACCGGGGGCCGGGTAGCGGCCACGGCGAAGCGCCGGACACCGTGTATCGGAACCCTTCCACGAACACC

IleLeuAlaGlyTyrGlyAlaGlyValAlaGlyValAlaAlaPheLysValMetSerGlyGluMetProSerThrGluAspLeuValAsnLeuProAlaIleLeuSerProGly
5881 ACATTCTGGGGGGTATGGAGCAGGAGTGGCCGGGGCGGTCGTGGCCTTTAAGGTCATGAGCGGGGAGATGCCCTCAACGGAGGACCTGGTCAATCTACTTCCTGCCATCCTCTCCTG
     TGTAAGACCCCCCAATACCTCGTCCTCACCGGCCCCGCGCCAGCACCGGAGCACGGCCGGAAATTCCAGTACTGCCCCTCTACTGAGCTTCCTGGCTCCTGACCAGTTAGATGAAGGACGGTAGGAGAGAGAGC
```

FIG. 2(11)

```
                AlaLeuValValGlyValValCysAlaAlaIleLeuArgArgHisValGlyProGlyGluGlyAlaValGlnTrpMetAsnArgLeuIleAlaPheAlaSerArgGlyAsnHisValSer
6001  GCGCCCTGGTCGTCGGGTGTGTGTGCAGCAATACTGCGTGCAGCGTGGGTCCGGGAGAGGGGCTGTGCAGTGGATGAACCGGCTGATAGCGTTCGCCTCGCGGGTAATCATGTTT
      CGGGGACCAGCAGCCCCAGCACACACCTGTTATGACGCAGCTGTGCACACGTCACTACTTGGCGACTATGCAAGCGGAGCGGAGCGCCCATTAGTACAAA

ProThrHisTyrValProGluSerAspAlaAlaAlaArgValThrGlnIleLeuSerSerLeuThrIleThrGlnLeuLeuLysArgLeuHisGlnTrpIleAsnGluCysSerThr
6121  CCCCACCCACTATGTCCTGAGCGACGCGCCAGGCGGTGTTACTCAGATCCTCTCAGCTCTCACTATCACTCAGCTGCTGAAAAGGCTCCACCAGTGGATTAATGAGACTGTCCA
      GCGGGTGCGTGATACAGGGACTCCTCGCGGCGGTGCGCACAATGAGTCTAGGAGAGGTCGGAATGGTAGTGAGACTGTTCCGAGGTGGTCACCTAATTACTTCTGACGAGGT

ProCysSerGlyTrpLeuArgAspValTrpAspTrpIleCysThrValLeuThrAspPheLysThrLeuGlnSerLysLeuLeuProGlnLeuProGlyValProPhePheSer
6241  CACCGTGTTCCGGCTCGTGGCTAAGGGATGTTTGGGACTGGATATGCACGGTGTTGACTGACTTCAAGACCTGCTCCAGTCCTCCGCCAGCTACCTGAGTCCCTTTTTCT
      GTGGCACAAGGCGAGCACCGATTCCCTACAAACCCTGACTACAAGTGCCACACCTGACTGAAGTTCTGACCGAGTCAGGTTCGAGGACGGGTCGATGACCTCAGGGAAAAAGA

CysGlnArgGlyTyrLysGlyValTrpArgGlyAspGlyIleMetGlnThrThrCysProCysGlyAlaGlnIleThrGlyHisValLysAsnGlySerMetArgIleValGlyProLys
6361  CGTGCCAACCCGGTACAAGGGAGTCTGGCGGGGAGAGACGGCATCATGCAAACCACCTGCCCATGTGCAGCACAGATCACCGGACATGTCAAAAACGGTTCCATGAGGATCGTGGGCCTA
      GCACGGTTGGCCCCATGTTCCCTCAGACGCCCTGCCTGCAGACGCCCCTCTGAGTACGTTTGGTGGACGGGTACACCTCGTGTCTAGTGCGTACTCTAGCAGCCGGAT

ThrCysSerAsnThrTrpHisGlyThrPheProIleAsnAlaTyrThrThrGlyProCysThrProSerProAlaProAsnTyrSerArgAlaLeuTrpArgValAlaAlaGluGluTyr
6481  AGACCTTCAGCAACAGTGGCATGGAACATTCCCATCAACGCATACACCACGGGCCCCTGCACACCCTCTCCAGCGCCAAACTATTCTAGGGCGTGTGGCGGGTTGCGCCCTGAGGAGT
      TCTGGACGTCGTTGTCCGTTGCACCGTTGTAAGGGGTAGTTGCGTATGTCGTTGGATGTGCCGGGAGGTTGATAAGATCCGCGGTTCGCGGTTCGCGGTTTGATAAGATCCGCGGGGTCGGCGCGGTTTGATAAGATCCGCGGGGACTCCTCA
```

FIG. 2(12)

```
                 ValGluValThrArgValGlyAspPheIleHisTyrValThrGlyMetThrThrAspAsnValLysCysProCysGlnValProAlaProGluPhePheSerGluValAspGlyValArgLeu
6601  ACTGGAGGTCACGCGGTCGGGGATTTCCACTACGTGACGGGCATGACCACTGACAACGTAAAGTGCCCATGCCCAGGTTCCGGCTCCTGAATTCTTCTGGAGGTGACGGAGTGCGGT
      TGCACCTTCCAGTGCCACCCCACCCCCTAAAGGTGATGCACTGCCCCTACTGGTGACTGTTGCATTTCACGGCTACGTCCAAGGCCGAGGACTTAAGAAGAGCCTCCACTGCCTCACGCCA

HisArgTyrAlaProAlaCysArgProLeuLeuArgGluGluValThrPheGlnValGlyLeuAsnGlnTyrLeuValGlySerGlnLeuProCysGluProGluProAspValAlaVal
6721  TGCACAGGTACGCTCCGGCGTGCAGGCCTCCTACGGGAGGAGGTTACATTCCAGGTCGGCTCAACCAATACTCGTTGGTCACAGTGTCACCAATGGAGCCCGAGCCGATGTAGCAG
      ACGTGTCCATGCGAGGCGCAGCGTCCGAGAGGATGCCCTCCTCCAATGTAAGGTCCAGCCGAGTTGGTATGGACCAACCCAGTGTCACTGGCCTGGGGCTTGGCCTACATCGTC

LeuThrSerMetLeuThrAspProSerHisIleThrAlaGluThrAlaLysArgArgGlySerProSerLeuAlaSerSerSerGlnLeuSerAlaProSer
6841  TGCTCACTTCCATGCTCACGGACCCCTCCCACATCCACAGCAGAGAAACGGCTAAGGCGTAGGTTGGCCAGGGGTCCCCCCTCCTTGGCCAGCTCTTCAGCTAGCCAGTTGTCTGGCCTT
      ACGAGTGAAGGTACGAGTGCCTGGGAGGGTGAGTGTCGTCTTTGCCGATTCGGCCTTCAACCGGTCCCCAGAGGGGAGGAACCGGTCGAGAAGTGATCGGTCAACAGACCGGAA

LeuLysAlaThrCysThrThrHisHisValSerProAspAspIleGluAlaAsnLeuLeuTrpArgGlnMetGlyGlyAsnIleThrArgValGluSerGluAsnLysVal
6961  CCTTGAAGGGACATGCACTACCACCATGTCTCTCCGGACGCTGACCTCATCGAGGCCAACCTCCTGTGGCGGCAGGAGATGGGCGGGAACATCACCCGCGTGAGTCGGAGAACAAGG
      GGAACTTCCGCTTGTACGTGATGGTGGTAGCTGATGTAGCAGAGAGGCCTGCGACTGGAGCTGGAGTTGGAGGACACCGCGTCCTCTACGGCGCACCTGTAGTGGGCGCACTCAGCCTCTTGTTCC

ValValLeuAspSerPheAspProLeuArgAlaGluGluAspGluArgGluValSerValProAlaGluIleLeuArgLysSerLysLysPheProAlaAlaMetProIleTrpAlaArg
7081  TGGTAGTCCTGGACTCTTTCGACCCTCTGAGCCGGCTTCGAGCGGAGGAGGATGAGAGGGAAGTATCCGTTCCGGCGGAGATCCTTGCGGAAATCCAAGAAGTTCCCCGCAGCGATGCCCATCTGGGCGC
      ACCATCAGGACCTGAGAAGCTGGGACGAGCGCCCCGAGCGCCTCCTCCTACTCTCCCTTCATAGGCAAGGCCGCCCTCTAGGACGCCTTAGTTCTTCAAGGGGCGTCGCTACCGGGTAGACCCGCG
```

FIG. 2(13)

```
     ProAspTyrAsnProProLeuGluSerTrpLysAspProAspTyrValProProValHisGlyCysProLeuProProIleLysAlaProProIleProProProArgArgLys
7201 GCCCGGATTACAACCCTCCACTGTTAGAGTCCTGGAAGGACCGGACTACGTCCCTCGGTGGTGCAGGGTGCCGTTGCCACCTATCAAGGCCCTCCAATACCACCTCCACGAGAA
     CGGGCCTAATGTTGGGAGGTGACAATCTCAGGACCTTCCTGGCCTGATGCAGGGAGGCCACCAGTGCCAGGGCAACGTGGATAGTTCCGGGAGGTTATGGTGGAGGTGCCTCTT

ArgThrValValLeuThrGluSerSerValSerSerAlaLeuAlaGluLeuAlaThrLysThrPheGlySerSerGluSerSerAlaValAspSerGlyThrAlaThrAlaLeuProAsp
7321 AGAGGACGGTTGTCCTAACAGAGTCCTCCGTGTTCTTCTGCCTTAGGGAGCTGCTACTAAGACCTTCGGCAGCTCCGAATCATGGCCGTTGACAGGGCACGGGGACGCCCTTCTG
     TCTCCTGCCAACAGGATTGTCTCAGGAGGCACAGAGAAGACGGAATCGCCTGAGGCTTAGTCCGGCAGCTGTCGCCGTGCCGCTGGGGGAAGGAC

GlnAlaSerAspAspGlyAspLysGlySerAspValGluSerTyrSerSerMetProProLeuGluGlyGluProGlyAspProAspLeuSerAspGlySerTrpSerThrValSerGlu
7441 ACCAGGCCTCCGACGACGGTGACAAAGGATCCGACGTTGAGTCGTACTCCTCCATGCCCCTTGAGGGGAACCGGGGGACCCCGATCTCAGTGACGGGTCTTGGTCTACGGTGAGCG
     TGGTCCGGAGGCTGCTGCCACTGTTCCTAGCCTGCAACTCAGCATGAGGAGGTACGGGGGGGAACTCCCCCTTGGCCCCTCTAGAGTCACTGCCCAGAACCAGATGCCACTCGC

GluAlaSerGluAspValValCysCysSerMetSerTyrThrTrpThrGlyAlaLeuIleThrProCysAlaAlaGluSerLysLeuProIleAsnAlaLeuSerAsnSerLeuLeu
7561 AGGAAGTCAGTGAGGATGTCGTCTGCTGCTGCTCAATGTCCTACACATGGACAGGGCCTTGATCACGGCCATGCCGTGGGAGGAAAGCAAGCTGCCATCAACGGTTGAGCAACTCTTTGC
     TCCTTCGATCACTCCTACAGACAGACGACGAGTTACAGGATGTGTACCTGTCCCGGAACTAGTGCCGTACGCGGCGCCTCCTTCGTTGCACGGTAGTTGCCAACTGTTGAGAAACG

ArgHisHisAsnMetValTyrAlaThrThrSerArgSerAlaGlyLeuArgGlnLysLysValThrPheAspArgLeuValLeuAspHisTyrArgAspLeuLysGluMet
7681 TGGCCACCATAACATGGTTTATGCCACAACATCTCGCAGCGCAGCGCTGCGGCAGACGCTGGGAGCAGAAGAAGGTCACCTTTGACAGACTGGAGCTCCTGGACGACCACTACCGGGACGTGCTCAAGGAGA
     ACCGGTGGTATTGTACCAAATACGGTGTTGTAGAGGCGTCGCGTCGCGTCGCGCGACCGCCGTCTTCTTCCAGTGGAAACTGTCTGACGTTCAGACCTGTGATGCCTGCACGAGTTCCTCT
```

FIG. 2(14)

```
                    LysAlaLysAlaSerThrValLysAlaLysLeuLeuSerValGluGluAlaCysLysLeuThrProProHisSerAlaLysSerLysPheGlyTyrGlyAlaLysAspValArgAsnLeu
7801    TGAAGGCAAGCGTCCACAGTTAAGGCTAAACTCCTATCCGTAGAGGAAGCCTGCAAGCTGACCCCCACATTCGGCCAAATCCAAGTTTGGCTATGGGGCAAAGGACGTCCGGAACC
        ACTTCCGCTTCCGCAGGTGTCAATTCGATTTGAGGATAGGCATCTCCTTCGGACGTTCGACTGCGGGGGTGTAACCGGTTAAGCCGGTTCAAACCGATACCCGTTCCTGCAGGCCTTGG

SerSerLysAlaValAsnHisIleHisSerValTrpLysAspLeuLeuGluAspThrValThrProIleAspThrThrIleMetAlaLysAsnGluValPheCysValGlnProGluLys
7921    TATCCAGCAAGGCGTTAACCACCATCCACTCCGTGTGGAAGGACTTGCTGGAAGACACTGTGACACCATGATTGACACCACCATCATGGCAAAAAATGAGGTTTTCTGTTCCAACCAGAGA
        ATAGGTCGTTCCGGCAATTGGTGTAGGTGAGGCACACCTTCCTGAACGACCTTCTGTGACACTGTGGTAGTACCGTTTTTTACTCCAAAAGACACAGGTTGGTCTCT

GlyGlyArgLysProAlaArgLeuIlePheProAspLeuGlyValArgValCysGluLysMetAlaLeuTyrAspValValSerThrLeuProGlnValValMetGlySerSerTyr
8041    AGGAGGCCGTAAGCCAGCCCGCCTTATCGTATTCCCAGATCTGGAGTCCGTGTATGCGAGAAGATGGCCCTCATGATGTGGTCTCCACCCTTCCTCAGGTCGTGATGGGCTCCTCAT
        TTCCTCCGGCATTCGGTCGGGCGGAATAGCATAAGGGTCTAGACCCTCAGGCACATAGCTCTTCTACCGGAGATACTACTCAGGAGTCCAGCACTACCGAGGAGTA

GlyPheGlnTyrSerProGlyGlnArgValGluPheLeuValAsnThrTrpLysSerLysAsnProMetGlyPheSerTyrAspThrArgCysPheAspSerPheValThrGluAsn
8161    ACGGATTCCAGTACTCTCCTGGGCAGCAGCCGTGAGTTCGAGTTCCTGGTGAATACCTGGAAATCAAAGAAAAACCCATGGCTTTCATATGACACTCGCTGTTTCGACTCAACGGTCACCGAGA
        TGCCTAAGGTCATGAGAGGACCCGTCGTCGACTCAAGGACCACTTAGGAGTTCTTTTTTGGGTACCCGAAAAGTATACTGTGAGCGACAAAGCTGAGTTGCCAGTGGCTCT

AspIleArgValGluSerIleTyrGlnCysCysAspLeuAlaAlaProGluAlaArgGlnAlaIleLysSerLeuThrGluArgLeuTyrIleGlyGlyProLeuThrAsnSerLysGly
8281    ACGACATCCGTGTTGAGGAGTCAATTTACCAATGTTGTGACTTGGCCCCCGAAGCCAGACAGGCCATAAAATCGCTCACAGAGGGCTTTATATCGGGGTCCTCTGACTAATTCAAAAG
        TGCTGTAGGCACACACTCCTCAGTTAAATGGTTACAACACTGAACGGGGGCTTGGTCGTCGGTAATTTAGCGAGTGTCTCGCGAAATATAGCCCCAGGAGAGACTGATTAAGTTTTC
```

FIG. 2(15)

```
       GlnAsnCysGlyTyrArgArgCysArgAlaSerGlyValLeuThrThrSerCysGlyAsnThrLeuThrCysTyrLeuLysAlaSerAlaAlaCysArgAlaAlaLysLeuGlnAspCys
8401   GCCAGAACTGCGGTTATCGCCGTTGCCGCCGAGCGGGTGCTGACGGTGCTGCGGTACCCCTCACATGTTACTTGAAGGCCTTGCAGCCTGTGAGCTGCCAAGCTGCAGGACT
       CGGTCTTGACGCCAATAGCGGCCACGCCGCGGCGCTCGCCGACGACTGCTGATGCACACTGGAGTGTACAATGAACTTCCGGAGACAGTCGACGCTTGAGGTCCTGA

ThrMetLeuValAlaAsnGlyAspAspLeuValIleCysGluSerAlaGlyThrGlnGluAspAlaAlaSerLeuArgValPheThrGluAlaMetThrArgTyrSerAlaProGly
8521   GCACGATGCTCGTGAACGGAGAGACGACCTCGTCGTTATCTGTGAAAGCCGGAACCCAAGAGACGCGGCAGCCTACAGGTCTTCACGGAGGCTATGACTAGGTACTCCGCCCCCCG
       CGTGCTACGAGCACTGCCTCTGCCTGGAGCAGCAATAGACACTTTCGCGCCTTGGGTTCTCGCGGCGCTCGATGCTCAGAAGTGCCTCCGATACTGATCCATGAGGCGGGGGGC

AspProProGlnProGluTyrAspLeuLeuIleThrSerCysSerSerAsnValSerValAlaHisAspAlaSerGlyLysArgValTyrTyrLeuThrArgAspProThrThrPro
8641   GGGACCCGCCCCAACCAGAATACGACTTGGAGCTGATAACATCATGTTCCTCCAATGTGCGTGCCCACGATGCATCAGGCAAAAGGGTGTACTACCTCACCCGTGATCCCACCACCC
       CCCTGGGCGGGGTTGGTCTTATGCTGAACCTCGACTATTGTAGTACAAGGAGTTACACAGCCAGCGGGTGCTACGTAGTCGGTTTCCCACATGGAGTGGGCACTAGGGTGGTGGG

LeuAlaArgAlaAlaAlaTrpGluThrAlaArgHisThrProValAsnSerTrpLeuGlyAsnIleIleMetTyrAlaProThrLeuTrpAlaArgMetIleLeuMetThrHisPhePheSer
8761   CCCTAGCACGGCTGCGTGGGAGACAGCTAGACACACTCCAGTTAACTCCTGGCTAGGCAACATTATTATGTATGCGCCCACTTTGTGGCAAGGATGATTCTGATGACTCACTTCTCT
       GGGATCGTGCCCGACGCACCCTCTGTCGATCGTGTGAGGTCAATTGAGGACCGATCCGTTGTAATAATACATAGCCGGTGAAACACCGTTCCTACTAAGACTACTGAGTGAAGAAGA

IleLeuLeuAlaGlnGluGlnLeuGluLysAlaLeuAspCysTyrSerIleGluProLeuAspLeuArgLeuHisGlyLeuSerAla
8881   CCATCCTTCTAGCGCAGGAGCAGCAACTTGAAAAAGCCCTGGACTGCTACAGCTGCCAGATCTGCCAGATCATTGACCTACCTCAGCCACTTAGCCCACTTACCATTGAGCCACTTACTCCATTGAGCCATTGAACGACTCCATGGCCTTAGCG
       GGTAGGAAGATCGCTCCTCGTCGTTGAACTTTTTCGGGACCTGACGGCTAGATGCCCGGACAATGAGGTAACTCGGTGAACTGAGGTAGCCGGAGTCTAGTAACTTGCTGAGTGAGTACCGAATCGC
```

FIG. 2(16)

```
                PheSerLeuHisSerTyrSerProGlyGluIleAsnArgValAlaSerCysLeuArgLysLeuGlyValProProLeuArgValTrpArgHisArgAlaArgSerValArgAlaArgLeu
9001  CATTTCACTCACTCCATAGTTACTTCCAGGTGAGATCAATAGGGTGGCTTCATCGTTCAGGAACTTGGGGTACCACCCCTTGCGAGTCTGGAGTCTGGGCCCAGGAGCGTCCCCGCTAGCC
      GTAAAGTGAGGTATCAATGAGAGGTCCACTCTAGTTATCCACCGAGTACGAGAGTCCTTTGAACCCATGTGGGAACCCTCAGACCCTCTGAGCCCGTCCTCGCAGGCCGGGATCCG

LeuSerGlnGlyGlyArgAlaAlaAlaThrCysGlyGlyLysTyrLeuPheAsnTrpAlaValLysThrLysLeuLysLeuThrProIleProAlaAlaSerArgLeuAspLeuSerGlyTrpPhe
9121  TACTGTCCAGGGAGGGAGGGCGCCGCCACTTGTGGCAAATACCTCTCAACTGGCAGTAAAAACCAAACTTAAACTCACTCCAATCCCGGCTGCTCCCCGTGACTTGTCCGGCTGGT
      ATGACAGGTCCCTCCCTCCCGCTGCGGCGGTGAACACCGTTATGGAGAAGTTGACCGTCATTTTTGGTTTGAATTGAGTGAGTTAGGCGCCGACCTGAACGGCCGACCA

ValAlaGlyTyrSerGlyGlyAspAleTyrHisSerLeuSerArgArgProArgTrpPheMetLeuCysLeuLeuLeuLeuSerValGlyValGlyIleTyrLeuLeuProAsnArg
9241  TGGTTGCTGGTTACAGCGGGGAGACATATATCACAGCCTGTCTCGTCCCGACCCGTTGGTTCATGCTGTGCCTACTCTTCTGTAGGGGTAGGCATCTACCTGCTCCCCAACC
      AGCAACGACCAATGTCGCCCCCTCTGTATATAGTGTCGGACAGAGCACGGGTGGGCAACCAAGTACGACACGGATGAGAATGAAAGACATCCCATCCGTAGATGGACGAGGGTTCG

9361  GATGAACGGGGAGATAAACACTCCAGGCCAATAGGCCATCCCCCTTTTTTTTTT
      CTACTTGCCCCTCTATTTGTGAGGTCCGGTTATCCGGTAGGGGGAAAAAAAAAA
```

NON-A, NON-B HEPATITIS VIRUS GENOMIC CDNA AND ANTIGEN POLYPEPTIDE

This is a division of application Ser. No. 08/324,977 filed Oct. 18, 1994, which was a continuation of application Ser. No. 08/099,706, filed Jul. 30, 1993, now abandoned, which was a division of application Ser. No. 08/769,996 filed Oct. 2, 1991, which was a continuation-in-part of application Ser. No. 07/635,451, filed Dec. 28, 1990 now abandoned.

BACKGROUND OF THE INVENTION

Field of the Invention

The present invention relates to a non-A, non-B hepatitis virus genomic cDNA and a non-A, non-B hepatitis virus genomic cDNA an a non-A, non-B hepatitis virus antigen polypeptide. More particularly, the present invention is concerned with a non-A, non-B hepatitis virus genomic cDNA which is useful for producing a non-A, non-B hepatitis virus antigen polypeptide and with a non-A, non-B hepatitis antigen polypeptide which is an expression product thereof. The non-A, non-B hepatitis virus genomic cDNA of the present invention is also useful for genetically diagnosing non-A, non-B hepatitis. Further, the non-A, non-B hepatitis antigen polypeptide of the present invention is useful for producing a vaccine for non-A, non-B hepatitis, an immunoglobulin, a polyclonal or monoclonal antibody, an immunological diagnostic reagent, an agent for screening blood for transfusion and an agent for use in affinity chromatography for removing non-A, non-B hepatitis virus from blood for transfusion.

Discussion of Related Art
Definition of non-A, non-B hepatitis virus

The viral hepatitis is a liver disease caused by the infection of a hepatitis virus. Heretofore, hepatitis A virus, hepatitis B virus and hepatitis D (delta) virus have been isolated and identified. The hepatitis D virus (delta-hepatitis virus) is a deficient virus which cannot multiply by itself and requires for its multiplication the co-presence of hepatitis B virus as a helper virus. Therefore, the hepatitis D virus is present only in a patient having hepatitis B. In 1974, it was reported that there were many patients having hepatitis caused by a factor other than the infection with either hepatitis A virus or hepatitis B virus. Such a hepatitis was named "non-A, non-B hepatitis", and researches on the non-A, non-B hepatitis virus have been made extensively and intensively throughout the world. Heretofore, it has been found that a plurality of types of non-A, non-B hepatitis viruses exist. Results of the researches up to now show that the non-A, non-B hepatitis virus is classified into two types according to the infection route, that is, an epidemic hepatitis virus, namely an enterically-transmitted non-A, non-B hepatitis virus, which is spread through blood by transfusion, etc. Of the non-A, non-B hepatitis viruses, only an enterically-transmitted non-A, non-B hepatitis virus which spreads over the areas of Africa, India and Southeast Asia has been virologically identified, but the blood-transmitted non-A, non-B hepatitis virus has not yet been identified.

Hereinbelow, the blood-transmitted non-A, non-B hepatitis is often referred to simply as "NANB hepatitis", and the blood-transmitted non-A, non-B hepatitis virus is often referred to simply as "NANBV". Current situation of the studies on NANB hepatitis and problems.

With respect to the epidemiology, clinical examination, diagnosis, treatment and prevention of the NANB hepatitis, virological studies have been made in the world by the comparison of NANBV with the other hepatitis viruses, based on the knowledge of diagnostics, histopathology, immunology, molecular biology and the like ["Japan Medical Journal", No. 3320, pp. 3–10 1987; "Igaku-no Ayumi (Progress of medicine)", 151(13) pp. 735–923, 1989; "Kan Tan Sui (Liver, Gallbladder, Pancreas)", 21(1) pp. 5–113, 1990; "Jikken Igaku (Experimental Medicine)", 8(3), pp. 201–233, 1990 ]. With respect to the NANB hepatitis, the following findings have been reported.

(1) Epidemiology: In Japan, according to the estimation by the Ministry of Health and Welfare, about 60% of chronic hepatitis patients (namely about 720 thousand patients), about 40% of hepatocirrhosis patients (namely about 100 thousand patients) and about 40% of liver cancer patients (namely about 7 thousand patients) are patients having NANB hepatitis. Further, the mortality attributed to the above-described NANB hepatitis reaches 16 thousand per year. In U.S.A., the number of post-transfusion hepatitis patients reaches 150 to 300 thousand per year and 90% of the post-transfusion hepatitis patients are patients having NANB hepatitis. Further, it is considered that 1 to 6% of the blood donors are NANBV carriers. Further, it is estimated that in the other countries also, the incidence of NANB hepatitis and the ratio of the NANBV carrier are equal to or higher than those in U.S.A. and Japan. Therefore, prevention, early diagnosis and early treatment of the NANB hepatitis are of global importance.

(2) Virology: The NANBV heretofore reported comprises an envelope and assumes a viral particle having a spherical shape of about 50 nm in diameter. The taxonomic observations suggest that the known NANBV is a virus similar to a togavirus or a flavivirus, or a virus of new type different from the togavirus or flavivirus. Further, the results of pathological observations of the cytoplasm of hepatocytes of a plurality of chimpanzees injected with serum of a patient having NANBV hepatitis show that the formation of a tubular structure occurs in the cytoplasm of a hepatocyte of some of the chimpanzees, but does not occur in the cytoplasm of a hepatocyte of the other chimpanzees, and that an intranuclear particle is formed in the cytoplasm of a hepatocyte of some of the chimpanzees. These results and the results of the epidemiological observations, tests on the presence or absence of the chloroform sensitivity and immunological diagnosis suggest that a plurality of types of NANBV-sexist (see, for example, "Science", Vol. 205, pp. 197–200, 1979, "Journal of Infectious Disease", Vol. 148, pp. 254–265, 1983 and "Biseibutsu"(Microorganism), Vol. 5, No. 5, pp. 463–475, 1989). The amount of the NANBV present in the blood of a patient having NANB hepatitis is extremely small as compared to either the amount of a hepatitis A virus present in the feces of a patient having hepatitis A or the amount of a hepatitis B virus present in the blood of a patient having hepatitis B. For example, the amount of hepatitis B virus in the blood of the patient is $10^8$ to $10^9$ per ml in terms of Chimpanzee Infectious dose (CID), whereas the amount of NANBV in the blood of the patient is only $10^4$ to $10^5$ per ml in terms of CID (Bradley, D. W.: Research perspective in post-transfusion non-A, non-B hepatitis, in "Infection, Immunity and Blood Transfusion", edited by Dodd, R. Y. & Barker, L. F., published by Alan R. Liss, Inc., New York (1985) pp. 81–97). Further it is known that except for human, there are no animals except chimpanzee that are sensitive to NANBV and that in the cytoplasm of the hepatocyte, a typical tubular structure is occasionally formed by NANBV infection. Since only chimpanzee can be used as an animal for experiment of the NANBV infection, a large number of chimpanzees are required to be used for the study of NANBV. However, the chimpanzee is not easily available and expensive. Therefore, the study of NANBV, identification of NANBV and search for a useful marker for NANBV, is necessarily restricted and delay. In order to solve these problems, various attempts have been made for the study of NANBV. For example, in an attempt, an NANBV genomic cDNA [(referred to as "hepatitis C virus (HCV)"] was cloned from blood plasma of chimpanzees suffering from NANB hepatitis (Science, Vol. 244, pp. 359–362, 1989), and it was confirmed that the antigen (referred to as "C-100") obtained by expressing the cDNA exhibited an antigen-antibody reaction with the antibody in the blood of an NANB hepatitis patient (Science, Vol. 244, pp. 362–364, 1989). Further, in another attempt, a chimpanzee was not used and an NANBV genomic cDNA was cloned from the blood plasma of NANB hepatitis patients, and it was confirmed that the antigen obtained by expressing the cDNA exhibited an antigen-antibody reaction with the antibody in the serum of an NANB hepatitis patient (Gastroenteriologia Japonica, Vol. 24 pp. 540–544 and pp. 545–548, 1989).

(3) Clinical observations: Hepatitis is generally classified either into epidemic hepatitis and sporadic hepatitis according to the number and frequency of the occurrences of hepatitis, or into acute hepatitis, fulminant hepatitis, subacute hepatitis, persistent hepatitis and chronic hepatitis according to the severeness and stage of the hepatitis patients. The latent period of the NANB hepatitis is 2 to 26 weeks. The symptom of NANB hepatitis in the early stage is mild as compared to that of hepatitis B. For example, a patient having NANB hepatitis only becomes feverish and complains of languor. Further, 70% of the patients have anicteric symptom. Therefore, the NANB hepatitis is frequently overlooked. However, the NANB hepatitis is very dangerous because the NANB hepatitis is likely to become chronic and, then, to progress to liver cirrhosis. Illustratively state, 40 to 50% of the patients having NANB hepatitis whose serum exhibits an increased aminotransferase activity develop chronic hepatitis. 10 to 20% of the cases of chronic hepatitis suffer from liver cirrhosis. Further, 0.5 to 1% of blood recipients per year becomes liver cirrhosis patients without subjective symptoms. More seriously, the liver cirrhosis may further progress to liver cancer or hepatoma. Therefore, for preventing biohazard caused by blood transfusion and bleeding, eradication of the NANB hepatitis is a matter of global importance from the viewpoint of public health.

(4) Diagnosis: As mentioned above, the NANBV (blood-transmitted type) has not yet been identified and a viral marker, such as an NANBV antigen, which is useful for the diagnosis of NANB hepatitis has not been known. Therefore, diagnosis of NANB hepatitis has been conducted by examining the titer of the antibody in serum of a patient, which is specific for each of the known pathogenic viruses, such as hepatitis A virus, hepatitis B virus, cytomegalovirus, EB virus, varicella virus and herpes simplex virus, and diagnosing the patient whose serum is negative with respect to the antibody specific for any of the above-mentioned viruses, as having NANB hepatitis, or by performing a histopathological examination through a biopsy of the liver ("Disease of the Liver and biliary system", 8th edition, S. Shenlock, pp. 326–333, 1989, Blackwell Scientific Publications). At the same time, another diagnosis method has also been used. For example, there have been used a method in which the activity of an enzyme in serum, such as GPT [glutamic-pyruvic transaminase, also known as "ALT" (alanine aminotransaminase)], GOT [glutamic-oxalo-acetic transaminase, also known as "AST" (aspartate aminotransferase)], and guanine deaminase (also known as "guanase") is determined ("Kan Tan Sui (Liver, Gallbladder, Pancreas)", Vol. 14, pp. 519–522, 1987). With respect to the GPT or GOT in serum mentioned above, a standard for the diagnosis of NANB hepatitis in which lasting and abnormally high activities of GPT and GOT are utilized as a criterion for the diagnosis of NANB hepatitis, is employed in Japan ("Journal of Blood Transfusion Society in Japan", Vol. 31, No. 4, pp. 316–320, 1985; and "Nippon Rinsho", Vol. 46, p. 2635–2638, 1988). Regarding the immunological diagnosis, in the present situation in which the isolation and identification of NANBV are difficult, an antigen-antibody reaction between an antigen obtained by expression of NANBV and cDNA clone (which has been isolated using the techniques of genetic engineering and the knowledge of immunology) and the serum of an NANB hepatitis patient is used as a criterion. Examples of known antigens include an expression product of an NANBV cDNA prepared from the plasma of an NANB hepatitis patient (European Patent Application Publication No. 363025), an expression product of "HCV" cDNA prepared from the plasma of a chimpanzee having the symptoms of NANB hepatitis (European Patent Application Publication No. 318216 and Japanese Patent Application Laid-Open Specification No. 2-500550) an expression product of an NANBV cDNA derived from the liver of an NANBV-infected chimpanzee (European Patent Application Publication No. 293274, Japanese Patent Publication Specification No. 64-2576 and Japanese Patent Application Laid-Open Specification No. 1-124387). As a method for determining the antigen-antibody reaction, RIA (radioimmunoassay) and EIA (enzyme immunoassay) are generally used. However, these expression products are different in antigenioity. The antigen which is an expression product of HCV cDNA (that is, the C-100 antigen mentioned above) can be some criterion or yardstick for the diagnosis of chronic hepatitis caused by the HCV infection. However, since the region in which the antigen (C-100) exhibits its antigenicity is limited ("Biseibutsu (Microorganism)", Vol. 5, pp. 453–475, 1989; "Kan Tan Sui (Liver, Gallbladder, Pancreas)", Vol. 20, pp. 47–51, 1990; and "Igaku-no Ayumi (Progress of Medicine)", Vol. 151, p. 871, 1989), this antigen is unsatisfactorily from the viewpoint of accurate diagnosis of NANB hepatitis and NANBV infection and from the viewpoint of accurate determination of the progress of a patient suffering from chronic hepatitis and acute hepatitis for treatment thereof. Therefore, it has been desired to obtain a reliable method for the diagnosis and prognosis of the NANB hepatitis.

(5) Therapy and Prevention: Recently, the usefulness of α- and β- interferons in the treatment of chronic NANB hepatitis have been reported ("Kan Tan Sui (Liver, Gallbladder, Pancreas)" vol. 20, pp. 59–64, 1990; "Igaku-no Ayumi (Progress of Medicine)", vol. 151, pp. 871–876, 1990). However, a suitable does of α- and β- interferons and a suitable period for administration thereof have not yet been established.

On the other hand, for prevention of NANB hepatitis, various vaccines are used in which the above-mentioned conventional expression products of NANBV cDNAs (European Patent Application Publication No. 363025) or HCV cDNAs (European Patent Application Publication No. 318216) are used as an antigen. However, as is apparent from the fact that the NANBV itself has not yet been isolated and identified before completion of the present invention, it has been impossible to specify an antigen useful for NANBV vaccines from the above-mentioned expression products each having a variety of antigenic determinants (epitopes) and determine the effectiveness and safety of such a specific antigen so that the antigen can be clinically used. Accordingly, there is no NANBV vaccine which can be advantageously put into practical use.

SUMMARY OF THE INVENTION

The present invention have made extensive and intensive studies with a view toward solving the above-mentioned problems by developing a novel NANBV genomic cDNA. As a result, the present invention have surprisingly succeeded in cloning an NANBV genomic cDNA, which not only has excellent reliability as compared to the known NANBV cDNA but also is larger in length than any know NANBV cDNAs and contains the entire region of the open reading frame of the NANBV antigen peptide which can reliably exhibit an antigen-antibody reaction specific for not only sera from patients having chronic NANB hepatitis but also sera from patients having acute NANB hepatitis. This success is attributed to a unique technique of the present inventors such that in order to obtain an authentic NANBV genome, NANBV RNAs are extracted directly from NANBV particles contained in whole blood of a patient having NANB hepatitis or a resected liver of a patient having NANB hepatitis and liver cancer in combination, without multiplying the NANBV in a chimpanzee having unknown factors which are considered to have rendered difficult the isolation of NANBV, although the amount of NANBV in the blood or resected liver is extremely small, that is, as small as about $\frac{1}{10,000}$ that of a hepatitis A virus or a hepatitis B virus, but with paying minute care in the operating procedure so that the NANBV and its genome do not undergo cleavage and/or decomposition by the action of body fluids or blood enzymes during the storage of fresh materials for NANBV genome. RNAs thus prepared from fresh human materials are then converted to double-stranded cDNA by means of a reverse transcriptase to obtain a cDNA library. In order to screen an NANBV genome from the cDNA library, the cDNAs are individually inserted in lambda gtll phage vectors and then expressed on the phage plaques at high concentration, followed by screening of NANBV genomic cDNAs by repeatedly conducting enzyme immunoassay (EIA) in which both serum from a convalescent patient having acute NANB hepatitis and serum from a patient having chronic NANB hepatitis are used. Thus, safe production of the NANBV antigen polypeptide with high purity on a large scale at low cost without biohazard, has for the first time been realized by expressing the cDNA of the present invention by recombinant DNA techniques. Based on the above, the present invention has been completed.

Therefore, it is an object of the present invention to provide an NANB hepatitis virus genomic cDNA.

It is another object of the present invention to provide an NANB hepatitis virus antigen polypeptide which is useful as an active ingredient for a diagnostic reagent and a vaccine for NANB hepatitis.

It is still another object of the present invention to provide a method for producing an NANBV antigen polypeptide.

It is a further object of the present invention to provide a diagnostic reagent for NANB hepatitis.

It is still a further object of the present invention to provide a vaccine for NANB hepatitis.

The foregoing and other objects, features and advantages of the present invention will be appended from the following detailed description, appended claims taken in connection with the accompanying drawings.

BRIEF DESCRIPTION OF THE DRAWINGS

In the Drawings:

FIG. 2(1) through FIG. 2(16) show the nucleotide sequence of the entire region of the NANBV genomic cDNA according to the present invention (SEQ ID NO: 1) and the amino acid sequence (SEQ ID NO: 2) coded for by the nucleotide sequence.

DETAILED DESCRIPTION OF THE INVENTION

Figure 1:
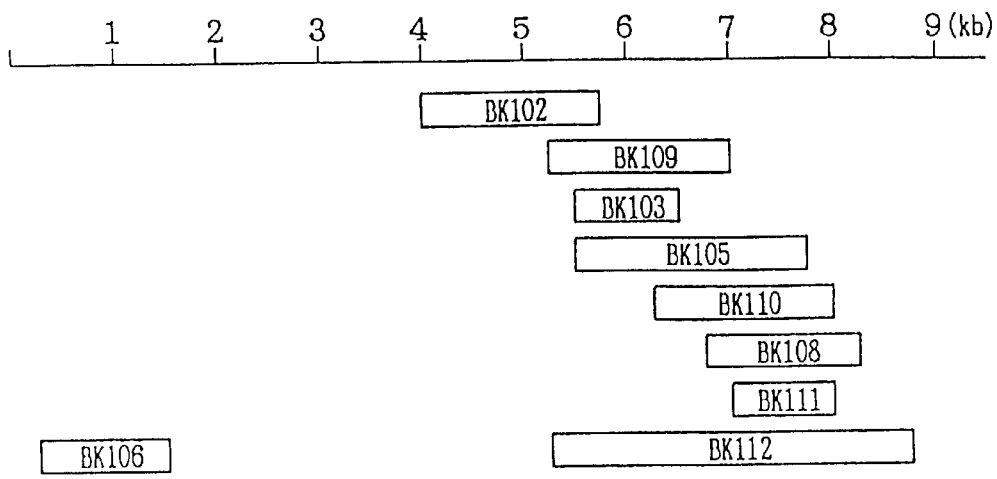
FIG. 1(1) and FIG. 1(2) are diagrams showing the relationships between the cDNA clones of the NANBV gene of the present invention, shown relative to the entire region of the NANBV genome.
Figure 1:
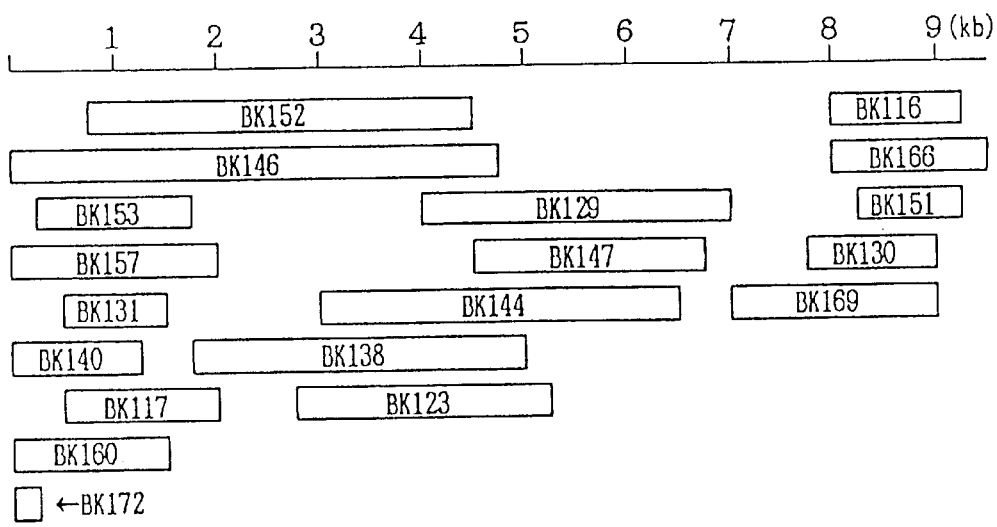

Essentially, according to the present invention there is provided an isolated deoxyribonucleic acid comprising at least one nucleotide sequence selected from the group consisting of a nucleotide sequence comprising at least part of the non-A, non-B hepatitis virus entire nucleotide sequence (SEQ ID NO: 1) from the 1st to 9416th nucleotides shown in FIG. 2(1) through FIG. 2(16) hereof and a nucleotide sequence complementary to said nucleotide sequence, or comprising at least one nucleotide sequence obtained by substituting at least one nucleotide of said nucleotide sequence in accordance with the degeneracy of the genetic code.

In another aspect of the present invention, there is provided an isolated antigen polypeptide comprising at least one amino acid sequence comprising at least part of an amino acid sequence coded for by a deoxyribonucleic acid comprising a coding region from the 333rd to 9362nd nucleotides of the non-A, non-B hepatitis virus nucleotide sequence (SEQ ID NO: 1) shown in FIG. 2(1) through FIG. 2(16) hereof.

In the present invention, unless otherwise specified, the left end and right end of the sequence of deoxyribonucleotides are the 5' end and 3' end, respectively. Further, unless otherwise specified, the left end and right end of the amino acid sequences of peptides are the N-terminus and C-terminus, respectively.

The NANBV genomic cDNA of the present invention and the NANBV antigen polypeptide as an expression product thereof can be prepared and identified in accordance with the following steps (I) to (VII).

Step (I): Selection and collection of a material for extracting an NANBV RNA.

As a material for extracting the NANBV RNA, there may be used, for example, blood, lymph, ascites and hepatocyte of an NANBV carrier, or of a human or a chimpanzee suffering from NANB hepatitis, and hepatocyte of a patient suffering from NANB hepatitis and liver cancer or hepatoma in combination. Since the materials derived from a chimpanzee may contain NANBV in a relatively small amount as compared to the materials derived from a human and a chimpanzee has unknown factors which are considered to have rendered difficult the isolation of NANBV, the use of the materials derived from a human is preferred. Of blood, lymph, ascites and hepatocytes from a human, blood can most easily be obtained in a large amount. For example, blood which is not acceptable for use as blood transfusion is available from a blood bank in a large amount. Such blood can advantageously be used as a material for extracting an NANBV RNA. When blood is used as a material, blood is separated into plasma and erthrocytes. The thus obtained plasma is examined to determine whether or not the plasma is negative to the surface antigen of hepatitis B virus (WHO expert committee on viral hepatitis: Advances in viral hepatitis, WHO Technical Report Series, 602, 28–33, 1977) and negative to a genomic DNA of hepatitis B virus (Brechot, C., Hadchouel, M., Scotto, J., Degos, F., Charnay, P., Trepo, C., Tiolais, P.: Detection of hepatitis B virus DNA in liver and serum: a direct appraisal of the chronic carrier state. Lancet 2: 765–768, 1981). Further, the plasma is examined with respect to the activities of enzymes, such as GPT (Wroblewski, F. & LaDue, J. S.: Serum glutamic-pyruvic transaminase in cardiac and hepatic disease, Proc. Soc. Exp. Biol. Med., 91, 569, 1956), GOT, guanase and the like, which are employed as the criterion for the diagnosis of NANB hepatitis. The above-mentioned procedures of the separation of blood into plasma and erthrocytes and the examination of the plasma are conducted with respect to blood of different lots. The plasma which is negative to both surface antigen and genomic cDNA of hepatitis B virus and exhibits extremely high activities of the above-mentioned enzymes, for example, a GPT activity of 35 IU/ml of more, is pooled.

The number of the NANB hepatitis virus particles in blood is extremely small as compared to that of the hepatitis B virus particles as mentioned hereinbelow. From the results of the infection experiment, the number of the NANB hepatitis virus particles in blood is estimated to be about $\frac{1}{10,000}$ of the number of the hepatitis B virus particles (Bradley, D. W., (1985); Research perspectives in post-transfusion non-A, non-B hepatitis, in "Infection, Immunity and Blood Transfusion", edited by Dodd, R. Y. & Barker, L. F., published by Alan R. Liss, Inc., New York, pp. 81–97). Therefore, for the extraction of the RNA, it is preferred to use blood in a large amount, for example, in an amount as large as about 3 to 10 liters. Fresh whole blood to be used as a material for extracting and NANB RNA from NANBV particles is stored at 1 to 5° C. in order to prevent NANBV and its gene from being denatured and to prevent its gene from being cleaved or decomposed by the action of an enzyme. It is also desirable to complete the preparation of NANBV RNAs by Step (II) within 48 to 72 hours from the collection of the fresh whole blood. When a hepatocyte is used as a material, about 1 to 3 g of a non-cancerous or a cancerous portion of a liver tissue resected from a patient having hepatoma or liver cancer which is a complication of a chronic NANB hepatitis may advantageously be used. Hepatocyte to be used as a material is stored in a frozen state at −70° C.

Step (II): Preparation of the NANBV RNA

From the material obtained in Step (I), the RNA may be extracted and purified by conventional methods. For example, when fresh whole blood is used as the material, about 2 to 10 liters of fresh whole blood is subjected to low-speed centrifugation to collect a plasma fraction as a supernatant. The virus fraction is obtained from the plasma through purification for use in the subsequent procedure for the extraction and purification of the RNA.

On the other hand, when hepatocyte is used as a material for extracting the NANBV RNA, about 5 to 30-fold volume of a diluent containing ribonuclease inhibitor is added to the liver tissue. Then, according to the conventional method using a homogenizer and the like, the liver tissue is crushed or disrupted to obtain a homogenate of hepatocyte. As a diluent, 10 to 150 mM of a conventional buffer may be used. Then, the homogenate is subjected to low-speed centrifugation to collect a supernatant. The collected supernatant is used as a original solution for the extraction and purification of the NANBV RNA. The extraction and purification of the NANBV RNA may be conducted by the conventional method, for example, an extraction method in which a mixture of a ribonuclease inhibitor, such as heparin, diethyl pyrocarbonate and guanidine thiocyanate, with a surfactant, a chelating agent, or a reducing agent capable of enhancing the denaturation of a protein, is used; a method in which fractionation is conducted by density gradient centrifugation using sucrose, cesium chloride, cesium trichloroacetate, Ficoll (Pharmacia Fine Chemicals AB, Sweden) or the like as a solute of a gradient; a method in which separation is conducted by affinity column utilizing the 3'-terminal poly A chain which an mRNA specifically has; a separation method in which an mRNA-bonded poly-some is obtained by the immunoprecipitation using an antibody specific for a protein synthesized on the polysome; a phenol extraction method based on a principle of two-phase separation; a precipitation method by the use of a polyethylene glycol, a dextran sulfate, an alcohol or the like. The above-mentioned methods may be used individually or in combination. The above-mentioned procedure for extracting and purifying the NANBV RNA may preferably be conducted at pH 3 to 10 in order to prevent the irreversible denaturation of the RNA.

Step (III): Preparation of a double-stranded cDNA from the NANBV RNA

Using the above-obtained NANBV RNA as a template, a cDNA may be prepared by a customary method. That is, using an oligodeoxythymidine and a random hexanucleotide primer as primers and using a reverse transcriptase, a cDNA complementary to the NANBV RNA is synthesized using the NANBV RNA as a template to obtain a double-strand comprising the cDNA and the NANBV RNA which are complementarily bonded to each other. Then, the thus obtained double-strand is reacted with ribonu-clease H so that the NANBV RNA is decomposed and removed from the cDNA. Thus, a single-stranded cDNA is obtained. Using the obtained single-stranded cDNA as a template, a double-stranded cDNA is synthesized by means of a DNA synthase. The double-stranded cDNA synthesis may easily be conducted using a commercially available kit for cDNA synthesis, for example, cDNA Synthesis System Plus® (manufactured and sold by Amersham, England), cDNA System Kit® (manufactured and sold by Pharmacia LKB, Sweden), cDNA Synthesis Kit® (manufactured and sold by Boehringer Mannheim GmbH, West Germany), and the like. When the quantity of the synthesized cDNA is small, the cDNA can be amplified using a conventional method, such as PCR (polymerase chain reaction) method ("PCR Technology", edit by H. A. Erlich, published by Stockton Press, 1989) using a PCR kit, such as AmpliTaq (manufactured and sold by Perkin Elmer Cetus, U.S.A.).

Step (IV): Preparation of a cDNA library

Using the cDNA prepared in Step (III), a cDNA library is prepared by a customary method. That is, the cDNA prepared in Step (III) is cut into fragments having different lengths and the resultant various cDNA fragments are individually ligated to replicable cloning vectors, to thereby obtain a cDNA library. As a replicable cloning vector, any known or commercially available vectors, such as phage genes, cosmids, plasmids and animal virus genes may be sued. When a phage gene or a cosmid is used as a replicable vector, in order to attain high stability and high transforming ability of the vector after each of the cDNA fragments has been individually inserted therein, the in vitro packaging of each of the cDNA-inserted vectors is conducted by a customary method. Thus, the cDNA-inserted vectors are obtained in the form of a recombinant phage particle. The obtained phage particles are used as a cDNA library for cDNA cloning. On the ether hand, when a plasmid is used as a replicable vector, the above-mentioned cDNA fragments are individually inserted in the plasmid vectors and the resultant cDNA-inserted vectors are then individually introduced into host cells, such as cells of *Escherichia coli, Bacillus subtilis,* yeast or the like, according to a customary method. The thus obtained transformants are used as a cDNA library for cDNA cloning. Further, when the animal virus gene is used as a replicable vector, the above-mentioned cDNA fragments are individually inserted in the virus gene vectors and the resultant recombinant viruses are then individually transfected into sensitive animal cells according to a standard method and multiplied in the cells. In the case of the recombinant virus, the obtained recombinant viruses as such are used as a cDNA library.

The preparation of the cDNA library may easily be conducted using a commercially available kit, for example, a cDNA cloning system lambda gt10 and lambda gt11 (manufactured and sold by Amersham, England; BRL Inc., U.S.A.; and Stratagene Inc., U.S.A.), an in vitro packaging system (manufactured and sold by Amersham, England; BRL Inc., U.S.A.; and Stratagene Inc., U.S.A.) and the like.

Step (V): Cloning of a cDNA containing an NANBV gene from the cDNA library

In this step, a cDNA clone containing a NANBV gene is obtained. When the cDNA library is comprised of transformants, the transformants are cultured on a standard agar medium to form colonies. On the other hand, when the cDNA library is comprised of recombinant phage particles or recombinant viruses, these phage particles or recombinant viruses are used to infect known sensitive host cells, such as *Escherichia coli, Bacillus subtilis,* yeast, animal cell culture and the like, and cultured to form a plaque, or to multiply the infected cells. The above-obtained transformant colonies, plagues or infected cells are subjected to immunoassay by as least one of the standard methods individually using serum from a convalescent patient having acute NANB hepatitis, serum from a patient having chronic NANB hepatitis, and serum from chimpanzee infected with an NANBV irrespective of whether or not the NANBV is of the type which causes a tubular structure to be formed in the cytoplasm of the hepatocyte of the chimpanzee, so that colonies, plaques or infected cells which have produced an NANBV antigen specifically reacted with at least one of the above-mentioned sera are selected and isolated. For the strict selection of the colonies, plaques and infected cells, it is preferred that the above procedure be repeated. From each of the thus selected and isolated colonies, plaques or the infected cells, a cDNA clone containing an NANBV gene is isolated according to a standard method described in T. Maniatis et al., Molecular Cloning, A Laboratory manual, published by Cold Spring Harbor Laboratory, U.S.A., pp. 309–433 (1982). The immunoassay may be conducted by, for example, an enzyme-labeled antibody technique in which an antibody labeled with an enzyme, such as peroxidase and alkaline phosphatase is used; and a fluorescent antibody technique in which an antibody labeled with fluorescein isothiocyanate, europium or the like is used. It is preferred that the immunoassay by the above-mentioned technique be conducted by an indirect method because with the indirect method, high sensitivity immunoassay can be attained even by the use of an extremely small amount of serum from a patient. As a primary antibody to be used in the indirect method, serum from a patient having NANB hepatitis or serum from a chimpanzee having NANB hepatitis may preferably be employed because these sera contain an antibody specific for an NANBV antigen in relatively large amount. As a secondary antibody to be used in the indirect method, a commercially available anti-human Ig (immunoglobulin) antibody labeled with an enzyme, a fluorescent substance or the like may be used.

A specimen to be subjected to immunoassay may be prepared according to a conventional method, for example, a blotting method in which nucleic acids and proteins of the colonies, plaques and infected cells are adsorbed on a filter membrane, a method in which a microplate or a slide glass for microscopy is used, or the like. When the blotting method is used in combination with an indirect, enzyme-labeled antibody technique, the selection of the intended colonies, plaques or infected cells from an extremely large number of the original colonies, original plaques or original infected cells can be conducted easily and promptly. In this case, blotting is conducted by contacting a commercially available filter made of nitrocellulose, cellulose acetate, nylon or the like, with the colonies, plaques or infected cells.

The above-obtained cDNA clone is a part of the NANBV gene. Therefore, in order to obtain cDNA clones covering the entire region of the NANBV gene, it is requisite to extend the cDNA clone by a method in which cDNA fragments adjacent to the cDNA clone are isolated by using 3'- and 5'-terminals of the cDNA clone as a probe. In this case, the technique which is known as "gene walking" (also known as "genomic walking" or "chromosome walking") may be employed ("DNA cloning volume III", edited by D. M. Glover, pp 37–39, IRL Press, 1987; "Molecular Cloning—a laboratory manual" 2nd edit., T. Maniatis et al, 3.21–3.23, 1989). by the repetition of the cloning procedure and the gene walking, the entire region of the NANBV gene can be obtained in the form of cDNA clones.

In this step, it is preferred to determine the nucleotide sequence of each of the obtained cDNA clones. The determination of the nucleotide sequence of the cDNA clone may generally be conducted according to a conventional method, for example, the Maxam-Gilbert method, the dideoxy chain termination method (Analytical Biochemistry, 152, 232–238, 1986), or the like.

Based on the determined nucleotide sequence, the amino acid sequence can be determined. The sequencing of the amino acids is conducted from the location of the initiation codon (ATG on the cDNA or AUG on the mRNA). Important portions of the amino acid sequence, for example, a hydrophilic portion, which is considered to constitute an epitope, can be identified by synthesizing a peptide corresponding to each hydrophillic portion and purifying the synthesized polypeptide by high performance liquid chromatography (HPLC), followed by subjecting the purified peptide to enzyme immunoasssy (EIA) or radioimmunoassay (RIA).

The cDNA clones are preferably classified into groups according to the respective properties of the NANBV antigen polypeptides coded for by the cDNA clones in order to distinguishing clones from one another. In this connection, the location of each cDNA clone on the restriction map of the NANBV gene can be used as a yardstick for the classification [see FIG. 1(1) and FIG. 1(2)]. Further, it has been found that some of NANBVs have the ability to cause a tubular structure to be formed in the cytoplasm of a hepatocyte of a chimpanzee, and some of NANBV do not have such ability (Science, 205, pp. 197–200, 1979). Therefore, the cDNA clones may be identified and classified by examining the serological reactivity of each cDNA clone with serum from a chimpanzee infected with an NANBV of the type which causes a tubular structure to be formed in the cytoplasm of the hepatocyte of the chimpanzee and with serum from a chimpanzee infected with an NANBV of the type which does not cause a tubular structure to be formed in the cytoplasm of the hepacyte of the chimpanzee. The examination of this serological reactivity may be conducted by immunoassay mentioned above.

In the present invention, as shown in FIGS. 1(1) and 1(2), the cDNA clones of the NANBV gene of the present invention are identified with prefix "BK".

FIG. 1(1) is a diagram showing the relationships between the cDNA clones of the NANBV gene of the present invention, shown relative to the entire region of the NANBV gene, and FIG. 1(2) is a diagram showing the relationships between the cDNA clones obtained by gene walking, shown relative to the entire region of the NANBV gene.

These BK NANBV cDNA clones include, for example, *Escherichia coli* BK 108 (deposited at Fermentation Research Institute, Japan under the accession number FERM BP-2971), *Escherichia coli* BK 129 (deposited at Fermentation Research Institute, Japan under the accession number FERM BP-2972), *Escherichia coli* BK 138 (deposited at Fermentation Research Institute, Japan under the accession number FERM BP-2975), and *Escherichia coli* BK 172 (deposited at Fermentation Research Institute, Japan under accession number FERM BP-2975). *Escherichia coli* BK 157, *Escherichia coli* BK 166 (deposited at Fermentation Research Institute, Japan under the accession number FERM BP-2975), and *Escherichia coli* BK 172 (deposited at Fermentation Research Institute, Japan under accession number FERM BP-2976). These seven BK NANBV cDNA clones are considered to cover at least the entire region of the open reading frame of the NANBV gene and probably the entire region of the NANBV gene.

The nucleotide sequence (SEQ ID NO: 1) of the entire region of the NANBV gene which is covered by the above-mentioned BK NANBV cDNA clones and the amino acid sequence (SEQ ID NO: 2) which is coded for by this nucleotide sequence are shown in FIG. 2(1) through FIG. 2(16). Based on the entire NANBV nucleotide sequence (SEQ ID NO: 1) and the entire NANBV amino acid sequence (SEQ ID NO: 2) shown in FIG. 2(1) through FIG. 2(16), various studies and observations can be made with respect to the homology of the nucleotide sequence and amino acid sequence of the NANBV gene to those of other virus genes, the hydrophobicity index (hydrophobicity/hydrophilicity profile), the structure of the NANBV gene, the regions of epitopes (antigenic determinants) and the like.

With respect to the homology, studies can be made by comparison of the nucleotide sequence and amino acid sequence of the NANBV gene with those of various viruses whose gene are well known (Japanese Patent Application Laid-Open specification No. 62-286930 and "Virology", Vol. 161, pp. 497–510, 1987) and those of other viruses, such as bovine virus diarrhea-mucosal disease virus ("Virology", Vol. 165, pp. 497–510, 1988), swine cholera virus ("Virology", Vol. 171, pp. 555–567, 1989), tobacco vein mottling virus ("Nucleic Acid Research, Vol. 165, pp. 5417–5430, 1986), etc.

With respect to the analysis of the hydrophobicity index, studies can be made by techniques using, for example, a genetic information processing software, SDC-Genetyx (manufactured and sold by SDC Software Co., Ltd., Japan), Doolittle's program (Journal of Molecular Biology, Vol. 157, pp. 105–132, 1982) and the like.

Figure 3:
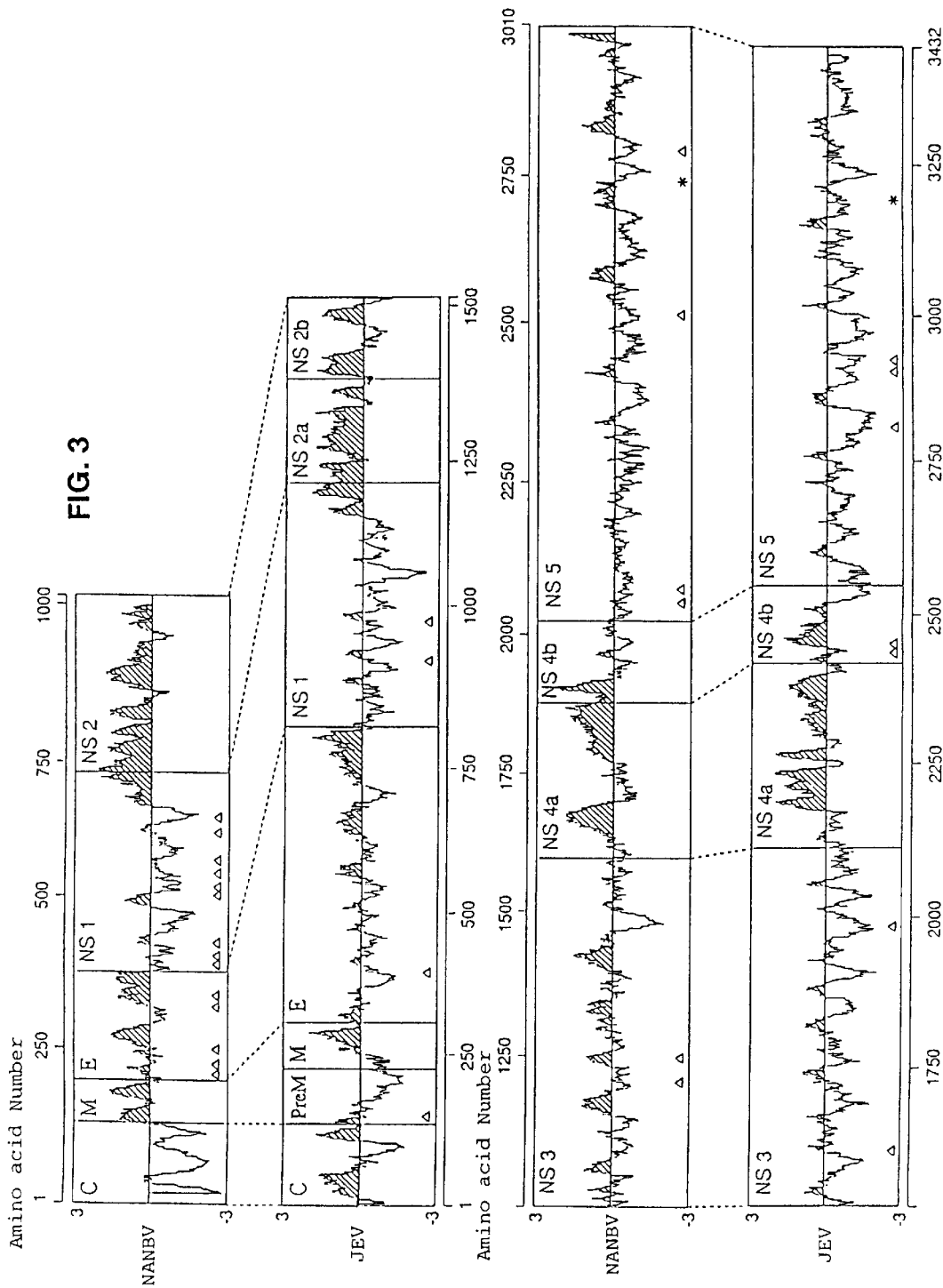
FIG. 3 is a diagram showing the hydrophobicity profiles of both of the NANBV of the present invention and the Japanese encephalitis virus (JEV), in which the hydrophobicity index of the NANBV is compared with that of the JEV.

FIG. 3 is a diagram showing the hydrophobic profiles of both of the NANBV of the present invention and the Japanese encephalitis virus (JEV), in which the respective hydrophobic indexes of both viruses are compared with each other. A significant similarity is found between the gene structure of the NANBV gene and that of the JEV gene. As shown in FIG. 3, the polypeptide of the NANBV of the present invention contains three structural proteins, namely, core protein (C), pre-matrix protein (PreM) that is further processes to matrix protein (M) and envelope protein (E), and seven nonstructural proteins, NS1, NS2a, NS2b, NS3, NS4a, NS4b and NS5. These proteins are, respectively, coded for by the following nucleotide sequences.

C protein: from the 333rd to 677th nucleotides
M protein: from the 678th to 905th nucleotides
E protein: from the 906th to 1499th nucleotides
NS1 protein: from the 1500th to 2519th nucleotides
NS2 protein: from the 2520th to 3350th nucleotides
NS3 protein: from the 3351st to 5177th nucleotides
NS4a protein: from the 5178th to 5918th nucleotides
NS4b protein: from the 5919th to 6371th nucleotides
NS5 protein: from the 6372nd to 9362nd nucleotides These nucleotide sequences are useful for the diagnosis of NANB hepatitis. Polypeptides respectively coded for by these nucleotide sequences are useful as antigens for not only vaccines but also diagnostic reagents for NANB hepatitis.

The above-mentioned three structural proteins are represented by the 1st(MET) to 389th(Gly) amino acids of SEQ ID NO: 2 shown in FIG. 2(1) through FIG. 2(3). The 1st methionine residue is the residue that is coded for by the initiation codon.

By further studies by the present inventors, it has been found that the following nucleotide sequences contain epitopes which are reactive to an anti-NANBV antibody:

nucleotide sequences respectively of the 333rd to 422nd nucleotides, of the 333rd to 1499th nucleotides, of the 333rd to 6371st nucleotides, of the 474th to 563rd nucleotides, of the 906th to 953rd nucleotides, of the 1020th to 1046th nucleotides, of the 1020th to 1121st nucleotides, of the 1194th to 1232nd nucleotides, of the 1209th to 1322nd nucleotides, of the 4485th to 4574th nucleotides and of the 5544th to 5633rd nucleotides of SEQ ID NO: 1.

As described hereinbelow, the above-mentioned nucleotide sequences or nucleotide sequences containing such nucleotide sequences as part of the whole sequences, can be effectively used not only for producing NANBV antigen polypeptides by recombinant DNA technique or chemical synthesis but also for diagnosing NANB hepatitis by hybridization or polymerase chain reaction (PCR).

Further, it has been found that a first nucleotide sequence comprising at least six nucleotides of the entire region from the 1st to 9416th nucleotides of SEQ ID NO: 1 shown in FIG. 2(1) through FIG. 2(16) is useful as a probe for hybridization or as a primer for polymerase chain reaction in the diagnosis of NANB hepatitis and that a polypeptide comprising at least four amino acids, which is coded for by a nucleotide sequence of at least twelve nucleotides of SEQ ID NO: 1 of the nucleotide sequence of the 333rd to 9362nd nucleotides of SEQ ID NO: 1 is effective as an antigen not only for a vaccine but also for a diagnostic reagent for NANB hepatitis. Further, as is well known in the art, a second nucleotide sequence complementary to the first nucleotide sequence is also useful as a probe for hybridization or as a primer for polymerase chain reaction in the diagnosis of NANB hepatitis. Further, a nucleotide sequence obtained by substituting at least one nucleotide of at least part of the coding region of the first nucleotide sequence of the NANBV in accordance with the degeneracy of the genetic code can also be used for producing the antigen polypeptide of the present invention by recombinant DNA technique.

Accordingly, the isolated deoxyribonucleic acid of the present invention comprises at least one nucleotide sequence selected from the group consisting of a first nucleotide sequence comprising at least part of the non-A, non-B hepatitis virus entire nucleotide sequence from the 1st to 9416th nucleotides of SEQ ID NO: 1 shown in FIG. 2(1) through FIG. 2(16) hereof and a second nucleotide sequence complementary to the first nucleotide sequence, or comprises at least one nucleotide sequence obtained by substituting at least one nucleotide of the first nucleotide sequence in accordance with the degeneracy of the genetic code.

In one preferred embodiment of the present invention with respect to the deoxyribonucleic acid, the first nucleotide sequence comprises at least six nucleotides of the non-A, non-B hepatitis virus entire nucleotide sequence from the 1st to 9416th nucleotides of SEQ ID NO: 1 shown in FIG. 2(1) through FIG. 2(16) hereof.

In another preferred embodiment of the present invention with respect to the deoxyribonucleic acid, the first nucleotide sequence comprises at least one nucleotide sequence selected from the group consisting of a nucleotide sequence of the 333rd to 422nd nucleotides, a nucleotide sequence of the 333rd to 677th nucleotides a nucleotide sequence of the 333rd to 1499th nucleotides, a nucleotide sequence of the 333rd to 6371st nucleotides, a nucleotide sequence of the 474th to 563rd nucleotides, a nucleotide sequence of the 678th to 905th nucleotides, a nucleotide sequence of 906th to 953rd nucleotides, a nucleotide sequence of the 906th to 1499th nucleotides, a nucleotide sequence of the 1020th to 1046th nucleotides, a nucleotide sequence of the 1020th to 1121st nucleotides, a nucleotide sequence of the 1194th to 1232nd nucleotides, a nucleotide sequence of the 1209th to 1322nd nucleotides, a nucleotide sequence of the 1500th to 2519th nucleotides, a nucleotide sequence of the 2520th to 3350th nucleotides, a nucleotide sequence of the 3351st to 5177th nucleotides, a nucleotide sequence of the 4485th to 4574th nucleotides, a nucleotide sequence of the 5178th to 4574the nucleotides, a nucleotide sequence of the 5178th to 5918th nucleotides, a nucleotide sequence of the 5544th to 5633rd nucleotides, a nucleotide sequence of the 5919th to 6371st nucleotides, a nucleotide sequence of the 6372nd to 9362nd nucleotides and a nucleotide sequence from the 1st to 9416th nucleotides of SEQ ID NO: 1.

The isolated antigen polypeptide of the present invention comprise at least one amino acid sequence comprising at least part of an amino acid sequence coded for by a deoxyribonucleic acid comprising a coding region from the 333rd to 9362nd nucleotides of the non-A, non-B hepatitis virus nucleotide sequence (SEQ ID NO: 1) shown in FIG. 2(1) through FIG. 2(16) hereof.

In one preferred embodiment of the present invention with respect to the antigen polypeptide, the antigen polypeptide comprises at least one amino acid sequence of at least four amino acids, which is coded for by a nucleotide sequence of at least twelve nucleotides of the nucleotide sequence of the 333rd to 9362nd nucleotides of SEQ ID NO: 1.

In another preferred embodiment of the present invention with respect to the antigen polypeptide, the antigen polypeptide comprises an amino acid sequence code for by a nucleotide sequence selected form the group consisting of a nucleotide sequence of the 333rd to 422nd nucleotides, a nucleotide sequence of the 333rd to 677th nucleotides, a nucleotide sequence of the 333rd to 1499th nucleotides, a nucleotide sequence of the 333rd to 6371st nucleotides, a nucleotide sequence of the 474th to 563rd nucleotides, a nucleotide sequence of the 678th to 905th nucleotides, a nucleotide sequence of the 906th to 953rd nucleotides, a nucleotide sequence of the 906th to 1499th nucleotides, a nucleotide sequence of the 1020th to 1046th nucleotides, a nucleotide sequence of the 1020th to 1121st nucleotides, a nucleotide sequence of the 1194th to 1232nd nucleotides, a nucleotide sequence of the 1209th to 1322nd nucleotides, a nucleotide sequence of the 1500th to 2519th nucleotides, a nucleotide sequence of the 2520th to 3350th nucleotides, a nucleotide sequence of the 3351st to 5177th nucleotides, a nucleotide sequence of the 4485th to 4574th nucleotides, a nucleotide sequence of the 5178th to 5918th nucleotides, a nucleotide sequence of the 5544th to 5633rd nucleotides, a nucleotide sequence of the 5919th to 6371st nucleotides, a nucleotide sequence of the 6372nd to 9362nd nucleotides and a nucleotide sequence of the 333rd to 9362nd nucleotides of SEQ ID NO: 1.

Furthermore, it should be noted that since a polypeptide coded for by the entire coding region of the NANBV (SEQ ID NO: 1) shown in FIG. 2(1) through FIG. 2(16), such a polypeptide has a broad antigen-antibody reaction spectrum and therefore can react to a wide variety of antibodies produced by infection with NANB hepatitis virus as compared to an antigen containing a single epitope, so that it has high sensitivity in detecting NANB hepatitis.

Step (VI): Expression of the NANBV genomic cDNA clone and a mass production of an NANBV antigen polypeptide.

In order to express the cloned cDNA of an NANBV antigen gene to produce an NANBV antigen polypeptide on a commercial scale, part or whole of the cloned cDNA present in the cDNA clone in taken out from the replicable cloning vector and recombined with a replicable expression vector. Illustratively stated, part or whole of the cDNA of each cDNA clone is cut off using a restriction enzyme to obtain a DNA fragment containing an NANBV antigen gene (hereafter referred to as "NANBV DNA fragment"). The NANBV DNA fragment is then inserted in a replicable expression vector by a customary method. When one DNA fragment is inserted in an expression vector, one type of antigen polypeptide can be produced by gene expression. When two or more of different DNA fragments are inserted in sequence in an expression vector, an antigen polypeptide can be produced by gene expression in the form of a fused polypeptide comprising polypeptides coded for the inserted DNA fragments.

As the replicable expression vector which may be used in this step, any conventionally known or commercially available expression vector can be used. Examples of expression vectors include plasmid vector pSN508 for enterobacteria (U.S. Pat. No. 4,703,005), plasmid vector pBH103 for yeast, and its series (Japanese Patent Application Laid-Open Specification No. 63-22098), plasmid pJM105 (Japanese Patent application Laid-Open Specification No. 62-286930), an attenuated chicken pox virus gene (Japanese Patent Application Laid-Open Specification No. 53-41202), an attenuated Marek's disease virus (The Journal of Japanese Society of Veterinary, 27, 20–24 (1974), and Gan Monograph on Cancer Research, 10, 91–107 (1971)), plasmid pTTQ series (manufactured and sold by Amersham, England), plasmid pSLV series (manufactured and sold by Pharmacia LKB, Sweden), and the like.

The NANBV DNA-inserted expression vectors are individually introduced or transfected into host cells sensitive to the vector according to a conventional method, to obtain transformants. Then, from the transformants, the transformant(s) which has produced an NANBV antigen polypeptide or an NANBV particle is selected. The production of an NANBV antigen polypeptide (or an NANBV particle) may be detected by the immunoassay mentioned above in Step (V). When an animal virus gene is used as an expression vector, a recombinant virus having an NANBV antigen polypeptide on the surface thereof may be obtained. Such a recombinant virus may advantageously be used as a raw material for a multifunctional vaccine having not only an antigenicity inherent in the virus vector but also an antigenicity of the NANBV.

By culturing the transformant or recombinant virus obtained above according to a customary method, an NANBV antigen polypeptide can be produced in the culture of the transformant or recombinant virus on a commercial scale. With respect to the details of the method in which an animal virus gene is used as an expression vector, reference may be made to European patent Application Publication No. 0 334 530 A1.

Accordingly, in still another aspect of the present invention, there is provided a method for producing a non-A, non-B hepatitis virus antigen polypeptide, which comprises:

(a) inserting a deoxyribonucleic acid into a replicable expression vector selected from a plasmid and an animal virus gene to obtain a replicable recombinant DNA comprising the plasmid and the deoxyribonucleic acid inserted therein when the replicable expression vector is a plasmid or obtain a recombinant virus comprising the animal virus gene and the deoxyribonucleic acid inserted therein when the expression vector is an animal virus gene, the deoxyribonucleic acid comprising a nucleotide sequence selected from the group consisting of a first nucleotide sequence comprising at least part of a region from the 1st to 1499th nucleotides or at least part of a region from the 1500th to 9416th nucleotides of the non-A, non-B hepatitis virus entire nucleotide sequence (SEQ ID NO:1) shown in FIG. 2(1) through FIG. 2(16) hereof and a nucleotide sequence obtained by substituting at least one nucleotide of the first nucleotide sequence in accordance with the degeneracy of the genetic code;

(b) transfecting cells of a microorganism or eukaryotic cell culture with the recombinant DNA when the replicable expression vector used in step (a) is a plasmid, to thereby form a transformant, followed by selection of the transformant from parent cells of the microorganism or eukaryotic cell culture;

(c) culturing the transformant obtained in step (b) to thereby express the deoxyribonucleic acid and produce a non-A, non-B hepatitis virus antigen peptide, or culturing the recombinant virus obtained in step (a) to thereby express the deoxyribonucleic acid and the animal virus gene and produce a non-A, non-B hepatitis virus antigen peptide in the form of a multiplied recombinant virus comprising an animal virus and a non-A, non-B hepatitis virus antigen peptide contained on the surface thereof; and (d) isolating the non-A, non-B hepatitis virus antigen peptide alone or in the form of the multiplied recombinant virus.

Furthermore, by using part or whole of the cDNA of FIG. 2(1) through FIG. 2(16) (SEQ ID NO: 1) as a template, an RNA or mRNA corresponding thereto can be synthesized by in vitro transcription according to a standard method. For example, an RNA or mRNA corresponding to the entire region of the cDNA of FIG. 2(1) through FIG 2(16) (SEQ ID NO:1) can synthesized using as a template the entire region of the cDNA which is prepared by digesting plasmid pDM-18 (constructed in Example 2) with restriction enzyme HindIII, followed by in vitro transcription by means of T7 RNA polymerase and cap analog. The thus synthesized RNA or mRNA covers the entire region of NANBV gene, that is, the RNA or mRNA is substantially naked NANBV genome. Therefore, when the mRNA is transfected into animal cells, an infectious NANBV particle can be obtained. The above-mentioned mRNA can be synthesized by means of, for example, a commercially available mRNA Capping Kit (manufactured and sold by Stratagene, U.S.A.) in a conventional manner. With respect to the details of the operating procedure for the synthesis, reference may be made to "Current Protocols in Molecular Biology", 10.17.1–10.17.5, published by John Wiley & Sons, 1989). The RNA which can be obtained using part or whole of the cDNA of FIG. 2(1) through FIG. 2(16) (SEQ ID NO: 1), is part or whole of the NANBV genome and, therefore, it is useful for studying NANBV and infectious disease caused thereby.

Step (VII): Purification of an NANBV antigen polypeptide

The NANBV antigen polypeptide produced in the culture of the transformant or recombinant virus may be purified using an appropriate combination of customary techniques selected from, for example, salting-out; adsorption and desorption using a silica gel, an activated carbon or the like; precipitation by an organic solvent; fractionation by ultracentrifugation; separation by ion exchange chromatography or affinity column chromatography; fractionation by high-performance liquid chromatography or electrophoresis, and the like.

When the NANBV antigen polypeptide is purified from the culture of an E. coli transformant or a yeast transformant, from the viewpoint of effective removal of allergens derived from E. coli and yeast which cause the quality of the final product of the NANBV antigen polypeptide to be markedly lowered, it is preferred that the purification be conducted by, for example, the steps of (1) adsorption and desorption using a silica gel, removal of impurities by adsorption on an activated carbon and (2) fractionation by density gradient centrifugation in this order (Japanese Patent Application Laid-Open Specification No. (63-297). When the NANBV antigen polypeptide is purified from the culture of a recombinant virus, e.g., the culture of a recombinant virus-infected cells, a high purity NANBV antigen polypeptide can be obtained by subjecting a crude solution containing the antigen to purification by ultracentrifugation and density gradient centrifugation repeatedly.

Thus, a solution containing a purified NANBV antigen polypeptide of the present invention is obtained. If desired, the solution may be lyophilized to obtain a purified NANBV antigen polypeptide in a dry form.

The mixed antigen polypeptide of the present invention may be obtained by mixing at least two different types of the NANBV antigen polypeptides obtained by gene expression of at least two different types of cDNAs having different nucleotide sequences.

As described above, the core protein (C protein), matrix protein (M protein) and envelope protein (E protein) of the NANBV are included in the region from the 1st (Met) to 389th (Gly) amino acids of SEQ ID NO:2 shown in FIG. 2(1) through FIG. 2(3). Therefore, the above-mentioned epitopes contained in this region, especially epitopes coded for by nucleotide sequences respectively of the 906th to 953rd nucleotides, of the 1020th to 1046th nucleotides and of the 1194th to 1232nd nucleotides of SEQ ID NO: 1, are extremely useful as antigens. The epitopes may be obtained by polypeptide synthesis. The polypeptide synthesis can be conducted by means of a commercially available polypeptide synthesizer, such as polypeptide synthesizer COUPLER 2100 (manufactured and sold by Du Pont, USA) and polypeptide synthesizer 430A (manufactured and sold by Applied Biosystems, USA). The synthesized antigen polypeptide may be used, for example, for producing a vaccine, a diagnostic reagent and an antibody.

In a further aspect of the present invention, there is provided a replicable recombinant comprising a replicable expression vector selected from a plasmid and an animal virus gene and a deoxyribonucleic acid comprising a nucleotide sequence selected from the group consisting of the first nucleotide sequence comprising at least part of a region from the 1st to 1499th nucleotides or at least part of a region from the 1500th to 9416th nucleotides of the non-A, non-B hepatitis virus nucleotide sequence (SEQ ID NO:1) shown in FIG. 2(1) through FIG. 2(16) hereof and a nucleotide sequence obtained by substituting at least one nucleotide of the first nucleotide sequence in accordance with the degeneracy of the genetic code.

The replicable recombinant can be used not only for producing the NANBV antigen polypeptide of the present invention but also for amplifying the NANBV genomic cDNA of the present invention by replication.

In a preferred embodiment of the present invention with respect to the replicable recombinant for amplifying the NANBV genomic cDNA by replication, the first nucleotide sequence comprises at least six nucleotides of the nucleotide sequence of the 1st to 1499th nucleotides or at least six nucleotides of the nucleotide sequence of the 1500th to 9416th nucleotides of SEQ ID NO:1.

In a preferred embodiment of the present invention with respect to the replicable recombinant for producing the NANB antigen polypeptide, the first nucleotide sequence comprises at least twelve nucleotides of the nucleotide sequence of the 333rd to 1499th nucleotides or at least twelve nucleotides of the nucleotide sequence of the 1500th to 9362nd nucleotides of SEQ ID NO:1.

In another preferred embodiment of the present invention with respect to the replicable recombinant for producing the NANBV antigen polypeptide, the first nucleotide sequence is selected from the group consisting of a nucleotide sequence of the 333rd to 422nd nucleotides, a nucleotide sequence of the 333rd to 677th nucleotides, a nucleotide sequence of the 333rd to 1499th nucleotides, a nucleotide sequence of the 474th to 563rd nucleotides, a nucleotide sequence of the 678th to 905th nucleotides, a nucleotide sequence of the 906th to 953rd nucleotides, a nucleotide sequence of the 906th to 1499th nucleotides, a nucleotide sequence of the 1020th 1046th nucleotides, a nucleotide sequence of the 1020th to 1121st nucleotides, a nucleotide sequence of the 1194th to 1232nd nucleotides, a nucleotide sequence of the 1209th to 1322nd nucleotides, a nucleotide sequence of the 1500th to 2519th nucleotides, a nucleotide sequence of the 2520th to 3350th nucleotides, a nucleotide sequence of the 3351st to 5177th nucleotides, a nucleotide sequence of the 4485th to 4574th nucleotides, a nucleotide sequence of the 5178th to 5918th nucleotides, a nucleotide sequence of the 5544th to 5633rd nucleotides, a nucleotide sequence of the 5919th to 6371st nucleotides and a nucleotide sequence of the 6327nd to 9362nd nucleotides of SEQ ID NO:1.

The purified NANBV antigen polypeptide of the present invention is useful as a diagnostic reagent for detecting NANB hepatitis.

The NANBV antigen polypeptide of the present invention can be formulated into a diagnostic reagent as follows. The purified NANBV antigen polypeptide solution obtained above is dispensed in a vessel, such as a vial and an ampul, and sealed. The antigen polypeptide solution put in a vessel may be lyophilized before the sealing, in the same manner as mentioned above. The amount of the NANBV antigen polypeptide put in a vessel is generally about 1 µg to about 10 mg. Alternatively, the NANBV antigen polypeptide may also be adsorbed on the surface of a customarily employed support, such as a microplate, polyethylene beads, filter paper or a membrane.

The determination of the reactivity of the serum with the NANBV antigen polypeptide may be conducted in substantially the same manner as described in Step (V) mentioned above. That is, the determination of the reactively may be conducted by a conventional immunoassay method, such as radioimmunoassay (RIA), enzyme-linked immunosorbent assay (ELISA), fluorescent antibody technique (FA), passive haemagglutination (PHA), reversed passive haemagglutination (rPHA) and the like. The amount of the NANBV antigen polypeptide to be used for the above immunoassay is generally from about 0.1 to about 100 mg/ml of serum. Particularly, the amounts of the NANBV antigen polypeptide to be used for RIA, ELISA, FA, PHA and rPHA are generally from 0.1 to 1 mg/ml, from 0.1 to 1 mg/ml, from 1 to 100 mg/ml, from 1 to 50 mg/ml and from 1 to 50 mg/ml, respectively.

The NANBV antigen polypeptide of the present invention may also be used for screening blood for transfusion. The screening method consists in:

a) isolating serum from whole blood;

b) contacting serum of an unknown blood with an isolated NANBV antigen polypeptide comprising at least one amino acid sequence comprising at least part of an amino acid sequence coded for by a deoxyribonucleic acid comprising a coding region from the 333rd to 9362nd nucleotides of the NANBV nucleotide sequence (SEQ ID NO:1) shown in FIG. 2(1) through FIG. 2(16);

c) determining whether the serum reacts with the NANBV antigen polypeptide;

d) classifying the serum as positive or negative to non-A, non-B hepatitis based on the reactivity; and e) effecting separation of the blood in accordance with the identification.

The contact of serum of an unknown blood with the NANBV antigen polypeptide of the present invention, and the determination of the reactivity of the serum of the blood with the NANBV antigen polypeptide may be conducted in the same manner as mentioned above with respect to the method for diagnosing NANB hepatitis. By the above method, a blood for transfusion free from the NANBV can be selected.

The polyclonal antibody and monoclonal antibody specific for the NANBV antigen polypeptide of the present invention may be used as an agent for removing NANBV from blood for transfusion. That is, NANBV present in blood can efficiently be removed by the polyclonal antibody or the monoclonal antibody by antigen-antibody reaction.

Further, the NANBV antigen polypeptide of the present invention may advantageously be used as an active ingredient of a vaccine for NANB hepatitis. The vaccine for NANB hepatitis may be prepared as follows. The culturing of a transformant containing a recombinant phage or plasmid carrying the cDNA coding for the NANBV antigen polypeptide, or a cell infected with the recombinant virus carrying the cDNA coding for the NANBV antigen polypeptide is conducted in the same manner as described above to thereby produce the NANBV antigen polypeptide in the culture. For detoxifying the NANBV antigen polypeptide in the culture to secure the safety of the antigen polypeptide and for fixing the antigen polypeptide to stabilize the immunogenicity and the antigenicity of the antigen polypeptide, it is preferred to add a conventional inactivating agent to the culture of the transformant or recombinant virus-infected cell, or to a culture medium obtained by removing the transformant cells or the recombinant virus-infected cell. For example, an inactivating agent, such as formalin, may be added in an amount of from 0.0001 to 0.001 v/v %, followed by incubation at 4 to 37° C. for 5 to 90 days. Then, the resultant culture or culture medium is subjected to purification in the same manner as mentioned above. Thus, an original NANB hepatitis vaccine solution containing the purified NANBV antigen polypeptide is obtained.

The original NANB hepatitis vaccine solution is filtered using a microfilter by a standard method to sterilize the solution. The filtrate is diluted with physiological saline so that the protein concentration is about 1 to about 500 $\mu$g/ml as measured by the Lowry method. To the resultant solution is then added aluminum hydroxide gel as an adjuvant so that the concentration of the added gel becomes about 0.01 to about 1.0 mg/ml. As an adjuvant, there may also be employed precipitating depositary adjuvants such as calcium phosphate gel, aluminum phosphate gel, aluminum sulfate, alumina and bentonite, and antibody-production inducing adjuvants such as muramyl peptide derivatives, polynucleotides, Krestin® (manufactured and sold by Kureha Chemical Industry Co., Ltd., Japan) and picibanil (both of which are an antineoplastic agent). Further, to the mixture, at least one stabilizing agent may be added. As the stabilizing agent, any commercially available stabilizing agent may be used. Examples of stabilizing agents include gelatin and hydrolysates thereof, albumin, saccharides such as glucose, fructose, galactose, sucrose and lactose, and amino acids such as glycine, alanine, lysine, arginine and glutamine.

Then, the thus obtained NANB hepatitis vaccine solution containing a gel-adsorbed NANBV antigen polypeptide is dispensed into a small vessel, such as an ampul and a vial, and sealed. Thus, there is obtained a purified adsorbed NANB hepatitis vaccine comprising an adsorbed NANBV antigen polypeptide.

The NANB hepatitis vaccine solution thus obtained may be lyophilized to obtain the NANB hepatitis vaccine in a dried form so that the product can be transported to and stored at a place of severe climate, for example, in an area in the tropics. The lyophilization may generally be conducted according to a standard method after the liquid adsorbed NANB hepatitis vaccine is dispensed in a vessel such as a vial and an ampul. After lyophilization, a nitrogen gas is introduced in the vessel containing the dried vaccine, followed by sealing. Incidentally, the quality of the vaccine produced is examined in accordance with "Adsorbed Hepatitis B Vaccine", "Dried Japanese Encephalitis Vaccine", and "Adsorbed Pertussis Vaccine" provided for in Notification No. 159 of the Ministry of Health and Welfare, Japan, "Minimum Requirements for Biological Products".

The NANB hepatitis vaccine may be prepared in the form of a mixed vaccine which contains an adsorbed NANBV antigen polypeptide mentioned above and at least one antigen other than the present NANBV antigen polypeptide. As the antigen other than the present NANBV antigen polypeptide, there may be employed any antigens that are conventionally used as active ingredients of the corresponding vaccines insofar as the side effects and adverse reactions caused by such other antigens and the NANBV antigen polypeptide are not additively or synergistically increased by the use of the NANBV antigen polypeptide and such other antigens in combination and the antigenicities and immunogenicities of the NANBV antigen polypeptide and such other antigens are not reduced by the interference between the NANBV antigen polypeptide and other antigens. The number and the types of the antigens which may be mixed with the NANBV antigen polypeptide are not limited insofar as the side effects and adverse reactions are not increased additively or synergistically and the antigenicity and immunogenicity of each of the NANBV antigen polypeptide and such antigens are not reduced as mentioned above. Generally, two to six types of antigens may be mixed with the NANBV antigen polypeptide. Examples of antigens which may be mixed with the present NANBV antigen polypeptide, include detoxified antigens, inactivated antigens or toxoids which are derived from Japanese encephalitis virus, HFRS (hemorrhagic fever with renal syndrome) virus, influenza virus, parainfluenza virus, hepatitis B virus, dengue fever virus, AIDS virus, *Bordetella pertussis*, diphtheria bacillus, tetanus bacillus, meningococcus, pneumococcus and the like.

Generally, the vaccine comprising the NANBV antigen polypeptide of the present invention may be contained and sealed in a vial, an ampul or the like. The vaccine of the present invention may generally be administered in the form of a liquid or suspension. In the case where the vaccine is in a dried form, the vaccine is dissolved or suspended in sterilized distilled water before administration, the amount of the distilled water being such that the volume becomes the original volume before being subjected to lyophilization. Generally, the vaccine may be administered subcutaneously. The dose of the vaccine per person may generally be about 0.5 ml. In general, the dose of the vaccine per child may be half as much as that of the vaccine per adult. The vaccine may generally be administered twice at an interval of about one week to one month and then, about half a year later, administered once more.

Further, the NANBV antigen polypeptide may be used for preparing an antibody, such as a polyclonal antibody and a monoclonal antibody, specific for the NANBV antigen polypeptide. For example, a polyclonal antibody specific for the NANBV antigen polypeptide may be prepared by a conventional method as follows. The purified NANBV antigen polypeptide of the present invention is inoculated subcutaneously, intramuscularly, intraperitoneally or intravenously to an animal, such as mouse, guinea pig and rabbit. The inoculation of the NANBV antigen polypeptide is generally conducted several times at intervals of 1 to 4 weeks, to thereby completely immunize the animal. In order to enhance the immunizing effect, a conventional and commercially available adjuvant may be used. Then, blood serum is collected from the immunized animal and an anti-NANBV antigen polypeptide polyclonal antibody is isolated and purified from the blood serum according to a standard method.

On the other hand, a monoclonal antibody specific for the NANBV antigen polypeptide may be prepared by a conventional method as described, for example, in Cell Technology, 1, 23–29 (1982). For example, splenic cells obtained from a mouse immunized with the purified NANBV antigen polypeptide are fused with commercially available mouse myeloma cells by cell fusion technique, to obtain hybridomas. The hybridomas are screened to obtain a hybridoma capable of producing an antibody reactive with the NANBV antigen polypeptide. The obtained hybridoma is cultured in a standard method. From the supernatant of the culture, an anti-NANBV antigen polypeptide monoclonal antibody is isolated and purified by a standard method.

The above-mentioned polyclonal antibody and monoclonal antibody may also be used as a diagnostic reagent for diagnosing NANB hepatitis. The diagnosis of NANB hepatitis using the antibody may be conducted by immunoassay in substantially the same manner as mentioned above with respect to the diagnosis of NANB hepatitis using the NANBV antigen polypeptide. By the use of the polyclonal antibody or the monoclonal antibody, the identification and quantification of the NANBV antigen polypeptide present in a liver tissue and blood can be conducted.

The NANBV genomic cDNA of the present invention can be prepared by digesting the NANBV genomic cDNA clone defined in the present invention with an appropriate restriction enzyme. Also, the NANBV genomic cDNA of the present invention can be prepared by the technique of DNA synthesis in accordance with the nucleotide sequence (SEQ ID NO:1) shown in FIG. 2(1) to FIG. 2(16) of the present application. The preparation of the NANBV genomic cDNA by way of DNA synthesis can be performed by means of a customary DNA synthesizer, such as DNA synthesizer Model 380B (manufactured and sold by Applied Biosystem, U.S.A.) and DNA Synthesizer Model 8700 (manufactured and sold by Biosearch, U.S.A.). The NANBV genomic cDNA of the present invention can be used to conduct the genetic diagnosis of NANBV infection. That is, the NANBV genomic cDNA of the present invention can be used as a primer for polymerase chain reaction (PCR) in the detection of an NANBV gene in the body fluid or cells from a patient. For the diagnosis by polymerase chain reaction, the NANBV genomic cDNA is used in an amount of 10 to 100 ng.

The NANBV genomic cDNA of the present invention may also be used for diagnosing NANB hepatitis by hybridization technique. That is, the NANBV genomic cDNA is labeled with, for example, biotin, alkaline phosphatase, radioisotope $^{32}$P or the like and used as a probe for hybridization. The cDNA to be used for the diagnosis by hybridization technique may be prepared by a standard method, for example, as follows. The recombinant phage containing the NANBV cDNA obtained in Step (V) mentioned above is digested with an appropriate restriction enzyme to cut off the DNA fragment containing the NANBV cDNA. The obtained DNA fragment is ligated to a commercially available replicable cloning plasmid to obtain a recombinant plasmid containing the DNA fragment. The recombinant plasmid is introduced in a host cell to form a transformant and the transformant is cultured to multiply the recombinant plasmid. The multiplied recombinant plasmid is isolated from the transformant and digested with a restriction enzyme. The resultant digest is subjected to low-melting point agarose gel electrophoresis to isolate and purify the cDNA coding for the NANBV antigen polypeptide. The thus obtained cDNA is labeled with biotin, alkaline phosphatase, radioisotope $^{32}$P or the like. The labeling of the cDNA may be conducted by using a commercially available nick translation kit or multiprime DNA labeling system (manufactured and sold by, for example, Amersham, England; Nippon Gene Co., Ltd., Japan; and the like). The labeled cDNA is put in a vessel having a volume of about 5 to 20 ml, such as a vial or an ampul, and sealed. The amount of the labeled cDNA put in a vessel is generally 1 to 100 µg per vessel. The labeled cDNA may be contained in the vessel in the form of a solution. Alternatively, the labeled cDNA may be contained in the vessel in a lyophilized state. The diagnosis of NANB hepatitis by the use of the labeled cDNA is conducted by a standard hybridization method. That is, plasma, serum or leukocytes obtained from a patient is placed in contact with the labeled cDNA and an RNA hybridized with the labeled cDNA is detected. The detection of the RNA hybridized with the labeled cDNA may be conducted by a standard method. When the cDNA is labeled with an enzyme, the detection is conducted by enzyme immunoassay. When the cDNA is labeled with a radioisotope, the detection is conducted by, for example, scintillation counting.

The NANBV genomic cDNA of the present invention is excellent in reliability and contains the entire region of the open reading frame of the NANBV gene.

The NANBV antigen polypeptide of the present invention is specifically reactive with the NANBV. Therefore, when the NANBV antigen polypeptide is used as a diagnostic reagent, the diagnosis of NANB hepatitis can be conducted easily with high reliability. Further, when the NANBV antigen polypeptide of the present invention is used for screening blood for transfusion, blood which is infected by NANBV can be selected easily with high reliability and removed from blood not infected by NANBV. Therefore, the post-transfusion. NANB hepatitis can be prevented.

Further, the NANBV antigen polypeptide of the present invention may advantageously be used as an active ingredient of a vaccine for preventing NANB hepatitis.

Further, by the use of the NANBV antigen polypeptide of the present invention, an antibody, particularly monoclonal antibody, specific for NANBV can easily be prepared. The antibody specific for NANBV can advantageously be used as not only a diagnostic reagent for detecting NANB hepatitis, but also an agent for removing NANBV from blood for transfusion.

Furthermore, it should be noted that the NANBV antigen polypeptide of the present invention is not produced by the infection of an animal with a virus, but produced by gene expression of the DNA coding for the present antigen polypeptide in a host cell. Hence, the possibility of infection during the steps for production of the present antigen polypeptide is substantially eliminated. Also, the production cost can be decreased. Moreover, since all of the materials used in the production process, e.g., medium for the incubation system, are well-known in respect of the composition thereof, purification is facile and an antigen polypeptide product having high purity can be obtained.

PREFERRED EMBODIMENT OF THE INVENTION

The present invention will now be described in detail with reference to the following Examples, which should not be construed to be limiting the scope of the present invention.

EXAMPLE 1

Step 1 (Preparation of a plasma-derived RNA for producing cDNA, which is complementary to NANBV genome RNA)

In order to obtain NANBV from plasma, 4.8 liters of human plasma exhibiting a glutamic=pyruvic transaminase (GPT) activity of 35 IU/ or more (as measured by the method of Wroblewski, F & J. S. LaDue: Serum glutamic-pyruvic transaminase in cardiac and hepatic disease. Proc. Soc. Exp. Biol. Med., 91:569, 1956) was superposed on a 30% (w/w) aqueous sucrose solution, and subjected to centrifugation under 48,000 x g at 4° C. and for 13 hours to obtain a precipitate. The precipitate was suspended in an aqueous solution containing 50 mM Tris.HCl (pH 8.0) and 1 mM EDTA, and once more subjected to centrifugation under 250,000 x g at 4° C. and for 3 hours to thereby obtain a precipitate. The obtained precipitate was dissolved in 75 ml of 5.5M GTC solution containing 5.5M quanidine thiocyanate, 20 mM sodium citrate (pH 7.0), 0.05% sarkosyl (sodium lauryl sarcosinate) and 0.1M 2-mercaptoethanol. The resultant solution was superposed on 16 ml of CsTFA-0.1M EDTA solution ($\rho$=1.51), and subjected to centrifugation under 140,000 x g at 15° C. and for 20 hours to thereby obtain a precipitate of RNA. The supernatant containing proteins and DNA was removed by suction, and the precipitate was dissolved in 200 $\mu$l of TE 10 mM Tris.HCl, pH 8.0 and 1 mM EDTA solution. 20 $\mu$l of 3M sodium chloride and ethanol were added to the solution, and allowed to stand still at –70° C. for 90 minutes. The mixture was centrifuged under 12,000 X g at 4° C. and for 30 minutes to obtain a precipitate. The precipitate was dissolved in TE, and sodium chloride and ethanol were added in the same manner as mentioned above. The mixture was allowed to stand still at –70° C. to obtain a precipitate. The precipitate was dissolved in 10 $\mu$l of TE to thereby obtain a purified RNA.

Step 2 (Preparation of a liver-derived RNA for producing a cDNA, which is complementary to NANBV genome RNA)

NANBV genome RNA was prepared from a liver tissue cut off from a NANBV hepatitis patient by the method of Okayama et al. (see H. Okayama, M. Kawaichi, M. Brownstein, F. Lee, T. Yokota, and K. Arai: High-Efficiency Cloning of Full-Length cDNA; Construction and Screening of cDNA Expression Libraries for Mammalian Cells, Methods in Enzymology 154.3–28, 1987).

Illustratively state, 1 g of liver tissue was cut into small pieces. The small pieces were suspended in 100 ml of 5.5M GTC solution as used in Step 1, and homogenized by means of a Teflon-glass homogenizer. Subsequently, the introduction of the homogenate into a syringe having #18 needle and the discharge of the homogenate from the syringe through the needle were repeated to thereby mechanically split DNA. The resultant homogenate was centrifuged under 1,500 x g (lower centrifugal force) at 4° C. and for 15 minutes to thereby obtain a supernatant. The supernatant was superposed on CsTFA solution and centrifuged in substantially the same manner as described in Step 1 to thereby obtain a precipitate as an RNA fraction. The thus obtained precipitate was suspended in 0.4 ml of 4M GTC solution. 10 $\mu$l of 1M acetic acid and 300 pl of ethanol were added to the suspension, and allowed to stand still at a temperature of –20° C. for at least 3 hours to thereby obtain a precipitate of RNA. The precipitate was separated by centrifugation under 12,000 x g at a temperature of 4° C. and for 10 minutes, and dissolved in 1 ml of TE solution. 100 $\mu$l of 2M sodium chloride solution and 3 ml of ethanol were added to the solution, and the mixture was allowed to stand at –20° C. for 3 hours. The resultant precipitate was collected by centrifugation and dissolved in 10 $\mu$l of TE to thereby obtain a purified, liver-derived RNA.

Step 3 (Preparation of a double-stranded cDNA using a cDNA synthesis kit)

A double-stranded cDNA was prepared using a commercially available cDNA synthesis kit (manufactured and sold by Amersham International, England).

Illustratively state, 0.75 $\mu$g of the purified RNA obtained in Step 1 and 2 $\mu$l of random hexanucleotide primer and 2 $\mu$l of reverse transcriptase taken from the reagents included in the kit were put in a reaction tube. Then, distilled water was added in an amount such that the total volume of the resultant mixture became 20 $\mu$l. The mixture was incubated at 42° C. for 40 minutes, thereby preparing a first strand of cDNA. Subsequently, a second strand of cDNA was synthesized while cooling the reaction mixture in ice water, as follows. To 20 $\mu$l of the reaction mixture were added 37.5 $\mu$l of buffer for second strand synthetic reaction, 1 $\mu$l of E. coli ribonuclease H and 6.6 $\mu$l of DNA polymerase I, which were taken from the reagents included in the kit, followed by addition of 34.9 $\mu$l of distilled water. The mixture was incubated at 12° C. for 60 minutes, 22° C. for 60 minutes and at 70° C. for 10 minutes. Then, the mixture was once more cooled with ice water. 1 $\mu$l of T4 DNA polymerase was added, incubated at a temperature of 37° C. for 10 minutes, and 4 $\mu$l of 0.25M EDTA (pH 8.0) was added to thereby terminate the reaction. The reaction mixture was mixed well with a mixture of phenol and chloroform, and centrifuged under 12,000 x g for one minute to thereby separate an aqueous layer. The aqueous layer was again subjected to the same extraction as mentioned above, and an equal amount of chloroform was added. The mixture was agitated well and centrifuged to separate an aqueous layer. Subsequently, an equal amount of 4M ammonium acetate and a two-fold amount of ethanol were added to the aqueous layer, and the mixture was cooled to –70° C., thereby obtaining a precipitate of purified double-stranded cDNA. The precipitate was dissolved in 50 $\mu$l of 2M ammonium acetate. To the mixture, 100 $\mu$l of ethanol was added, and the resultant mixture was cooled to –70° C. to thereby obtain a precipitate. The precipitate was collected by centrifugation under 12,000 x g for ten minutes. The collected precipitate was dried and then, dissolved in 20 $\mu$l of TE.

Step 4 (Preparation of a double-stranded cDNA by the Polymerase Chain Reaction (PCR) method)

The cDNAs which were prepared by means of a reverse transcriptase using as templates the RNAs prepared in Step 1 and Step 2, were individually amplified by the PCR method (see Saiki, R. K., Gelfand, D. H., Stoffer, S., Scharf, S. J., Higuchi, R., Horn, G. T., Mullis, K. B., and Erlich, H. A., Primer-directed enzymatic amplification of DNA with a thermostable DNA Polymerase, Science 239:487–491, 1988). That is, 5 to 1,000 ng of the RNA was incubated in 20 $\mu$l of a reverse transcriptase solution containing 50 mM Tris.HCl (pH 8.3), 40 mM KCl, 6 mM $MgCl_2$, 1 $\mu$M 3'-primer [synthesized oligonucleotide comprised of 25 nucleotides of nucleotide numbers 7949 to 7973 in FIG. 2(14)], 10 mM dNTP, and 0.5 unit of reverse transcriptase (product of New England Bio Lab., U.S.A.) at 37° C. for 30 minutes. To the resultant mixture was added 80 $\mu$l of a PCR reaction solution containing 18 mM Tris.HCl (pH 8.3), 48 mM KCl, 1.5 mM $MgCl_2$, 0.6 $\mu$M each of 5'-primer [synthesized oligonucleotide comprised of 25 nucleotides of nucleotide numbers 7612 to 7636 in FIG. 2(13)]and the above-mentioned 3'-primer, 10 mM dNTP and 2.5 units of Taq DNA polymerase (manufactured and sold by Perkin Elmer Cetus Co., Ltd., U.S.A.). The mixture was subjected to incubation at 94° C. for one minute, at 50° C. for 2 minutes and at 72° C. for 3 minutes. This incubation was repeated 40 times. The resultant mixture was subjected to electrophoresis using agarose gel, thereby obtaining amplified cDNA. The amplified cDNA was subjected to phenol treatment, ethanol precipitation and drying. The dried cDNA was dissolved in 10 μl of TE.

Step 5 (Preparation of a cDNA library using lambda gt11)

Using a commercially available cDNA cloning kit (manufactured and sold by Amersham International, England), a cDNA library was prepared. That is, to 130 ng of cDNA prepared in Step 3 were added 2 μl of L/K buffer, 2 μl of EcoRI adaptor and 2 μl of T4 DNA ligase, which were taken from the reagents included in the cloning kit. Distilled water was added to the solution in an amount such that the total volume of the resultant mixture became 20 μl. The mixture was incubated at a temperature of 15° C. for a period of from 16 to 20 hours, and 2 μl of 0.25M EDTA was added thereto, to thereby terminate the reaction. Subsequently, the mixture was passed through a size fractionating column included in the kit, thereby removing EcoRI adaptors which were not ligated to the cDNA. To 700 μl of the cDNA having EcoRI adaptor ligated thereto were added 83 μl of L/K buffer and 8 μl of T4 polynucleotidekinase. The mixture was incubated at a temperature of 37° C. for 30 minutes. The resultant mixture was subjected to phenol extraction twice, concentration to 350 to 400 μl by means of butanol and then ethanol precipitation, thereby obtaining a precipitate. The precipitate was dissolved in 5 μl of TE.

Subsequently, in order to insert the cDNA having EcoRI adaptor ligated thereto to the EcoRI site of cloning vector lambda gt11, 1 μl of L/K buffer, 2 μl (1 μg) lambda gt11 arm DNA and 2 μl of T4 DNA ligase were added to 1 μl (10 ng) of the above-mentioned cDNA having EcoRI adaptor ligated thereto. Distilled water was added to the mixture in an amount such that the total volume of the mixture became 10 μl. The mixture was incubated at a temperature of 15° C. for a period of from 16 to 20 hours. Thus, a recombinant lambda gt11 DNA solution was prepared. Further, a recombinant lambda phage was obtained by in vitro packaging using a commercially available in vitro packaging kit (manufactured and sold by Stratagene Co., Ltd., U.S.A.) including Gigapack II Gold solutions A and B, SM buffer and chloroform. That is, 10 μl of Gigapack II Gold solution A and 15 μl of Gigapack II Gold solution B were added to 4 μl of the above-mentioned recombinant lambda gt11 DNA solution. The mixture was incubated at 22° C. for 2 hours. After the incubation, 470 μl of SM buffer and 10 μl of chloroform were added to thereby obtain a recombinant phage, which was stored at 4° C.

Step 6 (Cloning of cDNA using *E. coli* plasmid pUC19)

Using a commercially available DNA ligation kit (manufactured and sold by Takara Shuzo Co., Ltd., Japan) including solutions A and B, the cDNA was inserted in *E. coli* plasmid pUC19 (C. Yanishi-Perron, J. Vieira, J. Messing, Gene 33, 103, 1985), and cloned in *E. coli*. That is, 40 μl of solution A and 10 μl of solution B were added to 5 μl of the cDNA prepared by polymerase chain reaction (PCR) in Step 4 and 4 μl (50 ng) of plasmid pUC19 DNA which had been digested with restriction enzyme SmaI and dephosphorylated. The mixture was incubated at a temperature of 15° C. for 16 hours. *E. coli* strain JM 109 (see Messing, J., Crea, R., and Seeburg, P. H., Nucleic Acids Res. 9, 309, 1981) was transformed with the above-obtained plasmid DNA according to the calcium chloride method (see Mandel, M. and A. Higa, J. Mol. Biol., 53, 154, 1970). Thus, a transformed *E. coli* containing the plasmid having the cDNA ligated thereto was obtained.

Step 7 (Screening of clone having NANBV gene from a cDNA library)

*E. coli* strain Y 1090 (see Richard A. Yound and Ronald W. Davis, Science, 222, 778, 1983) was cultured in 50 ml of LBM medium containing 1% tryptone, 0.5% yeast extract, 1% sodium chloride, 50 μg/ml amplicillin and 0.4% maltose at a temperature of 37° C. The *E. coli* cells in a logarithmic growth phase were suspended in 15 ml of 10 mM magnesium sulfate cooled with ice. The phage solution obtained in Step 5 was diluted with SM buffer containing 0.1M sodium chloride, 8 mM magnesium sulfate, 50 mM Tris.HCl (pH 7.5) and 0.01% gelatin. 0.1 ml of the diluted phage solution was mixed with an equal volume of the above-mentioned *E. coli* cell suspension, and the mixture was incubated at a temperature of 37° C. for 15 minutes. To the mixture was added 4 ml of soft agar medium heated to 45° C. and containing 1% tryptone, 0.5% yeast extract, 0.5% sodium chloride, 0.25% magnesium sulfate and 0.7% agar (pH 7.0). The mixture was spread on L-agar plate containing 1% tryptone, 0.5% yeast extract, 1% sodium chloride, 1.5% agar and 100 μg/ml ampicillin (pH 7.0), and incubated at a temperature of 42° C. for 3 hours. Subsequently, 10 mM IPTG (isopropyl β-D-thiogalactopyranoside) was infiltrated into a nitrocellulose filter, and the nitrocellulose filter was dried and closely contacted with the L-agar plate. The plate was incubated at a temperature of 37° C. for 3 hours. The filter was separated, and washed with TBS buffer three times. The washed filter was immersed in 2% bovine serum albumin solution, and incubated at room temperature for one hour. 1/20 volume of *E. coli* lysate solution included in a commercially available immunoscreening kit (manufactured and sold by Amersham International, England) was added to pooled serum from NANB hepatitis patients, and incubated at room temperature for 30 minutes. Thereafter, the serum was diluted to 50-fold with 0.2% bovine serum albumin-added TBS buffer, and the filter was immersed in the diluted serum solution, and incubated at room temperature for one hour.

The resultant filter was washed four times with a TBS buffer containing 0.05% Tween 20. The washed filter was immersed in an antibody solution which had been prepared by diluting a peroxidase-labeled anti-human IgG (manufactured and sold by Cappel Co., Ltd., Germany) 1,000-fold for one hour. The filter was washed with the above-mentioned Tween-TBS buffer, and immersed in a solution prepared by adding 0.4 ml of DAB (3,3'-diaminobenzidine tetrahydrochloride) and 15 μl of a 30% aqueous hydrogen peroxide solution to 50 ml of a TBS buffer, followed by incubation at room temperature for 5 to 30 minutes to allow color development. The resultant filter was completely washed with distilled water to terminate the reaction.

By the above-mentioned procedure, the obtained plaques were purified. As a result, 9 positive clones were isolated, which were, respectively, designated as BK 102, BK 103, BK 105, BK 106, BK 108, BK 109, BK 110, BK 111 and BK 112. All of these clones did not react with serum from a healthy human, but reacted with serum from a patient suffering from NANB hepatitis. See Table 1.

TABLE 1

Reactivity between the serum obtained from
a patient suffering from NANB hepatitis and
the recombinant lambda gt11 phage clone

| Clone | Serum from healthy person | Serum from NANB hepatitis patient |
|---|---|---|
| BK 102 | 0/10* | 10/11 |
| BK 103 | 0/10 | 9/11 |
| BK 105 | 0/10 | 11/11 |
| BK 106 | 0/10 | 11/11 |
| BK 108 | 0/10 | 9/11 |
| BK 109 | 0/10 | 9/11 |
| BK 110 | 0/10 | 9/11 |
| BK 111 | 0/10 | 9/11 |
| BK 112 | 0/10 | 10/11 |

*the number of positive samples/the number of specimens.

Step 8 (Determination of the nucleotide sequence of the obtained clones)

Recombinant phage DNAs of clones BK 102 to BK 112 were collected, and the collected DNAs were digested with restriction enzyme EcoRI. Then, cDNA fragments of NANBV were isolated and the isolated cDNAs were individually inserted into plasmid pUC19 at EcoRI site. Using the plasmids, E. coli strain JM 109 was transformed in substantially the same manner as in Step 7. Plasmid DNAs were obtained from the transformed E. coli and purified. The nucleotide sequence of each of the NANBV cDNAs was determined using 7-DEAZA sequencing kit (manufactured and sold by Takara Shuzo Co., Ltd., Japan; see Mizusawa, S., Nishimura, S. and Seela, F. Nucleic Acids Res., 14, 1319, 1986). The relationship between the nucleotide sequences of the obtained cDNA clones is shown in FIG. 1(1).

Step 9 9 (Cloning of NANBV cDNA clones from a cDNA library by Genomic Walking)

Probes were prepared by labeling with $^{32}$P-dCTP the cDNA fragments of clone BK 102, clone BK 106 and clone BK 112 which were obtained in Step 8. Using the probes, phage clones containing NANBV cDNAs were obtained by hybridization from the cDNA library of cloning vector lambda gt11 obtained in Step 5 and the above-mentioned probes. That is, plasmid DNAs were prepared from the transformed E. coli with clone BK 102, clone BK 106 and clone BK 112 obtained in Step 8 by the alkali method (see T. Maniatis, E. G. Fritsch, and J. Sambrook: Isolation of Bacteriophage λ and Plasmid DNA: "Molecular Cloning", Cold Spring Harbor Lab., pp 75–96.).

Plasmid DNA of clone BK 102 was digested with restriction enzymes NcoI and HincII, and the resultant 0.7 kb fragments having been on the 5'-terminus side of the DNA were subjected to electrophoresis with agarose gel, and collected. Plasmid DNAs of clone BK 106 and clone BK 112 were digested with restriction enzyme NcoI. In the same manner as mentioned above, 1.1 kb DNA fragments were collected from clone BK 106, and 0.7 kb fragments having been on the 3'-terminus side were collected from clone BK 112. 25 ng to 1 μg of DNA fragments were incubated with [α-$^{32}$P]dCTP (3000 Ci/mmol; manufactured by Amersham Co., Ltd., England) at a temperature of 37° C. for a period of from 3 to 5 hours, using commercially available DNA labeling kit (manufactured by Nippon Gene Co., Ltd.). Thus, probes for hybridization were prepared.

Subsequently, the cDNA library phage obtained in Step 5 was incubated at a temperature of 42° C. in L-agar medium for 3 hours, as described in Step 7. Further, the phage was incubated at a temperature of 37° C. for 3 hours, and was cooled. A nitrocellulose filter was disposed on the mixture, and was allowed to stand still for a period of from 30 to 60 seconds. Thus, the phage was adsorbed onto the filter.

The filter was subjected to alkali denaturation for a period of from 1 to 5 minutes using an aqueous solution containing 0.5N sodium hydroxide and 1.5M sodium chloride and to the neutralization with an aqueous solution containing 0.5M Tris.HCl (pH 8.0) and 1.5M sodium chloride for a period of from 1 to 5 minutes. The filter was washed with 2 x SSC solution containing 0.3M sodium chloride and 0.03M sodium citrate, air dried, and baked at a temperature of 80° C. for 2 hours.

The filter was incubated at a temperature of 42° C. for 6 hours in a solution for hybridization containing 50% formamide, 5 x SSC, 5 x Denhart solution, 50 mM phosphoric acid-citric acid buffer (pH 6.5), 100 μg/ml trout sperm DNA and 0.1% SDS. Then, the filter was immersed in 300 ml of the hybridization solution having 1 ml of the above-mentioned probe of about 4×10$^8$ cpm/ml added thereto, and incubated at a temperature of 42° C. for 16 to 20 hours. The filter was washed with an SDS solution containing 0.1% 2 x SSC four times and with an SDS solution containing 0.1% 0.1 x SSC twice. After the washing, the filter was dried, and was subjected to autoradiography. Thus, hybridization positive clones were isolated. As a result, 27 clones being reactive with the probe derived from clone BK 102, 14 clones being reactive with the probe derived from clone BK 106 and 13 clones being reactive with the probe derived from clone BK 112, were obtained, which were respectively designated as BK 114 to BK 169.

The nucleotide sequence of each of clones BK 114 to BK 169 was determined according to the method described in Step 8, followed by mapping for each of the clones. As a result, a map of nucleotide sequence having a length of about 9.5 kb considered to be the approximately total length of the NANBV genome was obtained [see FIG. 1(2)].

Clone BK 157 located on the 5' terminus side was digested with restriction enzyme KpnI to thereby collect a 0.55 kb fragment having been on the 4'-terminus side. Also, clone BK 116 located on the extreme 3'-terminus side was digested with restriction enzymes HpaI and EcoRI to thereby collect a 0.55 kb fragment having been on the 3'-terminus side. A probe labeled with $^{32}$P was prepared in the same manner as described above, and the cDNA library phage obtained in Step 5 was subjected to plaque hybridization. As a result, three new additional clones were separated by the probe derived from the clone BK 157. These new clones were, respectively, designated as clones BK 170, BK 171 and BK 172.

Step 10 (Analysis of the nucleotide sequence of cDNA)

The entire nucleotide sequence (SEQ ID NO:1) of NANBV gene was determined from the nucleotide sequences of the clones obtained in Steps 8 and 9, and shown in FIGS. 2(1) to 2(16). From the Figures, it was assumed that the cloned genomic cDNAs of NANBV were composed of 9416 nucleotides, wherein there was an open reading frame composed of 9030 nucleotides coding for a protein composed of 3010 amino acid residues. The hydrophilicity/hydrophobicity pattern of this protein was similar to that of flavivirus as already reported (see H. Sumiyoshi, C. Mori, I. Fuke et al., Complete Nucleotide Sequence of the Japanese Encephalitis Virus Genome RNA. Virology, 161, 497–510, 1987). Clone BK 157 covers nucleotide numbers 1 to 1962 of FIGS. 2(1) to 2(16), clone BK 172 covers nucleotide numbers 5 to 366, clone BK 153 covers nucleotide numbers 338 to 1802, clone BK 138 covers nucleotide numbers 1755 to 5124, clone BK 108 covers nucleotide numbers 6886 to 8344 and clone BK 166 covers nucleotide numbers 8082 to 9416. They are preserved as *Escherichia coli* BK 108 (deposited at Fermentation Research Institute, Japan under accession number FERM BP-2971), BK 129 (deposited at Fermentation Research Institute, Japan under accession number FERM BP-2972), BK 138 (deposited at Fermentation Research Institute, Japan under accession number FERM BP-2973), BK 153 (deposited at Fermentation Research Institute, Japan under accession number FERM BP-2974), BK 157, BK 166 (deposited at Fermentation Research Institute, Japan under accession number FERM BP-1975), and BK 172 (deposited at Fermentation Research Institute, Japan under accession number FERM BP-2976), respectively.

Step 11 (Production of NANBV-related antigens in *E. coli*, which antigens are related with the antibody-response accompanying NANBV infection)

Respective cDNAs of clone BK 106, clone BK 111 and clone BK 112 each obtained in Step 8 and cDNA of clone BK 147 obtained in Step 9 were individually inserted into plasmids, and the thus obtained plasmid DNAs were collected by the conventional alkali method. Subsequently, the collected DNA of clone BK 106 was digested with restriction enzymes EcoRI and ClaI to thereby obtain 0.5 μg of a DNA fragment of 0.34 kb in length. The thus obtained DNA fragment was incubated at 37° C. for 60 minutes in a T4 DNA polymerase solution containing 67 mM Tris.HCl (pH 8.8), 6.7 mM magnesium chloride, 16.6 mM ammonium sulfate, 10 mM 2-mercaptoethanol, 6.7 μM EDTA, 0.02% bovine serum albumin, 0.3 mM dNTP and 2–5 units of T4 DNA polymerase, thereby rendering both terminals blunt. The DNA of clone BK 102 was digested with restriction enzyme BamHI to thereby collect 0.5 μg of a DNA fragment of 0.7 kb in length, and the terminals of the DNA fragment were rendered blunt using T4 DNA polymerase in substantially the same manner as mentioned above. The DNA of clone BK 147 was digested with restriction enzyme Sau3AI to thereby obtain 0.5 μg of a DNA fragment of 1 kb in length and the terminals of the DNA fragment were rendered blunt in the same manner as mentioned above. Also, the DNA of clone BK 111 was digested with restriction enzyme EcoRI to thereby obtain 0.5 μg of a DNA fragment of 1 kg in length, and the terminals of the DNA fragment were rendered blunt in substantially the same manner as mentioned above. Subsequently, the DNA of expression vector pKK 233-2 (Amann, E. and J. Brosius. ATG vector for regulated high-level expression of cloned genes in *Escherichia coli*. Gene, Vol. 40, 183, 1985) was digested with restriction enzyme HindIII. 2 μg of the resultant DNA was incubated at 37° C. for 20 minute sin a S1 nuclease solution containing 0.3 M sodium chloride, 50 mM sodium acetate (pH 4.5), 1 mM zinc sulfate and 100–200 units of S1 nuclease, and the reaction was terminated by adding 1/10 volume of each of 0.12 M EDTA and 1 M Tris.HCl solution (pH 9.0). Then, phenol extraction was performed, and the vector DNA having blunt terminals was precipitated by ethanol and collected. On the other hand, the DNA of vector pKK 233-2 was digested with restricted with restriction enzyme PstI, and the digested DNA was purified by extraction with phenol and precipitation from ethanol. The terminals of 2 μg of the purified vector DNA which had been cleaved by restriction enzyme PstI were rendered blunt by the above-mentioned T4 DNA polymerase reaction. The thus obtained DNA fragments derived from clone BK 106 and clone BK 111 were each cleaved with restriction enzyme HindIII. 0.5 μg of each of the cleaved DNA fragments was mixed with 0.5 μg of a vector DNA having blunt terminals. The DNA fragments derived from clone BK 102 and clone BK 147 were each cleaved with restriction enzyme PstI. 0.5 μg of each of the claved DNA fragments was mixed with 0.5 μg of a vector DNA having terminals thereof rendered blunt. The volume of each of the mixtures was adjusted to 20 μl by adding 2 μl of 10× ligation solution containing 500 mM Tris.HCl (pH 7.5), 100 mM magnesium chloride, 100 mM DTT and 10 mM ATP, 300–400 units of T4 DNA ligase and distilled water. The mixtures were incubated at 14° C. for 12–18 hours, thereby obtaining plasmids, which were respectively designated as pCE-06, pE-11, pB-02 and pS-09. Using each of these plasmid DNAs, *E. coli* strain JM 109 was transformed in substantially the same manner as described in Step 6, thereby obtaining transformed *E. coli*. The transformed *E. coli* was cultured at 37° C. in LB medium (pH 7.5) containing 1 (w/v) % trypton, 0.5 (w/v) % yeast extract and 1 (w/v) % sodium chloride, and when it was in logarithmic growth phase, 1 mM IPTG (isopropyl-β-D-thiogalactopyranoside) was added to the medium. The culturing was further continued for 3 hours. Then, *E. coli* cells were collected by centrifugation (10,000×g for 15 minutes), and the collected cells were lysed in 50 mM Tris.HCl (pH 8.0). The mixture was subjected to ultrasonic treatment (20 KHz, 600 W, 5 minutes), and centrifuged at 10,000×g for 15 minutes to thereby obtain a supernatant fraction and a precipitate fraction. Each of the fractions was dissolved in a sample buffer containing of 20 (v/v) % glycerol, 0.1 M Tris.HCl (pH 6.8), 2 (w/v) % SDS, 2 (v/v) % 2-mercaptoethanol and 0.02% BPB, heated at 100° C. for 3 minute, and subjected to electrophoresis using 0.1% SDS-7.5% polyacrylamide gel to separate protein. After the electrophoresis, the protein was transferred to a nitrocellulose filter by trans blot cell (manufactured and sold by BIO.RAD Co., Ltd., U.S.A.). The filter was immersed in 3% gelatin solution, and allowed to stand still for 60 minutes. The filter was incubated together with serum from a patient suffering from NANB hepatitis, which had been diluted 100-fold, for 2 to 3 hours at room temperature. The filter was washed with distilled water and then with TTBS solution containing 0.02 M Tris.HCl (pH 7.5), 0.5 M sodium chloride and 0.05 (v/v)% Tween 20. Subsequently, the washed filter was immersed in a 2,000 fold-diluted solution of peroxidase-labeled anti-human IgG antibody, and incubated at room temperature for 90 minutes. The filter was washed with distilled water and then with TTBS solution. The washed filter was immersed in a buffer having, added thereto, coloring agent DAB and 30%, based on substrate, hydrogen peroxide as described in Step 7 for 5 to 30 minutes, following by washing with water, to terminate the reaction.

As a result, as shown in Table 2, all of the antigens produced by the plasmids specifically react with serum from a patient suffering from NANB hepatitis, thereby demonstrating that the proteins produced by the cDNAs inserted in the plasmids are clinically important.

TABLE 2

Reactivity evaluated by the Western blot method between proteins produced by various plasmids and sera from a patient suffering from NANB hepatitis.

| Plasmid | origin of cDNA | Extract | Serum from NANB hepatitis patient | Serum from healthy human |
|---|---|---|---|---|
| PCE-066 | BK 106 | S | ± | − |
|  |  | P | + | − |
| pE-11-89 | BK 111 | S | ± | − |
|  |  | P | + | − |
| pB-02-10 | BK 102 | S | + | − |
|  |  | P | − | − |
| ps-09-07 | BK 109 | S | ± | − |
|  |  | P | + | − |
| pKK 233-3 | — | S | − | − |
|  |  | P | − | − |

S: Supernatant by centrifugation
P: Precipitate by centrifugation
+: positive
±: slightly positive
−: negative Step 12 (Purification of NANBV-related antigens produced by E. coli and reactivity thereof with serum from a patient suffering form hepatitis)

The usefulness of the protein produced by the cDNA which was inserted into an expression vector was demonstrated by purifying the protein and using the purified protein as an antigen for ELISA or radioimmunoassay. That is, the lysate of the transformed E. coli which was obtained in Step 11 was subjected to centrifugation at 10,000×g for 15 minutes, thereby obtaining a supernatant and a precipitate. For example, the precipitate obtained from transformant JM 109/pCE 066 was suspended in a solution of 100 mM Tris.HCl (pH 8.0) and 0.1% Triton X-100, and the resultant suspension was subjected to ultrasonic treatment at a frequency of 20 KHz (600 W) for one minute, followed by centrifugation at 21,000×g for 15 minutes, thereby obtaining a precipitate. The precipitate was re-suspended in a solution of 100 mM Tris.HCl (pH 8.0) and 6 M urea, and then subjected to ultrasonic treatment followed by centrifugation.

The resultant supernatant was dialyzed against a solution of 10 mM phosphoric acid buffer (pH 7.5) and 6 M urea to thereby obtain an antigen solution. 20 ml of the antigen solution was passed through a column (21.5× 250 mm) packed with hydroxyapatite, which had been equilibrated with the above-mentioned buffer, to cause the antigen to be adsorbed onto the packing material. The column was subjected to high speed liquid chromatography (HPLC) wherein elution was performed with the above-mentioned buffer having, added thereto, sodium chloride, the concentration of which was varied from 0 to 2 M with a linear concentration gradient, thereby obtaining a fraction containing an antigen. The obtained fraction was dialyzed against a solution of 50 mM carbonate buffer (pH 9.6) and 0.05% sodium dodecyl sulfate (SDS).

Further, the supernatant obtained by centrifugation (at 10,000 g for 15 minutes) of the lysate of transformant JM 109/pB-02-10 was treated with 35% saturated ammonium sulfate, and the obtained precipitate was dissolved in a solution of 50 mM Tris.HCl (pH 8.5) and 100 mM 2-mercaptoethanol. The resultant solution was dialyzed against the above-mentioned buffer. Subsequently, 100 ml of the dialysed solution was passed through a column (22.0× 200 mm) packed with DEAE cellulose, which had been equilibrated with the above-mentioned buffer, to cause the antigen to be adsorbed onto the packing material. The column was subjected to high performance liquid chromatography wherein elution was performed with a solution of 50 mM Tris.HCl (pH 8.5) and 100 mM 2-mercaptoethanol having, added thereto, sodium chloride, the concentration of which was varied from 0 to 2 M with a linear concentration gradient, thereby pooling a fraction containing the antigen.

The fraction was dialyzed against a solution of 10 mM phosphate buffer (pH 6.8) and 100 mM 2-mercaptoethanol. The dialyzed solution was passed through the column of hydroxyapatite for high performance liquid chromatography, which had been equilibrated by the above-mentioned buffer, to cause the antigen to be adsorbed onto the packing material. The column was subjected to high speed liquid chromatography wherein elution was performed with phosphoric acid, the concentration of which was carried with a linear concentration gradient from 10 to 400 mM, thereby pooling a fraction containing the antigen. The resultant fraction was dialyzed against a solution of 50 mM carbonate buffer (pH 9.6) and 0.05% SDS.

The precipitate obtained by centrifugation of the lysate of transformant JM 109/pE-11-89 was suspended in 10 mM phosphate buffer (pH 5.5). The suspension was subjected to the above-mentioned ultrasonic treatment for one minute, and then subjected to centrifugation at 21,000×g for 15 minutes. The resultant precipitate was suspended in a solution of 100 mM carbonate buffer (pH 10.5), 500 mM sodium chloride and 10 mM EDTA. The resultant suspension was again subjected to the ultrasonic treatment for one minute, followed by centrifugation. The resultant supernatant was dialyzed against a solution of 30 mM phosphate buffer and 6 M urea. Subsequently, 20 ml of the dialyzed solution was passed through a CM cellulose column (22×200 mm) for high performance liquid chromatography (HPLC), which had been equilibrated with the same buffer as used for the above-mentioned dialysis, to thereby cause the antigen to be adsorbed onto the packing material. The column was subjected to high performance liquid chromatography wherein elution was performed with the above-mentioned buffer having, added thereto, sodium chloride, the concentration of which was varied from 0 to 1.5 M with a linear concentration gradient, obtaining a fraction containing the antigen. The fraction was dialyzed against a solution containing 50 mM carbonate buffer (pH 9.6) and 0.05% SDS, thereby obtaining a solution containing the antigen.

The antigens prepared above were used as an antigen for ELISA for the clinical diagnosis of infection with non-A, non-B hepatitis virus. The protein concentration of each of the above-mentioned purified antigens was adjusted to 1 μg/ml, and put in each well of Microplate Immulone 600 (manufactured and sold by Greiner, Co., Ltd., Germany) in an amount of 100 ml for use in ELISA, which well was allowed to stand still at 4° C. overnight. The contents of the individual wells were washed well three times with PBS-T buffer containing 10 mM phosphate buffer (pH 7.2), 0.8% sodium chloride and 0.05% Tween 20, and sample serum diluted with the PBS-T buffer was added in an amount of 100 μl/well, followed by reaction at 37° C. for one hour. The contents of the individual wells were washed three times with the PBS-T buffer, and a peroxidase-labeled anti-human IgG antibody (manufactured and sold by Cappel Co., Ltd., Germany) which had been diluted 8000-fold with PBS-T buffer containing 10% fetal calf serum was added in an amount of 100 μl/well. The individual well contents were reacted at 37° C. for one hour, and washed with the PBS-T buffer four times. A substrate coloring agent solution composed of 9 ml of 0.05 M citric acid-phosphate buffer and, contained therein, 0.5 μg of o-phenylenediamine and 20 μl of aqueous hydrogen peroxide, was added in an amount of 100 μl/well. The plate was light shielded, and allowed to stand still at room temperature for 60 minutes. 75 μl of 4 N sulfuric acid was added to each of the wells, and the absorbance at 490 nm was determined. The results are shown in Table 3. As apparent from the table, all of the antigens derived from the transformant specifically react with the serum from NANB hepatitis patient, thereby attesting to the usefulness in clinical diagnosis of the antigens produced by the transofrmants.

TABLE 3

Reactivity in ELISA between the purified antigens from various transformed *Escherichia coli* and the serum from NANB hepatitis patient

| origin of antigen | Serum from blood transfused patient of hepatitis | | | | |
|---|---|---|---|---|---|
| (transformed *Escherichia coli*) | acute | chronic | hepato-cirrhosis | hepatoma | healthy human serum |
| JM109/pCE-066 | 2/3* | 7/8 | 3/4 | 3/3 | 0/10 |
| JM109/pB-02-10 | 2/3 | 8/8 | 4/4 | 3/3 | 0/10 |
| JM109/pE-11-89 | 2/3 | 8/8 | 2/4 | 3/3 | 0/10 |

*the number of positive samples/the number of samples examined

The same results as shown in Table 3 were also obtained by radioimmunoassay using the above-mentioned antigens. That is, a polystyrene ball of ¼ inch in diameter (manufactured and sold by Pesel Co., Ltd., Germany) was put in 0.2 ml of each of the above-mentioned purified antigen solutions of 1 μg/ml in concentration, and allowed to stand still at 4° C. overnight. Then, the polystyrene ball was washed five times with the same PBS-T buffer as used in the above-mentioned ELISA, and a sample serum diluted 20 to 2500-fold with the PBS-T buffer was added in an amount of 200 μl/ball. Reaction was performed at 37° C. for 60 min. The polystyrene ball was washed five times with the PBS-T buffer, and $^{125}$I-labeled anti-human IgG antibody was added in an amount of 200 μl/ball. Reaction was performed at 37° C. for one hour and the ball was washed five times with the PBS-T buffer. The cpm of $^{125}$I bound to the polystyrene ball was measured, thereby obtaining the same results as shown in Table 3. Thus, the usefulness of the purified antigens obtained above in the clinical diagnosis of infection with NANB hepatitis virus, was demonstrated.

APPLICATION EXAMPLE 1

Assay of the reactivity of synthetic polypeptide

The antibody molecule reacts with a specific region structure known as "epitope" which exists on the antigen molecule, to thereby form a bonding therebetween. Such a specific region can be found in the hydrophilic region of the antigen molecule. The antigen polypeptide having such a specific region is believed to be useful for easily preparing a valuable clinical diagnostic reagent with high reaction specificity. The NANBV epitope is presumed from the hydrophilicity/hydrophobicity pattern of the amino acid sequence coded for by the NANBV genomic cDNA shown in FIGS. 2(1) to 2(16) Namely, polypeptides BKP-106-1, BKP-106-2, BKP-102-1 and BKP-147-1 were prepared, which were respectively comprised of amino acid residues coded for by nucleotide numbers 333 to 422 shown in FIG. 2(1), nucleotide numbers 474 to 563 shown in FIG. 2(1) through FIG. 2(2), nucleotide numbers 4485 to 4574 shown in FIG. 2(8), and nucleotide numbers 5544 to 5633 shown in FIG. 2(10) of SEQ ID NO:1. The concentration of each of the prepared polypeptides was adjusted to 1 μg/ml, applied to a microplate for ELISA according to the same method as described in Step 12 to thereby form a solid phase, and examined with respect to the reactivity thereof with the serum from NANB hepatitis patient by the method of ELISA. The results are shown in Table 4. As apparent from the table, all of the prepared polypeptides specifically reacted with the serum from NANB hepatitis patient, thereby demonstrating the importance in clinical diagnosis of the particular regions of nucleotide sequences described above.

TABLE 4

Reactivity of synthetic polypeptides with the serum from NANB hepatitis patient

| synthetic polypeptides | serum from NANB hepatitis patient | | healthy human |
|---|---|---|---|
| | acute | chronic | |
| BKP-106-1 | 2/5 | 5/5 | 0/5 |
| BKP-106-2 | 2/5 | 5/5 | 0/5 |
| BKP-102-1 | 3/5 | 5/5 | 0/5 |
| BKP-147-1 | 2/5 | 5/5 | 0/5 |

Moreover, presuming the epitopes of the envelop protein of NANBV, three types of proteins were prepared. That is, proteins coded for by nucleotide numbers 906 to 953 shown in FIG. 2(2), nucleotide numbers 1020 to 1046 shown in FIG. 2(2) and nucleotide numbers 1194 to 1232 shown in FIG. 2(2) through FIG. 2(3) of SEQ ID NO:1, were prepared. All of the thus prepared polypeptides correspond to the regions of the envelop where antigenic variation is believed to occur depending on the type of the NANBV strain, and the reactivity thereof in ELISA with the serum from a NANB hepatitis patient was confirmed. These attest to the importance and usefulness of the above-mentioned proteins in immunological survey, clinical diagnosis and vaccination.

APPLICATION EXAMPLE 2

Detection of NANBV nucleic acid according to PCT (Polymerase Chain Reaction) method For preventing NANB hepatitis caused by blood transfusion, it is important to determine whether or not any NANBV infection exists in the blood supplied for transfusion. Further, for diagnosing hepatitis, it is extremely clinically important to study whether or not any NANBV infection exists in liver tissue. The NANBV cDNA of the present invention can be advantageously used for producing a primer for polymerase chain reaction (PCR) useful for detecting NANB hepatitis. That is, as described in Step 1, the purification of RNA and the preparation of cDNA were performed from 1 ml of serum. Likewise, cDNA was prepared from liver cells as described in Step 2. Subsequently, as described in Step 4 , PCT and electrophoresis were conducted. According to the customary procedure, whether or not the amplified cDNA was derived from NANBV, was investigated by Southern hybridization using $^{32}$P-labeled probe prepared from the cDNA derived from NANBV cDNA clone BK 108.

The results are shown in Table 5. From the table, it is apparent that the NANBV nucleic acid in serum can be detected and the serum infection with NANBV can be diagnosed by the use of the primer prepared from the nucleotide sequence of the NANBV cDNA obtained according to the present invention and the fragment of cloned NANBV cDNA as a probe.

TABLE 5

Detection of NANBV nucleic acid by PCR

| sample | | antibody against NANBV | PCR |
|---|---|---|---|
| serum from chronic hepatitis patient | | | |
| NANB | 1 | + | + |
| | 2 | + | + |
| HBV carrier | 1 | − | − |
| | 2 | − | − |
| healthy human | 1 | − | − |
| | 2 | − | − |
| excised liver from NANB hepatoma-1 | | + | |
| cancerous site | | | + |
| non-cancerous site | | | + |
| excised liver from NANB hepatoma-2 | | + | |
| cancerous site | | | + |
| non-cancerous site | | | + |

What is claimed is:

1. An isolated antigen polypeptide comprising at least one amino acid sequence coded for by a nucleotide sequence selected from the group consisting of a nucleotide sequence of the 333rd to 422nd nucleotides, a nucleotide sequence of the 333rd to 677th nucleotides, nucleotide sequence of the 333rd to 1499th nucleotides, a nucleotide sequence of the 333rd to 6371st nucleotides, a nucleotide sequence of the 474th to 563rd nucleotides, a nucleotide sequence of the 678th to 905th nucleotides, a nucleotide sequence of the 906th to 953rd nucleotides, a nucleotide sequence of the 906th to 1499th nucleotides, a nucleotide sequence of the 1020th to 1046th nucleotides, a nucleotide sequence of the 1020th to 1121st nucleotides, a nucleotide sequence of the 1194th to 1232nd nucleotides, a nucleotide sequence of the 1209th to 1322nd nucleotides, a nucleotide sequence of the 1500th to 2519th nucleotides, a nucleotide sequence of the 3351st to 5177th nucleotides, a nucleotide sequence of the 4485th to 4574th nucleotides, a nucleotide sequence of the 5178th to 5918th nucleotides, a nucleotide sequence of the 5544th to 5633rd nucleotides, a nucleotide sequence of the 5919th to 6371st nucleotides, a nucleotide sequence of the 6372nd to 9362nd nucleotides and a nucleotide sequence of the 333rd to 9362nd nucleotides of the non-A, non-B hepatitis virus nucleotide sequence of SEQ ID NO:1.

2. A diagnostic reagent for the detection of non-A, non-B hepatitis by antigen-antibody reaction, comprising an isolated antigen polypeptide comprising at least one amino acid sequence coded for by a nucleotide sequence selected from the group consisting of a nucleotide sequence of the 333rd to 422nd nucleotides, a nucleotide sequence of the 333rd to 677th nucleotides, a nucleotide sequence of the 333rd to 1499th nucleotides, a nucleotide sequence of the 333rd to 6731st nucleotides, a nucleotide sequence of the 474th to 563rd nucleotides, a nucleotide sequence of the 678th to 905th nucleotides, a nucleotide sequence of the 906th to 953rd nucleotides, a nucleotide sequence of the 906th to 1499th nucleotides, a nucleotides sequence of the 1020th to 1046th nucleotides, a nucleotide sequence of the 1020th to 1121st nucleotides, a nucleotide sequence of the 1194th to 1232nd nucleotides, a nucleotide sequence of the 1209th to 1322nd nucleotides, a nucleotide sequence of the 1500th to 2519th nucleotides, a nucleotide sequence of the 3351st to 5177th nucleotides, a nucleotide sequence of the 4485th to 4574th nucleotides, a nucleotide sequence of the 5178th to 5918th nucleotides, a nucleotide sequence of the 5544th to 5633rd nucleotides, a nucleotide sequence of the 5919th to 6371st nucleotides, a nucleotide sequence of the 6372nd to 9362nd nucleotides and a nucleotide sequence of the 333rd to 9362nd nucleotides of the non-A, non-B hepatitis virus nucleotide sequence of SEQ ID NO:1.

* * * * *

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
      (A) LENGTH: 9416 base pairs
      (B) TYPE: nucleic acid
      (C) STRANDEDNESS: single
      (D) TOPOLOGY: linear (ii) MOLECULE TYPE: cDNA from genomic RNA (ix) FEATURE:
      (A) NAME/KEY: CDS
      (B) LOCATION: 333..9362

(xi) SEQUENCE DESCRIPTION: SEQ ID NO:1:

```
CGATTGGGGG CGACACTCCA CCATAGATCA CTCCCCTGTG AGGAACTACT GTCTTCACGC      60

AGAAAGCGTC TAGCCATGGC GTTAGTATGA GTGTCGTGCA GCCTCCAGGA CCCCCCCTCC     120

CGGGAGAGCC ATAGTGGTCT GCGGAACCGG TGAGTACACC GGAATTGCCA GGACGACCGG     180

GTCCTTTCTT GGATCAACCC GCTCAATGCC TGGAGATTTG GGCGTGCCCC CGCGAGACTG     240

CTAGCCGAGT AGTGTTGGGT CGCGAAAGGC CTTGTGGTAC TGCCTGATAG GGTGCTTGCG     300

AGTGCCCCGG GAGGTCTCGT AGACCGTGCA CC ATG AGC ACG AAT CCT AAA CCT      353
                                  Met Ser Thr Asn Pro Lys Pro
                                    1               5

CAA AGA AAA ACC AAA CGT AAC ACC AAC CGC CGC CCA CAG GAC GTC AAG      401
Gln Arg Lys Thr Lys Arg Asn Thr Asn Arg Arg Pro Gln Asp Val Lys
         10                  15                  20

TTC CCG GGC GGT GGT CAG ATC GTT GGT GGA GTT TAC CTG TTG CCG CGC      449
Phe Pro Gly Gly Gly Gln Ile Val Gly Gly Val Tyr Leu Leu Pro Arg
     25                  30                  35

AGG GGC CCC AGG TTG GGT GTG CGC GCG CCC AGG AAG ACT TCC GAG CGG      497
Arg Gly Pro Arg Leu Gly Val Arg Ala Pro Arg Lys Thr Ser Glu Arg
 40                  45                  50                  55

TCG CAA CCT CGT GGA AGG CGA CAA CCT ATC CCC AAG GCT CGC CGG CCC      545
Ser Gln Pro Arg Gly Arg Arg Gln Pro Ile Pro Lys Ala Arg Arg Pro
```

```
                    60                  65                  70
GAG GGC AGG ACC TGG GCT CAG CCC GGG TAC CCT TGG CCT CTC TAT GGC       593
Glu Gly Arg Thr Trp Ala Gln Pro Gly Tyr Pro Trp Pro Leu Tyr Gly
            75                  80                  85

AAT GAG GGC TTA GGG TGG GCA GGA TGG CTC CTG TCA CCC CGC GGC TCC       641
Asn Glu Gly Leu Gly Trp Ala Gly Trp Leu Leu Ser Pro Arg Gly Ser
        90                  95                  100

CGG CCT AGT TGG GGC CCC ACG GAC CCC CGG CGT AGG TCG CGT AAT TTG       689
Arg Pro Ser Trp Gly Pro Thr Asp Pro Arg Arg Ser Arg Asn Leu
    105                 110                 115

GGT AAG GTC ATC GAT ACC CTC ACA TGC GGC TTC GCC GAT CTC ATG GGG       737
Gly Lys Val Ile Asp Thr Leu Thr Cys Gly Phe Ala Asp Leu Met Gly
120                 125                 130                 135

TAC ATT CCG CTC GTC GGC GCC CCC CTG GGG GGC GCT GCC AGG GCC CTG       785
Tyr Ile Pro Leu Val Gly Ala Pro Leu Gly Gly Ala Ala Arg Ala Leu
                140                 145                 150

GCA CAT GGT GTC CGG GTT CTG GAG GAC GGC GTG AAC TAT GCA ACA GGG       833
Ala His Gly Val Arg Val Leu Glu Asp Gly Val Asn Tyr Ala Thr Gly
            155                 160                 165

AAT CTG CCC GGT TGC TCT TTT TCT ATC TTC CTC TTG GCT CTG CTG TCC       881
Asn Leu Pro Gly Cys Ser Phe Ser Ile Phe Leu Leu Ala Leu Leu Ser
        170                 175                 180

TGC CTG ACC ACC CCA GCT TCC GCT TAC GAA GTG CAC AAC GTG TCC GGG       929
Cys Leu Thr Thr Pro Ala Ser Ala Tyr Glu Val His Asn Val Ser Gly
    185                 190                 195

ATA TAT CAT GTC ACG AAC GAC TGC TCC AAC GCA AGC ATT GTG TAT GAG       977
Ile Tyr His Val Thr Asn Asp Cys Ser Asn Ala Ser Ile Val Tyr Glu
200                 205                 210                 215

GCA GCG GAC TTG ATC ATG CAT ACT CCT GGG TGC GTG CCC TGC GTT CGG      1025
Ala Ala Asp Leu Ile Met His Thr Pro Gly Cys Val Pro Cys Val Arg
                220                 225                 230

GAA GGC AAC TCC TCC CGC TGC TGG GTA GCG CTC ACT CCC ACG CTC GCA      1073
Glu Gly Asn Ser Ser Arg Cys Trp Val Ala Leu Thr Pro Thr Leu Ala
            235                 240                 245

GCC AGG AAC GTC ACC ATC CCC ACC ACG ACG ATA CGA CGC CAC GTC GAT      1121
Ala Arg Asn Val Thr Ile Pro Thr Thr Thr Ile Arg Arg His Val Asp
        250                 255                 260

CTG CTC GTT GGG GCG GCT GCT TTC TGT TCC GCT ATG TAC GTG GGG GAC      1169
Leu Leu Val Gly Ala Ala Ala Phe Cys Ser Ala Met Tyr Val Gly Asp
    265                 270                 275

CTC TGC GGA TCT GTT TTC CTC GTC TCT CAG CTG TTC ACC TTC TCG CCT      1217
Leu Cys Gly Ser Val Phe Leu Val Ser Gln Leu Phe Thr Phe Ser Pro
280                 285                 290                 295

CGC CGG CAT GTG ACA TTA CAG GAC TGT AAC TGC TCA ATT TAT CCC GGC      1265
Arg Arg His Val Thr Leu Gln Asp Cys Asn Cys Ser Ile Tyr Pro Gly
                300                 305                 310

CAT GTG TCG GGT CAC CGT ATG GCT TGG GAC ATG ATG ATG AAC TGG TCG      1313
His Val Ser Gly His Arg Met Ala Trp Asp Met Met Met Asn Trp Ser
            315                 320                 325

CCC ACA ACA GCC CTA GTG GTG TCG CAG TTA CTC CGG ATC CCA CAA GCC      1361
Pro Thr Thr Ala Leu Val Val Ser Gln Leu Leu Arg Ile Pro Gln Ala
        330                 335                 340

GTC GTG GAC ATG GTG GCG GGG GCC CAC TGG GGA GTC CTG GCG GGC CTT      1409
Val Val Asp Met Val Ala Gly Ala His Trp Gly Val Leu Ala Gly Leu
    345                 350                 355

GCC TAC TAT TCC ATG GCG GGG AAC TGG GCT AAG GTT CTG ATT GTG ATG      1457
Ala Tyr Tyr Ser Met Ala Gly Asn Trp Ala Lys Val Leu Ile Val Met
360                 365                 370                 375

CTA CTT TTT GCT GGC GTT GAC GGG GAT ACC CAC GTG ACA GGG GGG GCG      1505
Leu Leu Phe Ala Gly Val Asp Gly Asp Thr His Val Thr Gly Gly Ala
```

-continued

|  |  |  | 380 |  |  |  |  | 385 |  |  |  |  | 390 |  |  |  |
|---|---|---|---|---|---|---|---|---|---|---|---|---|---|---|---|---|
| CAA | GCC | AAA | ACC | ACC | AAC | AGG | CTC | GTG | TCC | ATG | TTC | GCA | AGT | GGG | CCG | 1553 |
| Gln | Ala | Lys | Thr | Thr | Asn | Arg | Leu | Val | Ser | Met | Phe | Ala | Ser | Gly | Pro |  |
|  |  |  | 395 |  |  |  |  | 400 |  |  |  |  | 405 |  |  |  |
| TCT | CAG | AAA | ATC | CAG | CTT | ATA | AAC | ACC | AAT | GGG | AGT | TGG | CAC | ATC | AAC | 1601 |
| Ser | Gln | Lys | Ile | Gln | Leu | Ile | Asn | Thr | Asn | Gly | Ser | Trp | His | Ile | Asn |  |
|  |  |  | 410 |  |  |  |  | 415 |  |  |  |  | 420 |  |  |  |
| AGG | ACT | GCC | CTG | AAC | TGC | AAT | GAC | TCT | CTC | CAG | ACT | GGG | TTT | CTT | GCC | 1649 |
| Arg | Thr | Ala | Leu | Asn | Cys | Asn | Asp | Ser | Leu | Gln | Thr | Gly | Phe | Leu | Ala |  |
|  |  | 425 |  |  |  |  | 430 |  |  |  |  | 435 |  |  |  |  |
| GCG | CTG | TTC | TAC | ACA | CAT | AGT | TTC | AAC | TCG | TCC | GGG | TGC | CCA | GAG | CGC | 1697 |
| Ala | Leu | Phe | Tyr | Thr | His | Ser | Phe | Asn | Ser | Ser | Gly | Cys | Pro | Glu | Arg |  |
| 440 |  |  |  |  | 445 |  |  |  |  | 450 |  |  |  |  | 455 |  |
| ATG | GCC | CAG | TGC | CGC | ACC | ATT | GAC | AAG | TTC | GAC | CAG | GGA | TGG | GGT | CCC | 1745 |
| Met | Ala | Gln | Cys | Arg | Thr | Ile | Asp | Lys | Phe | Asp | Gln | Gly | Trp | Gly | Pro |  |
|  |  |  |  | 460 |  |  |  |  | 465 |  |  |  |  | 470 |  |  |
| ATT | ACT | TAT | GCT | GAG | TCT | AGC | AGA | TCA | GAC | CAG | AGG | CCA | TAT | TGC | TGG | 1793 |
| Ile | Thr | Tyr | Ala | Glu | Ser | Ser | Arg | Ser | Asp | Gln | Arg | Pro | Tyr | Cys | Trp |  |
|  |  |  |  | 475 |  |  |  |  | 480 |  |  |  |  | 485 |  |  |
| CAC | TAC | CCA | CCT | CCA | CAA | TGT | ACC | ATC | GTA | CCT | GCG | TCG | GAG | GTG | TGC | 1841 |
| His | Tyr | Pro | Pro | Pro | Gln | Cys | Thr | Ile | Val | Pro | Ala | Ser | Glu | Val | Cys |  |
|  |  |  |  | 490 |  |  |  |  | 495 |  |  |  |  | 500 |  |  |
| GGC | CCA | GTG | TAC | TGC | TTC | ACC | CCA | AGC | CCT | GTC | GTC | GTG | GGG | ACG | ACC | 1889 |
| Gly | Pro | Val | Tyr | Cys | Phe | Thr | Pro | Ser | Pro | Val | Val | Val | Gly | Thr | Thr |  |
|  |  | 505 |  |  |  |  | 510 |  |  |  |  | 515 |  |  |  |  |
| GAT | CGT | TTC | GGT | GTC | CCT | ACG | TAT | AGA | TGG | GGG | GAG | AAC | GAG | ACT | GAC | 1937 |
| Asp | Arg | Phe | Gly | Val | Pro | Thr | Tyr | Arg | Trp | Gly | Glu | Asn | Glu | Thr | Asp |  |
| 520 |  |  |  |  | 525 |  |  |  |  | 530 |  |  |  |  | 535 |  |
| GTG | CTG | CTG | CTC | AAC | AAC | ACG | CGG | CCG | CCG | CAA | GGC | AAC | TGG | TTC | GGC | 1985 |
| Val | Leu | Leu | Leu | Asn | Asn | Thr | Arg | Pro | Pro | Gln | Gly | Asn | Trp | Phe | Gly |  |
|  |  |  | 540 |  |  |  |  | 545 |  |  |  |  | 550 |  |  |  |
| TGC | ACA | TGG | ATG | AAT | AGC | ACC | GGG | TTC | ACC | AAG | ACA | TGT | GGG | GGG | CCC | 2033 |
| Cys | Thr | Trp | Met | Asn | Ser | Thr | Gly | Phe | Thr | Lys | Thr | Cys | Gly | Gly | Pro |  |
|  |  |  | 555 |  |  |  |  | 560 |  |  |  |  | 565 |  |  |  |
| CCG | TGT | AAC | ATC | GGG | GGT | GTC | GGC | AAC | AAC | ACC | CTG | ACC | TGC | CCC | ACG | 2081 |
| Pro | Cys | Asn | Ile | Gly | Gly | Val | Gly | Asn | Asn | Thr | Leu | Thr | Cys | Pro | Thr |  |
|  |  | 570 |  |  |  |  | 575 |  |  |  |  | 580 |  |  |  |  |
| GAC | TGC | TTC | CGG | AAG | CAC | CCC | GAG | GCT | ACC | TAC | ACA | AAA | TGT | GGT | TCG | 2129 |
| Asp | Cys | Phe | Arg | Lys | His | Pro | Glu | Ala | Thr | Tyr | Thr | Lys | Cys | Gly | Ser |  |
|  | 585 |  |  |  |  | 590 |  |  |  |  | 595 |  |  |  |  |  |
| GGG | CCT | TGG | CTG | ACA | CCT | AGG | TGC | ATG | GTT | GAC | TAT | CCA | TAC | AGG | CTC | 2177 |
| Gly | Pro | Trp | Leu | Thr | Pro | Arg | Cys | Met | Val | Asp | Tyr | Pro | Tyr | Arg | Leu |  |
| 600 |  |  |  |  | 605 |  |  |  |  | 610 |  |  |  |  | 615 |  |
| TGG | CAT | TAC | CCC | TGC | ACT | GTT | AAC | TTT | ACC | ATC | TTC | AAG | GTT | AGG | ATG | 2225 |
| Trp | His | Tyr | Pro | Cys | Thr | Val | Asn | Phe | Thr | Ile | Phe | Lys | Val | Arg | Met |  |
|  |  |  | 620 |  |  |  |  | 625 |  |  |  |  | 630 |  |  |  |
| TAT | GTG | GGG | GGT | GTG | GAG | CAC | AGG | CTC | AAT | GCT | GCA | TGC | AAT | TGG | ACC | 2273 |
| Tyr | Val | Gly | Gly | Val | Glu | His | Arg | Leu | Asn | Ala | Ala | Cys | Asn | Trp | Thr |  |
|  |  | 635 |  |  |  |  | 640 |  |  |  |  | 645 |  |  |  |  |
| CGA | GGA | GAG | CGT | TGT | GAC | TTG | GAG | GAC | AGG | GAT | AGG | CCG | GAG | CTC | AGC | 2321 |
| Arg | Gly | Glu | Arg | Cys | Asp | Leu | Glu | Asp | Arg | Asp | Arg | Pro | Glu | Leu | Ser |  |
|  |  | 650 |  |  |  |  | 655 |  |  |  |  | 660 |  |  |  |  |
| CCG | CTG | CTG | CTG | TCT | ACA | ACA | GAG | TGG | CAG | GTA | CTG | CCC | TGT | TCC | TTC | 2369 |
| Pro | Leu | Leu | Leu | Ser | Thr | Thr | Glu | Trp | Gln | Val | Leu | Pro | Cys | Ser | Phe |  |
|  | 665 |  |  |  |  | 670 |  |  |  |  | 675 |  |  |  |  |  |
| ACC | ACC | CTA | CCA | GCT | CTG | TCC | ACT | GGC | TTG | ATT | CAC | CTC | CAT | CAG | AAC | 2417 |
| Thr | Thr | Leu | Pro | Ala | Leu | Ser | Thr | Gly | Leu | Ile | His | Leu | His | Gln | Asn |  |
| 680 |  |  |  |  | 685 |  |  |  |  | 690 |  |  |  |  | 695 |  |
| ATC | GTG | GAC | GTG | CAA | TAC | CTA | TAC | GGT | ATA | GGG | TCA | GCG | GTT | GTC | TCC | 2465 |
| Ile | Val | Asp | Val | Gln | Tyr | Leu | Tyr | Gly | Ile | Gly | Ser | Ala | Val | Val | Ser |  |

-continued

```
                    700                     705                     710
TTT GCA ATC AAA TGG GAG TAT GTC CTG TTG CTT TTC CTT CTC CTA GCG    2513
Phe Ala Ile Lys Trp Glu Tyr Val Leu Leu Phe Leu Leu Leu Ala
                715                     720                     725

GAC GCA CGT GTC TGT GCC TGC TTG TGG ATG ATG CTG CTG ATA GCC CAG    2561
Asp Ala Arg Val Cys Ala Cys Leu Trp Met Met Leu Leu Ile Ala Gln
            730                     735                     740

GCC GAG GCC GCC TTG GAG AAC CTG GTG GTC CTC AAT TCG GCG TCT GTG    2609
Ala Glu Ala Ala Leu Glu Asn Leu Val Val Leu Asn Ser Ala Ser Val
        745                     750                     755

GCC GGC GCA CAT GGC ATC CTC TCC TTC CTT GTG TTC TTC TGT GCC GCC    2657
Ala Gly Ala His Gly Ile Leu Ser Phe Leu Val Phe Phe Cys Ala Ala
760                     765                     770                     775

TGG TAC ATC AAA GGC AGG CTG GTC CCT GGG GCG ACA TAT GCT CTT TAT    2705
Trp Tyr Ile Lys Gly Arg Leu Val Pro Gly Ala Thr Tyr Ala Leu Tyr
                780                     785                     790

GGC GTG TGG CCG CTG CTC CTG CTC TTG CTG GCA TTA CCA CCG CGA GCT    2753
Gly Val Trp Pro Leu Leu Leu Leu Leu Ala Leu Pro Pro Arg Ala
            795                     800                     805

TAC GCC ATG GAC CGG GAG ATG GCT GCA TCG TGC GGA GGC GCG GTT TTT    2801
Tyr Ala Met Asp Arg Glu Met Ala Ala Ser Cys Gly Gly Ala Val Phe
        810                     815                     820

GTG GGT CTG GTA CTC CTG ACT TTG TCA CCA TAC TAC AAG GTG TTC CTC    2849
Val Gly Leu Val Leu Leu Thr Leu Ser Pro Tyr Tyr Lys Val Phe Leu
825                     830                     835

GCT AGG CTC ATA TGG TGG TTA CAA TAT TTT ACC ACC AGA GCC GAG GCG    2897
Ala Arg Leu Ile Trp Trp Leu Gln Tyr Phe Thr Thr Arg Ala Glu Ala
840                     845                     850                     855

GAC TTA CAT GTG TGG ATC CCC CCC CTC AAC GCT CGG GGA GGC CGC GAT    2945
Asp Leu His Val Trp Ile Pro Pro Leu Asn Ala Arg Gly Gly Arg Asp
                860                     865                     870

GCC ATC ATC CTC CTC ATG TGC GCA GTC CAT CCA GAG CTA ATC TTT GAC    2993
Ala Ile Ile Leu Leu Met Cys Ala Val His Pro Glu Leu Ile Phe Asp
            875                     880                     885

ATC ACC AAA CTT CTA ATT GCC ATA CTC GGT CCG CTC ATG GTG CTC CAA    3041
Ile Thr Lys Leu Leu Ile Ala Ile Leu Gly Pro Leu Met Val Leu Gln
        890                     895                     900

GCT GGC ATA ACC AGA GTG CCG TAC TTC GTG CGC GCT CAA GGG CTC ATT    3089
Ala Gly Ile Thr Arg Val Pro Tyr Phe Val Arg Ala Gln Gly Leu Ile
905                     910                     915

CAT GCA TGC ATG TTA GTG CGG AAG GTC GCT GGG GGT CAT TAT GTC CAA    3137
His Ala Cys Met Leu Val Arg Lys Val Ala Gly Gly His Tyr Val Gln
920                     925                     930                     935

ATG GCC TTC ATG AAG CTG GGC GCG CTG ACA GGC ACG TAC ATT TAC AAC    3185
Met Ala Phe Met Lys Leu Gly Ala Leu Thr Gly Thr Tyr Ile Tyr Asn
                940                     945                     950

CAT CTT ACC CCG CTA CGG GAT TGG CCA CGC GCG GGC CTA CGA GAC CTT    3233
His Leu Thr Pro Leu Arg Asp Trp Pro Arg Ala Gly Leu Arg Asp Leu
            955                     960                     965

GCG GTG GCA GTG GAG CCC GTC GTC TTC TCC GAC ATG GAG ACC AAG ATC    3281
Ala Val Ala Val Glu Pro Val Val Phe Ser Asp Met Glu Thr Lys Ile
        970                     975                     980

ATC ACC TGG GGA GCA GAC ACC GCG GCG TGT GGG GAC ATC ATC TTG GGT    3329
Ile Thr Trp Gly Ala Asp Thr Ala Ala Cys Gly Asp Ile Ile Leu Gly
985                     990                     995

CTG CCC GTC TCC GCC CGA AGG GGA AAG GAG ATA CTC CTG GGC CCG GCC    3377
Leu Pro Val Ser Ala Arg Arg Gly Lys Glu Ile Leu Leu Gly Pro Ala
1000                    1005                    1010                    1015

GAT AGT CTT GAA GGG CGG GGG TTG CGA CTC CTC GCG CCC ATC ACG GCC    3425
Asp Ser Leu Glu Gly Arg Gly Leu Arg Leu Leu Ala Pro Ile Thr Ala
```

-continued

```
                1020                1025                1030
TAC TCC CAA CAG ACG CGG GGC CTA CTT GGT TGC ATC ATC ACT AGC CTT      3473
Tyr Ser Gln Gln Thr Arg Gly Leu Leu Gly Cys Ile Ile Thr Ser Leu
                1035                1040                1045

ACA GGC CGG GAC AAG AAC CAG GTC GAG GGA GAG GTT CAG GTG GTT TCC      3521
Thr Gly Arg Asp Lys Asn Gln Val Glu Gly Glu Val Gln Val Val Ser
                1050                1055            1060

ACC GCA ACA CAA TCC TTC CTG GCG ACC TGC GTC AAC GGC GTG TGT TGG      3569
Thr Ala Thr Gln Ser Phe Leu Ala Thr Cys Val Asn Gly Val Cys Trp
            1065                1070                1075

ACC GTT TAC CAT GGT GCT GGC TCA AAG ACC TTA GCC GCG CCA AAG GGG      3617
Thr Val Tyr His Gly Ala Gly Ser Lys Thr Leu Ala Ala Pro Lys Gly
1080                1085                1090                1095

CCA ATC ACC CAG ATG TAC ACT AAT GTG GAC CAG GAC CTC GTC GGC TGG      3665
Pro Ile Thr Gln Met Tyr Thr Asn Val Asp Gln Asp Leu Val Gly Trp
                    1100                1105                1110

CCC AAG CCC CCC GGG GCG CGT TCC TTG ACA CCA TGC ACC TGT GGC AGC      3713
Pro Lys Pro Pro Gly Ala Arg Ser Leu Thr Pro Cys Thr Cys Gly Ser
                1115                1120                1125

TCA GAC CTT TAC TTG GTC ACG AGA CAT GCT GAC GTC ATT CCG GTG CGC      3761
Ser Asp Leu Tyr Leu Val Thr Arg His Ala Asp Val Ile Pro Val Arg
                1130                1135                1140

CGG CGG GGC GAC AGT AGG GGG AGC CTG CTC TCC CCC AGG CCT GTC TCC      3809
Arg Arg Gly Asp Ser Arg Gly Ser Leu Leu Ser Pro Arg Pro Val Ser
                1145                1150                1155

TAC TTG AAG GGC TCT TCG GGT GGT CCA CTG CTC TGC CCC TTC GGG CAC      3857
Tyr Leu Lys Gly Ser Ser Gly Gly Pro Leu Leu Cys Pro Phe Gly His
1160                1165                1170                1175

GCT GTG GGC ATC TTC CGG GCT GCC GTA TGC ACC CGG GGG GTT GCG AAG      3905
Ala Val Gly Ile Phe Arg Ala Ala Val Cys Thr Arg Gly Val Ala Lys
                1180                1185                1190

GCG GTG GAC TTT GTG CCC GTA GAG TCC ATG GAA ACT ACT ATG CGG TCT      3953
Ala Val Asp Phe Val Pro Val Glu Ser Met Glu Thr Thr Met Arg Ser
                1195                1200                1205

CCG GTC TTC ACG GAC AAC TCA TCC CCC CCG GCC GTA CCG CAG TCA TTT      4001
Pro Val Phe Thr Asp Asn Ser Ser Pro Pro Ala Val Pro Gln Ser Phe
                1210                1215                1220

CAA GTG GCC CAC CTA CAC GCT CCC ACT GGC AGC GGC AAG AGT ACT AAA      4049
Gln Val Ala His Leu His Ala Pro Thr Gly Ser Gly Lys Ser Thr Lys
                1225                1230                1235

GTG CCG GCT GCA TAT GCA GCC CAA GGG TAC AAG GTG CTC GTC CTC AAT      4097
Val Pro Ala Ala Tyr Ala Ala Gln Gly Tyr Lys Val Leu Val Leu Asn
1240                1245                1250                1255

CCG TCC GTT GCC GCT ACC TTA GGG TTT GGG GCG TAT ATG TCT AAG GCA      4145
Pro Ser Val Ala Ala Thr Leu Gly Phe Gly Ala Tyr Met Ser Lys Ala
                1260                1265                1270

CAC GGT ATT GAC CCC AAC ATC AGA ACT GGG GTA AGG ACC ATT ACC ACA      4193
His Gly Ile Asp Pro Asn Ile Arg Thr Gly Val Arg Thr Ile Thr Thr
                1275                1280                1285

GGC GCC CCC GTC ACA TAC TCT ACC TAT GGC AAG TTT CTT GCC GAT GGT      4241
Gly Ala Pro Val Thr Tyr Ser Thr Tyr Gly Lys Phe Leu Ala Asp Gly
                1290                1295                1300

GGT TGC TCT GGG GGC GCT TAT GAC ATC ATA ATA TGT GAT GAG TGC CAT      4289
Gly Cys Ser Gly Gly Ala Tyr Asp Ile Ile Ile Cys Asp Glu Cys His
1305                1310                1315

TCA ACT GAC TCG ACT ACA ATC TTG GGC ATC GGC ACA GTC CTG GAC CAA      4337
Ser Thr Asp Ser Thr Thr Ile Leu Gly Ile Gly Thr Val Leu Asp Gln
1320                1325                1330                1335

GCG GAG ACG GCT GGA GCG CGG CTT GTC GTG CTC GCC ACC GCT ACG CCT      4385
Ala Glu Thr Ala Gly Ala Arg Leu Val Val Leu Ala Thr Ala Thr Pro
```

-continued

```
                          1340               1345                1350
CCG GGA TCG GTC ACC GTG CCA CAC CCA AAC ATC GAG GAG GTG GCC CTG     4433
Pro Gly Ser Val Thr Val Pro His Pro Asn Ile Glu Glu Val Ala Leu
            1355                1360                1365

TCT AAT ACT GGA GAG ATC CCC TTC TAT GGC AAA GCC ATC CCC ATT GAA     4481
Ser Asn Thr Gly Glu Ile Pro Phe Tyr Gly Lys Ala Ile Pro Ile Glu
            1370                1375                1380

GCC ATC AGG GGG GGA AGG CAT CTC ATT TTC TGT CAT TCC AAG AAG AAG     4529
Ala Ile Arg Gly Gly Arg His Leu Ile Phe Cys His Ser Lys Lys Lys
            1385                1390                1395

TGC GAC GAG CTC GCC GCA AAG CTG TCA GGC CTC GGA ATC AAC GCT GTG     4577
Cys Asp Glu Leu Ala Ala Lys Leu Ser Gly Leu Gly Ile Asn Ala Val
1400                1405                1410                1415

GCG TAT TAC CGG GGG CTC GAT GTG TCC GTC ATA CCA ACT ATC GGA GAC     4625
Ala Tyr Tyr Arg Gly Leu Asp Val Ser Val Ile Pro Thr Ile Gly Asp
            1420                1425                1430

GTC GTT GTC GTG GCA ACA GAC GCT CTG ATG ACG GGC TAT ACG GGC GAC     4673
Val Val Val Val Ala Thr Asp Ala Leu Met Thr Gly Tyr Thr Gly Asp
            1435                1440                1445

TTT GAC TCA GTG ATC GAC TGT AAC ACA TGT GTC ACC CAG ACA GTC GAC     4721
Phe Asp Ser Val Ile Asp Cys Asn Thr Cys Val Thr Gln Thr Val Asp
            1450                1455                1460

TTC AGC TTG GAT CCC ACC TTC ACC ATT GAG ACG ACG ACC GTG CCT CAA     4769
Phe Ser Leu Asp Pro Thr Phe Thr Ile Glu Thr Thr Thr Val Pro Gln
            1465                1470                1475

GAC GCA GTG TCG CGC TCG CAG CGG CGG GGT AGG ACT GGC AGG GGT AGG     4817
Asp Ala Val Ser Arg Ser Gln Arg Arg Gly Arg Thr Gly Arg Gly Arg
1480                1485                1490                1495

AGA GGC ATC TAC AGG TTT GTG ACT CCG GGA GAA CGG CCC TCG GGC ATG     4865
Arg Gly Ile Tyr Arg Phe Val Thr Pro Gly Glu Arg Pro Ser Gly Met
            1500                1505                1510

TTC GAT TCC TCG GTC CTG TGT GAG TGC TAT GAC GCG GGC TGT GCT TGG     4913
Phe Asp Ser Ser Val Leu Cys Glu Cys Tyr Asp Ala Gly Cys Ala Trp
            1515                1520                1525

TAC GAG CTC ACC CCG GCC GAG ACC TCG GTT AGG TTG CGG GCC TAC CTG     4961
Tyr Glu Leu Thr Pro Ala Glu Thr Ser Val Arg Leu Arg Ala Tyr Leu
            1530                1535                1540

AAC ACA CCA GGG TTG CCC GTT TGC CAG GAC CAC CTG GAG TTC TGG GAG     5009
Asn Thr Pro Gly Leu Pro Val Cys Gln Asp His Leu Glu Phe Trp Glu
            1545                1550                1555

AGT GTC TTC ACA GGC CTC ACC CAT ATA GAT GCA CAC TTC TTG TCC CAG     5057
Ser Val Phe Thr Gly Leu Thr His Ile Asp Ala His Phe Leu Ser Gln
1560                1565                1570                1575

ACC AAG CAG GCA GGA GAC AAC TTC CCC TAC CTG GTA GCA TAC CAA GCC     5105
Thr Lys Gln Ala Gly Asp Asn Phe Pro Tyr Leu Val Ala Tyr Gln Ala
            1580                1585                1590

ACG GTG TGC GCC AGG GCT CAG GCC CCA CCT CCA TCA TGG GAT CAA ATG     5153
Thr Val Cys Ala Arg Ala Gln Ala Pro Pro Pro Ser Trp Asp Gln Met
            1595                1600                1605

TGG AAG TGT CTC ATA CGG CTG AAA CCT ACG CTG CAC GGG CCA ACA CCC     5201
Trp Lys Cys Leu Ile Arg Leu Lys Pro Thr Leu His Gly Pro Thr Pro
            1610                1615                1620

TTG CTG TAC AGG CTG GGA GCC GTC CAG AAT GAG GTC ACC CTC ACC CAC     5249
Leu Leu Tyr Arg Leu Gly Ala Val Gln Asn Glu Val Thr Leu Thr His
            1625                1630                1635

CCC ATA ACC AAA TAC ATC ATG GCA TGC ATG TCG GCT GAC CTG GAG GTC     5297
Pro Ile Thr Lys Tyr Ile Met Ala Cys Met Ser Ala Asp Leu Glu Val
1640                1645                1650                1655

GTC ACT AGC ACC TGG GTG CTG GTG GGC GGA GTC CTT GCA GCT CTG GCC     5345
Val Thr Ser Thr Trp Val Leu Val Gly Gly Val Leu Ala Ala Leu Ala
```

-continued

```
                 1660                  1665                  1670
GCG TAT TGC CTG ACA ACA GGC AGT GTG GTC ATT GTG GGT AGG ATT ATC         5393
Ala Tyr Cys Leu Thr Thr Gly Ser Val Val Ile Val Gly Arg Ile Ile
        1675                  1680                  1685

TTG TCC GGG AGG CCG GCC ATT GTT CCC GAC AGG GAG CTT CTC TAC CAG         5441
Leu Ser Gly Arg Pro Ala Ile Val Pro Asp Arg Glu Leu Leu Tyr Gln
        1690                  1695                  1700

GAG TTC GAT GAA ATG GAA GAG TGC GCC TCG CAC CTC CCT TAC ATC GAG         5489
Glu Phe Asp Glu Met Glu Glu Cys Ala Ser His Leu Pro Tyr Ile Glu
        1705                  1710                  1715

CAG GGA ATG CAG CTC GCC GAG CAA TTC AAG CAG AAA GCG CTC GGG TTA         5537
Gln Gly Met Gln Leu Ala Glu Gln Phe Lys Gln Lys Ala Leu Gly Leu
1720                  1725                  1730                  1735

CTG CAA ACA GCC ACC AAA CAA GCG GAG GCT GCT GCT CCC GTG GTG GAG         5585
Leu Gln Thr Ala Thr Lys Gln Ala Glu Ala Ala Ala Pro Val Val Glu
        1740                  1745                  1750

TCC AAG TGG CGA GCC CTT GAG ACA TTC TGG GCG AAG CAC ATG TGG AAT         5633
Ser Lys Trp Arg Ala Leu Glu Thr Phe Trp Ala Lys His Met Trp Asn
        1755                  1760                  1765

TTC ATC AGC GGG ATA CAG TAC TTA GCA GGC TTA TCC ACT CTG CCT GGG         5681
Phe Ile Ser Gly Ile Gln Tyr Leu Ala Gly Leu Ser Thr Leu Pro Gly
        1770                  1775                  1780

AAC CCC GCA ATA GCA TCA TTG ATG GCA TTC ACA GCC TCT ATC ACC AGC         5729
Asn Pro Ala Ile Ala Ser Leu Met Ala Phe Thr Ala Ser Ile Thr Ser
        1785                  1790                  1795

CCG CTC ACC ACC CAA AGT ACC CTC CTG TTT AAC ATC TTG GGG GGG TGG         5777
Pro Leu Thr Thr Gln Ser Thr Leu Leu Phe Asn Ile Leu Gly Gly Trp
1800                  1805                  1810                  1815

GTG GCT GCC CAA CTC GCC CCC CCC AGC GCC GCT TCG GCT TTC GTG GGC         5825
Val Ala Ala Gln Leu Ala Pro Pro Ser Ala Ala Ser Ala Phe Val Gly
        1820                  1825                  1830

GCC GGC ATC GCC GGT GCG GCT GTT GGC AGC ATA GGC CTT GGG AAG GTG         5873
Ala Gly Ile Ala Gly Ala Ala Val Gly Ser Ile Gly Leu Gly Lys Val
        1835                  1840                  1845

CTT GTG GAC ATT CTG GCG GGT TAT GGA GCA GGA GTG GCC GGC GCG CTC         5921
Leu Val Asp Ile Leu Ala Gly Tyr Gly Ala Gly Val Ala Gly Ala Leu
        1850                  1855                  1860

GTG GCC TTT AAG GTC ATG AGC GGC GAG ATG CCC TCC ACC GAG GAC CTG         5969
Val Ala Phe Lys Val Met Ser Gly Glu Met Pro Ser Thr Glu Asp Leu
        1865                  1870                  1875

GTC AAT CTA CTT CCT GCC ATC CTC TCT CCT GGC GCC CTG GTC GTC GGG         6017
Val Asn Leu Leu Pro Ala Ile Leu Ser Pro Gly Ala Leu Val Val Gly
1880                  1885                  1890                  1895

GTC GTG TGT GCA GCA ATA CTG CGT CGA CAC GTG GGT CCG GGA GAG GGG         6065
Val Val Cys Ala Ala Ile Leu Arg Arg His Val Gly Pro Gly Glu Gly
        1900                  1905                  1910

GCT GTG CAG TGG ATG AAC CGG CTG ATA GCG TTC GCC TCG CGG GGT AAT         6113
Ala Val Gln Trp Met Asn Arg Leu Ile Ala Phe Ala Ser Arg Gly Asn
        1915                  1920                  1925

CAT GTT TCC CCC ACG CAC TAT GTG CCT GAG AGC GAC GCC GCA GCG CGT         6161
His Val Ser Pro Thr His Tyr Val Pro Glu Ser Asp Ala Ala Ala Arg
        1930                  1935                  1940

GTT ACT CAG ATC CTC TCC AGC CTT ACC ATC ACT CAG CTG CTG AAA AGG         6209
Val Thr Gln Ile Leu Ser Ser Leu Thr Ile Thr Gln Leu Leu Lys Arg
        1945                  1950                  1955

CTC CAC CAG TGG ATT AAT GAA GAC TGC TCC ACA CCG TGT TCC GGC TCG         6257
Leu His Gln Trp Ile Asn Glu Asp Cys Ser Thr Pro Cys Ser Gly Ser
1960                  1965                  1970                  1975

TGG CTA AGG GAT GTT TGG GAC TGG ATA TGC ACG GTG TTG ACT GAC TTC         6305
Trp Leu Arg Asp Val Trp Asp Trp Ile Cys Thr Val Leu Thr Asp Phe
```

-continued

|  | 1980 | 1985 | 1990 | |
|---|---|---|---|---|
| AAG ACC TGG CTC CAG TCC AAG CTC CTG CCG CAG CTA CCT GGA GTC CCT | | | | 6353 |
| Lys Thr Trp Leu Gln Ser Lys Leu Leu Pro Gln Leu Pro Gly Val Pro | | | | |
|  | 1995 | 2000 | 2005 | |
| TTT TTC TCG TGC CAA CGC GGG TAC AAG GGA GTC TGG CGG GGA GAC GGC | | | | 6401 |
| Phe Phe Ser Cys Gln Arg Gly Tyr Lys Gly Val Trp Arg Gly Asp Gly | | | | |
|  | 2010 | 2015 | 2020 | |
| ATC ATG CAA ACC ACC TGC CCA TGT GGA GCA CAG ATC ACC GGA CAT GTC | | | | 6449 |
| Ile Met Gln Thr Thr Cys Pro Cys Gly Ala Gln Ile Thr Gly His Val | | | | |
|  | 2025 | 2030 | 2035 | |
| AAA AAC GGT TCC ATG AGG ATC GTC GGG CCT AAG ACC TGC AGC AAC ACG | | | | 6497 |
| Lys Asn Gly Ser Met Arg Ile Val Gly Pro Lys Thr Cys Ser Asn Thr | | | | |
| 2040 | 2045 | 2050 | 2055 | |
| TGG CAT GGA ACA TTC CCC ATC AAC GCA TAC ACC ACG GGC CCC TGC ACA | | | | 6545 |
| Trp His Gly Thr Phe Pro Ile Asn Ala Tyr Thr Thr Gly Pro Cys Thr | | | | |
|  | 2060 | 2065 | 2070 | |
| CCC TCT CCA GCG CCA AAC TAT TCT AGG GCG CTG TGG CGG GTG GCC GCT | | | | 6593 |
| Pro Ser Pro Ala Pro Asn Tyr Ser Arg Ala Leu Trp Arg Val Ala Ala | | | | |
|  | 2075 | 2080 | 2085 | |
| GAG GAG TAC GTG GAG GTC ACG CGG GTG GGG GAT TTC CAC TAC GTG ACG | | | | 6641 |
| Glu Glu Tyr Val Glu Val Thr Arg Val Gly Asp Phe His Tyr Val Thr | | | | |
|  | 2090 | 2095 | 2100 | |
| GGC ATG ACC ACT GAC AAC GTA AAG TGC CCA TGC CAG GTT CCG GCT CCT | | | | 6689 |
| Gly Met Thr Thr Asp Asn Val Lys Cys Pro Cys Gln Val Pro Ala Pro | | | | |
| 2105 | 2110 | 2115 | | |
| GAA TTC TTC TCG GAG GTG GAC GGA GTG CGG TTG CAC AGG TAC GCT CCG | | | | 6737 |
| Glu Phe Phe Ser Glu Val Asp Gly Val Arg Leu His Arg Tyr Ala Pro | | | | |
| 2120 | 2125 | 2130 | 2135 | |
| GCG TGC AGG CCT CTC CTA CGG GAG GAG GTT ACA TTC CAG GTC GGG CTC | | | | 6785 |
| Ala Cys Arg Pro Leu Leu Arg Glu Glu Val Thr Phe Gln Val Gly Leu | | | | |
|  | 2140 | 2145 | 2150 | |
| AAC CAA TAC CTG GTT GGG TCA CAG CTA CCA TGC GAG CCC GAA CCG GAT | | | | 6833 |
| Asn Gln Tyr Leu Val Gly Ser Gln Leu Pro Cys Glu Pro Glu Pro Asp | | | | |
|  | 2155 | 2160 | 2165 | |
| GTA GCA GTG CTC ACT TCC ATG CTC ACC GAC CCC TCC CAC ATC ACA GCA | | | | 6881 |
| Val Ala Val Leu Thr Ser Met Leu Thr Asp Pro Ser His Ile Thr Ala | | | | |
|  | 2170 | 2175 | 2180 | |
| GAA ACG GCT AAG CGT AGG TTG GCC AGG GGG TCT CCC CCC TCC TTG GCC | | | | 6929 |
| Glu Thr Ala Lys Arg Arg Leu Ala Arg Gly Ser Pro Pro Ser Leu Ala | | | | |
| 2185 | 2190 | 2195 | | |
| AGC TCT TCA GCT AGC CAG TTG TCT GCG CCT TCC TTG AAG GCG ACA TGC | | | | 6977 |
| Ser Ser Ser Ala Ser Gln Leu Ser Ala Pro Ser Leu Lys Ala Thr Cys | | | | |
| 2200 | 2205 | 2210 | 2215 | |
| ACT ACC CAC CAT GTC TCT CCG GAC GCT GAC CTC ATC GAG GCC AAC CTC | | | | 7025 |
| Thr Thr His His Val Ser Pro Asp Ala Asp Leu Ile Glu Ala Asn Leu | | | | |
|  | 2220 | 2225 | 2230 | |
| CTG TGG CGG CAG GAG ATG GGC GGG AAC ATC ACC CGC GTG GAG TCG GAG | | | | 7073 |
| Leu Trp Arg Gln Glu Met Gly Gly Asn Ile Thr Arg Val Glu Ser Glu | | | | |
|  | 2235 | 2240 | 2245 | |
| AAC AAG GTG GTA GTC CTG GAC TCT TTC GAC CCG CTT CGA GCG GAG GAG | | | | 7121 |
| Asn Lys Val Val Val Leu Asp Ser Phe Asp Pro Leu Arg Ala Glu Glu | | | | |
|  | 2250 | 2255 | 2260 | |
| GAT GAG AGG GAA GTA TCC GTT CCG GCG GAG ATC CTG CGG AAA TCC AAG | | | | 7169 |
| Asp Glu Arg Glu Val Ser Val Pro Ala Glu Ile Leu Arg Lys Ser Lys | | | | |
|  | 2265 | 2270 | 2275 | |
| AAG TTC CCC GCA GCG ATG CCC ATC TGG GCG CGC CCG GAT TAC AAC CCT | | | | 7217 |
| Lys Phe Pro Ala Ala Met Pro Ile Trp Ala Arg Pro Asp Tyr Asn Pro | | | | |
| 2280 | 2285 | 2290 | 2295 | |
| CCA CTG TTA GAG TCC TGG AAG GAC CCG GAC TAC GTC CCT CCG GTG GTG | | | | 7265 |
| Pro Leu Leu Glu Ser Trp Lys Asp Pro Asp Tyr Val Pro Pro Val Val | | | | |

-continued

```
                2300                    2305                    2310
CAC GGG TGC CCG TTG CCA CCT ATC AAG GCC CCT CCA ATA CCA CCT CCA     7313
His Gly Cys Pro Leu Pro Pro Ile Lys Ala Pro Pro Ile Pro Pro Pro
                2315                    2320                    2325

CGG AGA AAG AGG ACG GTT GTC CTA ACA GAG TCC TCC GTG TCT TCT GCC     7361
Arg Arg Lys Arg Thr Val Val Leu Thr Glu Ser Ser Val Ser Ser Ala
                2330                    2335                    2340

TTA GCG GAG CTC GCT ACT AAG ACC TTC GGC AGC TCC GAA TCA TCG GCC     7409
Leu Ala Glu Leu Ala Thr Lys Thr Phe Gly Ser Ser Glu Ser Ser Ala
                2345                    2350                    2355

GTC GAC AGC GGC ACG GCG ACC GCC CTT CCT GAC CAG GCC TCC GAC GAC     7457
Val Asp Ser Gly Thr Ala Thr Ala Leu Pro Asp Gln Ala Ser Asp Asp
2360                    2365                    2370                    2375

GGT GAC AAA GGA TCC GAC GTT GAG TCG TAC TCC TCC ATG CCC CCC CTT     7505
Gly Asp Lys Gly Ser Asp Val Glu Ser Tyr Ser Ser Met Pro Pro Leu
                2380                    2385                    2390

GAG GGG GAA CCG GGG GAC CCC GAT CTC AGT GAC GGG TCT TGG TCT ACC     7553
Glu Gly Glu Pro Gly Asp Pro Asp Leu Ser Asp Gly Ser Trp Ser Thr
                2395                    2400                    2405

GTG AGC GAG GAA GCT AGT GAG GAT GTC GTC TGC TGC TCA ATG TCC TAC     7601
Val Ser Glu Glu Ala Ser Glu Asp Val Val Cys Cys Ser Met Ser Tyr
                2410                    2415                    2420

ACA TGG ACA GGC GCC TTG ATC ACG CCA TGC GCT GCG GAG GAA AGC AAG     7649
Thr Trp Thr Gly Ala Leu Ile Thr Pro Cys Ala Ala Glu Glu Ser Lys
                2425                    2430                    2435

CTG CCC ATC AAC GCG TTG AGC AAC TCT TTG CTG CGC CAC CAT AAC ATG     7697
Leu Pro Ile Asn Ala Leu Ser Asn Ser Leu Leu Arg His His Asn Met
2440                    2445                    2450                    2455

GTT TAT GCC ACA ACA TCT CGC AGC GCA GGC CTG CGG CAG AAG AAG GTC     7745
Val Tyr Ala Thr Thr Ser Arg Ser Ala Gly Leu Arg Gln Lys Lys Val
                2460                    2465                    2470

ACC TTT GAC AGA CTG CAA GTC CTG GAC GAC CAC TAC CGG GAC GTG CTC     7793
Thr Phe Asp Arg Leu Gln Val Leu Asp Asp His Tyr Arg Asp Val Leu
                2475                    2480                    2485

AAG GAG ATG AAG GCG AAG GCG TCC ACA GTT AAG GCT AAA CTC CTA TCC     7841
Lys Glu Met Lys Ala Lys Ala Ser Thr Val Lys Ala Lys Leu Leu Ser
                2490                    2495                    2500

GTA GAG GAA GCC TGC AAG CTG ACG CCC CCA CAT TCG GCC AAA TCC AAG     7889
Val Glu Glu Ala Cys Lys Leu Thr Pro Pro His Ser Ala Lys Ser Lys
                2505                    2510                    2515

TTT GGC TAT GGG GCA AAG GAC GTC CGG AAC CTA TCC AGC AAG GCC GTT     7937
Phe Gly Tyr Gly Ala Lys Asp Val Arg Asn Leu Ser Ser Lys Ala Val
2520                    2525                    2530                    2535

AAC CAC ATC CAC TCC GTG TGG AAG GAC TTG CTG GAA GAC ACT GTG ACA     7985
Asn His Ile His Ser Val Trp Lys Asp Leu Leu Glu Asp Thr Val Thr
                2540                    2545                    2550

CCA ATT GAC ACC ACC ATC ATG GCA AAA AAT GAG GTT TTC TGT GTC CAA     8033
Pro Ile Asp Thr Thr Ile Met Ala Lys Asn Glu Val Phe Cys Val Gln
                2555                    2560                    2565

CCA GAG AAA GGA GGC CGT AAG CCA GCC CGC CTT ATC GTA TTC CCA GAT     8081
Pro Glu Lys Gly Gly Arg Lys Pro Ala Arg Leu Ile Val Phe Pro Asp
                2570                    2575                    2580

CTG GGA GTC CGT GTA TGC GAG AAG ATG GCC CTC TAT GAT GTG GTC TCC     8129
Leu Gly Val Arg Val Cys Glu Lys Met Ala Leu Tyr Asp Val Val Ser
                2585                    2590                    2595

ACC CTT CCT CAG GTC GTG ATG GGC TCC TCA TAC GGA TTC CAG TAC TCT     8177
Thr Leu Pro Gln Val Val Met Gly Ser Ser Tyr Gly Phe Gln Tyr Ser
2600                    2605                    2610                    2615

CCT GGG CAG CGA GTC GAG TTC CTG GTG AAT ACC TGG AAA TCA AAG AAA     8225
Pro Gly Gln Arg Val Glu Phe Leu Val Asn Thr Trp Lys Ser Lys Lys
```

```
                    2620                    2625                    2630
AAC CCC ATG GGC TTT TCA TAT GAC ACT CGC TGT TTC GAC TCA ACG GTC                8273
Asn Pro Met Gly Phe Ser Tyr Asp Thr Arg Cys Phe Asp Ser Thr Val
            2635                    2640                    2645

ACC GAG AAC GAC ATC CGT GTT GAG GAG TCA ATT TAC CAA TGT TGT GAC                8321
Thr Glu Asn Asp Ile Arg Val Glu Glu Ser Ile Tyr Gln Cys Cys Asp
            2650                    2655                    2660

TTG GCC CCC GAA GCC AGA CAG GCC ATA AAA TCG CTC ACA GAG CGG CTT                8369
Leu Ala Pro Glu Ala Arg Gln Ala Ile Lys Ser Leu Thr Glu Arg Leu
            2665                    2670                    2675

TAT ATC GGG GGT CCT CTG ACT AAT TCA AAA GGG CAG AAC TGC GGT TAT                8417
Tyr Ile Gly Gly Pro Leu Thr Asn Ser Lys Gly Gln Asn Cys Gly Tyr
2680                    2685                    2690                    2695

CGC CGG TGC CGC GCG AGC GGC GTG CTG ACG ACT AGC TGC GGT AAC ACC                8465
Arg Arg Cys Arg Ala Ser Gly Val Leu Thr Thr Ser Cys Gly Asn Thr
                2700                    2705                    2710

CTC ACA TGT TAC TTG AAG GCC TCT GCA GCC TGT CGA GCT GCG AAG CTC                8513
Leu Thr Cys Tyr Leu Lys Ala Ser Ala Ala Cys Arg Ala Ala Lys Leu
            2715                    2720                    2725

CAG GAC TGC ACG ATG CTC GTG AAC GGA GAC GAC CTC GTC GTT ATC TGT                8561
Gln Asp Cys Thr Met Leu Val Asn Gly Asp Asp Leu Val Val Ile Cys
            2730                    2735                    2740

GAA AGC GCG GGA ACC CAA GAG GAC GCG GCG AGC CTA CGA GTC TTC ACG                8609
Glu Ser Ala Gly Thr Gln Glu Asp Ala Ala Ser Leu Arg Val Phe Thr
2745                    2750                    2755

GAG GCT ATG ACT AGG TAC TCC GCC CCC CCC GGG GAC CCG CCC CAA CCA                8657
Glu Ala Met Thr Arg Tyr Ser Ala Pro Pro Gly Asp Pro Pro Gln Pro
2760                    2765                    2770                    2775

GAA TAC GAC TTG GAG CTG ATA ACA TCA TGT TCC TCC AAT GTG TCG GTC                8705
Glu Tyr Asp Leu Glu Leu Ile Thr Ser Cys Ser Ser Asn Val Ser Val
                2780                    2785                    2790

GCC CAC GAT GCA TCA GGC AAA AGG GTG TAC TAC CTC ACC CGT GAT CCC                8753
Ala His Asp Ala Ser Gly Lys Arg Val Tyr Tyr Leu Thr Arg Asp Pro
            2795                    2800                    2805

ACC ACC CCC CTA GCA CGG GCT GCG TGG GAG ACA GCT AGA CAC ACT CCA                8801
Thr Thr Pro Leu Ala Arg Ala Ala Trp Glu Thr Ala Arg His Thr Pro
            2810                    2815                    2820

GTT AAC TCC TGG CTA GGC AAC ATT ATT ATG TAT GCG CCC ACT TTG TGG                8849
Val Asn Ser Trp Leu Gly Asn Ile Ile Met Tyr Ala Pro Thr Leu Trp
            2825                    2830                    2835

GCA AGG ATG ATT CTG ATG ACT CAC TTC TTC TCC ATC CTT CTA GCG CAG                8897
Ala Arg Met Ile Leu Met Thr His Phe Phe Ser Ile Leu Leu Ala Gln
2840                    2845                    2850                    2855

GAG CAA CTT GAA AAA GCC CTG GAC TGC CAG ATC TAC GGG GCC TGT TAC                8945
Glu Gln Leu Glu Lys Ala Leu Asp Cys Gln Ile Tyr Gly Ala Cys Tyr
                2860                    2865                    2870

TCC ATT GAG CCA CTT GAC CTA CCT CAG ATC ATT GAA CGA CTC CAT GGC                8993
Ser Ile Glu Pro Leu Asp Leu Pro Gln Ile Ile Glu Arg Leu His Gly
            2875                    2880                    2885

CTT AGC GCA TTT TCA CTC CAT AGT TAC TCT CCA GGT GAG ATC AAT AGG                9041
Leu Ser Ala Phe Ser Leu His Ser Tyr Ser Pro Gly Glu Ile Asn Arg
            2890                    2895                    2900

GTG GCT TCA TGC CTC AGG AAA CTT GGG GTA CCA CCC TTG CGA GTC TGG                9089
Val Ala Ser Cys Leu Arg Lys Leu Gly Val Pro Pro Leu Arg Val Trp
            2905                    2910                    2915

AGA CAT CGG GCC AGG AGC GTC CGC GCT AGG CTA CTG TCC CAG GGA GGG                9137
Arg His Arg Ala Arg Ser Val Arg Ala Arg Leu Leu Ser Gln Gly Gly
2920                    2925                    2930                    2935

AGG GCC GCC ACT TGT GGC AAA TAC CTC TTC AAC TGG GCA GTA AAA ACC                9185
Arg Ala Ala Thr Cys Gly Lys Tyr Leu Phe Asn Trp Ala Val Lys Thr
```

```
                  2940              2945              2950
AAA CTT AAA CTC ACT CCA ATC CCG GCT GCG TCC CGG CTG GAC TTG TCC     9233
Lys Leu Lys Leu Thr Pro Ile Pro Ala Ala Ser Arg Leu Asp Leu Ser
            2955              2960              2965

GGC TGG TTC GTT GCT GGT TAC AGC GGG GGA GAC ATA TAT CAC AGC CTG     9281
Gly Trp Phe Val Ala Gly Tyr Ser Gly Gly Asp Ile Tyr His Ser Leu
        2970              2975              2980

TCT CGT GCC CGA CCC CGT TGG TTC ATG CTG TGC CTA CTC CTA CTT TCT     9329
Ser Arg Ala Arg Pro Arg Trp Phe Met Leu Cys Leu Leu Leu Leu Ser
        2985              2990              2995

GTA GGG GTA GGC ATC TAC CTG CTC CCC AAC CGA TGAACGGGGA GATAAACACT   9382
Val Gly Val Gly Ile Tyr Leu Leu Pro Asn Arg
3000            3005              3010

CCAGGCCAAT AGGCCATCCC CCTTTTTTTT TTTT                               9416

(2) INFORMATION FOR SEQ ID NO:2:

(i) SEQUENCE CHARACTERISTICS:
        (A) LENGTH: 3010 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Pro Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Pro Ala Ser Ala Tyr
            180                 185                 190

Glu Val His Asn Val Ser Gly Ile Tyr His Val Thr Asn Asp Cys Ser
        195                 200                 205

Asn Ala Ser Ile Val Tyr Glu Ala Ala Asp Leu Ile Met His Thr Pro
    210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Val Thr Ile Pro Thr Thr
                245                 250                 255
```

-continued

```
Thr Ile Arg Arg His Val Asp Leu Leu Val Gly Ala Ala Phe Cys
            260                 265                 270

Ser Ala Met Tyr Val Gly Asp Leu Cys Gly Ser Val Phe Leu Val Ser
            275                 280                 285

Gln Leu Phe Thr Phe Ser Pro Arg Arg His Val Thr Leu Gln Asp Cys
            290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                    325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Ala Gly Asn Trp
            355                 360                 365

Ala Lys Val Leu Ile Val Met Leu Leu Phe Ala Gly Val Asp Gly Asp
    370                 375                 380

Thr His Val Thr Gly Gly Ala Gln Ala Lys Thr Thr Asn Arg Leu Val
385                 390                 395                 400

Ser Met Phe Ala Ser Gly Pro Ser Gln Lys Ile Gln Leu Ile Asn Thr
                    405                 410                 415

Asn Gly Ser Trp His Ile Asn Arg Thr Ala Leu Asn Cys Asn Asp Ser
                420                 425                 430

Leu Gln Thr Gly Phe Leu Ala Ala Leu Phe Tyr Thr His Ser Phe Asn
            435                 440                 445

Ser Ser Gly Cys Pro Glu Arg Met Ala Gln Cys Arg Thr Ile Asp Lys
    450                 455                 460

Phe Asp Gln Gly Trp Gly Pro Ile Thr Tyr Ala Glu Ser Ser Arg Ser
465                 470                 475                 480

Asp Gln Arg Pro Tyr Cys Trp His Tyr Pro Pro Gln Cys Thr Ile
                    485                 490                 495

Val Pro Ala Ser Glu Val Cys Gly Pro Val Tyr Cys Phe Thr Pro Ser
                500                 505                 510

Pro Val Val Val Gly Thr Thr Asp Arg Phe Gly Val Pro Thr Tyr Arg
            515                 520                 525

Trp Gly Glu Asn Glu Thr Asp Val Leu Leu Leu Asn Asn Thr Arg Pro
    530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Val Gly Asn
            565                 570                 575

Asn Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Met
            595                 600                 605

Val Asp Tyr Pro Tyr Arg Leu Trp His Tyr Pro Cys Thr Val Asn Phe
    610                 615                 620

Thr Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asp Leu Glu Asp
                645                 650                 655

Arg Asp Arg Pro Glu Leu Ser Pro Leu Leu Leu Ser Thr Thr Glu Trp
                660                 665                 670

Gln Val Leu Pro Cys Ser Phe Thr Thr Leu Pro Ala Leu Ser Thr Gly
            675                 680                 685
```

```
Leu Ile His Leu His Gln Asn Ile Val Asp Val Gln Tyr Leu Tyr Gly
    690             695                 700
Ile Gly Ser Ala Val Val Ser Phe Ala Ile Lys Trp Glu Tyr Val Leu
705             710                 715                 720
Leu Leu Phe Leu Leu Leu Ala Asp Ala Arg Val Cys Ala Cys Leu Trp
                725                 730                 735
Met Met Leu Leu Ile Ala Gln Ala Glu Ala Ala Leu Glu Asn Leu Val
            740                 745                 750
Val Leu Asn Ser Ala Ser Val Ala Gly Ala His Gly Ile Leu Ser Phe
        755                 760                 765
Leu Val Phe Phe Cys Ala Ala Trp Tyr Ile Lys Gly Arg Leu Val Pro
    770                 775                 780
Gly Ala Thr Tyr Ala Leu Tyr Gly Val Trp Pro Leu Leu Leu Leu Leu
785                 790                 795                 800
Leu Ala Leu Pro Pro Arg Ala Tyr Ala Met Asp Arg Glu Met Ala Ala
                805                 810                 815
Ser Cys Gly Gly Ala Val Phe Val Gly Leu Val Leu Leu Thr Leu Ser
            820                 825                 830
Pro Tyr Tyr Lys Val Phe Leu Ala Arg Leu Ile Trp Trp Leu Gln Tyr
        835                 840                 845
Phe Thr Thr Arg Ala Glu Ala Asp Leu His Val Trp Ile Pro Pro Leu
    850                 855                 860
Asn Ala Arg Gly Gly Arg Asp Ala Ile Ile Leu Leu Met Cys Ala Val
865                 870                 875                 880
His Pro Glu Leu Ile Phe Asp Ile Thr Lys Leu Leu Ile Ala Ile Leu
                885                 890                 895
Gly Pro Leu Met Val Leu Gln Ala Gly Ile Thr Arg Val Pro Tyr Phe
            900                 905                 910
Val Arg Ala Gln Gly Leu Ile His Ala Cys Met Leu Val Arg Lys Val
        915                 920                 925
Ala Gly Gly His Tyr Val Gln Met Ala Phe Met Lys Leu Gly Ala Leu
    930                 935                 940
Thr Gly Thr Tyr Ile Tyr Asn His Leu Thr Pro Leu Arg Asp Trp Pro
945                 950                 955                 960
Arg Ala Gly Leu Arg Asp Leu Ala Val Ala Val Glu Pro Val Val Phe
                965                 970                 975
Ser Asp Met Glu Thr Lys Ile Ile Thr Trp Gly Ala Asp Thr Ala Ala
            980                 985                 990
Cys Gly Asp Ile Ile Leu Gly Leu Pro Val Ser Ala Arg Arg Gly Lys
        995                 1000                1005
Glu Ile Leu Leu Gly Pro Ala Asp Ser Leu Glu Gly Arg Gly Leu Arg
    1010                1015                1020
Leu Leu Ala Pro Ile Thr Ala Tyr Ser Gln Gln Thr Arg Gly Leu Leu
1025                1030                1035                1040
Gly Cys Ile Ile Thr Ser Leu Thr Gly Arg Asp Lys Asn Gln Val Glu
                1045                1050                1055
Gly Glu Val Gln Val Val Ser Thr Ala Thr Gln Ser Phe Leu Ala Thr
            1060                1065                1070
Cys Val Asn Gly Val Cys Trp Thr Val Tyr His Gly Ala Gly Ser Lys
        1075                1080                1085
Thr Leu Ala Ala Pro Lys Gly Pro Ile Thr Gln Met Tyr Thr Asn Val
    1090                1095                1100
Asp Gln Asp Leu Val Gly Trp Pro Lys Pro Pro Gly Ala Arg Ser Leu
```

-continued

```
         1105                1110                1115                1120
Thr Pro Cys Thr Cys Gly Ser Ser Asp Leu Tyr Leu Val Thr Arg His
                 1125                1130                1135
Ala Asp Val Ile Pro Val Arg Arg Gly Asp Ser Arg Gly Ser Leu
         1140                1145                1150
Leu Ser Pro Arg Pro Val Ser Tyr Leu Lys Gly Ser Ser Gly Gly Pro
         1155                1160                1165
Leu Leu Cys Pro Phe His Ala Val Gly Ile Phe Arg Ala Ala Val
         1170                1175                1180
Cys Thr Arg Gly Val Ala Lys Ala Val Asp Phe Val Pro Val Glu Ser
1185                1190                1195                1200
Met Glu Thr Thr Met Arg Ser Pro Val Phe Thr Asp Asn Ser Ser Pro
                 1205                1210                1215
Pro Ala Val Pro Gln Ser Phe Gln Val Ala His Leu His Ala Pro Thr
         1220                1225                1230
Gly Ser Gly Lys Ser Thr Lys Val Pro Ala Ala Tyr Ala Ala Gln Gly
         1235                1240                1245
Tyr Lys Val Leu Val Leu Asn Pro Ser Val Ala Ala Thr Leu Gly Phe
         1250                1255                1260
Gly Ala Tyr Met Ser Lys Ala His Gly Ile Asp Pro Asn Ile Arg Thr
1265                1270                1275                1280
Gly Val Arg Thr Ile Thr Thr Gly Ala Pro Val Thr Tyr Ser Thr Tyr
                 1285                1290                1295
Gly Lys Phe Leu Ala Asp Gly Gly Cys Ser Gly Gly Ala Tyr Asp Ile
         1300                1305                1310
Ile Ile Cys Asp Glu Cys His Ser Thr Asp Ser Thr Thr Ile Leu Gly
         1315                1320                1325
Ile Gly Thr Val Leu Asp Gln Ala Glu Thr Ala Gly Ala Arg Leu Val
         1330                1335                1340
Val Leu Ala Thr Ala Thr Pro Pro Gly Ser Val Thr Val Pro His Pro
1345                1350                1355                1360
Asn Ile Glu Glu Val Ala Leu Ser Asn Thr Gly Glu Ile Pro Phe Tyr
                 1365                1370                1375
Gly Lys Ala Ile Pro Ile Glu Ala Ile Arg Gly Gly Arg His Leu Ile
         1380                1385                1390
Phe Cys His Ser Lys Lys Lys Cys Asp Glu Leu Ala Ala Lys Leu Ser
         1395                1400                1405
Gly Leu Gly Ile Asn Ala Val Ala Tyr Tyr Arg Gly Leu Asp Val Ser
         1410                1415                1420
Val Ile Pro Thr Ile Gly Asp Val Val Val Ala Thr Asp Ala Leu
1425                1430                1435                1440
Met Thr Gly Tyr Thr Gly Asp Phe Asp Ser Val Ile Asp Cys Asn Thr
                 1445                1450                1455
Cys Val Thr Gln Thr Val Asp Phe Ser Leu Asp Pro Thr Phe Thr Ile
         1460                1465                1470
Glu Thr Thr Thr Val Pro Gln Asp Ala Val Ser Arg Ser Gln Arg Arg
         1475                1480                1485
Gly Arg Thr Gly Arg Gly Arg Arg Gly Ile Tyr Arg Phe Val Thr Pro
         1490                1495                1500
Gly Glu Arg Pro Ser Gly Met Phe Asp Ser Ser Val Leu Cys Glu Cys
1505                1510                1515                1520
Tyr Asp Ala Gly Cys Ala Trp Tyr Glu Leu Thr Pro Ala Glu Thr Ser
                 1525                1530                1535
```

-continued

```
Val Arg Leu Arg Ala Tyr Leu Asn Thr Pro Gly Leu Pro Val Cys Gln
        1540                1545                1550

Asp His Leu Glu Phe Trp Glu Ser Val Phe Thr Gly Leu Thr His Ile
        1555                1560                1565

Asp Ala His Phe Leu Ser Gln Thr Lys Gln Ala Gly Asp Asn Phe Pro
        1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
        1620                1625                1630

Asn Glu Val Thr Leu Thr His Pro Ile Thr Lys Tyr Ile Met Ala Cys
        1635                1640                1645

Met Ser Ala Asp Leu Glu Val Val Thr Ser Thr Trp Val Leu Val Gly
        1650                1655                1660

Gly Val Leu Ala Ala Leu Ala Ala Tyr Cys Leu Thr Thr Gly Ser Val
1665                1670                1675                1680

Val Ile Val Gly Arg Ile Ile Leu Ser Gly Arg Pro Ala Ile Val Pro
                1685                1690                1695

Asp Arg Glu Leu Leu Tyr Gln Glu Phe Asp Glu Met Glu Glu Cys Ala
        1700                1705                1710

Ser His Leu Pro Tyr Ile Glu Gln Gly Met Gln Leu Ala Glu Gln Phe
        1715                1720                1725

Lys Gln Lys Ala Leu Gly Leu Leu Gln Thr Ala Thr Lys Gln Ala Glu
        1730                1735                1740

Ala Ala Ala Pro Val Val Glu Ser Lys Trp Arg Ala Leu Glu Thr Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
        1780                1785                1790

Phe Thr Ala Ser Ile Thr Ser Pro Leu Thr Thr Gln Ser Thr Leu Leu
        1795                1800                1805

Phe Asn Ile Leu Gly Gly Trp Val Ala Ala Gln Leu Ala Pro Pro Ser
        1810                1815                1820

Ala Ala Ser Ala Phe Val Gly Ala Gly Ile Ala Gly Ala Ala Val Gly
1825                1830                1835                1840

Ser Ile Gly Leu Gly Lys Val Leu Val Asp Ile Leu Ala Gly Tyr Gly
                1845                1850                1855

Ala Gly Val Ala Gly Ala Leu Val Ala Phe Lys Val Met Ser Gly Glu
        1860                1865                1870

Met Pro Ser Thr Glu Asp Leu Val Asn Leu Leu Pro Ala Ile Leu Ser
        1875                1880                1885

Pro Gly Ala Leu Val Val Gly Val Val Cys Ala Ala Ile Leu Arg Arg
        1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Gln Ile Leu Ser Ser Leu Thr
        1940                1945                1950

Ile Thr Gln Leu Leu Lys Arg Leu His Gln Trp Ile Asn Glu Asp Cys
        1955                1960                1965
```

-continued

```
Ser Thr Pro Cys Ser Gly Ser Trp Leu Arg Asp Val Trp Asp Trp Ile
    1970                1975               1980

Cys Thr Val Leu Thr Asp Phe Lys Thr Trp Leu Gln Ser Lys Leu Leu
1985            1990                1995                2000

Pro Gln Leu Pro Gly Val Pro Phe Phe Ser Cys Gln Arg Gly Tyr Lys
                2005                2010                2015

Gly Val Trp Arg Gly Asp Gly Ile Met Gln Thr Thr Cys Pro Cys Gly
            2020                2025                2030

Ala Gln Ile Thr Gly His Val Lys Asn Gly Ser Met Arg Ile Val Gly
            2035                2040                2045

Pro Lys Thr Cys Ser Asn Thr Trp His Gly Thr Phe Pro Ile Asn Ala
    2050                2055                2060

Tyr Thr Thr Gly Pro Cys Thr Pro Ser Pro Ala Pro Asn Tyr Ser Arg
2065            2070                2075                2080

Ala Leu Trp Arg Val Ala Ala Glu Glu Tyr Val Glu Val Thr Arg Val
                2085                2090                2095

Gly Asp Phe His Tyr Val Thr Gly Met Thr Thr Asp Asn Val Lys Cys
                2100                2105                2110

Pro Cys Gln Val Pro Ala Pro Glu Phe Phe Ser Glu Val Asp Gly Val
        2115                2120                2125

Arg Leu His Arg Tyr Ala Pro Ala Cys Arg Pro Leu Leu Arg Glu Glu
    2130                2135                2140

Val Thr Phe Gln Val Gly Leu Asn Gln Tyr Leu Val Gly Ser Gln Leu
2145            2150                2155                2160

Pro Cys Glu Pro Glu Pro Asp Val Ala Val Leu Thr Ser Met Leu Thr
                2165                2170                2175

Asp Pro Ser His Ile Thr Ala Glu Thr Ala Lys Arg Arg Leu Ala Arg
            2180                2185                2190

Gly Ser Pro Pro Ser Leu Ala Ser Ser Ser Ala Ser Gln Leu Ser Ala
    2195                2200                2205

Pro Ser Leu Lys Ala Thr Cys Thr Thr His His Val Ser Pro Asp Ala
    2210                2215                2220

Asp Leu Ile Glu Ala Asn Leu Leu Trp Arg Gln Glu Met Gly Gly Asn
2225            2230                2235                2240

Ile Thr Arg Val Glu Ser Glu Asn Lys Val Val Leu Asp Ser Phe
            2245                2250                2255

Asp Pro Leu Arg Ala Glu Glu Asp Glu Arg Glu Val Ser Val Pro Ala
            2260                2265                2270

Glu Ile Leu Arg Lys Ser Lys Lys Phe Pro Ala Ala Met Pro Ile Trp
        2275                2280                2285

Ala Arg Pro Asp Tyr Asn Pro Pro Leu Leu Glu Ser Trp Lys Asp Pro
    2290                2295                2300

Asp Tyr Val Pro Pro Val Val His Gly Cys Pro Leu Pro Pro Ile Lys
2305            2310                2315                2320

Ala Pro Pro Ile Pro Pro Pro Arg Arg Lys Arg Thr Val Val Leu Thr
                2325                2330                2335

Glu Ser Ser Val Ser Ser Ala Leu Ala Glu Leu Ala Thr Lys Thr Phe
            2340                2345                2350

Gly Ser Ser Glu Ser Ser Ala Val Asp Ser Gly Thr Ala Thr Ala Leu
    2355                2360                2365

Pro Asp Gln Ala Ser Asp Asp Gly Asp Lys Gly Ser Asp Val Glu Ser
    2370                2375                2380

Tyr Ser Ser Met Pro Pro Leu Glu Gly Glu Pro Gly Asp Pro Asp Leu
```

```
2385            2390             2395            2400

Ser Asp Gly Ser Trp Ser Thr Val Ser Glu Glu Ala Ser Glu Asp Val
                2405             2410            2415

Val Cys Cys Ser Met Ser Tyr Thr Trp Thr Gly Ala Leu Ile Thr Pro
                2420             2425            2430

Cys Ala Ala Glu Glu Ser Lys Leu Pro Ile Asn Ala Leu Ser Asn Ser
                2435             2440            2445

Leu Leu Arg His His Asn Met Val Tyr Ala Thr Thr Ser Arg Ser Ala
                2450             2455            2460

Gly Leu Arg Gln Lys Lys Val Thr Phe Asp Arg Leu Gln Val Leu Asp
2465            2470             2475            2480

Asp His Tyr Arg Asp Val Leu Lys Glu Met Lys Ala Lys Ala Ser Thr
                2485             2490            2495

Val Lys Ala Lys Leu Leu Ser Val Glu Glu Ala Cys Lys Leu Thr Pro
                2500             2505            2510

Pro His Ser Ala Lys Ser Lys Phe Gly Tyr Gly Ala Lys Asp Val Arg
                2515             2520            2525

Asn Leu Ser Ser Lys Ala Val Asn His Ile His Ser Val Trp Lys Asp
                2530             2535            2540

Leu Leu Glu Asp Thr Val Thr Pro Ile Asp Thr Thr Ile Met Ala Lys
2545            2550             2555            2560

Asn Glu Val Phe Cys Val Gln Pro Glu Lys Gly Gly Arg Lys Pro Ala
                2565             2570            2575

Arg Leu Ile Val Phe Pro Asp Leu Gly Val Arg Val Cys Glu Lys Met
                2580             2585            2590

Ala Leu Tyr Asp Val Val Ser Thr Leu Pro Gln Val Val Met Gly Ser
                2595             2600            2605

Ser Tyr Gly Phe Gln Tyr Ser Pro Gly Gln Arg Val Glu Phe Leu Val
                2610             2615            2620

Asn Thr Trp Lys Ser Lys Lys Asn Pro Met Gly Phe Ser Tyr Asp Thr
2625            2630             2635            2640

Arg Cys Phe Asp Ser Thr Val Thr Glu Asn Asp Ile Arg Val Glu Glu
                2645             2650            2655

Ser Ile Tyr Gln Cys Cys Asp Leu Ala Pro Glu Ala Arg Gln Ala Ile
                2660             2665            2670

Lys Ser Leu Thr Glu Arg Leu Tyr Ile Gly Gly Pro Leu Thr Asn Ser
                2675             2680            2685

Lys Gly Gln Asn Cys Gly Tyr Arg Arg Cys Arg Ala Ser Gly Val Leu
                2690             2695            2700

Thr Thr Ser Cys Gly Asn Thr Leu Thr Cys Tyr Leu Lys Ala Ser Ala
2705            2710             2715            2720

Ala Cys Arg Ala Ala Lys Leu Gln Asp Cys Thr Met Leu Val Asn Gly
                2725             2730            2735

Asp Asp Leu Val Val Ile Cys Glu Ser Ala Gly Thr Gln Glu Asp Ala
                2740             2745            2750

Ala Ser Leu Arg Val Phe Thr Glu Ala Met Thr Arg Tyr Ser Ala Pro
                2755             2760            2765

Pro Gly Asp Pro Pro Gln Pro Glu Tyr Asp Leu Glu Leu Ile Thr Ser
                2770             2775            2780

Cys Ser Ser Asn Val Ser Val Ala His Asp Ala Ser Gly Lys Arg Val
2785            2790             2795            2800

Tyr Tyr Leu Thr Arg Asp Pro Thr Thr Pro Leu Ala Arg Ala Ala Trp
                2805             2810            2815
```

```
Glu Thr Ala Arg His Thr Pro Val Asn Ser Trp Leu Gly Asn Ile Ile
        2820                2825                2830
Met Tyr Ala Pro Thr Leu Trp Ala Arg Met Ile Leu Met Thr His Phe
        2835                2840                2845
Phe Ser Ile Leu Leu Ala Gln Glu Gln Leu Glu Lys Ala Leu Asp Cys
2850                2855                2860
Gln Ile Tyr Gly Ala Cys Tyr Ser Ile Glu Pro Leu Asp Leu Pro Gln
2865                2870                2875                2880
Ile Ile Glu Arg Leu His Gly Leu Ser Ala Phe Ser Leu His Ser Tyr
            2885                2890                2895
Ser Pro Gly Glu Ile Asn Arg Val Ala Ser Cys Leu Arg Lys Leu Gly
            2900                2905                2910
Val Pro Pro Leu Arg Val Trp Arg His Arg Ala Arg Ser Val Arg Ala
        2915                2920                2925
Arg Leu Leu Ser Gln Gly Gly Arg Ala Ala Thr Cys Gly Lys Tyr Leu
        2930                2935                2940
Phe Asn Trp Ala Val Lys Thr Lys Leu Lys Leu Thr Pro Ile Pro Ala
2945                2950                2955                2960
Ala Ser Arg Leu Asp Leu Ser Gly Trp Phe Val Ala Gly Tyr Ser Gly
            2965                2970                2975
Gly Asp Ile Tyr His Ser Leu Ser Arg Ala Arg Pro Arg Trp Phe Met
        2980                2985                2990
Leu Cys Leu Leu Leu Leu Ser Val Gly Val Gly Ile Tyr Leu Leu Pro
        2995                3000                3005
Asn Arg
    3010

(2) INFORMATION FOR SEQ ID NO:3:

(i) SEQUENCE CHARACTERISTICS:
        (A) LENGTH: 1499 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: CDS
        (B) LOCATION: 333..1499

(ix) FEATURE:
        (A) NAME/KEY: misc_feature
        (B) LOCATION: 1..1499
        (D) OTHER INFORMATION: /note= "sequence = 1 - 1499 of SEQ
            ID NO: 1"

(xi) SEQUENCE DESCRIPTION: SEQ ID NO:3:

CGATTGGGGG CGACACTCCA CCATAGATCA CTCCCCTGTG AGGAACTACT GTCTTCACGC      60

AGAAAGCGTC TAGCCATGGC GTTAGTATGA GTGTCGTGCA GCCTCCAGGA CCCCCCCTCC     120

CGGGAGAGCC ATAGTGGTCT GCGGAACCGG TGAGTACACC GGAATTGCCA GGACGACCGG     180

GTCCTTTCTT GGATCAACCC GCTCAATGCC TGGAGATTTG GGCGTGCCCC CGCGAGACTG     240

CTAGCCGAGT AGTGTTGGGT CGCGAAAGGC CTTGTGGTAC TGCCTGATAG GGTGCTTGCG     300

AGTGCCCCGG GAGGTCTCGT AGACCGTGCA CC ATG AGC ACG AAT CCT AAA CCT        353
                                  Met Ser Thr Asn Pro Lys Pro
                                   1               5

CAA AGA AAA ACC AAA CGT AAC ACC AAC CGC CGC CCA CAG GAC GTC AAG        401
Gln Arg Lys Thr Lys Arg Asn Thr Asn Arg Arg Pro Gln Asp Val Lys
        10                  15                  20
```

| | | | | | | | | | | | | | | | |
|---|---|---|---|---|---|---|---|---|---|---|---|---|---|---|---|
| TTC | CCG | GGC | GGT | GGT | CAG | ATC | GTT | GGT | GGA | GTT | TAC | CTG | TTG | CCG | CGC | 449 |
| Phe | Pro | Gly | Gly | Gly | Gln | Ile | Val | Gly | Gly | Val | Tyr | Leu | Leu | Pro | Arg |
| 25 | | | | | 30 | | | | | | 35 | | | | |

```
TTC CCG GGC GGT GGT CAG ATC GTT GGT GGA GTT TAC CTG TTG CCG CGC      449
Phe Pro Gly Gly Gly Gln Ile Val Gly Gly Val Tyr Leu Leu Pro Arg
 25              30                  35

AGG GGC CCC AGG TTG GGT GTG CGC GCG CCC AGG AAG ACT TCC GAG CGG      497
Arg Gly Pro Arg Leu Gly Val Arg Ala Pro Arg Lys Thr Ser Glu Arg
 40              45                  50                  55

TCG CAA CCT CGT GGA AGG CGA CAA CCT ATC CCC AAG GCT CGC CGG CCC      545
Ser Gln Pro Arg Gly Arg Arg Gln Pro Ile Pro Lys Ala Arg Arg Pro
             60                  65                  70

GAG GGC AGG ACC TGG GCT CAG CCC GGG TAC CCT TGG CCT CTC TAT GGC      593
Glu Gly Arg Thr Trp Ala Gln Pro Gly Tyr Pro Trp Pro Leu Tyr Gly
             75                  80                  85

AAT GAG GGC TTA GGG TGG GCA GGA TGG CTC CTG TCA CCC CGC GGC TCC      641
Asn Glu Gly Leu Gly Trp Ala Gly Trp Leu Leu Ser Pro Arg Gly Ser
         90                  95                 100

CGG CCT AGT TGG GGC CCC ACG GAC CCC CGG CGT AGG TCG CGT AAT TTG      689
Arg Pro Ser Trp Gly Pro Thr Asp Pro Arg Arg Ser Arg Asn Leu
105                 110                 115

GGT AAG GTC ATC GAT ACC CTC ACA TGC GGC TTC GCC GAT CTC ATG GGG      737
Gly Lys Val Ile Asp Thr Leu Thr Cys Gly Phe Ala Asp Leu Met Gly
120             125                 130                 135

TAC ATT CCG CTC GTC GGC GCC CCC CTG GGG GGC GCT GCC AGG GCC CTG      785
Tyr Ile Pro Leu Val Gly Ala Pro Leu Gly Gly Ala Ala Arg Ala Leu
            140                 145                 150

GCA CAT GGT GTC CGG GTT CTG GAG GAC GGC GTG AAC TAT GCA ACA GGG      833
Ala His Gly Val Arg Val Leu Glu Asp Gly Val Asn Tyr Ala Thr Gly
            155                 160                 165

AAT CTG CCC GGT TGC TCT TTT TCT ATC TTC CTC TTG GCT CTG CTG TCC      881
Asn Leu Pro Gly Cys Ser Phe Ser Ile Phe Leu Leu Ala Leu Leu Ser
        170                 175                 180

TGC CTG ACC ACC CCA GCT TCC GCT TAC GAA GTG CAC AAC GTG TCC GGG      929
Cys Leu Thr Thr Pro Ala Ser Ala Tyr Glu Val His Asn Val Ser Gly
185                 190                 195

ATA TAT CAT GTC ACG AAC GAC TGC TCC AAC GCA AGC ATT GTG TAT GAG      977
Ile Tyr His Val Thr Asn Asp Cys Ser Asn Ala Ser Ile Val Tyr Glu
200                 205                 210                 215

GCA GCG GAC TTG ATC ATG CAT ACT CCT GGG TGC GTG CCC TGC GTT CGG     1025
Ala Ala Asp Leu Ile Met His Thr Pro Gly Cys Val Pro Cys Val Arg
                220                 225                 230

GAA GGC AAC TCC TCC CGC TGC TGG GTA GCG CTC ACT CCC ACG CTC GCA     1073
Glu Gly Asn Ser Ser Arg Cys Trp Val Ala Leu Thr Pro Thr Leu Ala
                235                 240                 245

GCC AGG AAC GTC ACC ATC CCC ACC ACG ACG ATA CGA CGC CAC GTC GAT     1121
Ala Arg Asn Val Thr Ile Pro Thr Thr Thr Ile Arg Arg His Val Asp
        250                 255                 260

CTG CTC GTT GGG GCG GCT GCT TTC TGT TCC GCT ATG TAC GTG GGG GAC     1169
Leu Leu Val Gly Ala Ala Ala Phe Cys Ser Ala Met Tyr Val Gly Asp
265                 270                 275

CTC TGC GGA TCT GTT TTC CTC GTC TCT CAG CTG TTC ACC TTC TCG CCT     1217
Leu Cys Gly Ser Val Phe Leu Val Ser Gln Leu Phe Thr Phe Ser Pro
280             285                 290                 295

CGC CGG CAT GTG ACA TTA CAG GAC TGT AAC TGC TCA ATT TAT CCC GGC     1265
Arg Arg His Val Thr Leu Gln Asp Cys Asn Cys Ser Ile Tyr Pro Gly
            300                 305                 310

CAT GTG TCG GGT CAC CGT ATG GCT TGG GAC ATG ATG ATG AAC TGG TCG     1313
His Val Ser Gly His Arg Met Ala Trp Asp Met Met Met Asn Trp Ser
            315                 320                 325

CCC ACA ACA GCC CTA GTG GTG TCG CAG TTA CTC CGG ATC CCA CAA GCC     1361
Pro Thr Thr Ala Leu Val Val Ser Gln Leu Leu Arg Ile Pro Gln Ala
        330                 335                 340
```

```
GTC GTG GAC ATG GTG GCG GGG GCC CAC TGG GGA GTC CTG GCG GGC CTT        1409
Val Val Asp Met Val Ala Gly Ala His Trp Gly Val Leu Ala Gly Leu
345                 350                 355

GCC TAC TAT TCC ATG GCG GGG AAC TGG GCT AAG GTT CTG ATT GTG ATG        1457
Ala Tyr Tyr Ser Met Ala Gly Asn Trp Ala Lys Val Leu Ile Val Met
360                 365                 370                 375

CTA CTT TTT GCT GGC GTT GAC GGG GAT ACC CAC GTG ACA GGG                1499
Leu Leu Phe Ala Gly Val Asp Gly Asp Thr His Val Thr Gly
                380                 385
```

(2) INFORMATION FOR SEQ ID NO:4:

(i) SEQUENCE CHARACTERISTICS:
        (A) LENGTH: 389 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Pro Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Tyr
            180                 185                 190

Glu Val His Asn Val Ser Gly Ile Tyr His Val Thr Asn Asp Cys Ser
        195                 200                 205

Asn Ala Ser Ile Val Tyr Glu Ala Ala Asp Leu Ile Met His Thr Pro
    210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Val Thr Ile Pro Thr Thr
                245                 250                 255

Thr Ile Arg Arg His Val Asp Leu Leu Val Gly Ala Ala Ala Phe Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Val Thr Leu Gln Asp Cys
    290                 295                 300
```

```
Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
            325                 330                 335

Leu Leu Arg Ile Pro Gln Ala Val Asp Met Val Ala Gly Ala His
        340                 345                 350

Trp Gly Val Leu Ala Gly Leu Ala Tyr Tyr Ser Met Ala Gly Asn Trp
            355                 360                 365

Ala Lys Val Leu Ile Val Met Leu Leu Phe Ala Gly Val Asp Gly Asp
    370                 375                 380

Thr His Val Thr Gly
385
```

(2) INFORMATION FOR SEQ ID NO:5:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..90
        (D) OTHER INFORMATION: /note: "sequence = 333 - 422 of
            SEQ ID NO: 1"

(ix) FEATURE:
        (A) NAME/KEY: CDS
        (B) LOCATION: 1..90

(xi) SEQUENCE DESCRIPTION: SEQ ID NO:5:

```
ATG AGC ACG AAT CCT AAA CCT CAA AGA AAA ACC AAA CGT AAC ACC AAC    48
Met Ser Thr Asn Pro Lys Pro Gln Arg Lys Thr Lys Arg Asn Thr Asn
1               5                   10                  15

CGC CGC CCA CAG GAC GTC AAG TTC CCG GGC GGT GGT CAG ATC            90
Arg Arg Pro Gln Asp Val Lys Phe Pro Gly Gly Gly Gln Ile
            20                  25                  30
```

(2) INFORMATION FOR SEQ ID NO:6:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile
            20                  25                  30
```

(2) INFORMATION FOR SEQ ID NO:7:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: cDNA from genomic RNA (ix) FEATURE:

(A) NAME/KEY: misc_feature
        (B) LOCATION: 1..345
        (D) OTHER INFORMATION: /note: "sequence = 333 - 677 of
            SEQ ID NO: 1"

(ix) FEATURE:
        (A) NAME/KEY: CDS
        (B) LOCATION: 1..345

(xi) SEQUENCE DESCRIPTION: SEQ ID NO:7:

```
ATG AGC ACG AAT CCT AAA CCT CAA AGA AAA ACC AAA CGT AAC ACC AAC        48
Met Ser Thr Asn Pro Lys Pro Gln Arg Lys Thr Lys Arg Asn Thr Asn
 1               5                  10                  15

CGC CGC CCA CAG GAC GTC AAG TTC CCG GGC GGT GGT CAG ATC GTT GGT        96
Arg Arg Pro Gln Asp Val Lys Phe Pro Gly Gly Gly Gln Ile Val Gly
                20                  25                  30

GGA GTT TAC CTG TTG CCG CGC AGG GGC CCC AGG TTG GGT GTG CGC GCG       144
Gly Val Tyr Leu Leu Pro Arg Arg Gly Pro Arg Leu Gly Val Arg Ala
            35                  40                  45

CCC AGG AAG ACT TCC GAG CGG TCG CAA CCT CGT GGA AGG CGA CAA CCT       192
Pro Arg Lys Thr Ser Glu Arg Ser Gln Pro Arg Gly Arg Arg Gln Pro
 50                  55                  60

ATC CCC AAG GCT CGC CGG CCC GAG GGC AGG ACC TGG GCT CAG CCC GGG       240
Ile Pro Lys Ala Arg Arg Pro Glu Gly Arg Thr Trp Ala Gln Pro Gly
 65                  70                  75                  80

TAC CCT TGG CCT CTC TAT GGC AAT GAG GGC TTA GGG TGG GCA GGA TGG       288
Tyr Pro Trp Pro Leu Tyr Gly Asn Glu Gly Leu Gly Trp Ala Gly Trp
                85                  90                  95

CTC CTG TCA CCC CGC GGC TCC CGG CCT AGT TGG GGC CCC ACG GAC CCC       336
Leu Leu Ser Pro Arg Gly Ser Arg Pro Ser Trp Gly Pro Thr Asp Pro
            100                 105                 110

CGG CGT AGG                                                           345
Arg Arg Arg
        115
```

(2) INFORMATION FOR SEQ ID NO:8:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Pro Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg
        115
```

(2) INFORMATION FOR SEQ ID NO:9:

(i) SEQUENCE CHARACTERISTICS:
        (A) LENGTH: 1167 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..1167
        (D) OTHER INFORMATION: /note: "sequence = 333 - 1499 of
            SEQ ID NO: 1"

(ix) FEATURE:
        (A) NAME/KEY: CDS
        (B) LOCATION: 1..1167

(xi) SEQUENCE DESCRIPTION: SEQ ID NO:9:

```
ATG AGC ACG AAT CCT AAA CCT CAA AGA AAA ACC AAA CGT AAC ACC AAC       48
Met Ser Thr Asn Pro Lys Pro Gln Arg Lys Thr Lys Arg Asn Thr Asn
 1               5                  10                  15

CGC CGC CCA CAG GAC GTC AAG TTC CCG GGC GGT GGT CAG ATC GTT GGT       96
Arg Arg Pro Gln Asp Val Lys Phe Pro Gly Gly Gly Gln Ile Val Gly
                20                  25                  30

GGA GTT TAC CTG TTG CCG CGC AGG GGC CCC AGG TTG GGT GTG CGC GCG      144
Gly Val Tyr Leu Leu Pro Arg Arg Gly Pro Arg Leu Gly Val Arg Ala
        35                  40                  45

CCC AGG AAG ACT TCC GAG CGG TCG CAA CCT CGT GGA AGG CGA CAA CCT      192
Pro Arg Lys Thr Ser Glu Arg Ser Gln Pro Arg Gly Arg Arg Gln Pro
50                  55                  60

ATC CCC AAG GCT CGC CGG CCC GAG GGC AGG ACC TGG GCT CAG CCC GGG      240
Ile Pro Lys Ala Arg Arg Pro Glu Gly Arg Thr Trp Ala Gln Pro Gly
65                  70                  75                  80

TAC CCT TGG CCT CTC TAT GGC AAT GAG GGC TTA GGG TGG GCA GGA TGG      288
Tyr Pro Trp Pro Leu Tyr Gly Asn Glu Gly Leu Gly Trp Ala Gly Trp
                85                  90                  95

CTC CTG TCA CCC CGC GGC TCC CGG CCT AGT TGG GGC CCC ACG GAC CCC      336
Leu Leu Ser Pro Arg Gly Ser Arg Pro Ser Trp Gly Pro Thr Asp Pro
            100                 105                 110

CGG CGT AGG TCG CGT AAT TTG GGT AAG GTC ATC GAT ACC CTC ACA TGC      384
Arg Arg Arg Ser Arg Asn Leu Gly Lys Val Ile Asp Thr Leu Thr Cys
        115                 120                 125

GGC TTC GCC GAT CTC ATG GGG TAC ATT CCG CTC GTC GGC GCC CCC CTG      432
Gly Phe Ala Asp Leu Met Gly Tyr Ile Pro Leu Val Gly Ala Pro Leu
    130                 135                 140

GGG GGC GCT GCC AGG GCC CTG GCA CAT GGT GTC CGG GTT CTG GAG GAC      480
Gly Gly Ala Ala Arg Ala Leu Ala His Gly Val Arg Val Leu Glu Asp
145                 150                 155                 160

GGC GTG AAC TAT GCA ACA GGG AAT CTG CCC GGT TGC TCT TTT TCT ATC      528
Gly Val Asn Tyr Ala Thr Gly Asn Leu Pro Gly Cys Ser Phe Ser Ile
                165                 170                 175

TTC CTC TTG GCT CTG CTG TCC TGC CTG ACC ACC CCA GCT TCC GCT TAC      576
Phe Leu Leu Ala Leu Leu Ser Cys Leu Thr Thr Pro Ala Ser Ala Tyr
            180                 185                 190

GAA GTG CAC AAC GTG TCC GGG ATA TAT CAT GTC ACG AAC GAC TGC TCC      624
Glu Val His Asn Val Ser Gly Ile Tyr His Val Thr Asn Asp Cys Ser
        195                 200                 205

AAC GCA AGC ATT GTG TAT GAG GCA GCG GAC TTG ATC ATG CAT ACT CCT      672
Asn Ala Ser Ile Val Tyr Glu Ala Ala Asp Leu Ile Met His Thr Pro
    210                 215                 220

GGG TGC GTG CCC TGC GTT CGG GAA GGC AAC TCC TCC CGC TGC TGG GTA      720
Gly Cys Val Pro Cys Val Arg Glu Gly Asn Ser Ser Arg Cys Trp Val
```

```
GCG CTC ACT CCC ACG CTC GCA GCC AGG AAC GTC ACC ATC CCC ACC ACG      768
Ala Leu Thr Pro Thr Leu Ala Ala Arg Asn Val Thr Ile Pro Thr Thr
            245                 250                 255

ACG ATA CGA CGC CAC GTC GAT CTG CTC GTT GGG GCG GCT GCT TTC TGT      816
Thr Ile Arg Arg His Val Asp Leu Leu Val Gly Ala Ala Ala Phe Cys
            260                 265                 270

TCC GCT ATG TAC GTG GGG GAC CTC TGC GGA TCT GTT TTC CTC GTC TCT      864
Ser Ala Met Tyr Val Gly Asp Leu Cys Gly Ser Val Phe Leu Val Ser
            275                 280                 285

CAG CTG TTC ACC TTC TCG CCT CGC CGG CAT GTG ACA TTA CAG GAC TGT      912
Gln Leu Phe Thr Phe Ser Pro Arg Arg His Val Thr Leu Gln Asp Cys
        290                 295                 300

AAC TGC TCA ATT TAT CCC GGC CAT GTG TCG GGT CAC CGT ATG GCT TGG      960
Asn Cys Ser Ile Tyr Pro Gly His Val Ser Gly His Arg Met Ala Trp
305                 310                 315                 320

GAC ATG ATG ATG AAC TGG TCG CCC ACA ACA GCC CTA GTG GTG TCG CAG     1008
Asp Met Met Met Asn Trp Ser Pro Thr Thr Ala Leu Val Val Ser Gln
                325                 330                 335

TTA CTC CGG ATC CCA CAA GCC GTC GTG GAC ATG GTG GCG GGG GCC CAC     1056
Leu Leu Arg Ile Pro Gln Ala Val Val Asp Met Val Ala Gly Ala His
            340                 345                 350

TGG GGA GTC CTG GCG GGC CTT GCC TAC TAT TCC ATG GCG GGG AAC TGG     1104
Trp Gly Val Leu Ala Gly Leu Ala Tyr Tyr Ser Met Ala Gly Asn Trp
        355                 360                 365

GCT AAG GTT CTG ATT GTG ATG CTA CTT TTT GCT GGC GTT GAC GGG GAT     1152
Ala Lys Val Leu Ile Val Met Leu Leu Phe Ala Gly Val Asp Gly Asp
370                 375                 380

ACC CAC GTG ACA GGG                                                  1167
Thr His Val Thr Gly
385
```

(2) INFORMATION FOR SEQ ID NO:10:

(i) SEQUENCE CHARACTERISTICS:
        (A) LENGTH: 389 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Pro Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140
```

```
Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
            165                 170                 175

Phe Leu Leu Ala Leu Leu Ser Cys Leu Thr Thr Pro Ala Ser Ala Tyr
            180                 185                 190

Glu Val His Asn Val Ser Gly Ile Tyr His Val Thr Asn Asp Cys Ser
            195                 200                 205

Asn Ala Ser Ile Val Tyr Glu Ala Ala Asp Leu Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Val Thr Ile Pro Thr Thr
                245                 250                 255

Thr Ile Arg Arg His Val Asp Leu Leu Val Gly Ala Ala Ala Phe Cys
                260                 265                 270

Ser Ala Met Tyr Val Gly Asp Leu Cys Gly Ser Val Phe Leu Val Ser
            275                 280                 285

Gln Leu Phe Thr Phe Ser Pro Arg Arg His Val Thr Leu Gln Asp Cys
290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
                340                 345                 350

Trp Gly Val Leu Ala Gly Leu Ala Tyr Tyr Ser Met Ala Gly Asn Trp
            355                 360                 365

Ala Lys Val Leu Ile Val Met Leu Leu Phe Ala Gly Val Asp Gly Asp
    370                 375                 380

Thr His Val Thr Gly
385

(2) INFORMATION FOR SEQ ID NO:11:

(i) SEQUENCE CHARACTERISTICS:
        (A) LENGTH: 6039 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..6039
        (D) OTHER INFORMATION: /note: "sequence = 333 - 6371 of
            SEQ ID NO: 1"

(ix) FEATURE:
        (A) NAME/KEY: CDS
        (B) LOCATION: 1..6039

(xi) SEQUENCE DESCRIPTION: SEQ ID NO:11:

ATG AGC ACG AAT CCT AAA CCT CAA AGA AAA ACC AAA CGT AAC ACC AAC       48
Met Ser Thr Asn Pro Lys Pro Gln Arg Lys Thr Lys Arg Asn Thr Asn
1               5                   10                  15

CGC CGC CCA CAG GAC GTC AAG TTC CCG GGC GGT GGT CAG ATC GTT GGT       96
Arg Arg Pro Gln Asp Val Lys Phe Pro Gly Gly Gly Gln Ile Val Gly
            20                  25                  30
```

-continued

```
GGA GTT TAC CTG TTG CCG CGC AGG GGC CCC AGG TTG GGT GTG CGC GCG      144
Gly Val Tyr Leu Leu Pro Arg Arg Gly Pro Arg Leu Gly Val Arg Ala
         35                  40                  45

CCC AGG AAG ACT TCC GAG CGG TCG CAA CCT CGT GGA AGG CGA CAA CCT      192
Pro Arg Lys Thr Ser Glu Arg Ser Gln Pro Arg Gly Arg Arg Gln Pro
 50                  55                  60

ATC CCC AAG GCT CGC CGG CCC GAG GGC AGG ACC TGG GCT CAG CCC GGG      240
Ile Pro Lys Ala Arg Arg Pro Glu Gly Arg Thr Trp Ala Gln Pro Gly
 65                  70                  75                  80

TAC CCT TGG CCT CTC TAT GGC AAT GAG GGC TTA GGG TGG GCA GGA TGG      288
Tyr Pro Trp Pro Leu Tyr Gly Asn Glu Gly Leu Gly Trp Ala Gly Trp
                     85                  90                  95

CTC CTG TCA CCC CGC GGC TCC CGG CCT AGT TGG GGC CCC ACG GAC CCC      336
Leu Leu Ser Pro Arg Gly Ser Arg Pro Ser Trp Gly Pro Thr Asp Pro
                100                 105                 110

CGG CGT AGG TCG CGT AAT TTG GGT AAG GTC ATC GAT ACC CTC ACA TGC      384
Arg Arg Arg Ser Arg Asn Leu Gly Lys Val Ile Asp Thr Leu Thr Cys
            115                 120                 125

GGC TTC GCC GAT CTC ATG GGG TAC ATT CCG CTC GTC GGC GCC CCC CTG      432
Gly Phe Ala Asp Leu Met Gly Tyr Ile Pro Leu Val Gly Ala Pro Leu
130                 135                 140

GGG GGC GCT GCC AGG GCC CTG GCA CAT GGT GTC CGG GTT CTG GAG GAC      480
Gly Gly Ala Ala Arg Ala Leu Ala His Gly Val Arg Val Leu Glu Asp
145                 150                 155                 160

GGC GTG AAC TAT GCA ACA GGG AAT CTG CCC GGT TGC TCT TTT TCT ATC      528
Gly Val Asn Tyr Ala Thr Gly Asn Leu Pro Gly Cys Ser Phe Ser Ile
                165                 170                 175

TTC CTC TTG GCT CTG CTG TCC TGC CTG ACC ACC CCA GCT TCC GCT TAC      576
Phe Leu Leu Ala Leu Leu Ser Cys Leu Thr Thr Pro Ala Ser Ala Tyr
                180                 185                 190

GAA GTG CAC AAC GTG TCC GGG ATA TAT CAT GTC ACG AAC GAC TGC TCC      624
Glu Val His Asn Val Ser Gly Ile Tyr His Val Thr Asn Asp Cys Ser
            195                 200                 205

AAC GCA AGC ATT GTG TAT GAG GCA GCG GAC TTG ATC ATG CAT ACT CCT      672
Asn Ala Ser Ile Val Tyr Glu Ala Ala Asp Leu Ile Met His Thr Pro
210                 215                 220

GGG TGC GTG CCC TGC GTT CGG GAA GGC AAC TCC TCC CGC TGC TGG GTA      720
Gly Cys Val Pro Cys Val Arg Glu Gly Asn Ser Ser Arg Cys Trp Val
225                 230                 235                 240

GCG CTC ACT CCC ACG CTC GCA GCC AGG AAC GTC ACC ATC CCC ACC ACG      768
Ala Leu Thr Pro Thr Leu Ala Ala Arg Asn Val Thr Ile Pro Thr Thr
                245                 250                 255

ACG ATA CGA CGC CAC GTC GAT CTG CTC GTT GGG GCG GCT GCT TTC TGT      816
Thr Ile Arg Arg His Val Asp Leu Leu Val Gly Ala Ala Ala Phe Cys
            260                 265                 270

TCC GCT ATG TAC GTG GGG GAC CTC TGC GGA TCT GTT TTC CTC GTC TCT      864
Ser Ala Met Tyr Val Gly Asp Leu Cys Gly Ser Val Phe Leu Val Ser
275                 280                 285

CAG CTG TTC ACC TTC TCG CCT CGC CGG CAT GTG ACA TTA CAG GAC TGT      912
Gln Leu Phe Thr Phe Ser Pro Arg Arg His Val Thr Leu Gln Asp Cys
290                 295                 300

AAC TGC TCA ATT TAT CCC GGC CAT GTG TCG GGT CAC CGT ATG GCT TGG      960
Asn Cys Ser Ile Tyr Pro Gly His Val Ser Gly His Arg Met Ala Trp
305                 310                 315                 320

GAC ATG ATG ATG AAC TGG TCG CCC ACA ACA GCC CTA GTG GTG TCG CAG      1008
Asp Met Met Met Asn Trp Ser Pro Thr Thr Ala Leu Val Val Ser Gln
                325                 330                 335

TTA CTC CGG ATC CCA CAA GCC GTC GTG GAC ATG GTG GCG GGG GCC CAC      1056
Leu Leu Arg Ile Pro Gln Ala Val Val Asp Met Val Ala Gly Ala His
                340                 345                 350
```

```
TGG GGA GTC CTG GCG GGC CTT GCC TAC TAT TCC ATG GCG GGG AAC TGG      1104
Trp Gly Val Leu Ala Gly Leu Ala Tyr Tyr Ser Met Ala Gly Asn Trp
        355                 360                 365

GCT AAG GTT CTG ATT GTG ATG CTA CTT TTT GCT GGC GTT GAC GGG GAT      1152
Ala Lys Val Leu Ile Val Met Leu Leu Phe Ala Gly Val Asp Gly Asp
370                 375                 380

ACC CAC GTG ACA GGG GGC GCG CAA GCC AAA ACC ACC AAC AGG CTC GTG      1200
Thr His Val Thr Gly Gly Ala Gln Ala Lys Thr Thr Asn Arg Leu Val
385                 390                 395                 400

TCC ATG TTC GCA AGT GGG CCG TCT CAG AAA ATC CAG CTT ATA AAC ACC      1248
Ser Met Phe Ala Ser Gly Pro Ser Gln Lys Ile Gln Leu Ile Asn Thr
            405                 410                 415

AAT GGG AGT TGG CAC ATC AAC AGG ACT GCC CTG AAC TGC AAT GAC TCT      1296
Asn Gly Ser Trp His Ile Asn Arg Thr Ala Leu Asn Cys Asn Asp Ser
            420                 425                 430

CTC CAG ACT GGG TTT CTT GCC GCG CTG TTC TAC ACA CAT AGT TTC AAC      1344
Leu Gln Thr Gly Phe Leu Ala Ala Leu Phe Tyr Thr His Ser Phe Asn
            435                 440                 445

TCG TCC GGG TGC CCA GAG CGC ATG GCC CAG TGC CGC ACC ATT GAC AAG      1392
Ser Ser Gly Cys Pro Glu Arg Met Ala Gln Cys Arg Thr Ile Asp Lys
450                 455                 460

TTC GAC CAG GGA TGG GGT CCC ATT ACT TAT GCT GAG TCT AGC AGA TCA      1440
Phe Asp Gln Gly Trp Gly Pro Ile Thr Tyr Ala Glu Ser Ser Arg Ser
465                 470                 475                 480

GAC CAG AGG CCA TAT TGC TGG CAC TAC CCA CCT CCA CAA TGT ACC ATC      1488
Asp Gln Arg Pro Tyr Cys Trp His Tyr Pro Pro Pro Gln Cys Thr Ile
            485                 490                 495

GTA CCT GCG TCG GAG GTG TGC GGC CCA GTG TAC TGC TTC ACC CCA AGC      1536
Val Pro Ala Ser Glu Val Cys Gly Pro Val Tyr Cys Phe Thr Pro Ser
            500                 505                 510

CCT GTC GTC GTG GGG ACG ACC GAT CGT TTC GGT GTC CCT ACG TAT AGA      1584
Pro Val Val Val Gly Thr Thr Asp Arg Phe Gly Val Pro Thr Tyr Arg
            515                 520                 525

TGG GGG GAG AAC GAG ACT GAC GTG CTG CTG CTC AAC AAC ACG CGG CCG      1632
Trp Gly Glu Asn Glu Thr Asp Val Leu Leu Leu Asn Asn Thr Arg Pro
530                 535                 540

CCG CAA GGC AAC TGG TTC GGC TGC ACA TGG ATG AAT AGC ACC GGG TTC      1680
Pro Gln Gly Asn Trp Phe Gly Cys Thr Trp Met Asn Ser Thr Gly Phe
545                 550                 555                 560

ACC AAG ACA TGT GGG GGG CCC CCG TGT AAC ATC GGG GGG GTC GGC AAC      1728
Thr Lys Thr Cys Gly Gly Pro Pro Cys Asn Ile Gly Gly Val Gly Asn
            565                 570                 575

AAC ACC CTG ACC TGC CCC ACG GAC TGC TTC CGG AAG CAC CCC GAG GCT      1776
Asn Thr Leu Thr Cys Pro Thr Asp Cys Phe Arg Lys His Pro Glu Ala
            580                 585                 590

ACC TAC ACA AAA TGT GGT TCG GGG CCT TGG CTG ACA CCT AGG TGC ATG      1824
Thr Tyr Thr Lys Cys Gly Ser Gly Pro Trp Leu Thr Pro Arg Cys Met
            595                 600                 605

GTT GAC TAT CCA TAC AGG CTC TGG CAT TAC CCC TGC ACT GTT AAC TTT      1872
Val Asp Tyr Pro Tyr Arg Leu Trp His Tyr Pro Cys Thr Val Asn Phe
            610                 615                 620

ACC ATC TTC AAG GTT AGG ATG TAT GTG GGG GGG GTG GAG CAC AGG CTC      1920
Thr Ile Phe Lys Val Arg Met Tyr Val Gly Gly Val Glu His Arg Leu
625                 630                 635                 640

AAT GCT GCA TGC AAT TGG ACC CGA GGA GAG CGT TGT GAC TTG GAG GAC      1968
Asn Ala Ala Cys Asn Trp Thr Arg Gly Glu Arg Cys Asp Leu Glu Asp
            645                 650                 655

AGG GAT AGG CCG GAG CTC AGC CCG CTG CTG CTG TCT ACA ACA GAG TGG      2016
Arg Asp Arg Pro Glu Leu Ser Pro Leu Leu Leu Ser Thr Thr Glu Trp
            660                 665                 670
```

```
CAG GTA CTG CCC TGT TCC TTC ACC ACC CTA CCA GCT CTG TCC ACT GGC     2064
Gln Val Leu Pro Cys Ser Phe Thr Thr Leu Pro Ala Leu Ser Thr Gly
            675                 680                 685

TTG ATT CAC CTC CAT CAG AAC ATC GTG GAC GTG CAA TAC CTA TAC GGT     2112
Leu Ile His Leu His Gln Asn Ile Val Asp Val Gln Tyr Leu Tyr Gly
690                 695                 700

ATA GGG TCA GCG GTT GTC TCC TTT GCA ATC AAA TGG GAG TAT GTC CTG     2160
Ile Gly Ser Ala Val Val Ser Phe Ala Ile Lys Trp Glu Tyr Val Leu
705                 710                 715                 720

TTG CTT TTC CTT CTC CTA GCG GAC GCA CGT GTC TGT GCC TGC TTG TGG     2208
Leu Leu Phe Leu Leu Leu Ala Asp Ala Arg Val Cys Ala Cys Leu Trp
            725                 730                 735

ATG ATG CTG CTG ATA GCC CAG GCC GAG GCC GCC TTG GAG AAC CTG GTG     2256
Met Met Leu Leu Ile Ala Gln Ala Glu Ala Ala Leu Glu Asn Leu Val
                740                 745                 750

GTC CTC AAT TCG GCG TCT GTG GCC GGC GCA CAT GGC ATC CTC TCC TTC     2304
Val Leu Asn Ser Ala Ser Val Ala Gly Ala His Gly Ile Leu Ser Phe
                    755                 760                 765

CTT GTG TTC TTC TGT GCC GCC TGG TAC ATC AAA GGC AGG CTG GTC CCT     2352
Leu Val Phe Phe Cys Ala Ala Trp Tyr Ile Lys Gly Arg Leu Val Pro
770                 775                 780

GGG GCG ACA TAT GCT CTT TAT GGC GTG TGG CCG CTC CTG CTC TTG         2400
Gly Ala Thr Tyr Ala Leu Tyr Gly Val Trp Pro Leu Leu Leu Leu
785                 790                 795                 800

CTG GCA TTA CCA CCG CGA GCT TAC GCC ATG GAC CGG GAG ATG GCT GCA     2448
Leu Ala Leu Pro Pro Arg Ala Tyr Ala Met Asp Arg Glu Met Ala Ala
            805                 810                 815

TCG TGC GGA GGC GCG GTT TTT GTG GGT CTG GTA CTC CTG ACT TTG TCA     2496
Ser Cys Gly Gly Ala Val Phe Val Gly Leu Val Leu Leu Thr Leu Ser
                820                 825                 830

CCA TAC TAC AAG GTG TTC CTC GCT AGG CTC ATA TGG TGG TTA CAA TAT     2544
Pro Tyr Tyr Lys Val Phe Leu Ala Arg Leu Ile Trp Trp Leu Gln Tyr
                    835                 840                 845

TTT ACC ACC AGA GCC GAG GCG GAC TTA CAT GTG TGG ATC CCC CCC CTC     2592
Phe Thr Thr Arg Ala Glu Ala Asp Leu His Val Trp Ile Pro Pro Leu
850                 855                 860

AAC GCT CGG GGA GGC CGC GAT GCC ATC ATC CTC CTC ATG TGC GCA GTC     2640
Asn Ala Arg Gly Gly Arg Asp Ala Ile Ile Leu Leu Met Cys Ala Val
865                 870                 875                 880

CAT CCA GAG CTA ATC TTT GAC ATC ACC AAA CTT CTA ATT GCC ATA CTC     2688
His Pro Glu Leu Ile Phe Asp Ile Thr Lys Leu Leu Ile Ala Ile Leu
                885                 890                 895

GGT CCG CTC ATG GTG CTC CAA GCT GGC ATA ACC AGA GTG CCG TAC TTC     2736
Gly Pro Leu Met Val Leu Gln Ala Gly Ile Thr Arg Val Pro Tyr Phe
                    900                 905                 910

GTG CGC GCT CAA GGG CTC ATT CAT GCA TGC ATG TTA GTG CGG AAG GTC     2784
Val Arg Ala Gln Gly Leu Ile His Ala Cys Met Leu Val Arg Lys Val
                915                 920                 925

GCT GGG GGT CAT TAT GTC CAA ATG GCC TTC ATG AAG CTG GGC GCG CTG     2832
Ala Gly Gly His Tyr Val Gln Met Ala Phe Met Lys Leu Gly Ala Leu
            930                 935                 940

ACA GGC ACG TAC ATT TAC AAC CAT CTT ACC CCG CTA CGG GAT TGG CCA     2880
Thr Gly Thr Tyr Ile Tyr Asn His Leu Thr Pro Leu Arg Asp Trp Pro
945                 950                 955                 960

CGC GCG GGC CTA CGA GAC CTT GCG GTG GCA GTG GAG CCC GTC GTC TTC     2928
Arg Ala Gly Leu Arg Asp Leu Ala Val Ala Val Glu Pro Val Val Phe
                965                 970                 975

TCC GAC ATG GAG ACC AAG ATC ATC ACC TGG GGA GCA GAC ACC GCG GCG     2976
Ser Asp Met Glu Thr Lys Ile Ile Thr Trp Gly Ala Asp Thr Ala Ala
                    980                 985                 990
```

```
TGT GGG GAC ATC ATC TTG GGT CTG CCC GTC TCC GCC CGA AGG GGA AAG          3024
Cys Gly Asp Ile Ile Leu Gly Leu Pro Val Ser Ala Arg Arg Gly Lys
            995                 1000                1005

GAG ATA CTC CTG GGC CCG GCC GAT AGT CTT GAA GGG CGG GGG TTG CGA          3072
Glu Ile Leu Leu Gly Pro Ala Asp Ser Leu Glu Gly Arg Gly Leu Arg
1010                1015                1020

CTC CTC GCG CCC ATC ACG GCC TAC TCC CAA CAG ACG CGG GGC CTA CTT          3120
Leu Leu Ala Pro Ile Thr Ala Tyr Ser Gln Gln Thr Arg Gly Leu Leu
1025                1030                1035                1040

GGT TGC ATC ATC ACT AGC CTT ACA GGC CGG GAC AAG AAC CAG GTC GAG          3168
Gly Cys Ile Ile Thr Ser Leu Thr Gly Arg Asp Lys Asn Gln Val Glu
            1045                1050                1055

GGA GAG GTT CAG GTG GTT TCC ACC GCA ACA CAA TCC TTC CTG GCG ACC          3216
Gly Glu Val Gln Val Val Ser Thr Ala Thr Gln Ser Phe Leu Ala Thr
                1060                1065                1070

TGC GTC AAC GGC GTG TGT TGG ACC GTT TAC CAT GGT GCT GGC TCA AAG          3264
Cys Val Asn Gly Val Cys Trp Thr Val Tyr His Gly Ala Gly Ser Lys
                1075                1080                1085

ACC TTA GCC GCG CCA AAG GGG CCA ATC ACC CAG ATG TAC ACT AAT GTG          3312
Thr Leu Ala Ala Pro Lys Gly Pro Ile Thr Gln Met Tyr Thr Asn Val
            1090                1095                1100

GAC CAG GAC CTC GTC GGC TGG CCC AAG CCC CCC GGG GCG CGT TCC TTG          3360
Asp Gln Asp Leu Val Gly Trp Pro Lys Pro Pro Gly Ala Arg Ser Leu
1105                1110                1115                1120

ACA CCA TGC ACC TGT GGC AGC TCA GAC CTT TAC TTG GTC ACG AGA CAT          3408
Thr Pro Cys Thr Cys Gly Ser Ser Asp Leu Tyr Leu Val Thr Arg His
                1125                1130                1135

GCT GAC GTC ATT CCG GTG CGC CGG CGG GGC GAC AGT AGG GGG AGC CTG          3456
Ala Asp Val Ile Pro Val Arg Arg Arg Gly Asp Ser Arg Gly Ser Leu
                1140                1145                1150

CTC TCC CCC AGG CCT GTC TCC TAC TTG AAG GGC TCT TCG GGT GGT CCA          3504
Leu Ser Pro Arg Pro Val Ser Tyr Leu Lys Gly Ser Ser Gly Gly Pro
            1155                1160                1165

CTG CTC TGC CCC TTC GGG CAC GCT GTG GGC ATC TTC CGG GCT GCC GTA          3552
Leu Leu Cys Pro Phe Gly His Ala Val Gly Ile Phe Arg Ala Ala Val
1170                1175                1180

TGC ACC CGG GGG GTT GCG AAG GCG GTG GAC TTT GTG CCC GTA GAG TCC          3600
Cys Thr Arg Gly Val Ala Lys Ala Val Asp Phe Val Pro Val Glu Ser
1185                1190                1195                1200

ATG GAA ACT ACT ATG CGG TCT CCG GTC TTC ACG GAC AAC TCA TCC CCC          3648
Met Glu Thr Thr Met Arg Ser Pro Val Phe Thr Asp Asn Ser Ser Pro
                1205                1210                1215

CCG GCC GTA CCG CAG TCA TTT CAA GTG GCC CAC CTA CAC GCT CCC ACT          3696
Pro Ala Val Pro Gln Ser Phe Gln Val Ala His Leu His Ala Pro Thr
            1220                1225                1230

GGC AGC GGC AAG AGT ACT AAA GTG CCG GCT GCA TAT GCA GCC CAA GGG          3744
Gly Ser Gly Lys Ser Thr Lys Val Pro Ala Ala Tyr Ala Ala Gln Gly
            1235                1240                1245

TAC AAG GTG CTC GTC CTC AAT CCG TCC GTT GCC GCT ACC TTA GGG TTT          3792
Tyr Lys Val Leu Val Leu Asn Pro Ser Val Ala Ala Thr Leu Gly Phe
            1250                1255                1260

GGG GCG TAT ATG TCT AAG GCA CAC GGT ATT GAC CCC AAC ATC AGA ACT          3840
Gly Ala Tyr Met Ser Lys Ala His Gly Ile Asp Pro Asn Ile Arg Thr
1265                1270                1275                1280

GGG GTA AGG ACC ATT ACC ACA GGC GCC CCC GTC ACA TAC TCT ACC TAT          3888
Gly Val Arg Thr Ile Thr Thr Gly Ala Pro Val Thr Tyr Ser Thr Tyr
                1285                1290                1295

GGC AAG TTT CTT GCC GAT GGT GGT TGC TCT GGG GGC GCT TAT GAC ATC          3936
Gly Lys Phe Leu Ala Asp Gly Gly Cys Ser Gly Gly Ala Tyr Asp Ile
            1300                1305                1310
```

-continued

| | | |
|---|---|---|
| ATA ATA TGT GAT GAG TGC CAT TCA ACT GAC TCG ACT ACA ATC TTG GGC<br>Ile Ile Cys Asp Glu Cys His Ser Thr Asp Ser Thr Thr Ile Leu Gly<br>1315                                  1320                                1325 | 3984 |
| ATC GGC ACA GTC CTG GAC CAA GCG GAG ACG GCT GGA GCG CGG CTT GTC<br>Ile Gly Thr Val Leu Asp Gln Ala Glu Thr Ala Gly Ala Arg Leu Val<br>1330                                 1335                               1340 | 4032 |
| GTG CTC GCC ACC GCT ACG CCT CCG GGA TCG GTC ACC GTG CCA CAC CCA<br>Val Leu Ala Thr Ala Thr Pro Pro Gly Ser Val Thr Val Pro His Pro<br>1345                                 1350                               1355                          1360 | 4080 |
| AAC ATC GAG GAG GTG GCC CTG TCT AAT ACT GGA GAG ATC CCC TTC TAT<br>Asn Ile Glu Glu Val Ala Leu Ser Asn Thr Gly Glu Ile Pro Phe Tyr<br>                                1365                               1370                          1375 | 4128 |
| GGC AAA GCC ATC CCC ATT GAA GCC ATC AGG GGG GGA AGG CAT CTC ATT<br>Gly Lys Ala Ile Pro Ile Glu Ala Ile Arg Gly Gly Arg His Leu Ile<br>                1380                               1385                               1390 | 4176 |
| TTC TGT CAT TCC AAG AAG AAG TGC GAC GAG CTC GCC GCA AAG CTG TCA<br>Phe Cys His Ser Lys Lys Lys Cys Asp Glu Leu Ala Ala Lys Leu Ser<br>                1395                               1400                               1405 | 4224 |
| GGC CTC GGA ATC AAC GCT GTG GCG TAT TAC CGG GGG CTC GAT GTG TCC<br>Gly Leu Gly Ile Asn Ala Val Ala Tyr Tyr Arg Gly Leu Asp Val Ser<br>                1410                               1415                               1420 | 4272 |
| GTC ATA CCA ACT ATC GGA GAC GTC GTT GTC GTG GCA ACA GAC GCT CTG<br>Val Ile Pro Thr Ile Gly Asp Val Val Val Val Ala Thr Asp Ala Leu<br>1425                                   1430                               1435                          1440 | 4320 |
| ATG ACG GGC TAT ACG GGC GAC TTT GAC TCA GTG ATC GAC TGT AAC ACA<br>Met Thr Gly Tyr Thr Gly Asp Phe Asp Ser Val Ile Asp Cys Asn Thr<br>                1445                               1450                               1455 | 4368 |
| TGT GTC ACC CAG ACA GTC GAC TTC AGC TTG GAT CCC ACC TTC ACC ATT<br>Cys Val Thr Gln Thr Val Asp Phe Ser Leu Asp Pro Thr Phe Thr Ile<br>                1460                               1465                               1470 | 4416 |
| GAG ACG ACG ACC GTG CCT CAA GAC GCA GTG TCG CGC TCG CAG CGG CGG<br>Glu Thr Thr Thr Val Pro Gln Asp Ala Val Ser Arg Ser Gln Arg Arg<br>                1475                               1480                               1485 | 4464 |
| GGT AGG ACT GGC AGG GGT AGG AGA GGC ATC TAC AGG TTT GTG ACT CCG<br>Gly Arg Thr Gly Arg Gly Arg Arg Gly Ile Tyr Arg Phe Val Thr Pro<br>                1490                               1495                               1500 | 4512 |
| GGA GAA CGG CCC TCG GGC ATG TTC GAT TCC TCG GTC CTG TGT GAG TGC<br>Gly Glu Arg Pro Ser Gly Met Phe Asp Ser Ser Val Leu Cys Glu Cys<br>1505                                   1510                               1515                          1520 | 4560 |
| TAT GAC GCG GGC TGT GCT TGG TAC GAG CTC ACC CCG GCC GAG ACC TCG<br>Tyr Asp Ala Gly Cys Ala Trp Tyr Glu Leu Thr Pro Ala Glu Thr Ser<br>                1525                               1530                               1535 | 4608 |
| GTT AGG TTG CGG GCC TAC CTG AAC ACA CCA GGG TTG CCC GTT TGC CAG<br>Val Arg Leu Arg Ala Tyr Leu Asn Thr Pro Gly Leu Pro Val Cys Gln<br>                1540                               1545                               1550 | 4656 |
| GAC CAC CTG GAG TTC TGG GAG AGT GTC TTC ACA GGC CTC ACC CAT ATA<br>Asp His Leu Glu Phe Trp Glu Ser Val Phe Thr Gly Leu Thr His Ile<br>                1555                               1560                               1565 | 4704 |
| GAT GCA CAC TTC TTG TCC CAG ACC AAG CAG GCA GGA GAC AAC TTC CCC<br>Asp Ala His Phe Leu Ser Gln Thr Lys Gln Ala Gly Asp Asn Phe Pro<br>1570                                   1575                               1580 | 4752 |
| TAC CTG GTA GCA TAC CAA GCC ACG GTG TGC GCC AGG GCT CAG GCC CCA<br>Tyr Leu Val Ala Tyr Gln Ala Thr Val Cys Ala Arg Ala Gln Ala Pro<br>1585                                   1590                               1595                          1600 | 4800 |
| CCT CCA TCA TGG GAT CAA ATG TGG AAG TGT CTC ATA CGG CTG AAA CCT<br>Pro Pro Ser Trp Asp Gln Met Trp Lys Cys Leu Ile Arg Leu Lys Pro<br>                1605                               1610                               1615 | 4848 |
| ACG CTG CAC GGG CCA ACA CCC TTG CTG TAC AGG CTG GGA GCC GTC CAG<br>Thr Leu His Gly Pro Thr Pro Leu Leu Tyr Arg Leu Gly Ala Val Gln<br>                1620                               1625                               1630 | 4896 |

-continued

| | | |
|---|---|---|
| AAT GAG GTC ACC CTC ACC CAC CCC ATA ACC AAA TAC ATC ATG GCA TGC<br>Asn Glu Val Thr Leu Thr His Pro Ile Thr Lys Tyr Ile Met Ala Cys<br>　　　1635　　　　　　　1640　　　　　　　1645 | 4944 |
| ATG TCG GCT GAC CTG GAG GTC GTC ACT AGC ACC TGG GTG CTG GTG GGC<br>Met Ser Ala Asp Leu Glu Val Val Thr Ser Thr Trp Val Leu Val Gly<br>1650　　　　　　　1655　　　　　　　1660 | 4992 |
| GGA GTC CTT GCA GCT CTG GCC GCG TAT TGC CTG ACA ACA GGC AGT GTG<br>Gly Val Leu Ala Ala Leu Ala Ala Tyr Cys Leu Thr Thr Gly Ser Val<br>1665　　　　　　　1670　　　　　　　1675　　　　　　　1680 | 5040 |
| GTC ATT GTG GGT AGG ATT ATC TTG TCC GGG AGG CCG GCC ATT GTT CCC<br>Val Ile Val Gly Arg Ile Ile Leu Ser Gly Arg Pro Ala Ile Val Pro<br>　　　　　　　1685　　　　　　　1690　　　　　　　1695 | 5088 |
| GAC AGG GAG CTT CTC TAC CAG GAG TTC GAT GAA ATG GAA GAG TGC GCC<br>Asp Arg Glu Leu Leu Tyr Gln Glu Phe Asp Glu Met Glu Glu Cys Ala<br>　　　1700　　　　　　　1705　　　　　　　1710 | 5136 |
| TCG CAC CTC CCT TAC ATC GAG CAG GGA ATG CAG CTC GCC GAG CAA TTC<br>Ser His Leu Pro Tyr Ile Glu Gln Gly Met Gln Leu Ala Glu Gln Phe<br>1715　　　　　　　1720　　　　　　　1725 | 5184 |
| AAG CAG AAA GCG CTC GGG TTA CTG CAA ACA GCC ACC AAA CAA GCG GAG<br>Lys Gln Lys Ala Leu Gly Leu Leu Gln Thr Ala Thr Lys Gln Ala Glu<br>1730　　　　　　　1735　　　　　　　1740 | 5232 |
| GCT GCT GCT CCC GTG GTG GAG TCC AAG TGG CGA GCC CTT GAG ACA TTC<br>Ala Ala Ala Pro Val Val Glu Ser Lys Trp Arg Ala Leu Glu Thr Phe<br>1745　　　　　　　1750　　　　　　　1755　　　　　　　1760 | 5280 |
| TGG GCG AAG CAC ATG TGG AAT TTC ATC AGC GGG ATA CAG TAC TTA GCA<br>Trp Ala Lys His Met Trp Asn Phe Ile Ser Gly Ile Gln Tyr Leu Ala<br>　　　　　　　1765　　　　　　　1770　　　　　　　1775 | 5328 |
| GGC TTA TCC ACT CTG CCT GGG AAC CCC GCA ATA GCA TCA TTG ATG GCA<br>Gly Leu Ser Thr Leu Pro Gly Asn Pro Ala Ile Ala Ser Leu Met Ala<br>　　　1780　　　　　　　1785　　　　　　　1790 | 5376 |
| TTC ACA GCC TCT ATC ACC AGC CCG CTC ACC ACC CAA AGT ACC CTC CTG<br>Phe Thr Ala Ser Ile Thr Ser Pro Leu Thr Thr Gln Ser Thr Leu Leu<br>1795　　　　　　　1800　　　　　　　1805 | 5424 |
| TTT AAC ATC TTG GGG GGG TGG GTG GCT GCC CAA CTC GCC CCC CCC AGC<br>Phe Asn Ile Leu Gly Gly Trp Val Ala Ala Gln Leu Ala Pro Pro Ser<br>1810　　　　　　　1815　　　　　　　1820 | 5472 |
| GCC GCT TCG GCT TTC GTG GGC GCC GGC ATC GCC GGT GCG GCT GTT GGC<br>Ala Ala Ser Ala Phe Val Gly Ala Gly Ile Ala Gly Ala Ala Val Gly<br>1825　　　　　　　1830　　　　　　　1835　　　　　　　1840 | 5520 |
| AGC ATA GGC CTT GGG AAG GTG CTT GTG GAC ATT CTG GCG GGT TAT GGA<br>Ser Ile Gly Leu Gly Lys Val Leu Val Asp Ile Leu Ala Gly Tyr Gly<br>　　　　　　　1845　　　　　　　1850　　　　　　　1855 | 5568 |
| GCA GGA GTG GCC GGC GCG CTC GTG GCC TTT AAG GTC ATG AGC GGC GAG<br>Ala Gly Val Ala Gly Ala Leu Val Ala Phe Lys Val Met Ser Gly Glu<br>　　　1860　　　　　　　1865　　　　　　　1870 | 5616 |
| ATG CCC TCC ACC GAG GAC CTG GTC AAT CTA CTT CCT GCC ATC CTC TCT<br>Met Pro Ser Thr Glu Asp Leu Val Asn Leu Leu Pro Ala Ile Leu Ser<br>1875　　　　　　　1880　　　　　　　1885 | 5664 |
| CCT GGC GCC CTG GTC GTC GGG GTC GTG TGT GCA GCA ATA CTG CGT CGA<br>Pro Gly Ala Leu Val Val Gly Val Val Cys Ala Ala Ile Leu Arg Arg<br>1890　　　　　　　1895　　　　　　　1900 | 5712 |
| CAC GTG GGT CCG GGA GAG GGG GCT GTG CAG TGG ATG AAC CGG CTG ATA<br>His Val Gly Pro Gly Glu Gly Ala Val Gln Trp Met Asn Arg Leu Ile<br>1905　　　　　　　1910　　　　　　　1915　　　　　　　1920 | 5760 |
| GCG TTC GCC TCG CGG GGT AAT CAT GTT TCC CCC ACG CAC TAT GTG CCT<br>Ala Phe Ala Ser Arg Gly Asn His Val Ser Pro Thr His Tyr Val Pro<br>　　　　　　　1925　　　　　　　1930　　　　　　　1935 | 5808 |
| GAG AGC GAC GCC GCA GCG CGT GTT ACT CAG ATC CTC TCC AGC CTT ACC<br>Glu Ser Asp Ala Ala Ala Arg Val Thr Gln Ile Leu Ser Ser Leu Thr<br>　　　1940　　　　　　　1945　　　　　　　1950 | 5856 |

```
ATC ACT CAG CTG CTG AAA AGG CTC CAC CAG TGG ATT AAT GAA GAC TGC      5904
Ile Thr Gln Leu Leu Lys Arg Leu His Gln Trp Ile Asn Glu Asp Cys
        1955                1960                1965

TCC ACA CCG TGT TCC GGC TCG TGG CTA AGG GAT GTT TGG GAC TGG ATA      5952
Ser Thr Pro Cys Ser Gly Ser Trp Leu Arg Asp Val Trp Asp Trp Ile
    1970                1975                1980

TGC ACG GTG TTG ACT GAC TTC AAG ACC TGG CTC CAG TCC AAG CTC CTG      6000
Cys Thr Val Leu Thr Asp Phe Lys Thr Trp Leu Gln Ser Lys Leu Leu
1985            1990                1995                2000

CCG CAG CTA CCT GGA GTC CCT TTT TTC TCG TGC CAA CGC                  6039
Pro Gln Leu Pro Gly Val Pro Phe Phe Ser Cys Gln Arg
            2005                2010
```

(2) INFORMATION FOR SEQ ID NO:12:

(i) SEQUENCE CHARACTERISTICS:
        (A) LENGTH: 2013 amino acids
        (B) TYPE: amino acid
        (D) TOPOLOGY: linear (ii) MOLECULE TYPE: protein (xi) SEQUENCE DESCRIPTION: SEQ ID NO:12:

```
Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Pro Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Tyr
            180                 185                 190

Glu Val His Asn Val Ser Gly Ile Tyr His Val Thr Asn Asp Cys Ser
        195                 200                 205

Asn Ala Ser Ile Val Tyr Glu Ala Ala Asp Leu Ile Met His Thr Pro
210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Val Thr Ile Pro Thr Thr
                245                 250                 255

Thr Ile Arg Arg His Val Asp Leu Leu Val Gly Ala Ala Ala Phe Cys
            260                 265                 270

Ser Ala Met Tyr Val Gly Asp Leu Cys Gly Ser Val Phe Leu Val Ser
```

-continued

```
                275                 280                 285
Gln Leu Phe Thr Phe Ser Pro Arg Arg His Val Thr Leu Gln Asp Cys
    290                 295                 300
Asn Cys Ser Ile Tyr Pro Gly His Val Ser Gly His Arg Met Ala Trp
305                 310                 315                 320
Asp Met Met Met Asn Trp Ser Pro Thr Thr Ala Leu Val Val Ser Gln
                325                 330                 335
Leu Leu Arg Ile Pro Gln Ala Val Val Asp Met Val Ala Gly Ala His
                340                 345                 350
Trp Gly Val Leu Ala Gly Leu Ala Tyr Tyr Ser Met Ala Gly Asn Trp
            355                 360                 365
Ala Lys Val Leu Ile Val Met Leu Leu Phe Ala Gly Val Asp Gly Asp
370                 375                 380
Thr His Val Thr Gly Gly Ala Gln Ala Lys Thr Thr Asn Arg Leu Val
385                 390                 395                 400
Ser Met Phe Ala Ser Gly Pro Ser Gln Lys Ile Gln Leu Ile Asn Thr
                405                 410                 415
Asn Gly Ser Trp His Ile Asn Arg Thr Ala Leu Asn Cys Asn Asp Ser
            420                 425                 430
Leu Gln Thr Gly Phe Leu Ala Ala Leu Phe Tyr Thr His Ser Phe Asn
        435                 440                 445
Ser Ser Gly Cys Pro Glu Arg Met Ala Gln Cys Arg Thr Ile Asp Lys
450                 455                 460
Phe Asp Gln Gly Trp Gly Pro Ile Thr Tyr Ala Glu Ser Ser Arg Ser
465                 470                 475                 480
Asp Gln Arg Pro Tyr Cys Trp His Tyr Pro Pro Gln Cys Thr Ile
                485                 490                 495
Val Pro Ala Ser Glu Val Cys Gly Pro Val Tyr Cys Phe Thr Pro Ser
                500                 505                 510
Pro Val Val Val Gly Thr Thr Asp Arg Phe Gly Val Pro Thr Tyr Arg
            515                 520                 525
Trp Gly Glu Asn Glu Thr Asp Val Leu Leu Leu Asn Asn Thr Arg Pro
    530                 535                 540
Pro Gln Gly Asn Trp Phe Gly Cys Thr Trp Met Asn Ser Thr Gly Phe
545                 550                 555                 560
Thr Lys Thr Cys Gly Gly Pro Pro Cys Asn Ile Gly Gly Val Gly Asn
                565                 570                 575
Asn Thr Leu Thr Cys Pro Thr Asp Cys Phe Arg Lys His Pro Glu Ala
            580                 585                 590
Thr Tyr Thr Lys Cys Gly Ser Gly Pro Trp Leu Thr Pro Arg Cys Met
        595                 600                 605
Val Asp Tyr Pro Tyr Arg Leu Trp His Tyr Pro Cys Thr Val Asn Phe
    610                 615                 620
Thr Ile Phe Lys Val Arg Met Tyr Val Gly Gly Val Glu His Arg Leu
625                 630                 635                 640
Asn Ala Ala Cys Asn Trp Thr Arg Gly Glu Arg Cys Asp Leu Glu Asp
                645                 650                 655
Arg Asp Arg Pro Glu Leu Ser Pro Leu Leu Leu Ser Thr Thr Glu Trp
                660                 665                 670
Gln Val Leu Pro Cys Ser Phe Thr Thr Leu Pro Ala Leu Ser Thr Gly
            675                 680                 685
Leu Ile His Leu His Gln Asn Ile Val Asp Val Gln Tyr Leu Tyr Gly
    690                 695                 700
```

-continued

```
Ile Gly Ser Ala Val Val Ser Phe Ala Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala Ala Leu Glu Asn Leu Val
            740                 745                 750

Val Leu Asn Ser Ala Ser Val Ala Gly Ala His Gly Ile Leu Ser Phe
        755                 760                 765

Leu Val Phe Phe Cys Ala Ala Trp Tyr Ile Lys Gly Arg Leu Val Pro
    770                 775                 780

Gly Ala Thr Tyr Ala Leu Tyr Gly Val Trp Pro Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Val Leu Leu Thr Leu Ser
            820                 825                 830

Pro Tyr Tyr Lys Val Phe Leu Ala Arg Leu Ile Trp Trp Leu Gln Tyr
        835                 840                 845

Phe Thr Thr Arg Ala Glu Ala Asp Leu His Val Trp Ile Pro Pro Leu
    850                 855                 860

Asn Ala Arg Gly Gly Arg Asp Ala Ile Ile Leu Leu Met Cys Ala Val
865                 870                 875                 880

His Pro Glu Leu Ile Phe Asp Ile Thr Lys Leu Leu Ile Ala Ile Leu
                885                 890                 895

Gly Pro Leu Met Val Leu Gln Ala Gly Ile Thr Arg Val Pro Tyr Phe
            900                 905                 910

Val Arg Ala Gln Gly Leu Ile His Ala Cys Met Leu Val Arg Lys Val
        915                 920                 925

Ala Gly Gly His Tyr Val Gln Met Ala Phe Met Lys Leu Gly Ala Leu
    930                 935                 940

Thr Gly Thr Tyr Ile Tyr Asn His Leu Thr Pro Leu Arg Asp Trp Pro
945                 950                 955                 960

Arg Ala Gly Leu Arg Asp Leu Ala Val Ala Val Glu Pro Val Val Phe
                965                 970                 975

Ser Asp Met Glu Thr Lys Ile Ile Thr Trp Gly Ala Asp Thr Ala Ala
            980                 985                 990

Cys Gly Asp Ile Ile Leu Gly Leu Pro Val Ser Ala Arg Arg Gly Lys
        995                 1000                1005

Glu Ile Leu Leu Gly Pro Ala Asp Ser Leu Glu Gly Arg Gly Leu Arg
    1010                1015                1020

Leu Leu Ala Pro Ile Thr Ala Tyr Ser Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Val Val Ser Thr Ala Thr Gln Ser Phe Leu Ala Thr
            1060                1065                1070

Cys Val Asn Gly Val Cys Trp Thr Val Tyr His Gly Ala Gly Ser Lys
        1075                1080                1085

Thr Leu Ala Ala Pro Lys Gly Pro Ile Thr Gln Met Tyr Thr Asn Val
    1090                1095                1100

Asp Gln Asp Leu Val Gly Trp Pro Lys Pro Gly Ala Arg Ser Leu
1105                1110                1115                1120

Thr Pro Cys Thr Cys Gly Ser Ser Asp Leu Tyr Leu Val Thr Arg His
                1125                1130                1135
```

```
Ala Asp Val Ile Pro Val Arg Arg Gly Asp Ser Arg Gly Ser Leu
         1140                1145                1150

Leu Ser Pro Arg Pro Val Ser Tyr Leu Lys Gly Ser Ser Gly Pro
         1155                1160                1165

Leu Leu Cys Pro Phe Gly His Ala Val Gly Ile Phe Arg Ala Val
         1170                1175                1180

Cys Thr Arg Gly Val Ala Lys Ala Val Asp Phe Val Pro Val Glu Ser
1185                1190                1195                1200

Met Glu Thr Thr Met Arg Ser Pro Val Phe Thr Asp Asn Ser Ser Pro
                1205                1210                1215

Pro Ala Val Pro Gln Ser Phe Gln Val Ala His Leu His Ala Pro Thr
                1220                1225                1230

Gly Ser Gly Lys Ser Thr Lys Val Pro Ala Ala Tyr Ala Ala Gln Gly
                1235                1240                1245

Tyr Lys Val Leu Val Leu Asn Pro Ser Val Ala Ala Thr Leu Gly Phe
                1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Ala Pro Val Thr Tyr Ser Thr Tyr
                1285                1290                1295

Gly Lys Phe Leu Ala Asp Gly Gly Cys Ser Gly Gly Ala Tyr Asp Ile
                1300                1305                1310

Ile Ile Cys Asp Glu Cys His Ser Thr Asp Ser Thr Thr Ile Leu Gly
                1315                1320                1325

Ile Gly Thr Val Leu Asp Gln Ala Glu Thr Ala Gly Ala Arg Leu Val
                1330                1335                1340

Val Leu Ala Thr Ala Thr Pro Pro Gly Ser Val Thr Val Pro His Pro
1345                1350                1355                1360

Asn Ile Glu Glu Val Ala Leu Ser Asn Thr Gly Glu Ile Pro Phe Tyr
                1365                1370                1375

Gly Lys Ala Ile Pro Ile Glu Ala Ile Arg Gly Gly Arg His Leu Ile
                1380                1385                1390

Phe Cys His Ser Lys Lys Lys Cys Asp Glu Leu Ala Ala Lys Leu Ser
                1395                1400                1405

Gly Leu Gly Ile Asn Ala Val Ala Tyr Tyr Arg Gly Leu Asp Val Ser
         1410                1415                1420

Val Ile Pro Thr Ile Gly Asp Val Val Val Ala Thr Asp Ala Leu
1425                1430                1435                1440

Met Thr Gly Tyr Thr Gly Asp Phe Asp Ser Val Ile Asp Cys Asn Thr
                1445                1450                1455

Cys Val Thr Gln Thr Val Asp Phe Ser Leu Asp Pro Thr Phe Thr Ile
                1460                1465                1470

Glu Thr Thr Thr Val Pro Gln Asp Ala Val Ser Arg Ser Gln Arg Arg
                1475                1480                1485

Gly Arg Thr Gly Arg Gly Arg Arg Gly Ile Tyr Arg Phe Val Thr Pro
         1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Ser
                1525                1530                1535

Val Arg Leu Arg Ala Tyr Leu Asn Thr Pro Gly Leu Pro Val Cys Gln
                1540                1545                1550

Asp His Leu Glu Phe Trp Glu Ser Val Phe Thr Gly Leu Thr His Ile
```

-continued

```
                1555                1560                1565
Asp Ala His Phe Leu Ser Gln Thr Lys Gln Ala Gly Asp Asn Phe Pro
    1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
    1620                1625                1630

Asn Glu Val Thr Leu Thr His Pro Ile Thr Lys Tyr Ile Met Ala Cys
    1635                1640                1645

Met Ser Ala Asp Leu Glu Val Val Thr Ser Thr Trp Val Leu Val Gly
    1650                1655                1660

Gly Val Leu Ala Ala Leu Ala Ala Tyr Cys Leu Thr Thr Gly Ser Val
1665                1670                1675                1680

Val Ile Val Gly Arg Ile Ile Leu Ser Gly Arg Pro Ala Ile Val Pro
                1685                1690                1695

Asp Arg Glu Leu Leu Tyr Gln Glu Phe Asp Glu Met Glu Glu Cys Ala
                1700                1705                1710

Ser His Leu Pro Tyr Ile Glu Gln Gly Met Gln Leu Ala Glu Gln Phe
    1715                1720                1725

Lys Gln Lys Ala Leu Gly Leu Leu Gln Thr Ala Thr Lys Gln Ala Glu
    1730                1735                1740

Ala Ala Ala Pro Val Val Glu Ser Lys Trp Arg Ala Leu Glu Thr Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
                1780                1785                1790

Phe Thr Ala Ser Ile Thr Ser Pro Leu Thr Thr Gln Ser Thr Leu Leu
                1795                1800                1805

Phe Asn Ile Leu Gly Gly Trp Val Ala Ala Gln Leu Ala Pro Pro Ser
    1810                1815                1820

Ala Ala Ser Ala Phe Val Gly Ala Gly Ile Ala Gly Ala Ala Val Gly
1825                1830                1835                1840

Ser Ile Gly Leu Gly Lys Val Leu Val Asp Ile Leu Ala Gly Tyr Gly
                1845                1850                1855

Ala Gly Val Ala Gly Ala Leu Val Ala Phe Lys Val Met Ser Gly Glu
                1860                1865                1870

Met Pro Ser Thr Glu Asp Leu Val Asn Leu Leu Pro Ala Ile Leu Ser
    1875                1880                1885

Pro Gly Ala Leu Val Val Gly Val Val Cys Ala Ala Ile Leu Arg Arg
    1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Gln Ile Leu Ser Ser Leu Thr
                1940                1945                1950

Ile Thr Gln Leu Leu Lys Arg Leu His Gln Trp Ile Asn Glu Asp Cys
                1955                1960                1965

Ser Thr Pro Cys Ser Gly Ser Trp Leu Arg Asp Val Trp Asp Trp Ile
    1970                1975                1980
```

-continued

```
Cys Thr Val Leu Thr Asp Phe Lys Thr Trp Leu Gln Ser Lys Leu Leu
1985                1990                1995                2000

Pro Gln Leu Pro Gly Val Pro Phe Phe Ser Cys Gln Arg
                2005                2010
```

(2) INFORMATION FOR SEQ ID NO:13:

(i) SEQUENCE CHARACTERISTICS:
        (A) LENGTH: 9030 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..9030
        (D) OTHER INFORMATION: /note: "sequence = 333 - 9362 of
            SEQ ID NO: 1"

(ix) FEATURE:
        (A) NAME/KEY: CDS
        (B) LOCATION: 1..9030

(xi) SEQUENCE DESCRIPTION: SEQ ID NO:13:

```
ATG AGC ACG AAT CCT AAA CCT CAA AGA AAA ACC AAA CGT AAC ACC AAC        48
Met Ser Thr Asn Pro Lys Pro Gln Arg Lys Thr Lys Arg Asn Thr Asn
1               5                   10                  15

CGC CGC CCA CAG GAC GTC AAG TTC CCG GGC GGT GGT CAG ATC GTT GGT        96
Arg Arg Pro Gln Asp Val Lys Phe Pro Gly Gly Gly Gln Ile Val Gly
                20                  25                  30

GGA GTT TAC CTG TTG CCG CGC AGG GGC CCC AGG TTG GGT GTG CGC GCG       144
Gly Val Tyr Leu Leu Pro Arg Arg Gly Pro Arg Leu Gly Val Arg Ala
        35                  40                  45

CCC AGG AAG ACT TCC GAG CGG TCG CAA CCT CGT GGA AGG CGA CAA CCT       192
Pro Arg Lys Thr Ser Glu Arg Ser Gln Pro Arg Gly Arg Arg Gln Pro
50                  55                  60

ATC CCC AAG GCT CGC CGG CCC GAG GGC AGG ACC TGG GCT CAG CCC GGG       240
Ile Pro Lys Ala Arg Arg Pro Glu Gly Arg Thr Trp Ala Gln Pro Gly
65                  70                  75                  80

TAC CCT TGG CCT CTC TAT GGC AAT GAG GGC TTA GGG TGG GCA GGA TGG       288
Tyr Pro Trp Pro Leu Tyr Gly Asn Glu Gly Leu Gly Trp Ala Gly Trp
                85                  90                  95

CTC CTG TCA CCC CGC GGC TCC CGG CCT AGT TGG GGC CCC ACG GAC CCC       336
Leu Leu Ser Pro Arg Gly Ser Arg Pro Ser Trp Gly Pro Thr Asp Pro
                100                 105                 110

CGG CGT AGG TCG CGT AAT TTG GGT AAG GTC ATC GAT ACC CTC ACA TGC       384
Arg Arg Arg Ser Arg Asn Leu Gly Lys Val Ile Asp Thr Leu Thr Cys
            115                 120                 125

GGC TTC GCC GAT CTC ATG GGG TAC ATT CCG CTC GTC GGC GCC CCC CTG       432
Gly Phe Ala Asp Leu Met Gly Tyr Ile Pro Leu Val Gly Ala Pro Leu
130                 135                 140

GGG GGC GCT GCC AGG GCC CTG GCA CAT GGT GTC CGG GTT CTG GAG GAC       480
Gly Gly Ala Ala Arg Ala Leu Ala His Gly Val Arg Val Leu Glu Asp
145                 150                 155                 160

GGC GTG AAC TAT GCA ACA GGG AAT CTG CCC GGT TGC TCT TTT TCT ATC       528
Gly Val Asn Tyr Ala Thr Gly Asn Leu Pro Gly Cys Ser Phe Ser Ile
                165                 170                 175

TTC CTC TTG GCT CTG CTG TCC TGC CTG ACC ACC CCA GCT TCC GCT TAC       576
Phe Leu Leu Ala Leu Leu Ser Cys Leu Thr Thr Pro Ala Ser Ala Tyr
                180                 185                 190

GAA GTG CAC AAC GTG TCC GGG ATA TAT CAT GTC ACG AAC GAC TGC TCC       624
Glu Val His Asn Val Ser Gly Ile Tyr His Val Thr Asn Asp Cys Ser
                195                 200                 205
```

```
AAC GCA AGC ATT GTG TAT GAG GCA GCG GAC TTG ATC ATG CAT ACT CCT    672
Asn Ala Ser Ile Val Tyr Glu Ala Ala Asp Leu Ile Met His Thr Pro
        210             215             220

GGG TGC GTG CCC TGC GTT CGG GAA GGC AAC TCC TCC CGC TGC TGG GTA    720
Gly Cys Val Pro Cys Val Arg Glu Gly Asn Ser Ser Arg Cys Trp Val
225             230             235             240

GCG CTC ACT CCC ACG CTC GCA GCC AGG AAC GTC ACC ATC CCC ACC ACG    768
Ala Leu Thr Pro Thr Leu Ala Ala Arg Asn Val Thr Ile Pro Thr Thr
            245             250             255

ACG ATA CGA CGC CAC GTC GAT CTG CTC GTT GGG GCG GCT GCT TTC TGT    816
Thr Ile Arg Arg His Val Asp Leu Leu Val Gly Ala Ala Ala Phe Cys
        260             265             270

TCC GCT ATG TAC GTG GGG GAC CTC TGC GGA TCT GTT TTC CTC GTC TCT    864
Ser Ala Met Tyr Val Gly Asp Leu Cys Gly Ser Val Phe Leu Val Ser
        275             280             285

CAG CTG TTC ACC TTC TCG CCT CGC CGG CAT GTG ACA TTA CAG GAC TGT    912
Gln Leu Phe Thr Phe Ser Pro Arg Arg His Val Thr Leu Gln Asp Cys
        290             295             300

AAC TGC TCA ATT TAT CCC GGC CAT GTG TCG GGT CAC CGT ATG GCT TGG    960
Asn Cys Ser Ile Tyr Pro Gly His Val Ser Gly His Arg Met Ala Trp
305             310             315             320

GAC ATG ATG ATG AAC TGG TCG CCC ACA ACA GCC CTA GTG GTG TCG CAG   1008
Asp Met Met Met Asn Trp Ser Pro Thr Thr Ala Leu Val Val Ser Gln
            325             330             335

TTA CTC CGG ATC CCA CAA GCC GTC GTG GAC ATG GTG GCG GGG GCC CAC   1056
Leu Leu Arg Ile Pro Gln Ala Val Val Asp Met Val Ala Gly Ala His
        340             345             350

TGG GGA GTC CTG GCG GGC CTT GCC TAC TAT TCC ATG GCG GGG AAC TGG   1104
Trp Gly Val Leu Ala Gly Leu Ala Tyr Tyr Ser Met Ala Gly Asn Trp
        355             360             365

GCT AAG GTT CTG ATT GTG ATG CTA CTT TTT GCT GGC GTT GAC GGG GAT   1152
Ala Lys Val Leu Ile Val Met Leu Leu Phe Ala Gly Val Asp Gly Asp
        370             375             380

ACC CAC GTG ACA GGG GGG GCG CAA GCC AAA ACC ACC AAC AGG CTC GTG   1200
Thr His Val Thr Gly Gly Ala Gln Ala Lys Thr Thr Asn Arg Leu Val
385             390             395             400

TCC ATG TTC GCA AGT GGG CCG TCT CAG AAA ATC CAG CTT ATA AAC ACC   1248
Ser Met Phe Ala Ser Gly Pro Ser Gln Lys Ile Gln Leu Ile Asn Thr
            405             410             415

AAT GGG AGT TGG CAC ATC AAC AGG ACT GCC CTG AAC TGC AAT GAC TCT   1296
Asn Gly Ser Trp His Ile Asn Arg Thr Ala Leu Asn Cys Asn Asp Ser
        420             425             430

CTC CAG ACT GGG TTT CTT GCC GCG CTG TTC TAC ACA CAT AGT TTC AAC   1344
Leu Gln Thr Gly Phe Leu Ala Ala Leu Phe Tyr Thr His Ser Phe Asn
        435             440             445

TCG TCC GGG TGC CCA GAG CGC ATG GCC CAG TGC CGC ACC ATT GAC AAG   1392
Ser Ser Gly Cys Pro Glu Arg Met Ala Gln Cys Arg Thr Ile Asp Lys
450             455             460

TTC GAC CAG GGA TGG GGT CCC ATT ACT TAT GCT GAG TCT AGC AGA TCA   1440
Phe Asp Gln Gly Trp Gly Pro Ile Thr Tyr Ala Glu Ser Ser Arg Ser
465             470             475             480

GAC CAG AGG CCA TAT TGC TGG CAC TAC CCA CCT CCA CAA TGT ACC ATC   1488
Asp Gln Arg Pro Tyr Cys Trp His Tyr Pro Pro Pro Gln Cys Thr Ile
            485             490             495

GTA CCT GCG TCG GAG GTG TGC GGC CCA GTG TAC TGC TTC ACC CCA AGC   1536
Val Pro Ala Ser Glu Val Cys Gly Pro Val Tyr Cys Phe Thr Pro Ser
            500             505             510

CCT GTC GTC GTG GGG ACG ACC GAT CGT TTC GGT GTC CCT ACG TAT AGA   1584
Pro Val Val Val Gly Thr Thr Asp Arg Phe Gly Val Pro Thr Tyr Arg
        515             520             525
```

```
TGG GGG GAG AAC GAG ACT GAC GTG CTG CTG CTC AAC AAC ACG CGG CCG      1632
Trp Gly Glu Asn Glu Thr Asp Val Leu Leu Leu Asn Asn Thr Arg Pro
        530                 535                 540

CCG CAA GGC AAC TGG TTC GGC TGC ACA TGG ATG AAT AGC ACC GGG TTC      1680
Pro Gln Gly Asn Trp Phe Gly Cys Thr Trp Met Asn Ser Thr Gly Phe
545                 550                 555                 560

ACC AAG ACA TGT GGG GGG CCC CCG TGT AAC ATC GGG GGG GTC GGC AAC      1728
Thr Lys Thr Cys Gly Gly Pro Pro Cys Asn Ile Gly Gly Val Gly Asn
                565                 570                 575

AAC ACC CTG ACC TGC CCC ACG GAC TGC TTC CGG AAG CAC CCC GAG GCT      1776
Asn Thr Leu Thr Cys Pro Thr Asp Cys Phe Arg Lys His Pro Glu Ala
            580                 585                 590

ACC TAC ACA AAA TGT GGT TCG GGG CCT TGG CTG ACA CCT AGG TGC ATG      1824
Thr Tyr Thr Lys Cys Gly Ser Gly Pro Trp Leu Thr Pro Arg Cys Met
        595                 600                 605

GTT GAC TAT CCA TAC AGG CTC TGG CAT TAC CCC TGC ACT GTT AAC TTT      1872
Val Asp Tyr Pro Tyr Arg Leu Trp His Tyr Pro Cys Thr Val Asn Phe
    610                 615                 620

ACC ATC TTC AAG GTT AGG ATG TAT GTG GGG GGG GTG GAG CAC AGG CTC      1920
Thr Ile Phe Lys Val Arg Met Tyr Val Gly Gly Val Glu His Arg Leu
625                 630                 635                 640

AAT GCT GCA TGC AAT TGG ACC CGA GGA GAG CGT TGT GAC TTG GAG GAC      1968
Asn Ala Ala Cys Asn Trp Thr Arg Gly Glu Arg Cys Asp Leu Glu Asp
                645                 650                 655

AGG GAT AGG CCG GAG CTC AGC CCG CTG CTG CTG TCT ACA ACA GAG TGG      2016
Arg Asp Arg Pro Glu Leu Ser Pro Leu Leu Leu Ser Thr Thr Glu Trp
            660                 665                 670

CAG GTA CTG CCC TGT TCC TTC ACC ACC CTA CCA GCT CTG TCC ACT GGC      2064
Gln Val Leu Pro Cys Ser Phe Thr Thr Leu Pro Ala Leu Ser Thr Gly
        675                 680                 685

TTG ATT CAC CTC CAT CAG AAC ATC GTG GAC GTG CAA TAC CTA TAC GGT      2112
Leu Ile His Leu His Gln Asn Ile Val Asp Val Gln Tyr Leu Tyr Gly
    690                 695                 700

ATA GGG TCA GCG GTT GTC TCC TTT GCA ATC AAA TGG GAG TAT GTC CTG      2160
Ile Gly Ser Ala Val Val Ser Phe Ala Ile Lys Trp Glu Tyr Val Leu
705                 710                 715                 720

TTG CTT TTC CTT CTC CTA GCG GAC GCA CGT GTC TGT GCC TGC TTG TGG      2208
Leu Leu Phe Leu Leu Leu Ala Asp Ala Arg Val Cys Ala Cys Leu Trp
                725                 730                 735

ATG ATG CTG CTG ATA GCC CAG GCC GAG GCC GCC TTG GAG AAC CTG GTG      2256
Met Met Leu Leu Ile Ala Gln Ala Glu Ala Ala Leu Glu Asn Leu Val
            740                 745                 750

GTC CTC AAT TCG GCG TCT GTG GCC GGC GCA CAT GGC ATC CTC TCC TTC      2304
Val Leu Asn Ser Ala Ser Val Ala Gly Ala His Gly Ile Leu Ser Phe
        755                 760                 765

CTT GTG TTC TTC TGT GCC GCC TGG TAC ATC AAA GGC AGG CTG GTC CCT      2352
Leu Val Phe Phe Cys Ala Ala Trp Tyr Ile Lys Gly Arg Leu Val Pro
    770                 775                 780

GGG GCG ACA TAT GCT CTT TAT GGC GTG TGG CCG CTG CTC CTG CTC TTG      2400
Gly Ala Thr Tyr Ala Leu Tyr Gly Val Trp Pro Leu Leu Leu Leu Leu
785                 790                 795                 800

CTG GCA TTA CCA CCG CGA GCT TAC GCC ATG GAC CGG GAG ATG GCT GCA      2448
Leu Ala Leu Pro Pro Arg Ala Tyr Ala Met Asp Arg Glu Met Ala Ala
                805                 810                 815

TCG TGC GGA GGC GCG GTT TTT GTG GGT CTG GTA CTC CTG ACT TTG TCA      2496
Ser Cys Gly Gly Ala Val Phe Val Gly Leu Val Leu Leu Thr Leu Ser
            820                 825                 830

CCA TAC TAC AAG GTG TTC CTC GCT AGG CTC ATA TGG TGG TTA CAA TAT      2544
Pro Tyr Tyr Lys Val Phe Leu Ala Arg Leu Ile Trp Trp Leu Gln Tyr
        835                 840                 845
```

| | |
|---|---|
| TTT ACC ACC AGA GCC GAG GCG GAC TTA CAT GTG TGG ATC CCC CCC CTC<br>Phe Thr Thr Arg Ala Glu Ala Asp Leu His Val Trp Ile Pro Pro Leu<br>850                            855                           860 | 2592 |
| AAC GCT CGG GGA GGC CGC GAT GCC ATC ATC CTC CTC ATG TGC GCA GTC<br>Asn Ala Arg Gly Gly Arg Asp Ala Ile Ile Leu Leu Met Cys Ala Val<br>865                            870                           875                           880 | 2640 |
| CAT CCA GAG CTA ATC TTT GAC ATC ACC AAA CTT CTA ATT GCC ATA CTC<br>His Pro Glu Leu Ile Phe Asp Ile Thr Lys Leu Leu Ile Ala Ile Leu<br>                           885                           890                           895 | 2688 |
| GGT CCG CTC ATG GTG CTC CAA GCT GGC ATA ACC AGA GTG CCG TAC TTC<br>Gly Pro Leu Met Val Leu Gln Ala Gly Ile Thr Arg Val Pro Tyr Phe<br>                    900                           905                           910 | 2736 |
| GTG CGC GCT CAA GGG CTC ATT CAT GCA TGC ATG TTA GTG CGG AAG GTC<br>Val Arg Ala Gln Gly Leu Ile His Ala Cys Met Leu Val Arg Lys Val<br>                915                           920                           925 | 2784 |
| GCT GGG GGT CAT TAT GTC CAA ATG GCC TTC ATG AAG CTG GGC GCG CTG<br>Ala Gly Gly His Tyr Val Gln Met Ala Phe Met Lys Leu Gly Ala Leu<br>930                            935                           940 | 2832 |
| ACA GGC ACG TAC ATT TAC AAC CAT CTT ACC CCG CTA CGG GAT TGG CCA<br>Thr Gly Thr Tyr Ile Tyr Asn His Leu Thr Pro Leu Arg Asp Trp Pro<br>945                            950                           955                           960 | 2880 |
| CGC GCG GGC CTA CGA GAC CTT GCG GTG GCA GTG GAG CCC GTC GTC TTC<br>Arg Ala Gly Leu Arg Asp Leu Ala Val Ala Val Glu Pro Val Val Phe<br>                    965                           970                           975 | 2928 |
| TCC GAC ATG GAG ACC AAG ATC ATC ACC TGG GGA GCA GAC ACC GCG GCG<br>Ser Asp Met Glu Thr Lys Ile Ile Thr Trp Gly Ala Asp Thr Ala Ala<br>                980                           985                           990 | 2976 |
| TGT GGG GAC ATC ATC TTG GGT CTG CCC GTC TCC GCC GGA AGG GGA AAG<br>Cys Gly Asp Ile Ile Leu Gly Leu Pro Val Ser Ala Arg Arg Gly Lys<br>             995                         1000                       1005 | 3024 |
| GAG ATA CTC CTG GGC CCG GCC GAT AGT CTT GAA GGG CGG GGG TTG CGA<br>Glu Ile Leu Leu Gly Pro Ala Asp Ser Leu Glu Gly Arg Gly Leu Arg<br>          1010                       1015                       1020 | 3072 |
| CTC CTC GCG CCC ATC ACG GCC TAC TCC CAA CAG ACG CGG GGC CTA CTT<br>Leu Leu Ala Pro Ile Thr Ala Tyr Ser Gln Gln Thr Arg Gly Leu Leu<br>1025                        1030                       1035                       1040 | 3120 |
| GGT TGC ATC ATC ACT AGC CTT ACA GGC CGG GAC AAG AAC CAG GTC GAG<br>Gly Cys Ile Ile Thr Ser Leu Thr Gly Arg Asp Lys Asn Gln Val Glu<br>                    1045                       1050                       1055 | 3168 |
| GGA GAG GTT CAG GTG GTT TCC ACC GCA ACA CAA TCC TTC CTG GCG ACC<br>Gly Glu Val Gln Val Val Ser Thr Ala Thr Gln Ser Phe Leu Ala Thr<br>               1060                       1065                       1070 | 3216 |
| TGC GTC AAC GGC GTG TGT TGG ACC GTT TAC CAT GGT GCT GGC TCA AAG<br>Cys Val Asn Gly Val Cys Trp Thr Val Tyr His Gly Ala Gly Ser Lys<br>          1075                       1080                       1085 | 3264 |
| ACC TTA GCC GCG CCA AAG GGG CCA ATC ACC CAG ATG TAC ACT AAT GTG<br>Thr Leu Ala Ala Pro Lys Gly Pro Ile Thr Gln Met Tyr Thr Asn Val<br>1090                        1095                       1100 | 3312 |
| GAC CAG GAC CTC GTC GGC TGG CCC AAG CCC CCC GGG GCG CGT TCC TTG<br>Asp Gln Asp Leu Val Gly Trp Pro Lys Pro Pro Gly Ala Arg Ser Leu<br>1105                        1110                       1115                       1120 | 3360 |
| ACA CCA TGC ACC TGT GGC AGC TCA GAC CTT TAC TTG GTC ACG AGA CAT<br>Thr Pro Cys Thr Cys Gly Ser Ser Asp Leu Tyr Leu Val Thr Arg His<br>                    1125                       1130                       1135 | 3408 |
| GCT GAC GTC ATT CCG GTG CGC CGG CGG GGC GAC AGT AGG GGG AGC CTG<br>Ala Asp Val Ile Pro Val Arg Arg Arg Gly Asp Ser Arg Gly Ser Leu<br>               1140                       1145                       1150 | 3456 |
| CTC TCC CCC AGG CCT GTC TCC TAC TTG AAG GGC TCT TCG GGT GGT CCA<br>Leu Ser Pro Arg Pro Val Ser Tyr Leu Lys Gly Ser Ser Gly Gly Pro<br>          1155                       1160                       1165 | 3504 |

| | | |
|---|---|---|
| CTG CTC TGC CCC TTC GGG CAC GCT GTG GGC ATC TTC CGG GCT GCC GTA | 3552 | |
| Leu Leu Cys Pro Phe Gly His Ala Val Gly Ile Phe Arg Ala Ala Val | | |
| 1170       1175       1180 | | |
| TGC ACC CGG GGG GTT GCG AAG GCG GTG GAC TTT GTG CCC GTA GAG TCC | 3600 | |
| Cys Thr Arg Gly Val Ala Lys Ala Val Asp Phe Val Pro Val Glu Ser | | |
| 1185       1190       1195       1200 | | |
| ATG GAA ACT ACT ATG CGG TCT CCG GTC TTC ACG GAC AAC TCA TCC CCC | 3648 | |
| Met Glu Thr Thr Met Arg Ser Pro Val Phe Thr Asp Asn Ser Ser Pro | | |
|       1205       1210       1215 | | |
| CCG GCC GTA CCG CAG TCA TTT CAA GTG GCC CAC CTA CAC GCT CCC ACT | 3696 | |
| Pro Ala Val Pro Gln Ser Phe Gln Val Ala His Leu His Ala Pro Thr | | |
|       1220       1225       1230 | | |
| GGC AGC GGC AAG AGT ACT AAA GTG CCG GCT GCA TAT GCA GCC CAA GGG | 3744 | |
| Gly Ser Gly Lys Ser Thr Lys Val Pro Ala Ala Tyr Ala Ala Gln Gly | | |
|       1235       1240       1245 | | |
| TAC AAG GTG CTC GTC CTC AAT CCG TCC GTT GCC GCT ACC TTA GGG TTT | 3792 | |
| Tyr Lys Val Leu Val Leu Asn Pro Ser Val Ala Ala Thr Leu Gly Phe | | |
|       1250       1255       1260 | | |
| GGG GCG TAT ATG TCT AAG GCA CAC GGT ATT GAC CCC AAC ATC AGA ACT | 3840 | |
| Gly Ala Tyr Met Ser Lys Ala His Gly Ile Asp Pro Asn Ile Arg Thr | | |
| 1265       1270       1275       1280 | | |
| GGG GTA AGG ACC ATT ACC ACA GGC GCC CCC GTC ACA TAC TCT ACC TAT | 3888 | |
| Gly Val Arg Thr Ile Thr Thr Gly Ala Pro Val Thr Tyr Ser Thr Tyr | | |
|       1285       1290       1295 | | |
| GGC AAG TTT CTT GCC GAT GGT GGT TGC TCT GGG GCG CTA TAT GAC ATC | 3936 | |
| Gly Lys Phe Leu Ala Asp Gly Gly Cys Ser Gly Ala Tyr Asp Ile | | |
|       1300       1305       1310 | | |
| ATA ATA TGT GAT GAG TGC CAT TCA ACT GAC TCG ACT ACA ATC TTG GGC | 3984 | |
| Ile Ile Cys Asp Glu Cys His Ser Thr Asp Ser Thr Thr Ile Leu Gly | | |
|       1315       1320       1325 | | |
| ATC GGC ACA GTC CTG GAC CAA GCG GAG ACG GCT GGA GCG CGG CTT GTC | 4032 | |
| Ile Gly Thr Val Leu Asp Gln Ala Glu Thr Ala Gly Ala Arg Leu Val | | |
| 1330       1335       1340 | | |
| GTG CTC GCC ACC GCT ACG CCT CCG GGA TCG GTC ACC GTG CCA CAC CCA | 4080 | |
| Val Leu Ala Thr Ala Thr Pro Pro Gly Ser Val Thr Val Pro His Pro | | |
| 1345       1350       1355       1360 | | |
| AAC ATC GAG GAG GTG GCC CTG TCT AAT ACT GGA GAG ATC CCC TTC TAT | 4128 | |
| Asn Ile Glu Glu Val Ala Leu Ser Asn Thr Gly Glu Ile Pro Phe Tyr | | |
|       1365       1370       1375 | | |
| GGC AAA GCC ATC CCC ATT GAA GCC ATC AGG GGG GGA AGG CAT CTC ATT | 4176 | |
| Gly Lys Ala Ile Pro Ile Glu Ala Ile Arg Gly Gly Arg His Leu Ile | | |
|       1380       1385       1390 | | |
| TTC TGT CAT TCC AAG AAG AAG TGC GAC GAG CTC GCC GCA AAG CTG TCA | 4224 | |
| Phe Cys His Ser Lys Lys Lys Cys Asp Glu Leu Ala Ala Lys Leu Ser | | |
|       1395       1400       1405 | | |
| GGC CTC GGA ATC AAC GCT GTG GCG TAT TAC CGG GGG CTC GAT GTG TCC | 4272 | |
| Gly Leu Gly Ile Asn Ala Val Ala Tyr Tyr Arg Gly Leu Asp Val Ser | | |
|       1410       1415       1420 | | |
| GTC ATA CCA ACT ATC GGA GAC GTC GTT GTC GTG GCA ACA GAC GCT CTG | 4320 | |
| Val Ile Pro Thr Ile Gly Asp Val Val Val Val Ala Thr Asp Ala Leu | | |
| 1425       1430       1435       1440 | | |
| ATG ACG GGC TAT ACG GGC GAC TTT GAC TCA GTG ATC GAC TGT AAC ACA | 4368 | |
| Met Thr Gly Tyr Thr Gly Asp Phe Asp Ser Val Ile Asp Cys Asn Thr | | |
|       1445       1450       1455 | | |
| TGT GTC ACC CAG ACA GTC GAC TTC AGC TTG GAT CCC ACC TTC ACC ATT | 4416 | |
| Cys Val Thr Gln Thr Val Asp Phe Ser Leu Asp Pro Thr Phe Thr Ile | | |
|       1460       1465       1470 | | |
| GAG ACG ACG ACC GTG CCT CAA GAC GCA GTG TCG CGC TCG CAG CGG CGG | 4464 | |
| Glu Thr Thr Thr Val Pro Gln Asp Ala Val Ser Arg Ser Gln Arg Arg | | |
|       1475       1480       1485 | | |

```
GGT AGG ACT GGC AGG GGT AGG AGA GGC ATC TAC AGG TTT GTG ACT CCG    4512
Gly Arg Thr Gly Arg Gly Arg Arg Gly Ile Tyr Arg Phe Val Thr Pro
        1490                1495                1500

GGA GAA CGG CCC TCG GGC ATG TTC GAT TCC TCG GTC CTG TGT GAG TGC    4560
Gly Glu Arg Pro Ser Gly Met Phe Asp Ser Ser Val Leu Cys Glu Cys
1505                1510                1515                1520

TAT GAC GCG GGC TGT GCT TGG TAC GAG CTC ACC CCG GCC GAG ACC TCG    4608
Tyr Asp Ala Gly Cys Ala Trp Tyr Glu Leu Thr Pro Ala Glu Thr Ser
                1525                1530                1535

GTT AGG TTG CGG GCC TAC CTG AAC ACA CCA GGG TTG CCC GTT TGC CAG    4656
Val Arg Leu Arg Ala Tyr Leu Asn Thr Pro Gly Leu Pro Val Cys Gln
        1540                1545                1550

GAC CAC CTG GAG TTC TGG GAG AGT GTC TTC ACA GGC CTC ACC CAT ATA    4704
Asp His Leu Glu Phe Trp Glu Ser Val Phe Thr Gly Leu Thr His Ile
        1555                1560                1565

GAT GCA CAC TTC TTG TCC CAG ACC AAG CAG GCA GGA GAC AAC TTC CCC    4752
Asp Ala His Phe Leu Ser Gln Thr Lys Gln Ala Gly Asp Asn Phe Pro
        1570                1575                1580

TAC CTG GTA GCA TAC CAA GCC ACG GTG TGC GCC AGG GCT CAG GCC CCA    4800
Tyr Leu Val Ala Tyr Gln Ala Thr Val Cys Ala Arg Ala Gln Ala Pro
1585                1590                1595                1600

CCT CCA TCA TGG GAT CAA ATG TGG AAG TGT CTC ATA CGG CTG AAA CCT    4848
Pro Pro Ser Trp Asp Gln Met Trp Lys Cys Leu Ile Arg Leu Lys Pro
                1605                1610                1615

ACG CTG CAC GGG CCA ACA CCC TTG CTG TAC AGG CTG GGA GCC GTC CAG    4896
Thr Leu His Gly Pro Thr Pro Leu Leu Tyr Arg Leu Gly Ala Val Gln
        1620                1625                1630

AAT GAG GTC ACC CTC ACC CAC CCC ATA ACC AAA TAC ATC ATG GCA TGC    4944
Asn Glu Val Thr Leu Thr His Pro Ile Thr Lys Tyr Ile Met Ala Cys
        1635                1640                1645

ATG TCG GCT GAC CTG GAG GTC GTC ACT AGC ACC TGG GTG CTG GTG GGC    4992
Met Ser Ala Asp Leu Glu Val Val Thr Ser Thr Trp Val Leu Val Gly
        1650                1655                1660

GGA GTC CTT GCA GCT CTG GCC GCG TAT TGC CTG ACA ACA GGC AGT GTG    5040
Gly Val Leu Ala Ala Leu Ala Ala Tyr Cys Leu Thr Thr Gly Ser Val
1665                1670                1675                1680

GTC ATT GTG GGT AGG ATT ATC TTG TCC GGG AGG CCG GCC ATT GTT CCC    5088
Val Ile Val Gly Arg Ile Ile Leu Ser Gly Arg Pro Ala Ile Val Pro
                1685                1690                1695

GAC AGG GAG CTT CTC TAC CAG GAG TTC GAT GAA ATG GAA GAG TGC GCC    5136
Asp Arg Glu Leu Leu Tyr Gln Glu Phe Asp Glu Met Glu Glu Cys Ala
        1700                1705                1710

TCG CAC CTC CCT TAC ATC GAG CAG GGA ATG CAG CTC GCC GAG CAA TTC    5184
Ser His Leu Pro Tyr Ile Glu Gln Gly Met Gln Leu Ala Glu Gln Phe
        1715                1720                1725

AAG CAG AAA GCG CTC GGG TTA CTG CAA ACA GCC ACC AAA CAA GCG GAG    5232
Lys Gln Lys Ala Leu Gly Leu Leu Gln Thr Ala Thr Lys Gln Ala Glu
        1730                1735                1740

GCT GCT GCT CCC GTG GTG GAG TCC AAG TGG CGA GCC CTT GAG ACA TTC    5280
Ala Ala Ala Pro Val Val Glu Ser Lys Trp Arg Ala Leu Glu Thr Phe
1745                1750                1755                1760

TGG GCG AAG CAC ATG TGG AAT TTC ATC AGC GGG ATA CAG TAC TTA GCA    5328
Trp Ala Lys His Met Trp Asn Phe Ile Ser Gly Ile Gln Tyr Leu Ala
                1765                1770                1775

GGC TTA TCC ACT CTG CCT GGG AAC CCC GCA ATA GCA TCA TTG ATG GCA    5376
Gly Leu Ser Thr Leu Pro Gly Asn Pro Ala Ile Ala Ser Leu Met Ala
        1780                1785                1790

TTC ACA GCC TCT ATC ACC AGC CCG CTC ACC ACC CAA AGT ACC CTC CTG    5424
Phe Thr Ala Ser Ile Thr Ser Pro Leu Thr Thr Gln Ser Thr Leu Leu
        1795                1800                1805
```

```
TTT AAC ATC TTG GGG GGG TGG GTG GCT GCC CAA CTC GCC CCC CCC AGC    5472
Phe Asn Ile Leu Gly Gly Trp Val Ala Ala Gln Leu Ala Pro Pro Ser
        1810                1815                1820

GCC GCT TCG GCT TTC GTG GGC GCC GGC ATC GCC GGT GCG GCT GTT GGC    5520
Ala Ala Ser Ala Phe Val Gly Ala Gly Ile Ala Gly Ala Ala Val Gly
1825                1830                1835                1840

AGC ATA GGC CTT GGG AAG GTG CTT GTG GAC ATT CTG GCG GGT TAT GGA    5568
Ser Ile Gly Leu Gly Lys Val Leu Val Asp Ile Leu Ala Gly Tyr Gly
                    1845                1850                1855

GCA GGA GTG GCC GGC GCG CTC GTG GCC TTT AAG GTC ATG AGC GGC GAG    5616
Ala Gly Val Ala Gly Ala Leu Val Ala Phe Lys Val Met Ser Gly Glu
            1860                1865                1870

ATG CCC TCC ACC GAG GAC CTG GTC AAT CTA CTT CCT GCC ATC CTC TCT    5664
Met Pro Ser Thr Glu Asp Leu Val Asn Leu Leu Pro Ala Ile Leu Ser
        1875                1880                1885

CCT GGC GCC CTG GTC GTC GGG GTC GTG TGT GCA GCA ATA CTG CGT CGA    5712
Pro Gly Ala Leu Val Val Gly Val Val Cys Ala Ala Ile Leu Arg Arg
    1890                1895                1900

CAC GTG GGT CCG GGA GAG GGG GCT GTG CAG TGG ATG AAC CGG CTG ATA    5760
His Val Gly Pro Gly Glu Gly Ala Val Gln Trp Met Asn Arg Leu Ile
1905                1910                1915                1920

GCG TTC GCC TCG CGG GGT AAT CAT GTT TCC CCC ACG CAC TAT GTG CCT    5808
Ala Phe Ala Ser Arg Gly Asn His Val Ser Pro Thr His Tyr Val Pro
                    1925                1930                1935

GAG AGC GAC GCC GCA GCG CGT GTT ACT CAG ATC CTC TCC AGC CTT ACC    5856
Glu Ser Asp Ala Ala Ala Arg Val Thr Gln Ile Leu Ser Ser Leu Thr
            1940                1945                1950

ATC ACT CAG CTG CTG AAA AGG CTC CAC CAG TGG ATT AAT GAA GAC TGC    5904
Ile Thr Gln Leu Leu Lys Arg Leu His Gln Trp Ile Asn Glu Asp Cys
        1955                1960                1965

TCC ACA CCG TGT TCC GGC TCG TGG CTA AGG GAT GTT TGG GAC TGG ATA    5952
Ser Thr Pro Cys Ser Gly Ser Trp Leu Arg Asp Val Trp Asp Trp Ile
    1970                1975                1980

TGC ACG GTG TTG ACT GAC TTC AAG ACC TGG CTC CAG TCC AAG CTC CTG    6000
Cys Thr Val Leu Thr Asp Phe Lys Thr Trp Leu Gln Ser Lys Leu Leu
1985                1990                1995                2000

CCG CAG CTA CCT GGA GTC CCT TTT TTC TCG TGC CAA CGC GGG TAC AAG    6048
Pro Gln Leu Pro Gly Val Pro Phe Phe Ser Cys Gln Arg Gly Tyr Lys
                    2005                2010                2015

GGA GTC TGG CGG GGA GAC GGC ATC ATG CAA ACC ACC TGC CCA TGT GGA    6096
Gly Val Trp Arg Gly Asp Gly Ile Met Gln Thr Thr Cys Pro Cys Gly
            2020                2025                2030

GCA CAG ATC ACC GGA CAT GTC AAA AAC GGT TCC ATG AGG ATC GTC GGG    6144
Ala Gln Ile Thr Gly His Val Lys Asn Gly Ser Met Arg Ile Val Gly
        2035                2040                2045

CCT AAG ACC TGC AGC AAC ACG TGG CAT GGA ACA TTC CCC ATC AAC GCA    6192
Pro Lys Thr Cys Ser Asn Thr Trp His Gly Thr Phe Pro Ile Asn Ala
    2050                2055                2060

TAC ACC ACG GGC CCC TGC ACA CCC TCT CCA GCG CCA AAC TAT TCT AGG    6240
Tyr Thr Thr Gly Pro Cys Thr Pro Ser Pro Ala Pro Asn Tyr Ser Arg
2065                2070                2075                2080

GCG CTG TGG CGG GTG GCC GCT GAG GAG TAC GTG GAG GTC ACG CGG GTG    6288
Ala Leu Trp Arg Val Ala Ala Glu Glu Tyr Val Glu Val Thr Arg Val
                    2085                2090                2095

GGG GAT TTC CAC TAC GTG ACG GGC ATG ACC ACT GAC AAC GTA AAG TGC    6336
Gly Asp Phe His Tyr Val Thr Gly Met Thr Thr Asp Asn Val Lys Cys
            2100                2105                2110

CCA TGC CAG GTT CCG GCT CCT GAA TTC TTC TCG GAG GTG GAC GGA GTG    6384
Pro Cys Gln Val Pro Ala Pro Glu Phe Phe Ser Glu Val Asp Gly Val
        2115                2120                2125
```

```
CGG TTG CAC AGG TAC GCT CCG GCG TGC AGG CCT CTC CTA CGG GAG GAG      6432
Arg Leu His Arg Tyr Ala Pro Ala Cys Arg Pro Leu Leu Arg Glu Glu
    2130                2135                2140

GTT ACA TTC CAG GTC GGG CTC AAC CAA TAC CTG GTT GGG TCA CAG CTA      6480
Val Thr Phe Gln Val Gly Leu Asn Gln Tyr Leu Val Gly Ser Gln Leu
2145                2150                2155                2160

CCA TGC GAG CCC GAA CCG GAT GTA GCA GTG CTC ACT TCC ATG CTC ACC      6528
Pro Cys Glu Pro Glu Pro Asp Val Ala Val Leu Thr Ser Met Leu Thr
                2165                2170                2175

GAC CCC TCC CAC ATC ACA GCA GAA ACG GCT AAG CGT AGG TTG GCC AGG      6576
Asp Pro Ser His Ile Thr Ala Glu Thr Ala Lys Arg Arg Leu Ala Arg
            2180                2185                2190

GGG TCT CCC CCC TCC TTG GCC AGC TCT TCA GCT AGC CAG TTG TCT GCG      6624
Gly Ser Pro Pro Ser Leu Ala Ser Ser Ser Ala Ser Gln Leu Ser Ala
        2195                2200                2205

CCT TCC TTG AAG GCG ACA TGC ACT ACC CAC CAT GTC TCT CCG GAC GCT      6672
Pro Ser Leu Lys Ala Thr Cys Thr Thr His His Val Ser Pro Asp Ala
    2210                2215                2220

GAC CTC ATC GAG GCC AAC CTC CTG TGG CGG CAG GAG ATG GGC GGG AAC      6720
Asp Leu Ile Glu Ala Asn Leu Leu Trp Arg Gln Glu Met Gly Gly Asn
2225                2230                2235                2240

ATC ACC CGC GTG GAG TCG GAG AAC AAG GTG GTA GTC CTG GAC TCT TTC      6768
Ile Thr Arg Val Glu Ser Glu Asn Lys Val Val Val Leu Asp Ser Phe
                2245                2250                2255

GAC CCG CTT CGA GCG GAG GAG GAT GAG AGG GAA GTA TCC GTT CCG GCG      6816
Asp Pro Leu Arg Ala Glu Glu Asp Glu Arg Glu Val Ser Val Pro Ala
            2260                2265                2270

GAG ATC CTG CGG AAA TCC AAG AAG TTC CCC GCA GCG ATG CCC ATC TGG      6864
Glu Ile Leu Arg Lys Ser Lys Lys Phe Pro Ala Ala Met Pro Ile Trp
        2275                2280                2285

GCG CGC CCG GAT TAC AAC CCT CCA CTG TTA GAG TCC TGG AAG GAC CCG      6912
Ala Arg Pro Asp Tyr Asn Pro Pro Leu Leu Glu Ser Trp Lys Asp Pro
    2290                2295                2300

GAC TAC GTC CCT CCG GTG GTG CAC GGG TGC CCG TTG CCA CCT ATC AAG      6960
Asp Tyr Val Pro Pro Val Val His Gly Cys Pro Leu Pro Pro Ile Lys
2305                2310                2315                2320

GCC CCT CCA ATA CCA CCT CCA CGG AGA AAG AGG ACG GTT GTC CTA ACA      7008
Ala Pro Pro Ile Pro Pro Pro Arg Arg Lys Arg Thr Val Val Leu Thr
                2325                2330                2335

GAG TCC TCC GTG TCT TCT GCC TTA GCG GAG CTC GCT ACT AAG ACC TTC      7056
Glu Ser Ser Val Ser Ser Ala Leu Ala Glu Leu Ala Thr Lys Thr Phe
            2340                2345                2350

GGC AGC TCC GAA TCA TCG GCC GTC GAC AGC GGC ACG GCG ACC GCC CTT      7104
Gly Ser Ser Glu Ser Ser Ala Val Asp Ser Gly Thr Ala Thr Ala Leu
        2355                2360                2365

CCT GAC CAG GCC TCC GAC GAC GGT GAC AAA GGA TCC GAC GTT GAG TCG      7152
Pro Asp Gln Ala Ser Asp Asp Gly Asp Lys Gly Ser Asp Val Glu Ser
    2370                2375                2380

TAC TCC TCC ATG CCC CCC CTT GAG GGG GAA CCG GGG GAC CCC GAT CTC      7200
Tyr Ser Ser Met Pro Pro Leu Glu Gly Glu Pro Gly Asp Pro Asp Leu
2385                2390                2395                2400

AGT GAC GGG TCT TGG TCT ACC GTG AGC GAG GAA GCT AGT GAG GAT GTC      7248
Ser Asp Gly Ser Trp Ser Thr Val Ser Glu Glu Ala Ser Glu Asp Val
                2405                2410                2415

GTC TGC TGC TCA ATG TCC TAC ACA TGG ACA GGC GCC TTG ATC ACG CCA      7296
Val Cys Cys Ser Met Ser Tyr Thr Trp Thr Gly Ala Leu Ile Thr Pro
            2420                2425                2430

TGC GCT GCG GAG GAA AGC AAG CTG CCC ATC AAC GCG TTG AGC AAC TCT      7344
Cys Ala Ala Glu Glu Ser Lys Leu Pro Ile Asn Ala Leu Ser Asn Ser
        2435                2440                2445
```

```
TTG CTG CGC CAC CAT AAC ATG GTT TAT GCC ACA ACA TCT CGC AGC GCA      7392
Leu Leu Arg His His Asn Met Val Tyr Ala Thr Thr Ser Arg Ser Ala
    2450                2455                2460

GGC CTG CGG CAG AAG AAG GTC ACC TTT GAC AGA CTG CAA GTC CTG GAC      7440
Gly Leu Arg Gln Lys Lys Val Thr Phe Asp Arg Leu Gln Val Leu Asp
2465                2470                2475                2480

GAC CAC TAC CGG GAC GTG CTC AAG GAG ATG AAG GCG AAG GCG TCC ACA      7488
Asp His Tyr Arg Asp Val Leu Lys Glu Met Lys Ala Lys Ala Ser Thr
                2485                2490                2495

GTT AAG GCT AAA CTC CTA TCC GTA GAG GAA GCC TGC AAG CTG ACG CCC      7536
Val Lys Ala Lys Leu Leu Ser Val Glu Glu Ala Cys Lys Leu Thr Pro
            2500                2505                2510

CCA CAT TCG GCC AAA TCC AAG TTT GGC TAT GGG GCA AAG GAC GTC CGG      7584
Pro His Ser Ala Lys Ser Lys Phe Gly Tyr Gly Ala Lys Asp Val Arg
        2515                2520                2525

AAC CTA TCC AGC AAG GCC GTT AAC CAC ATC CAC TCC GTG TGG AAG GAC      7632
Asn Leu Ser Ser Lys Ala Val Asn His Ile His Ser Val Trp Lys Asp
    2530                2535                2540

TTG CTG GAA GAC ACT GTG ACA CCA ATT GAC ACC ACC ATC ATG GCA AAA      7680
Leu Leu Glu Asp Thr Val Thr Pro Ile Asp Thr Thr Ile Met Ala Lys
2545                2550                2555                2560

AAT GAG GTT TTC TGT GTC CAA CCA GAG AAA GGA GGC CGT AAG CCA GCC      7728
Asn Glu Val Phe Cys Val Gln Pro Glu Lys Gly Gly Arg Lys Pro Ala
                2565                2570                2575

CGC CTT ATC GTA TTC CCA GAT CTG GGA GTC CGT GTA TGC GAG AAG ATG      7776
Arg Leu Ile Val Phe Pro Asp Leu Gly Val Arg Val Cys Glu Lys Met
            2580                2585                2590

GCC CTC TAT GAT GTG GTC TCC ACC CTT CCT CAG GTC GTG ATG GGC TCC      7824
Ala Leu Tyr Asp Val Val Ser Thr Leu Pro Gln Val Val Met Gly Ser
        2595                2600                2605

TCA TAC GGA TTC CAG TAC TCT CCT GGG CAG CGA GTC GAG TTC CTG GTG      7872
Ser Tyr Gly Phe Gln Tyr Ser Pro Gly Gln Arg Val Glu Phe Leu Val
    2610                2615                2620

AAT ACC TGG AAA TCA AAG AAA AAC CCC ATG GGC TTT TCA TAT GAC ACT      7920
Asn Thr Trp Lys Ser Lys Lys Asn Pro Met Gly Phe Ser Tyr Asp Thr
2625                2630                2635                2640

CGC TGT TTC GAC TCA ACG GTC ACC GAG AAC GAC ATC CGT GTT GAG GAG      7968
Arg Cys Phe Asp Ser Thr Val Thr Glu Asn Asp Ile Arg Val Glu Glu
                2645                2650                2655

TCA ATT TAC CAA TGT TGT GAC TTG GCC CCC GAA GCC AGA CAG GCC ATA      8016
Ser Ile Tyr Gln Cys Cys Asp Leu Ala Pro Glu Ala Arg Gln Ala Ile
            2660                2665                2670

AAA TCG CTC ACA GAG CGG CTT TAT ATC GGG GGT CCT CTG ACT AAT TCA      8064
Lys Ser Leu Thr Glu Arg Leu Tyr Ile Gly Gly Pro Leu Thr Asn Ser
        2675                2680                2685

AAA GGG CAG AAC TGC GGT TAT CGC CGG TGC CGC GCG AGC GGC GTG CTG      8112
Lys Gly Gln Asn Cys Gly Tyr Arg Arg Cys Arg Ala Ser Gly Val Leu
    2690                2695                2700

ACG ACT AGC TGC GGT AAC ACC CTC ACA TGT TAC TTG AAG GCC TCT GCA      8160
Thr Thr Ser Cys Gly Asn Thr Leu Thr Cys Tyr Leu Lys Ala Ser Ala
2705                2710                2715                2720

GCC TGT CGA GCT GCG AAG CTC CAG GAC TGC ACG ATG CTC GTG AAC GGA      8208
Ala Cys Arg Ala Ala Lys Leu Gln Asp Cys Thr Met Leu Val Asn Gly
                2725                2730                2735

GAC GAC CTC GTC GTT ATC TGT GAA AGC GCG GGA ACC CAA GAG GAC GCG      8256
Asp Asp Leu Val Val Ile Cys Glu Ser Ala Gly Thr Gln Glu Asp Ala
            2740                2745                2750

GCG AGC CTA CGA GTC TTC ACG GAG GCT ATG ACT AGG TAC TCC GCC CCC      8304
Ala Ser Leu Arg Val Phe Thr Glu Ala Met Thr Arg Tyr Ser Ala Pro
        2755                2760                2765
```

```
CCC GGG GAC CCG CCC CAA CCA GAA TAC GAC TTG GAG CTG ATA ACA TCA      8352
Pro Gly Asp Pro Pro Gln Pro Glu Tyr Asp Leu Glu Leu Ile Thr Ser
    2770            2775                2780

TGT TCC TCC AAT GTG TCG GTC GCC CAC GAT GCA TCA GGC AAA AGG GTG      8400
Cys Ser Ser Asn Val Ser Val Ala His Asp Ala Ser Gly Lys Arg Val
2785            2790                2795                2800

TAC TAC CTC ACC CGT GAT CCC ACC ACC CCC CTA GCA CGG GCT GCG TGG      8448
Tyr Tyr Leu Thr Arg Asp Pro Thr Thr Pro Leu Ala Arg Ala Ala Trp
                2805                2810                2815

GAG ACA GCT AGA CAC ACT CCA GTT AAC TCC TGG CTA GGC AAC ATT ATT      8496
Glu Thr Ala Arg His Thr Pro Val Asn Ser Trp Leu Gly Asn Ile Ile
            2820                2825                2830

ATG TAT GCG CCC ACT TTG TGG GCA AGG ATG ATT CTG ATG ACT CAC TTC      8544
Met Tyr Ala Pro Thr Leu Trp Ala Arg Met Ile Leu Met Thr His Phe
        2835                2840                2845

TTC TCC ATC CTT CTA GCG CAG GAG CAA CTT GAA AAA GCC CTG GAC TGC      8592
Phe Ser Ile Leu Leu Ala Gln Glu Gln Leu Glu Lys Ala Leu Asp Cys
    2850                2855                2860

CAG ATC TAC GGG GCC TGT TAC TCC ATT GAG CCA CTT GAC CTA CCT CAG      8640
Gln Ile Tyr Gly Ala Cys Tyr Ser Ile Glu Pro Leu Asp Leu Pro Gln
2865            2870                2875                2880

ATC ATT GAA CGA CTC CAT GGC CTT AGC GCA TTT TCA CTC CAT AGT TAC      8688
Ile Ile Glu Arg Leu His Gly Leu Ser Ala Phe Ser Leu His Ser Tyr
                2885                2890                2895

TCT CCA GGT GAG ATC AAT AGG GTG GCT TCA TGC CTC AGG AAA CTT GGG      8736
Ser Pro Gly Glu Ile Asn Arg Val Ala Ser Cys Leu Arg Lys Leu Gly
            2900                2905                2910

GTA CCA CCC TTG CGA GTC TGG AGA CAT CGG GCC AGG AGC GTC CGC GCT      8784
Val Pro Pro Leu Arg Val Trp Arg His Arg Ala Arg Ser Val Arg Ala
        2915                2920                2925

AGG CTA CTG TCC CAG GGA GGG AGG GCC GCC ACT TGT GGC AAA TAC CTC      8832
Arg Leu Leu Ser Gln Gly Gly Arg Ala Ala Thr Cys Gly Lys Tyr Leu
    2930                2935                2940

TTC AAC TGG GCA GTA AAA ACC AAA CTT AAA CTC ACT CCA ATC CCG GCT      8880
Phe Asn Trp Ala Val Lys Thr Lys Leu Lys Leu Thr Pro Ile Pro Ala
2945            2950                2955                2960

GCG TCC CGG CTG GAC TTG TCC GGC TGG TTC GTT GCT GGT TAC AGC GGG      8928
Ala Ser Arg Leu Asp Leu Ser Gly Trp Phe Val Ala Gly Tyr Ser Gly
                2965                2970                2975

GGA GAC ATA TAT CAC AGC CTG TCT CGT GCC CGA CCC CGT TGG TTC ATG      8976
Gly Asp Ile Tyr His Ser Leu Ser Arg Ala Arg Pro Arg Trp Phe Met
            2980                2985                2990

CTG TGC CTA CTC CTA CTT TCT GTA GGG GTA GGC ATC TAC CTG CTC CCC      9024
Leu Cys Leu Leu Leu Leu Ser Val Gly Val Gly Ile Tyr Leu Leu Pro
        2995                3000                3005

AAC CGA                                                              9030
Asn Arg
3010

(2) INFORMATION FOR SEQ ID NO:14:

(i) SEQUENCE CHARACTERISTICS:
        (A) LENGTH: 3010 amino acids
        (B) TYPE: amino acid
        (D) TOPOLOGY: linear (ii) MOLECULE TYPE: protein (xi) SEQUENCE DESCRIPTION: SEQ ID NO:14:

Met Ser Thr Asn Pro Lys Pro Gln Arg Lys Thr Lys Arg Asn Thr Asn
1               5                   10                  15
```

-continued

```
Arg Arg Pro Gln Asp Val Lys Phe Pro Gly Gly Gln Ile Val Gly
             20                  25                  30

Gly Val Tyr Leu Leu Pro Arg Arg Gly Pro Arg Leu Gly Val Arg Ala
         35                  40                  45

Pro Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Tyr
            180                 185                 190

Glu Val His Asn Val Ser Gly Ile Tyr His Val Thr Asn Asp Cys Ser
            195                 200                 205

Asn Ala Ser Ile Val Tyr Glu Ala Ala Asp Leu Ile Met His Thr Pro
    210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Val Thr Ile Pro Thr Thr
                245                 250                 255

Thr Ile Arg Arg His Val Asp Leu Leu Val Gly Ala Ala Phe Cys
                260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Val Thr Leu Gln Asp Cys
    290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
            325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Ala Gly Asn Trp
        355                 360                 365

Ala Lys Val Leu Ile Val Met Leu Leu Phe Ala Gly Val Asp Gly Asp
    370                 375                 380

Thr His Val Thr Gly Gly Ala Gln Ala Lys Thr Thr Asn Arg Leu Val
385                 390                 395                 400

Ser Met Phe Ala Ser Gly Pro Ser Gln Lys Ile Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Leu Ala Ala Leu Phe Tyr Thr His Ser Phe Asn
        435                 440                 445
```

```
Ser Ser Gly Cys Pro Glu Arg Met Ala Gln Cys Arg Thr Ile Asp Lys
    450                 455                 460
Phe Asp Gln Gly Trp Gly Pro Ile Thr Tyr Ala Glu Ser Ser Arg Ser
465                 470                 475                 480
Asp Gln Arg Pro Tyr Cys Trp His Tyr Pro Pro Gln Cys Thr Ile
                    485                 490                 495
Val Pro Ala Ser Glu Val Cys Gly Pro Val Tyr Cys Phe Thr Pro Ser
                    500                 505                 510
Pro Val Val Gly Thr Thr Asp Arg Phe Gly Val Pro Thr Tyr Arg
                515                 520                 525
Trp Gly Glu Asn Glu Thr Asp Val Leu Leu Asn Asn Thr Arg Pro
            530                 535                 540
Pro Gln Gly Asn Trp Phe Gly Cys Thr Trp Met Asn Ser Thr Gly Phe
545                 550                 555                 560
Thr Lys Thr Cys Gly Gly Pro Pro Cys Asn Ile Gly Gly Val Gly Asn
                    565                 570                 575
Asn Thr Leu Thr Cys Pro Thr Asp Cys Phe Arg Lys His Pro Glu Ala
                580                 585                 590
Thr Tyr Thr Lys Cys Gly Ser Gly Pro Trp Leu Thr Pro Arg Cys Met
                595                 600                 605
Val Asp Tyr Pro Tyr Arg Leu Trp His Tyr Pro Cys Thr Val Asn Phe
610                 615                 620
Thr Ile Phe Lys Val Arg Met Tyr Val Gly Gly Val Glu His Arg Leu
625                 630                 635                 640
Asn Ala Ala Cys Asn Trp Thr Arg Gly Glu Arg Cys Asp Leu Glu Asp
                645                 650                 655
Arg Asp Arg Pro Glu Leu Ser Pro Leu Leu Leu Ser Thr Thr Glu Trp
                660                 665                 670
Gln Val Leu Pro Cys Ser Phe Thr Thr Leu Pro Ala Leu Ser Thr Gly
                675                 680                 685
Leu Ile His Leu His Gln Asn Ile Val Asp Val Gln Tyr Leu Tyr Gly
            690                 695                 700
Ile Gly Ser Ala Val Val Ser Phe Ala Ile Lys Trp Glu Tyr Val Leu
705                 710                 715                 720
Leu Leu Phe Leu Leu Leu Ala Asp Ala Arg Val Cys Ala Cys Leu Trp
                725                 730                 735
Met Met Leu Leu Ile Ala Gln Ala Glu Ala Leu Glu Asn Leu Val
            740                 745                 750
Val Leu Asn Ser Ala Ser Val Ala Gly Ala His Gly Ile Leu Ser Phe
                755                 760                 765
Leu Val Phe Phe Cys Ala Ala Trp Tyr Ile Lys Gly Arg Leu Val Pro
            770                 775                 780
Gly Ala Thr Tyr Ala Leu Tyr Gly Val Trp Pro Leu Leu Leu Leu Leu
785                 790                 795                 800
Leu Ala Leu Pro Pro Arg Ala Tyr Ala Met Asp Arg Glu Met Ala Ala
                805                 810                 815
Ser Cys Gly Gly Ala Val Phe Val Gly Leu Val Leu Leu Thr Leu Ser
                820                 825                 830
Pro Tyr Tyr Lys Val Phe Leu Ala Arg Leu Ile Trp Trp Leu Gln Tyr
            835                 840                 845
Phe Thr Thr Arg Ala Glu Ala Asp Leu His Val Trp Ile Pro Pro Leu
            850                 855                 860
Asn Ala Arg Gly Gly Arg Asp Ala Ile Ile Leu Leu Met Cys Ala Val
```

-continued

```
              865                 870                 875                 880

His Pro Glu Leu Ile Phe Asp Ile Thr Lys Leu Leu Ile Ala Ile Leu
                    885                 890                 895

Gly Pro Leu Met Val Leu Gln Ala Gly Ile Thr Arg Val Pro Tyr Phe
                900                 905                 910

Val Arg Ala Gln Gly Leu Ile His Ala Cys Met Leu Val Arg Lys Val
            915                 920                 925

Ala Gly Gly His Tyr Val Gln Met Ala Phe Met Lys Leu Gly Ala Leu
        930                 935                 940

Thr Gly Thr Tyr Ile Tyr Asn His Leu Thr Pro Leu Arg Asp Trp Pro
945                 950                 955                 960

Arg Ala Gly Leu Arg Asp Leu Ala Val Ala Val Glu Pro Val Val Phe
                965                 970                 975

Ser Asp Met Glu Thr Lys Ile Ile Thr Trp Gly Ala Asp Thr Ala Ala
                980                 985                 990

Cys Gly Asp Ile Ile Leu Gly Leu Pro Val Ser Ala Arg Arg Gly Lys
            995                 1000                1005

Glu Ile Leu Leu Gly Pro Ala Asp Ser Leu Glu Gly Arg Gly Leu Arg
        1010                1015                1020

Leu Leu Ala Pro Ile Thr Ala Tyr Ser Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Val Val Ser Thr Ala Thr Gln Ser Phe Leu Ala Thr
                1060                1065                1070

Cys Val Asn Gly Val Cys Trp Thr Val Tyr His Gly Ala Gly Ser Lys
            1075                1080                1085

Thr Leu Ala Ala Pro Lys Gly Pro Ile Thr Gln Met Tyr Thr Asn Val
        1090                1095                1100

Asp Gln Asp Leu Val Gly Trp Pro Lys Pro Pro Gly Ala Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
                1140                1145                1150

Leu Ser Pro Arg Pro Val Ser Tyr Leu Lys Gly Ser Ser Gly Gly Pro
            1155                1160                1165

Leu Leu Cys Pro Phe Gly His Ala Val Gly Ile Phe Arg Ala Ala Val
        1170                1175                1180

Cys Thr Arg Gly Val Ala Lys Ala Val Asp Phe Val Pro Val Glu Ser
1185                1190                1195                1200

Met Glu Thr Thr Met Arg Ser Pro Val Phe Thr Asp Asn Ser Ser Pro
                1205                1210                1215

Pro Ala Val Pro Gln Ser Phe Gln Val Ala His Leu His Ala Pro Thr
                1220                1225                1230

Gly Ser Gly Lys Ser Thr Lys Val Pro Ala Ala Tyr Ala Ala Gln Gly
            1235                1240                1245

Tyr Lys Val Leu Val Leu Asn Pro Ser Val Ala Ala Thr Leu Gly Phe
        1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Ala Pro Val Thr Tyr Ser Thr Tyr
                1285                1290                1295
```

-continued

```
Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ser Thr Thr Ile Leu Gly
            1315                1320            1325

Ile Gly Thr Val Leu Asp Gln Ala Glu Thr Ala Gly Ala Arg Leu Val
            1330                1335                1340

Val Leu Ala Thr Ala Thr Pro Pro Gly Ser Val Thr Val Pro His Pro
1345                1350                1355                1360

Asn Ile Glu Glu Val Ala Leu Ser Asn Thr Gly Glu Ile Pro Phe Tyr
            1365                1370                1375

Gly Lys Ala Ile Pro Ile Glu Ala Ile Arg Gly Gly Arg His Leu Ile
            1380                1385                1390

Phe Cys His Ser Lys Lys Lys Cys Asp Glu Leu Ala Ala Lys Leu Ser
            1395                1400            1405

Gly Leu Gly Ile Asn Ala Val Ala Tyr Tyr Arg Gly Leu Asp Val Ser
            1410                1415                1420

Val Ile Pro Thr Ile Gly Asp Val Val Val Ala Thr Asp Ala Leu
1425                1430                1435                1440

Met Thr Gly Tyr Thr Gly Asp Phe Asp Ser Val Ile Asp Cys Asn Thr
            1445                1450                1455

Cys Val Thr Gln Thr Val Asp Phe Ser Leu Asp Pro Thr Phe Thr Ile
            1460                1465                1470

Glu Thr Thr Thr Val Pro Gln Asp Ala Val Ser Arg Ser Gln Arg Arg
            1475                1480                1485

Gly Arg Thr Gly Arg Gly Arg Arg Gly Ile Tyr Arg Phe Val Thr Pro
            1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Ser
            1525                1530                1535

Val Arg Leu Arg Ala Tyr Leu Asn Thr Pro Gly Leu Pro Val Cys Gln
            1540                1545                1550

Asp His Leu Glu Phe Trp Glu Ser Val Phe Thr Gly Leu Thr His Ile
            1555                1560                1565

Asp Ala His Phe Leu Ser Gln Thr Lys Gln Ala Gly Asp Asn Phe Pro
            1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
            1620                1625                1630

Asn Glu Val Thr Leu Thr His Pro Ile Thr Lys Tyr Ile Met Ala Cys
            1635                1640                1645

Met Ser Ala Asp Leu Glu Val Val Thr Ser Thr Trp Val Leu Val Gly
1650                1655                1660

Gly Val Leu Ala Ala Leu Ala Ala Tyr Cys Leu Thr Thr Gly Ser Val
1665                1670                1675                1680

Val Ile Val Gly Arg Ile Ile Leu Ser Gly Arg Pro Ala Ile Val Pro
            1685                1690                1695

Asp Arg Glu Leu Leu Tyr Gln Glu Phe Asp Glu Met Glu Glu Cys Ala
            1700                1705                1710

Ser His Leu Pro Tyr Ile Glu Gln Gly Met Gln Leu Ala Glu Gln Phe
            1715                1720                1725
```

-continued

```
Lys Gln Lys Ala Leu Gly Leu Leu Gln Thr Ala Thr Lys Gln Ala Glu
            1730                1735                1740

Ala Ala Ala Pro Val Val Glu Ser Lys Trp Arg Ala Leu Glu Thr Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
            1780                1785                1790

Phe Thr Ala Ser Ile Thr Ser Pro Leu Thr Thr Gln Ser Thr Leu Leu
            1795                1800                1805

Phe Asn Ile Leu Gly Gly Trp Val Ala Ala Gln Leu Ala Pro Pro Ser
        1810                1815                1820

Ala Ala Ser Ala Phe Val Gly Ala Gly Ile Ala Gly Ala Ala Val Gly
1825                1830                1835                1840

Ser Ile Gly Leu Gly Lys Val Leu Val Asp Ile Leu Ala Gly Tyr Gly
                1845                1850                1855

Ala Gly Val Ala Gly Ala Leu Val Ala Phe Lys Val Met Ser Gly Glu
            1860                1865                1870

Met Pro Ser Thr Glu Asp Leu Val Asn Leu Leu Pro Ala Ile Leu Ser
            1875                1880                1885

Pro Gly Ala Leu Val Val Gly Val Val Cys Ala Ala Ile Leu Arg Arg
            1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Gln Ile Leu Ser Ser Leu Thr
            1940                1945                1950

Ile Thr Gln Leu Leu Lys Arg Leu His Gln Trp Ile Asn Glu Asp Cys
            1955                1960                1965

Ser Thr Pro Cys Ser Gly Ser Trp Leu Arg Asp Val Trp Asp Trp Ile
            1970                1975                1980

Cys Thr Val Leu Thr Asp Phe Lys Thr Trp Leu Gln Ser Lys Leu Leu
1985                1990                1995                2000

Pro Gln Leu Pro Gly Val Pro Phe Phe Ser Cys Gln Arg Gly Tyr Lys
                2005                2010                2015

Gly Val Trp Arg Gly Asp Gly Ile Met Gln Thr Thr Cys Pro Cys Gly
                2020                2025                2030

Ala Gln Ile Thr Gly His Val Lys Asn Gly Ser Met Arg Ile Val Gly
            2035                2040                2045

Pro Lys Thr Cys Ser Asn Thr Trp His Gly Thr Phe Pro Ile Asn Ala
2050                2055                2060

Tyr Thr Thr Gly Pro Cys Thr Pro Ser Pro Ala Pro Asn Tyr Ser Arg
2065                2070                2075                2080

Ala Leu Trp Arg Val Ala Ala Glu Glu Tyr Val Glu Val Thr Arg Val
                2085                2090                2095

Gly Asp Phe His Tyr Val Thr Gly Met Thr Thr Asp Asn Val Lys Cys
            2100                2105                2110

Pro Cys Gln Val Pro Ala Pro Glu Phe Phe Ser Glu Val Asp Gly Val
            2115                2120                2125

Arg Leu His Arg Tyr Ala Pro Ala Cys Arg Pro Leu Leu Arg Glu Glu
        2130                2135                2140

Val Thr Phe Gln Val Gly Leu Asn Gln Tyr Leu Val Gly Ser Gln Leu
```

-continued

```
            2145                2150                2155                2160
Pro Cys Glu Pro Glu Pro Asp Val Ala Val Leu Thr Ser Met Leu Thr
                    2165                2170                2175
Asp Pro Ser His Ile Thr Ala Glu Thr Ala Lys Arg Arg Leu Ala Arg
                2180                2185                2190
Gly Ser Pro Pro Ser Leu Ala Ser Ser Ala Ser Gln Leu Ser Ala
            2195                2200                2205
Pro Ser Leu Lys Ala Thr Cys Thr Thr His His Val Ser Pro Asp Ala
        2210                2215                2220
Asp Leu Ile Glu Ala Asn Leu Leu Trp Arg Gln Glu Met Gly Gly Asn
2225                2230                2235                2240
Ile Thr Arg Val Glu Ser Glu Asn Lys Val Val Leu Asp Ser Phe
                2245                2250                2255
Asp Pro Leu Arg Ala Glu Glu Asp Glu Arg Glu Val Ser Val Pro Ala
            2260                2265                2270
Glu Ile Leu Arg Lys Ser Lys Lys Phe Pro Ala Ala Met Pro Ile Trp
        2275                2280                2285
Ala Arg Pro Asp Tyr Asn Pro Pro Leu Leu Glu Ser Trp Lys Asp Pro
    2290                2295                2300
Asp Tyr Val Pro Pro Val Val His Gly Cys Pro Leu Pro Pro Ile Lys
2305                2310                2315                2320
Ala Pro Pro Ile Pro Pro Pro Arg Arg Lys Arg Thr Val Val Leu Thr
                2325                2330                2335
Glu Ser Ser Val Ser Ser Ala Leu Ala Glu Leu Ala Thr Lys Thr Phe
            2340                2345                2350
Gly Ser Ser Glu Ser Ser Ala Val Asp Ser Gly Thr Ala Thr Ala Leu
            2355                2360                2365
Pro Asp Gln Ala Ser Asp Asp Gly Asp Lys Gly Ser Asp Val Glu Ser
        2370                2375                2380
Tyr Ser Ser Met Pro Pro Leu Glu Gly Glu Pro Gly Asp Pro Asp Leu
2385                2390                2395                2400
Ser Asp Gly Ser Trp Ser Thr Val Ser Glu Glu Ala Ser Glu Asp Val
                2405                2410                2415
Val Cys Cys Ser Met Ser Tyr Thr Trp Thr Gly Ala Leu Ile Thr Pro
                2420                2425                2430
Cys Ala Ala Glu Glu Ser Lys Leu Pro Ile Asn Ala Leu Ser Asn Ser
            2435                2440                2445
Leu Leu Arg His His Asn Met Val Tyr Ala Thr Thr Ser Arg Ser Ala
        2450                2455                2460
Gly Leu Arg Gln Lys Lys Val Thr Phe Asp Arg Leu Gln Val Leu Asp
2465                2470                2475                2480
Asp His Tyr Arg Asp Val Leu Lys Glu Met Lys Ala Lys Ala Ser Thr
                2485                2490                2495
Val Lys Ala Lys Leu Leu Ser Val Glu Glu Ala Cys Lys Leu Thr Pro
                2500                2505                2510
Pro His Ser Ala Lys Ser Lys Phe Gly Tyr Gly Ala Lys Asp Val Arg
            2515                2520                2525
Asn Leu Ser Ser Lys Ala Val Asn His Ile His Ser Val Trp Lys Asp
        2530                2535                2540
Leu Leu Glu Asp Thr Val Thr Pro Ile Asp Thr Thr Ile Met Ala Lys
2545                2550                2555                2560
Asn Glu Val Phe Cys Val Gln Pro Glu Lys Gly Gly Arg Lys Pro Ala
                2565                2570                2575
```

-continued

```
Arg Leu Ile Val Phe Pro Asp Leu Gly Val Arg Val Cys Glu Lys Met
            2580                2585                2590

Ala Leu Tyr Asp Val Val Ser Thr Leu Pro Gln Val Val Met Gly Ser
            2595                2600                2605

Ser Tyr Gly Phe Gln Tyr Ser Pro Gly Gln Arg Val Glu Phe Leu Val
            2610                2615                2620

Asn Thr Trp Lys Ser Lys Lys Asn Pro Met Gly Phe Ser Tyr Asp Thr
2625                2630                2635                2640

Arg Cys Phe Asp Ser Thr Val Thr Glu Asn Asp Ile Arg Val Glu Glu
            2645                2650                2655

Ser Ile Tyr Gln Cys Cys Asp Leu Ala Pro Glu Ala Arg Gln Ala Ile
            2660                2665                2670

Lys Ser Leu Thr Glu Arg Leu Tyr Ile Gly Gly Pro Leu Thr Asn Ser
            2675                2680                2685

Lys Gly Gln Asn Cys Gly Tyr Arg Arg Cys Arg Ala Ser Gly Val Leu
            2690                2695                2700

Thr Thr Ser Cys Gly Asn Thr Leu Thr Cys Tyr Leu Lys Ala Ser Ala
2705                2710                2715                2720

Ala Cys Arg Ala Ala Lys Leu Gln Asp Cys Thr Met Leu Val Asn Gly
            2725                2730                2735

Asp Asp Leu Val Val Ile Cys Glu Ser Ala Gly Thr Gln Glu Asp Ala
            2740                2745                2750

Ala Ser Leu Arg Val Phe Thr Glu Ala Met Thr Arg Tyr Ser Ala Pro
            2755                2760                2765

Pro Gly Asp Pro Pro Gln Pro Glu Tyr Asp Leu Glu Leu Ile Thr Ser
            2770                2775                2780

Cys Ser Ser Asn Val Ser Val Ala His Asp Ala Ser Gly Lys Arg Val
2785                2790                2795                2800

Tyr Tyr Leu Thr Arg Asp Pro Thr Thr Pro Leu Ala Arg Ala Ala Trp
            2805                2810                2815

Glu Thr Ala Arg His Thr Pro Val Asn Ser Trp Leu Gly Asn Ile Ile
            2820                2825                2830

Met Tyr Ala Pro Thr Leu Trp Ala Arg Met Ile Leu Met Thr His Phe
            2835                2840                2845

Phe Ser Ile Leu Leu Ala Gln Glu Gln Leu Glu Lys Ala Leu Asp Cys
            2850                2855                2860

Gln Ile Tyr Gly Ala Cys Tyr Ser Ile Glu Pro Leu Asp Leu Pro Gln
2865                2870                2875                2880

Ile Ile Glu Arg Leu His Gly Leu Ser Ala Phe Ser Leu His Ser Tyr
            2885                2890                2895

Ser Pro Gly Glu Ile Asn Arg Val Ala Ser Cys Leu Arg Lys Leu Gly
            2900                2905                2910

Val Pro Pro Leu Arg Val Trp Arg His Arg Ala Arg Ser Val Arg Ala
            2915                2920                2925

Arg Leu Leu Ser Gln Gly Gly Arg Ala Ala Thr Cys Gly Lys Tyr Leu
            2930                2935                2940

Phe Asn Trp Ala Val Lys Thr Lys Leu Lys Leu Thr Pro Ile Pro Ala
2945                2950                2955                2960

Ala Ser Arg Leu Asp Leu Ser Gly Trp Phe Val Ala Gly Tyr Ser Gly
            2965                2970                2975

Gly Asp Ile Tyr His Ser Leu Ser Arg Ala Arg Pro Arg Trp Phe Met
            2980                2985                2990

Leu Cys Leu Leu Leu Leu Ser Val Gly Val Gly Ile Tyr Leu Leu Pro
            2995                3000                3005
```

Asn Arg
     3010

(2) INFORMATION FOR SEQ ID NO:15:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..90
        (D) OTHER INFORMATION: /note: "sequence = 474 - 563 of
            SEQ ID NO: 1"

(ix) FEATURE:
        (A) NAME/KEY: CDS
        (B) LOCATION: 1..90

(xi) SEQUENCE DESCRIPTION: SEQ ID NO:15:

```
GCG CCC AGG AAG ACT TCC GAG CGG TCG CAA CCT CGT GGA AGG CGA CAA        48
Ala Pro Arg Lys Thr Ser Glu Arg Ser Gln Pro Arg Gly Arg Arg Gln
 1               5                  10                  15

CCT ATC CCC AAG GCT CGC CGG CCC GAG GGC AGG ACC TGG GCT                90
Pro Ile Pro Lys Ala Arg Arg Pro Glu Gly Arg Thr Trp Ala
             20                  25                  30
```

(2) INFORMATION FOR SEQ ID NO:16:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO:16:

```
Ala Pro Arg Lys Thr Ser Glu Arg Ser Gln Pro Arg Gly Arg Arg Gln
 1               5                  10                  15

Pro Ile Pro Lys Ala Arg Arg Pro Glu Gly Arg Thr Trp Ala
             20                  25                  30
```

(2) INFORMATION FOR SEQ ID NO:17:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..228
        (D) OTHER INFORMATION: /note: "sequence = 678 - 905 of
            SEQ ID NO: 1"

(ix) FEATURE:
        (A) NAME/KEY: CDS
        (B) LOCATION: 1..228

(xi) SEQUENCE DESCRIPTION: SEQ ID NO:17:

```
TCG CGT AAT TTG GGT AAG GTC ATC GAT ACC CTC ACA TGC GGC TTC GCC        48
Ser Arg Asn Leu Gly Lys Val Ile Asp Thr Leu Thr Cys Gly Phe Ala
 1               5                  10                  15
```

```
GAT CTC ATG GGG TAC ATT CCG CTC GTC GGC GCC CCC CTG GGG GGC GCT      96
Asp Leu Met Gly Tyr Ile Pro Leu Val Gly Ala Pro Leu Gly Gly Ala
             20                  25                  30

GCC AGG GCC CTG GCA CAT GGT GTC CGG GTT CTG GAG GAC GGC GTG AAC     144
Ala Arg Ala Leu Ala His Gly Val Arg Val Leu Glu Asp Gly Val Asn
         35                  40                  45

TAT GCA ACA GGG AAT CTG CCC GGT TGC TCT TTT TCT ATC TTC CTC TTG     192
Tyr Ala Thr Gly Asn Leu Pro Gly Cys Ser Phe Ser Ile Phe Leu Leu
     50                  55                  60

GCT CTG CTG TCC TGC CTG ACC ACC CCA GCT TCC GCT                     228
Ala Leu Leu Ser Cys Leu Thr Thr Pro Ala Ser Ala
 65                  70                  75
```

(2) INFORMATION FOR SEQ ID NO:18:

(i) SEQUENCE CHARACTERISTICS:
        (A) LENGTH: 76 amino acids
        (B) TYPE: amino acid
        (D) TOPOLOGY: linear (ii) MOLECULE TYPE: protein (xi) SEQUENCE DESCRIPTION: SEQ ID NO:18:

```
Ser Arg Asn Leu Gly Lys Val Ile Asp Thr Leu Thr Cys Gly Phe Ala
 1               5                  10                  15

Asp Leu Met Gly Tyr Ile Pro Leu Val Gly Ala Pro Leu Gly Gly Ala
             20                  25                  30

Ala Arg Ala Leu Ala His Gly Val Arg Val Leu Glu Asp Gly Val Asn
         35                  40                  45

Tyr Ala Thr Gly Asn Leu Pro Gly Cys Ser Phe Ser Ile Phe Leu Leu
     50                  55                  60

Ala Leu Leu Ser Cys Leu Thr Thr Pro Ala Ser Ala
 65                  70                  75
```

(2) INFORMATION FOR SEQ ID NO:19:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..48
        (D) OTHER INFORMATION: /note: "sequence = 906 - 953 of
            SEQ ID NO: 1"

(ix) FEATURE:
        (A) NAME/KEY: CDS
        (B) LOCATION: 1..48

(xi) SEQUENCE DESCRIPTION: SEQ ID NO:19:

```
TAC GAA GTG CAC AAC GTG TCC GGG ATA TAT CAT GTC ACG AAC GAC TGC      48
Tyr Glu Val His Asn Val Ser Gly Ile Tyr His Val Thr Asn Asp Cys
 1               5                  10                  15
```

(2) INFORMATION FOR SEQ ID NO:20:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:20:

```
Tyr Glu Val His Asn Val Ser Gly Ile Tyr His Val Thr Asn Asp Cys
  1               5                  10                  15
```

(2) INFORMATION FOR SEQ ID NO:21:

(i) SEQUENCE CHARACTERISTICS:
        (A) LENGTH: 594 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..594
        (D) OTHER INFORMATION: /note: "sequence = 906 - 1499 of
            SEQ ID NO: 1"

(ix) FEATURE:
        (A) NAME/KEY: CDS
        (B) LOCATION: 1..594

(xi) SEQUENCE DESCRIPTION: SEQ ID NO:21:

```
TAC GAA GTG CAC AAC GTG TCC GGG ATA TAT CAT GTC ACG AAC GAC TGC         48
Tyr Glu Val His Asn Val Ser Gly Ile Tyr His Val Thr Asn Asp Cys
  1               5                  10                  15

TCC AAC GCA AGC ATT GTG TAT GAG GCA GCG GAC TTG ATC ATG CAT ACT         96
Ser Asn Ala Ser Ile Val Tyr Glu Ala Ala Asp Leu Ile Met His Thr
                 20                  25                  30

CCT GGG TGC GTG CCC TGC GTT CGG GAA GGC AAC TCC TCC CGC TGC TGG        144
Pro Gly Cys Val Pro Cys Val Arg Glu Gly Asn Ser Ser Arg Cys Trp
             35                  40                  45

GTA GCG CTC ACT CCC ACG CTC GCA GCC AGG AAC GTC ACC ATC CCC ACC        192
Val Ala Leu Thr Pro Thr Leu Ala Ala Arg Asn Val Thr Ile Pro Thr
         50                  55                  60

ACG ACG ATA CGA CGC CAC GTC GAT CTG CTC GTT GGG GCG GCT GCT TTC        240
Thr Thr Ile Arg Arg His Val Asp Leu Leu Val Gly Ala Ala Ala Phe
 65                  70                  75                  80

TGT TCC GCT ATG TAC GTG GGG GAC CTC TGC GGA TCT GTT TTC CTC GTC        288
Cys Ser Ala Met Tyr Val Gly Asp Leu Cys Gly Ser Val Phe Leu Val
                 85                  90                  95

TCT CAG CTG TTC ACC TTC TCG CCT CGC CGG CAT GTG ACA TTA CAG GAC        336
Ser Gln Leu Phe Thr Phe Ser Pro Arg Arg His Val Thr Leu Gln Asp
                100                 105                 110

TGT AAC TGC TCA ATT TAT CCC GGC CAT GTG TCG GGT CAC CGT ATG GCT        384
Cys Asn Cys Ser Ile Tyr Pro Gly His Val Ser Gly His Arg Met Ala
            115                 120                 125

TGG GAC ATG ATG ATG AAC TGG TCG CCC ACA ACA GCC CTA GTG GTG TCG        432
Trp Asp Met Met Met Asn Trp Ser Pro Thr Thr Ala Leu Val Val Ser
130                 135                 140

CAG TTA CTC CGG ATC CCA CAA GCC GTC GTG GAC ATG GTG GCG GGG GCC        480
Gln Leu Leu Arg Ile Pro Gln Ala Val Val Asp Met Val Ala Gly Ala
145                 150                 155                 160

CAC TGG GGA GTC CTG GCG GGC CTT GCC TAC TAT TCC ATG GCG GGG AAC        528
His Trp Gly Val Leu Ala Gly Leu Ala Tyr Tyr Ser Met Ala Gly Asn
                165                 170                 175

TGG GCT AAG GTT CTG ATT GTG ATG CTA CTT TTT GCT GGC GTT GAC GGG        576
Trp Ala Lys Val Leu Ile Val Met Leu Leu Phe Ala Gly Val Asp Gly
            180                 185                 190

GAT ACC CAC GTG ACA GGG                                                594
Asp Thr His Val Thr Gly
            195
```

(2) INFORMATION FOR SEQ ID NO:22:

(i) SEQUENCE CHARACTERISTICS:
        (A) LENGTH: 198 amino acids
        (B) TYPE: amino acid
        (D) TOPOLOGY: linear (ii) MOLECULE TYPE: protein (xi) SEQUENCE DESCRIPTION: SEQ ID NO:22:

```
Tyr Glu Val His Asn Val Ser Gly Ile Tyr His Val Thr Asn Asp Cys
 1               5                  10                  15

Ser Asn Ala Ser Ile Val Tyr Glu Ala Ala Asp Leu Ile Met His Thr
                20                  25                  30

Pro Gly Cys Val Pro Cys Val Arg Glu Gly Asn Ser Ser Arg Cys Trp
            35                  40                  45

Val Ala Leu Thr Pro Thr Leu Ala Ala Arg Asn Val Thr Ile Pro Thr
        50                  55                  60

Thr Thr Ile Arg Arg His Val Asp Leu Leu Val Gly Ala Ala Ala Phe
 65                  70                  75                  80

Cys Ser Ala Met Tyr Val Gly Asp Leu Cys Gly Ser Val Phe Leu Val
                85                  90                  95

Ser Gln Leu Phe Thr Phe Ser Pro Arg Arg His Val Thr Leu Gln Asp
                100                 105                 110

Cys Asn Cys Ser Ile Tyr Pro Gly His Val Ser Gly His Arg Met Ala
            115                 120                 125

Trp Asp Met Met Met Asn Trp Ser Pro Thr Thr Ala Leu Val Val Ser
        130                 135                 140

Gln Leu Leu Arg Ile Pro Gln Ala Val Val Asp Met Val Ala Gly Ala
145                 150                 155                 160

His Trp Gly Val Leu Ala Gly Leu Ala Tyr Tyr Ser Met Ala Gly Asn
                165                 170                 175

Trp Ala Lys Val Leu Ile Val Met Leu Leu Phe Ala Gly Val Asp Gly
                180                 185                 190

Asp Thr His Val Thr Gly
                195
```

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..27
        (D) OTHER INFORMATION: /note: "sequence = 1020 - 1046 of
            SEQ ID NO: 1"

(ix) FEATURE:
        (A) NAME/KEY: CDS
        (B) LOCATION: 1..27

(xi) SEQUENCE DESCRIPTION: SEQ ID NO:23:

```
GTT CGG GAA GGC AAC TCC TCC CGC TGC                          27
Val Arg Glu Gly Asn Ser Ser Arg Cys
 1               5
```

(2) INFORMATION FOR SEQ ID NO:24:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO:24:

Val Arg Glu Gly Asn Ser Ser Arg Cys
 1               5

(2) INFORMATION FOR SEQ ID NO:25:

(i) SEQUENCE CHARACTERISTICS:
            (A) LENGTH: 102 base pairs
            (B) TYPE: nucleic acid
            (C) STRANDEDNESS: single
            (D) TOPOLOGY: linear (ii) MOLECULE TYPE: cDNA from genomic RNA (ix) FEATURE:
            (A) NAME/KEY: misc_feature
            (B) LOCATION: 1..102
            (D) OTHER INFORMATION: /note: "sequence = 1020 - 1121 of
                SEQ ID NO: 1"

(ix) FEATURE:
            (A) NAME/KEY: CDS
            (B) LOCATION: 1..102

(xi) SEQUENCE DESCRIPTION: SEQ ID NO:25:

GTT CGG GAA GGC AAC TCC TCC CGC TGC TGG GTA GCG CTC ACT CCC ACG      48
Val Arg Glu Gly Asn Ser Ser Arg Cys Trp Val Ala Leu Thr Pro Thr
 1               5                  10                  15

CTC GCA GCC AGG AAC GTC ACC ATC CCC ACC ACG ACA ATA CGA CGC CAC      96
Leu Ala Ala Arg Asn Val Thr Ile Pro Thr Thr Thr Ile Arg Arg His
                20                  25                  30

GTC GAT                                                             102
Val Asp (2) INFORMATION FOR SEQ ID NO:26:

(i) SEQUENCE CHARACTERISTICS:
            (A) LENGTH: 34 amino acids
            (B) TYPE: amino acid
            (D) TOPOLOGY: linear (ii) MOLECULE TYPE: protein (xi) SEQUENCE DESCRIPTION: SEQ ID NO:26:

Val Arg Glu Gly Asn Ser Ser Arg Cys Trp Val Ala Leu Thr Pro Thr
 1               5                  10                  15

Leu Ala Ala Arg Asn Val Thr Ile Pro Thr Thr Thr Ile Arg Arg His
                20                  25                  30

Val Asp (2) INFORMATION FOR SEQ ID NO:27:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: cDNA from genomic RNA (ix) FEATURE:
            (A) NAME/KEY: misc_feature (B) LOCATION: 1..39
            (D) OTHER INFORMATION: /note: "sequence = 1194 - 1232 of
                  SEQ ID NO: 1"

(ix) FEATURE:
            (A) NAME/KEY: CDS
            (B) LOCATION: 1..39

(xi) SEQUENCE DESCRIPTION: SEQ ID NO:27:

TCT CAG CTG TTC ACC TTC TCG CCT CGC CGG CAT GTG ACA                    39
Ser Gln Leu Phe Thr Phe Ser Pro Arg Arg His Val Thr
 1               5                  10

(2) INFORMATION FOR SEQ ID NO:28:

(i) SEQUENCE CHARACTERISTICS:
            (A) LENGTH: 13 amino acids
            (B) TYPE: amino acid
            (D) TOPOLOGY: linear (ii) MOLECULE TYPE: protein (xi) SEQUENCE DESCRIPTION: SEQ ID NO:28:

Ser Gln Leu Phe Thr Phe Ser Pro Arg Arg His Val Thr
 1               5                  10

(2) INFORMATION FOR SEQ ID NO:29:

(i) SEQUENCE CHARACTERISTICS:
            (A) LENGTH: 114 base pairs
            (B) TYPE: nucleic acid
            (C) STRANDEDNESS: single
            (D) TOPOLOGY: linear (ii) MOLECULE TYPE: cDNA from genomic RNA (ix) FEATURE:
            (A) NAME/KEY: misc_feature
            (B) LOCATION: 1..114
            (D) OTHER INFORMATION: /note: "sequence = 1209 - 1322 of
                  SEQ ID NO: 1"

(ix) FEATURE:
            (A) NAME/KEY: CDS
            (B) LOCATION: 1..114

(xi) SEQUENCE DESCRIPTION: SEQ ID NO:29:

TTC TCG CCT CGC CGG CAT GTG ACA TTA CAG GAC TGT AAC TGC TCA ATT        48
Phe Ser Pro Arg Arg His Val Thr Leu Gln Asp Cys Asn Cys Ser Ile
 1               5                  10                  15

TAT CCC GGC CAT GTG TCG GGT CAC CGT ATG GCT TGG GAC ATG ATG ATG        96
Tyr Pro Gly His Val Ser Gly His Arg Met Ala Trp Asp Met Met Met
             20                  25                  30

AAC TGG TCG CCC ACA ACA                                               114
Asn Trp Ser Pro Thr Thr
         35

(2) INFORMATION FOR SEQ ID NO:30:

(i) SEQUENCE CHARACTERISTICS:
            (A) LENGTH: 38 amino acids
            (B) TYPE: amino acid
            (D) TOPOLOGY: linear (ii) MOLECULE TYPE: protein (xi) SEQUENCE DESCRIPTION: SEQ ID NO:30:

Phe Ser Pro Arg Arg His Val Thr Leu Gln Asp Cys Asn Cys Ser Ile
 1               5                  10                  15

Tyr Pro Gly His Val Ser Gly His Arg Met Ala Trp Asp Met Met Met

|         |         | 20      |         |         |         | 25      |         |         |         | 30      |         |      |
|---------|---------|---------|---------|---------|---------|---------|---------|---------|---------|---------|---------|------|

Asn Trp Ser Pro Thr Thr
          35

(2) INFORMATION FOR SEQ ID NO:31:

(i) SEQUENCE CHARACTERISTICS:
        (A) LENGTH: 7917 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: CDS
        (B) LOCATION: 1..7862

(ix) FEATURE:
        (A) NAME/KEY: misc_feature
        (B) LOCATION: 1..7916
        (D) OTHER INFORMATION: /note= "sequence = 1500 - 9416 of
            SEQ ID NO: 1"

(xi) SEQUENCE DESCRIPTION: SEQ ID NO:31:

```
GGG GCG CAA GCC AAA ACC ACC AAC AGG CTC GTG TCC ATG TTC GCA AGT        48
Gly Ala Gln Ala Lys Thr Thr Asn Arg Leu Val Ser Met Phe Ala Ser
 1               5                  10                  15

GGG CCG TCT CAG AAA ATC CAG CTT ATA AAC ACC AAT GGG AGT TGG CAC        96
Gly Pro Ser Gln Lys Ile Gln Leu Ile Asn Thr Asn Gly Ser Trp His
             20                  25                  30

ATC AAC AGG ACT GCC CTG AAC TGC AAT GAC TCT CTC CAG ACT GGG TTT       144
Ile Asn Arg Thr Ala Leu Asn Cys Asn Asp Ser Leu Gln Thr Gly Phe
         35                  40                  45

CTT GCC GCG CTG TTC TAC ACA CAT AGT TTC AAC TCG TCC GGG TGC CCA       192
Leu Ala Ala Leu Phe Tyr Thr His Ser Phe Asn Ser Ser Gly Cys Pro
     50                  55                  60

GAG CGC ATG GCC CAG TGC CGC ACC ATT GAC AAG TTC GAC CAG GGA TGG       240
Glu Arg Met Ala Gln Cys Arg Thr Ile Asp Lys Phe Asp Gln Gly Trp
 65                  70                  75                  80

GGT CCC ATT ACT TAT GCT GAG TCT AGC AGA TCA GAC CAG AGG CCA TAT       288
Gly Pro Ile Thr Tyr Ala Glu Ser Ser Arg Ser Asp Gln Arg Pro Tyr
                 85                  90                  95

TGC TGG CAC TAC CCA CCT CCA CAA TGT ACC ATC GTA CCT GCG TCG GAG       336
Cys Trp His Tyr Pro Pro Pro Gln Cys Thr Ile Val Pro Ala Ser Glu
            100                 105                 110

GTG TGC GGC CCA GTG TAC TGC TTC ACC CCA AGC CCT GTC GTC GTG GGG       384
Val Cys Gly Pro Val Tyr Cys Phe Thr Pro Ser Pro Val Val Val Gly
        115                 120                 125

ACG ACC GAT CGT TTC GGT GTC CCT ACG TAT AGA TGG GGG GAG AAC GAG       432
Thr Thr Asp Arg Phe Gly Val Pro Thr Tyr Arg Trp Gly Glu Asn Glu
    130                 135                 140

ACT GAC GTG CTG CTC CTC AAC AAC ACG CGG CCG CCG CAA GGC AAC TGG       480
Thr Asp Val Leu Leu Leu Asn Asn Thr Arg Pro Pro Gln Gly Asn Trp
145                 150                 155                 160

TTC GGC TGC ACA TGG ATG AAT AGC ACC GGG TTC ACC AAG ACA TGT GGG       528
Phe Gly Cys Thr Trp Met Asn Ser Thr Gly Phe Thr Lys Thr Cys Gly
                165                 170                 175

GGG CCC CCG TGT AAC ATC GGG GGG GTC GGC AAC AAC ACC CTG ACC TGC       576
Gly Pro Pro Cys Asn Ile Gly Gly Val Gly Asn Asn Thr Leu Thr Cys
            180                 185                 190

CCC ACG GAC TGC TTC CGG AAG CAC CCC GAG GCT ACC TAC ACA AAA TGT       624
Pro Thr Asp Cys Phe Arg Lys His Pro Glu Ala Thr Tyr Thr Lys Cys
        195                 200                 205
```

```
                                                              -continued

GGT TCG GGG CCT TGG CTG ACA CCT AGG TGC ATG GTT GAC TAT CCA TAC    672
Gly Ser Gly Pro Trp Leu Thr Pro Arg Cys Met Val Asp Tyr Pro Tyr
210             215                 220

AGG CTC TGG CAT TAC CCC TGC ACT GTT AAC TTT ACC ATC TTC AAG GTT    720
Arg Leu Trp His Tyr Pro Cys Thr Val Asn Phe Thr Ile Phe Lys Val
225             230                 235                 240

AGG ATG TAT GTG GGG GGG GTG GAG CAC AGG CTC AAT GCT GCA TGC AAT    768
Arg Met Tyr Val Gly Gly Val Glu His Arg Leu Asn Ala Ala Cys Asn
                245                 250                 255

TGG ACC CGA GGA GAG CGT TGT GAC TTG GAG GAC AGG GAT AGG CCG GAG    816
Trp Thr Arg Gly Glu Arg Cys Asp Leu Glu Asp Arg Asp Arg Pro Glu
            260                 265                 270

CTC AGC CCG CTG CTG CTG TCT ACA ACA GAG TGG CAG GTA CTG CCC TGT    864
Leu Ser Pro Leu Leu Leu Ser Thr Thr Glu Trp Gln Val Leu Pro Cys
        275                 280                 285

TCC TTC ACC ACC CTA CCA GCT CTG TCC ACT GGC TTG ATT CAC CTC CAT    912
Ser Phe Thr Thr Leu Pro Ala Leu Ser Thr Gly Leu Ile His Leu His
    290                 295                 300

CAG AAC ATC GTG GAC GTG CAA TAC CTA TAC GGT ATA GGG TCA GCG GTT    960
Gln Asn Ile Val Asp Val Gln Tyr Leu Tyr Gly Ile Gly Ser Ala Val
305                 310                 315                 320

GTC TCC TTT GCA ATC AAA TGG GAG TAT GTC CTG TTG CTT TTC CTT CTC    1008
Val Ser Phe Ala Ile Lys Trp Glu Tyr Val Leu Leu Leu Phe Leu Leu
                325                 330                 335

CTA GCG GAC GCA CGT GTC TGT GCC TGC TTG TGG ATG ATG CTG CTG ATA    1056
Leu Ala Asp Ala Arg Val Cys Ala Cys Leu Trp Met Met Leu Leu Ile
            340                 345                 350

GCC CAG GCC GAG GCC GCC TTG GAG AAC CTG GTG GTC CTC AAT TCG GCG    1104
Ala Gln Ala Glu Ala Ala Leu Glu Asn Leu Val Val Leu Asn Ser Ala
        355                 360                 365

TCT GTG GCC GGC GCA CAT GGC ATC CTC TCC TTC CTT GTG TTC TTC TGT    1152
Ser Val Ala Gly Ala His Gly Ile Leu Ser Phe Leu Val Phe Phe Cys
    370                 375                 380

GCC GCC TGG TAC ATC AAA GGC AGG CTG GTC CCT GGG GCG ACA TAT GCT    1200
Ala Ala Trp Tyr Ile Lys Gly Arg Leu Val Pro Gly Ala Thr Tyr Ala
385                 390                 395                 400

CTT TAT GGC GTG TGG CCG CTG CTC CTG CTC TTG CTG GCA TTA CCA CCG    1248
Leu Tyr Gly Val Trp Pro Leu Leu Leu Leu Leu Ala Leu Pro Pro
                405                 410                 415

CGA GCT TAC GCC ATG GAC CGG GAG ATG GCT GCA TCG TGC GGA GGC GCG    1296
Arg Ala Tyr Ala Met Asp Arg Glu Met Ala Ala Ser Cys Gly Gly Ala
            420                 425                 430

GTT TTT GTG GGT CTG GTA CTC CTG ACT TTG TCA CCA TAC TAC AAG GTG    1344
Val Phe Val Gly Leu Val Leu Leu Thr Leu Ser Pro Tyr Tyr Lys Val
        435                 440                 445

TTC CTC GCT AGG CTC ATA TGG TGG TTA CAA TAT TTT ACC ACC AGA GCC    1392
Phe Leu Ala Arg Leu Ile Trp Trp Leu Gln Tyr Phe Thr Thr Arg Ala
    450                 455                 460

GAG GCG GAC TTA CAT GTG TGG ATC CCC CCC CTC AAC GCT CGG GGA GGC    1440
Glu Ala Asp Leu His Val Trp Ile Pro Pro Leu Asn Ala Arg Gly Gly
465                 470                 475                 480

CGC GAT GCC ATC ATC CTC CTC ATG TGC GCA GTC CAT CCA GAG CTA ATC    1488
Arg Asp Ala Ile Ile Leu Leu Met Cys Ala Val His Pro Glu Leu Ile
                485                 490                 495

TTT GAC ATC ACC AAA CTT CTA ATT GCC ATA CTC GGT CCG CTC ATG GTG    1536
Phe Asp Ile Thr Lys Leu Leu Ile Ala Ile Leu Gly Pro Leu Met Val
            500                 505                 510

CTC CAA GCT GGC ATA ACC AGA GTG CCG TAC TTC GTG CGC GCT CAA GGG    1584
Leu Gln Ala Gly Ile Thr Arg Val Pro Tyr Phe Val Arg Ala Gln Gly
        515                 520                 525
```

```
CTC ATT CAT GCA TGC ATG TTA GTG CGG AAG GTC GCT GGG GGT CAT TAT     1632
Leu Ile His Ala Cys Met Leu Val Arg Lys Val Ala Gly Gly His Tyr
        530                 535                 540

GTC CAA ATG GCC TTC ATG AAG CTG GGC GCG CTG ACA GGC ACG TAC ATT     1680
Val Gln Met Ala Phe Met Lys Leu Gly Ala Leu Thr Gly Thr Tyr Ile
545                 550                 555                 560

TAC AAC CAT CTT ACC CCG CTA CGG GAT TGG CCA CGC GCG GGC CTA CGA     1728
Tyr Asn His Leu Thr Pro Leu Arg Asp Trp Pro Arg Ala Gly Leu Arg
                565                 570                 575

GAC CTT GCG GTG GCA GTG GAG CCC GTC GTC TTC TCC GAC ATG GAG ACC     1776
Asp Leu Ala Val Ala Val Glu Pro Val Val Phe Ser Asp Met Glu Thr
            580                 585                 590

AAG ATC ATC ACC TGG GGA GCA GAC ACC GCG GCG TGT GGG GAC ATC ATC     1824
Lys Ile Ile Thr Trp Gly Ala Asp Thr Ala Ala Cys Gly Asp Ile Ile
        595                 600                 605

TTG GGT CTG CCC GTC TCC GCC CGA AGG GGA AAG GAG ATA CTC CTG GGC     1872
Leu Gly Leu Pro Val Ser Ala Arg Arg Gly Lys Glu Ile Leu Leu Gly
610                 615                 620

CCG GCC GAT AGT CTT GAA GGG CGG GGG TTG CGA CTC CTC GCG CCC ATC     1920
Pro Ala Asp Ser Leu Glu Gly Arg Gly Leu Arg Leu Leu Ala Pro Ile
625                 630                 635                 640

ACG GCC TAC TCC CAA CAG ACG CGG GGC CTA CTT GGT TGC ATC ATC ACT     1968
Thr Ala Tyr Ser Gln Gln Thr Arg Gly Leu Leu Gly Cys Ile Ile Thr
                645                 650                 655

AGC CTT ACA GGC CGG GAC AAG AAC CAG GTC GAG GGA GAG GTT CAG GTG     2016
Ser Leu Thr Gly Arg Asp Lys Asn Gln Val Glu Gly Glu Val Gln Val
            660                 665                 670

GTT TCC ACC GCA ACA CAA TCC TTC CTG GCG ACC TGC GTC AAC GGC GTG     2064
Val Ser Thr Ala Thr Gln Ser Phe Leu Ala Thr Cys Val Asn Gly Val
        675                 680                 685

TGT TGG ACC GTT TAC CAT GGT GCT GGC TCA AAG ACC TTA GCC GCG CCA     2112
Cys Trp Thr Val Tyr His Gly Ala Gly Ser Lys Thr Leu Ala Ala Pro
690                 695                 700

AAG GGG CCA ATC ACC CAG ATG TAC ACT AAT GTG GAC CAG GAC CTC GTC     2160
Lys Gly Pro Ile Thr Gln Met Tyr Thr Asn Val Asp Gln Asp Leu Val
705                 710                 715                 720

GGC TGG CCC AAG CCC CCC GGG GCG CGT TCC TTG ACA CCA TGC ACC TGT     2208
Gly Trp Pro Lys Pro Pro Gly Ala Arg Ser Leu Thr Pro Cys Thr Cys
                725                 730                 735

GGC AGC TCA GAC CTT TAC TTG GTC ACG AGA CAT GCT GAC GTC ATT CCG     2256
Gly Ser Ser Asp Leu Tyr Leu Val Thr Arg His Ala Asp Val Ile Pro
            740                 745                 750

GTG CGC CGG CGG GGC GAC AGT AGG GGG AGC CTG CTC TCC CCC AGG CCT     2304
Val Arg Arg Arg Gly Asp Ser Arg Gly Ser Leu Leu Ser Pro Arg Pro
        755                 760                 765

GTC TCC TAC TTG AAG GGC TCT TCG GGT GGT CCA CTG CTC TGC CCC TTC     2352
Val Ser Tyr Leu Lys Gly Ser Ser Gly Gly Pro Leu Leu Cys Pro Phe
770                 775                 780

GGG CAC GCT GTG GGC ATC TTC CGG GCT GCC GTA TGC ACC CGG GGG GTT     2400
Gly His Ala Val Gly Ile Phe Arg Ala Ala Val Cys Thr Arg Gly Val
785                 790                 795                 800

GCG AAG GCG GTG GAC TTT GTG CCC GTA GAG TCC ATG GAA ACT ACT ATG     2448
Ala Lys Ala Val Asp Phe Val Pro Val Glu Ser Met Glu Thr Thr Met
                805                 810                 815

CGG TCT CCG GTC TTC ACG GAC AAC TCA TCC CCC CCG GCC GTA CCG CAG     2496
Arg Ser Pro Val Phe Thr Asp Asn Ser Ser Pro Pro Ala Val Pro Gln
            820                 825                 830

TCA TTT CAA GTG GCC CAC CTA CAC GCT CCC ACT GGC AGC GGC AAG AGT     2544
Ser Phe Gln Val Ala His Leu His Ala Pro Thr Gly Ser Gly Lys Ser
        835                 840                 845
```

| | | |
|---|---|---|
| ACT AAA GTG CCG GCT GCA TAT GCA GCC CAA GGG TAC AAG GTG CTC GTC<br>Thr Lys Val Pro Ala Ala Tyr Ala Ala Gln Gly Tyr Lys Val Leu Val<br>850                                855                              860 | 2592 |
| CTC AAT CCG TCC GTT GCC GCT ACC TTA GGG TTT GGG GCG TAT ATG TCT<br>Leu Asn Pro Ser Val Ala Ala Thr Leu Gly Phe Gly Ala Tyr Met Ser<br>865                       870                             875                       880 | 2640 |
| AAG GCA CAC GGT ATT GAC CCC AAC ATC AGA ACT GGG GTA AGG ACC ATT<br>Lys Ala His Gly Ile Asp Pro Asn Ile Arg Thr Gly Val Arg Thr Ile<br>                          885                               890                             895 | 2688 |
| ACC ACA GGC GCC CCC GTC ACA TAC TCT ACC TAT GGC AAG TTT CTT GCC<br>Thr Thr Gly Ala Pro Val Thr Tyr Ser Thr Tyr Gly Lys Phe Leu Ala<br>                  900                             905                           910 | 2736 |
| GAT GGT GGT TGC TCT GGG GGC GCT TAT GAC ATC ATA ATA TGT GAT GAG<br>Asp Gly Gly Cys Ser Gly Gly Ala Tyr Asp Ile Ile Ile Cys Asp Glu<br>                915                           920                           925 | 2784 |
| TGC CAT TCA ACT GAC TCG ACT ACA ATC TTG GGC ATC GGC ACA GTC CTG<br>Cys His Ser Thr Asp Ser Thr Thr Ile Leu Gly Ile Gly Thr Val Leu<br>930                                935                             940 | 2832 |
| GAC CAA GCG GAG ACG GCT GGA GCG CGG CTT GTC GTG CTC GCC ACC GCT<br>Asp Gln Ala Glu Thr Ala Gly Ala Arg Leu Val Val Leu Ala Thr Ala<br>945                                950                            955                      960 | 2880 |
| ACG CCT CCG GGA TCG GTC ACC GTG CCA CAC CCA AAC ATC GAG GAG GTG<br>Thr Pro Pro Gly Ser Val Thr Val Pro His Pro Asn Ile Glu Glu Val<br>                965                           970                           975 | 2928 |
| GCC CTG TCT AAT ACT GGA GAG ATC CCC TTC TAT GGC AAA GCC ATC CCC<br>Ala Leu Ser Asn Thr Gly Glu Ile Pro Phe Tyr Gly Lys Ala Ile Pro<br>                980                           985                           990 | 2976 |
| ATT GAA GCC ATC AGG GGG GGA AGG CAT CTC ATT TTC TGT CAT TCC AAG<br>Ile Glu Ala Ile Arg Gly Gly Arg His Leu Ile Phe Cys His Ser Lys<br>                  995                       1000                        1005 | 3024 |
| AAG AAG TGC GAC GAG CTC GCC GCA AAG CTG TCA GGC CTC GGA ATC AAC<br>Lys Lys Cys Asp Glu Leu Ala Ala Lys Leu Ser Gly Leu Gly Ile Asn<br>1010                             1015                           1020 | 3072 |
| GCT GTG GCG TAT TAC CGG GGG CTC GAT GTG TCC GTC ATA CCA ACT ATC<br>Ala Val Ala Tyr Tyr Arg Gly Leu Asp Val Ser Val Ile Pro Thr Ile<br>1025                         1030                           1035                     1040 | 3120 |
| GGA GAC GTC GTT GTC GTG GCA ACA GAC GCT CTG ATG ACG GGC TAT ACG<br>Gly Asp Val Val Val Ala Thr Asp Ala Leu Met Thr Gly Tyr Thr<br>                          1045                           1050                     1055 | 3168 |
| GGC GAC TTT GAC TCA GTG ATC GAC TGT AAC ACA TGT GTC ACC CAG ACA<br>Gly Asp Phe Asp Ser Val Ile Asp Cys Asn Thr Cys Val Thr Gln Thr<br>                   1060                         1065                           1070 | 3216 |
| GTC GAC TTC AGC TTG GAT CCC ACC TTC ACC ATT GAG ACG ACG ACC GTG<br>Val Asp Phe Ser Leu Asp Pro Thr Phe Thr Ile Glu Thr Thr Thr Val<br>             1075                         1080                         1085 | 3264 |
| CCT CAA GAC GCA GTG TCG CGC TCG CAG CGG CGG GGT AGG ACT GGC AGG<br>Pro Gln Asp Ala Val Ser Arg Ser Gln Arg Arg Gly Arg Thr Gly Arg<br>          1090                         1095                           1100 | 3312 |
| GGT AGG AGA GGC ATC TAC AGG TTT GTG ACT CCG GGA GAA CGG CCC TCG<br>Gly Arg Arg Gly Ile Tyr Arg Phe Val Thr Pro Gly Glu Arg Pro Ser<br>1105                       1110                        1115                     1120 | 3360 |
| GGC ATG TTC GAT TCC TCG GTC CTG TGT GAG TGC TAT GAC GCG GGC TGT<br>Gly Met Phe Asp Ser Ser Val Leu Cys Glu Cys Tyr Asp Ala Gly Cys<br>             1125                         1130                       1135 | 3408 |
| GCT TGG TAC GAG CTC ACC CCG GCC GAG ACC TCG GTT AGG TTG CGG GCC<br>Ala Trp Tyr Glu Leu Thr Pro Ala Glu Thr Ser Val Arg Leu Arg Ala<br>                 1140                         1145                     1150 | 3456 |
| TAC CTG AAC ACA CCA GGG TTG CCC GTT TGC CAG GAC CAC CTG GAG TTC<br>Tyr Leu Asn Thr Pro Gly Leu Pro Val Cys Gln Asp His Leu Glu Phe<br>                   1155                         1160                           1165 | 3504 |

-continued

| | | |
|---|---|---|
| TGG GAG AGT GTC TTC ACA GGC CTC ACC CAT ATA GAT GCA CAC TTC TTG<br>Trp Glu Ser Val Phe Thr Gly Leu Thr His Ile Asp Ala His Phe Leu<br>1170                          1175                       1180 | 3552 |
| TCC CAG ACC AAG CAG GCA GGA GAC AAC TTC CCC TAC CTG GTA GCA TAC<br>Ser Gln Thr Lys Gln Ala Gly Asp Asn Phe Pro Tyr Leu Val Ala Tyr<br>1185                          1190                       1195                       1200 | 3600 |
| CAA GCC ACG GTG TGC GCC AGG GCT CAG GCC CCA CCT CCA TCA TGG GAT<br>Gln Ala Thr Val Cys Ala Arg Ala Gln Ala Pro Pro Pro Ser Trp Asp<br>                   1205                       1210                       1215 | 3648 |
| CAA ATG TGG AAG TGT CTC ATA CGG CTG AAA CCT ACG CTG CAC GGG CCA<br>Gln Met Trp Lys Cys Leu Ile Arg Leu Lys Pro Thr Leu His Gly Pro<br>                1220                       1225                       1230 | 3696 |
| ACA CCC TTG CTG TAC AGG CTG GGA GCC GTC CAG AAT GAG GTC ACC CTC<br>Thr Pro Leu Leu Tyr Arg Leu Gly Ala Val Gln Asn Glu Val Thr Leu<br>                   1235                       1240                       1245 | 3744 |
| ACC CAC CCC ATA ACC AAA TAC ATC ATG GCA TGC ATG TCG GCT GAC CTG<br>Thr His Pro Ile Thr Lys Tyr Ile Met Ala Cys Met Ser Ala Asp Leu<br>1250                          1255                       1260 | 3792 |
| GAG GTC GTC ACT AGC ACC TGG GTG CTG GTG GGC GGA GTC CTT GCA GCT<br>Glu Val Val Thr Ser Thr Trp Val Leu Val Gly Gly Val Leu Ala Ala<br>1265                          1270                       1275                       1280 | 3840 |
| CTG GCC GCG TAT TGC CTG ACA ACA GGC AGT GTG GTC ATT GTG GGT AGG<br>Leu Ala Ala Tyr Cys Leu Thr Thr Gly Ser Val Val Ile Val Gly Arg<br>                   1285                       1290                       1295 | 3888 |
| ATT ATC TTG TCC GGG AGG CCG GCC ATT GTT CCC GAC AGG GAG CTT CTC<br>Ile Ile Leu Ser Gly Arg Pro Ala Ile Val Pro Asp Arg Glu Leu Leu<br>                1300                       1305                       1310 | 3936 |
| TAC CAG GAG TTC GAT GAA ATG GAA GAG TGC GCC TCG CAC CTC CCT TAC<br>Tyr Gln Glu Phe Asp Glu Met Glu Glu Cys Ala Ser His Leu Pro Tyr<br>                   1315                       1320                       1325 | 3984 |
| ATC GAG CAG GGA ATG CAG CTC GCC GAG CAA TTC AAG CAG AAA GCG CTC<br>Ile Glu Gln Gly Met Gln Leu Ala Glu Gln Phe Lys Gln Lys Ala Leu<br>1330                          1335                       1340 | 4032 |
| GGG TTA CTG CAA ACA GCC ACC AAA CAA GCG GAG GCT GCT GCT CCC GTG<br>Gly Leu Leu Gln Thr Ala Thr Lys Gln Ala Glu Ala Ala Ala Pro Val<br>1345                          1350                       1355                       1360 | 4080 |
| GTG GAG TCC AAG TGG CGA GCC CTT GAG ACA TTC TGG GCG AAG CAC ATG<br>Val Glu Ser Lys Trp Arg Ala Leu Glu Thr Phe Trp Ala Lys His Met<br>                   1365                       1370                       1375 | 4128 |
| TGG AAT TTC ATC AGC GGG ATA CAG TAC TTA GCA GGC TTA TCC ACT CTG<br>Trp Asn Phe Ile Ser Gly Ile Gln Tyr Leu Ala Gly Leu Ser Thr Leu<br>                1380                       1385                       1390 | 4176 |
| CCT GGG AAC CCC GCA ATA GCA TCA TTG ATG GCA TTC ACA GCC TCT ATC<br>Pro Gly Asn Pro Ala Ile Ala Ser Leu Met Ala Phe Thr Ala Ser Ile<br>                   1395                       1400                       1405 | 4224 |
| ACC AGC CCG CTC ACC ACC CAA AGT ACC CTC CTG TTT AAC ATC TTG GGG<br>Thr Ser Pro Leu Thr Thr Gln Ser Thr Leu Leu Phe Asn Ile Leu Gly<br>1410                          1415                       1420 | 4272 |
| GGG TGG GTG GCT GCC CAA CTC GCC CCC CCC AGC GCC GCT TCG GCT TTC<br>Gly Trp Val Ala Ala Gln Leu Ala Pro Pro Ser Ala Ala Ser Ala Phe<br>1425                          1430                       1435                       1440 | 4320 |
| GTG GGC GCC GGC ATC GCC GGT GCG GCT GTT GGC AGC ATA GGC CTT GGG<br>Val Gly Ala Gly Ile Ala Gly Ala Ala Val Gly Ser Ile Gly Leu Gly<br>                   1445                       1450                       1455 | 4368 |
| AAG GTG CTT GTG GAC ATT CTG GCG GGT TAT GGA GCA GGA GTG GCC GGC<br>Lys Val Leu Val Asp Ile Leu Ala Gly Tyr Gly Ala Gly Val Ala Gly<br>                1460                       1465                       1470 | 4416 |
| GCG CTC GTG GCC TTT AAG GTC ATG AGC GGC GAG ATG CCC TCC ACC GAG<br>Ala Leu Val Ala Phe Lys Val Met Ser Gly Glu Met Pro Ser Thr Glu<br>                   1475                       1480                       1485 | 4464 |

-continued

```
GAC CTG GTC AAT CTA CTT CCT GCC ATC CTC TCT CCT GGC GCC CTG GTC    4512
Asp Leu Val Asn Leu Leu Pro Ala Ile Leu Ser Pro Gly Ala Leu Val
        1490                1495                1500

GTC GGG GTC GTG TGT GCA GCA ATA CTG CGT CGA CAC GTG GGT CCG GGA    4560
Val Gly Val Val Cys Ala Ala Ile Leu Arg Arg His Val Gly Pro Gly
1505                1510                1515                1520

GAG GGG GCT GTG CAG TGG ATG AAC CGG CTG ATA GCG TTC GCC TCG CGG    4608
Glu Gly Ala Val Gln Trp Met Asn Arg Leu Ile Ala Phe Ala Ser Arg
                1525                1530                1535

GGT AAT CAT GTT TCC CCC ACG CAC TAT GTG CCT GAG AGC GAC GCC GCA    4656
Gly Asn His Val Ser Pro Thr His Tyr Val Pro Glu Ser Asp Ala Ala
                    1540                1545                1550

GCG CGT GTT ACT CAG ATC CTC TCC AGC CTT ACC ATC ACT CAG CTG CTG    4704
Ala Arg Val Thr Gln Ile Leu Ser Ser Leu Thr Ile Thr Gln Leu Leu
        1555                1560                1565

AAA AGG CTC CAC CAG TGG ATT AAT GAA GAC TGC TCC ACA CCG TGT TCC    4752
Lys Arg Leu His Gln Trp Ile Asn Glu Asp Cys Ser Thr Pro Cys Ser
        1570                1575                1580

GGC TCG TGG CTA AGG GAT GTT TGG GAC TGG ATA TGC ACG GTG TTG ACT    4800
Gly Ser Trp Leu Arg Asp Val Trp Asp Trp Ile Cys Thr Val Leu Thr
1585                1590                1595                1600

GAC TTC AAG ACC TGG CTC CAG TCC AAG CTC CTG CCG CAG CTA CCT GGA    4848
Asp Phe Lys Thr Trp Leu Gln Ser Lys Leu Leu Pro Gln Leu Pro Gly
                1605                1610                1615

GTC CCT TTT TTC TCG TGC CAA CGC GGG TAC AAG GGA GTC TGG CGG GGA    4896
Val Pro Phe Phe Ser Cys Gln Arg Gly Tyr Lys Gly Val Trp Arg Gly
                    1620                1625                1630

GAC GGC ATC ATG CAA ACC ACC TGC CCA TGT GGA GCA CAG ATC ACC GGA    4944
Asp Gly Ile Met Gln Thr Thr Cys Pro Cys Gly Ala Gln Ile Thr Gly
        1635                1640                1645

CAT GTC AAA AAC GGT TCC ATG AGG ATC GTC GGG CCT AAG ACC TGC AGC    4992
His Val Lys Asn Gly Ser Met Arg Ile Val Gly Pro Lys Thr Cys Ser
        1650                1655                1660

AAC ACG TGG CAT GGA ACA TTC CCC ATC AAC GCA TAC ACC ACG GGC CCC    5040
Asn Thr Trp His Gly Thr Phe Pro Ile Asn Ala Tyr Thr Thr Gly Pro
1665                1670                1675                1680

TGC ACA CCC TCT CCA GCG CCA AAC TAT TCT AGG GCG CTG TGG CGG GTG    5088
Cys Thr Pro Ser Pro Ala Pro Asn Tyr Ser Arg Ala Leu Trp Arg Val
                1685                1690                1695

GCC GCT GAG GAG TAC GTG GAG GTC ACG CGG GTG GGG GAT TTC CAC TAC    5136
Ala Ala Glu Glu Tyr Val Glu Val Thr Arg Val Gly Asp Phe His Tyr
                1700                1705                1710

GTG ACG GGC ATG ACC ACT GAC AAC GTA AAG TGC CCA TGC CAG GTT CCG    5184
Val Thr Gly Met Thr Thr Asp Asn Val Lys Cys Pro Cys Gln Val Pro
        1715                1720                1725

GCT CCT GAA TTC TTC TCG GAG GTG GAC GGA GTG CGG TTG CAC AGG TAC    5232
Ala Pro Glu Phe Phe Ser Glu Val Asp Gly Val Arg Leu His Arg Tyr
        1730                1735                1740

GCT CCG GCG TGC AGG CCT CTC CTA CGG GAG GAG GTT ACA TTC CAG GTC    5280
Ala Pro Ala Cys Arg Pro Leu Leu Arg Glu Glu Val Thr Phe Gln Val
1745                1750                1755                1760

GGG CTC AAC CAA TAC CTG GTT GGG TCA CAG CTA CCA TGC GAG CCC GAA    5328
Gly Leu Asn Gln Tyr Leu Val Gly Ser Gln Leu Pro Cys Glu Pro Glu
                1765                1770                1775

CCG GAT GTA GCA GTG CTC ACT TCC ATG CTC ACC GAC CCC TCC CAC ATC    5376
Pro Asp Val Ala Val Leu Thr Ser Met Leu Thr Asp Pro Ser His Ile
                    1780                1785                1790

ACA GCA GAA ACG GCT AAG CGT AGG TTG GCC AGG GGG TCT CCC CCC TCC    5424
Thr Ala Glu Thr Ala Lys Arg Arg Leu Ala Arg Gly Ser Pro Pro Ser
        1795                1800                1805
```

-continued

| | | |
|---|---|---|
| TTG GCC AGC TCT TCA GCT AGC CAG TTG TCT GCG CCT TCC TTG AAG GCG<br>Leu Ala Ser Ser Ser Ala Ser Gln Leu Ser Ala Pro Ser Leu Lys Ala<br>1810                       1815                   1820 | 5472 |
| ACA TGC ACT ACC CAC CAT GTC TCT CCG GAC GCT GAC CTC ATC GAG GCC<br>Thr Cys Thr Thr His His Val Ser Pro Asp Ala Asp Leu Ile Glu Ala<br>1825                  1830                 1835                  1840 | 5520 |
| AAC CTC CTG TGG CGG CAG GAG ATG GGC GGG AAC ATC ACC CGC GTG GAG<br>Asn Leu Leu Trp Arg Gln Glu Met Gly Gly Asn Ile Thr Arg Val Glu<br>                1845                  1850                  1855 | 5568 |
| TCG GAG AAC AAG GTG GTA GTC CTG GAC TCT TTC GAC CCG CTT CGA GCG<br>Ser Glu Asn Lys Val Val Val Leu Asp Ser Phe Asp Pro Leu Arg Ala<br>                1860                  1865                  1870 | 5616 |
| GAG GAG GAT GAG AGG GAA GTA TCC GTT CCG GCG GAG ATC CTG CGG AAA<br>Glu Glu Asp Glu Arg Glu Val Ser Val Pro Ala Glu Ile Leu Arg Lys<br>1875                       1880                   1885 | 5664 |
| TCC AAG AAG TTC CCC GCA GCG ATG CCC ATC TGG GCG CGC CCG GAT TAC<br>Ser Lys Lys Phe Pro Ala Ala Met Pro Ile Trp Ala Arg Pro Asp Tyr<br>       1890                  1895                  1900 | 5712 |
| AAC CCT CCA CTG TTA GAG TCC TGG AAG GAC CCG GAC TAC GTC CCT CCG<br>Asn Pro Pro Leu Leu Glu Ser Trp Lys Asp Pro Asp Tyr Val Pro Pro<br>1905                       1910                   1915                  1920 | 5760 |
| GTG GTG CAC GGG TGC CCG TTG CCA CCT ATC AAG GCC CCT CCA ATA CCA<br>Val Val His Gly Cys Pro Leu Pro Pro Ile Lys Ala Pro Pro Ile Pro<br>                1925                  1930                  1935 | 5808 |
| CCT CCA CGG AGA AAG AGG ACG GTT GTC CTA ACA GAG TCC TCC GTG TCT<br>Pro Pro Arg Arg Lys Arg Thr Val Val Leu Thr Glu Ser Ser Val Ser<br>                1940                  1945                  1950 | 5856 |
| TCT GCC TTA GCG GAG CTC GCT ACT AAG ACC TTC GGC AGC TCC GAA TCA<br>Ser Ala Leu Ala Glu Leu Ala Thr Lys Thr Phe Gly Ser Ser Glu Ser<br>                1955                  1960                  1965 | 5904 |
| TCG GCC GTC GAC AGC GGC ACG GCG ACC GCC CTT CCT GAC CAG GCC TCC<br>Ser Ala Val Asp Ser Gly Thr Ala Thr Ala Leu Pro Asp Gln Ala Ser<br>1970                       1975                   1980 | 5952 |
| GAC GAC GGT GAC AAA GGA TCC GAC GTT GAG TCG TAC TCC TCC ATG CCC<br>Asp Asp Gly Asp Lys Gly Ser Asp Val Glu Ser Tyr Ser Ser Met Pro<br>1985                       1990                   1995                  2000 | 6000 |
| CCC CTT GAG GGG GAA CCG GGG GAC CCC GAT CTC AGT GAC GGG TCT TGG<br>Pro Leu Glu Gly Glu Pro Gly Asp Pro Asp Leu Ser Asp Gly Ser Trp<br>                2005                  2010                  2015 | 6048 |
| TCT ACC GTG AGC GAG GAA GCT AGT GAG GAT GTC GTC TGC TGC TCA ATG<br>Ser Thr Val Ser Glu Glu Ala Ser Glu Asp Val Val Cys Cys Ser Met<br>2020                       2025                   2030 | 6096 |
| TCC TAC ACA TGG ACA GGC GCC TTG ATC ACG CCA TGC GCT GCG GAG GAA<br>Ser Tyr Thr Trp Thr Gly Ala Leu Ile Thr Pro Cys Ala Ala Glu Glu<br>       2035                  2040                  2045 | 6144 |
| AGC AAG CTG CCC ATC AAC GCG TTG AGC AAC TCT TTG CTG CGC CAC CAT<br>Ser Lys Leu Pro Ile Asn Ala Leu Ser Asn Ser Leu Leu Arg His His<br>                2050                  2055                  2060 | 6192 |
| AAC ATG GTT TAT GCC ACA ACA TCT CGC AGC GCA GGC CTG CGG CAG AAG<br>Asn Met Val Tyr Ala Thr Thr Ser Arg Ser Ala Gly Leu Arg Gln Lys<br>2065                       2070                   2075                  2080 | 6240 |
| AAG GTC ACC TTT GAC AGA CTG CAA GTC CTG GAC GAC CAC TAC CGG GAC<br>Lys Val Thr Phe Asp Arg Leu Gln Val Leu Asp Asp His Tyr Arg Asp<br>                2085                  2090                  2095 | 6288 |
| GTG CTC AAG GAG ATG AAG GCG AAG GCG TCC ACA GTT AAG GCT AAA CTC<br>Val Leu Lys Glu Met Lys Ala Lys Ala Ser Thr Val Lys Ala Lys Leu<br>2100                       2105                   2110 | 6336 |
| CTA TCC GTA GAG GAA GCC TGC AAG CTG ACG CCC CCA CAT TCG GCC AAA<br>Leu Ser Val Glu Glu Ala Cys Lys Leu Thr Pro Pro His Ser Ala Lys<br>                2115                  2120                  2125 | 6384 |

| | | |
|---|---|---|
| TCC AAG TTT GGC TAT GGG GCA AAG GAC GTC CGG AAC CTA TCC AGC AAG<br>Ser Lys Phe Gly Tyr Gly Ala Lys Asp Val Arg Asn Leu Ser Ser Lys<br>            2130                          2135                         2140 | 6432 |
| GCC GTT AAC CAC ATC CAC TCC GTG TGG AAG GAC TTG CTG GAA GAC ACT<br>Ala Val Asn His Ile His Ser Val Trp Lys Asp Leu Leu Glu Asp Thr<br>2145                        2150                        2155                        2160 | 6480 |
| GTG ACA CCA ATT GAC ACC ACC ATC ATG GCA AAA AAT GAG GTT TTC TGT<br>Val Thr Pro Ile Asp Thr Thr Ile Met Ala Lys Asn Glu Val Phe Cys<br>            2165                          2170                         2175 | 6528 |
| GTC CAA CCA GAG AAA GGA GGC CGT AAG CCA GCC CGC CTT ATC GTA TTC<br>Val Gln Pro Glu Lys Gly Gly Arg Lys Pro Ala Arg Leu Ile Val Phe<br>2180                        2185                        2190 | 6576 |
| CCA GAT CTG GGA GTC CGT GTA TGC GAG AAG ATG GCC CTC TAT GAT GTG<br>Pro Asp Leu Gly Val Arg Val Cys Glu Lys Met Ala Leu Tyr Asp Val<br>            2195                          2200                         2205 | 6624 |
| GTC TCC ACC CTT CCT CAG GTC GTG ATG GGC TCC TCA TAC GGA TTC CAG<br>Val Ser Thr Leu Pro Gln Val Val Met Gly Ser Ser Tyr Gly Phe Gln<br>2210                        2215                        2220 | 6672 |
| TAC TCT CCT GGG CAG CGA GTC GAG TTC CTG GTG AAT ACC TGG AAA TCA<br>Tyr Ser Pro Gly Gln Arg Val Glu Phe Leu Val Asn Thr Trp Lys Ser<br>2225                        2230                        2235                        2240 | 6720 |
| AAG AAA AAC CCC ATG GGC TTT TCA TAT GAC ACT CGC TGT TTC GAC TCA<br>Lys Lys Asn Pro Met Gly Phe Ser Tyr Asp Thr Arg Cys Phe Asp Ser<br>                        2245                        2250                        2255 | 6768 |
| ACG GTC ACC GAG AAC GAC ATC CGT GTT GAG GAG TCA ATT TAC CAA TGT<br>Thr Val Thr Glu Asn Asp Ile Arg Val Glu Glu Ser Ile Tyr Gln Cys<br>            2260                          2265                         2270 | 6816 |
| TGT GAC TTG GCC CCC GAA GCC AGA CAG GCC ATA AAA TCG CTC ACA GAG<br>Cys Asp Leu Ala Pro Glu Ala Arg Gln Ala Ile Lys Ser Leu Thr Glu<br>2275                        2280                        2285 | 6864 |
| CGG CTT TAT ATC GGG GGT CCT CTG ACT AAT TCA AAA GGG CAG AAC TGC<br>Arg Leu Tyr Ile Gly Gly Pro Leu Thr Asn Ser Lys Gly Gln Asn Cys<br>2290                        2295                        2300 | 6912 |
| GGT TAT CGC CGG TGC CGC GCG AGC GGC GTG CTG ACG ACT AGC TGC GGT<br>Gly Tyr Arg Arg Cys Arg Ala Ser Gly Val Leu Thr Thr Ser Cys Gly<br>2305                        2310                        2315                        2320 | 6960 |
| AAC ACC CTC ACA TGT TAC TTG AAG GCC TCT GCA GCC TGT CGA GCT GCG<br>Asn Thr Leu Thr Cys Tyr Leu Lys Ala Ser Ala Ala Cys Arg Ala Ala<br>                        2325                        2330                        2335 | 7008 |
| AAG CTC CAG GAC TGC ACG ATG CTC GTG AAC GGA GAC GAC CTC GTC GTT<br>Lys Leu Gln Asp Cys Thr Met Leu Val Asn Gly Asp Asp Leu Val Val<br>2340                        2345                        2350 | 7056 |
| ATC TGT GAA AGC GCG GGA ACC CAA GAG GAC GCG GCG AGC CTA CGA GTC<br>Ile Cys Glu Ser Ala Gly Thr Gln Glu Asp Ala Ala Ser Leu Arg Val<br>            2355                          2360                         2365 | 7104 |
| TTC ACG GAG GCT ATG ACT AGG TAC TCC GCC CCC CCC GGG GAC CCG CCC<br>Phe Thr Glu Ala Met Thr Arg Tyr Ser Ala Pro Pro Gly Asp Pro Pro<br>2370                        2375                        2380 | 7152 |
| CAA CCA GAA TAC GAC TTG GAG CTG ATA ACA TCA TGT TCC TCC AAT GTG<br>Gln Pro Glu Tyr Asp Leu Glu Leu Ile Thr Ser Cys Ser Ser Asn Val<br>2385                        2390                        2395                        2400 | 7200 |
| TCG GTC GCC CAC GAT GCA TCA GGC AAA AGG GTG TAC TAC CTC ACC CGT<br>Ser Val Ala His Asp Ala Ser Gly Lys Arg Val Tyr Tyr Leu Thr Arg<br>            2405                          2410                         2415 | 7248 |
| GAT CCC ACC ACC CCC CTA GCA CGG GCT GCG TGG GAG ACA GCT AGA CAC<br>Asp Pro Thr Thr Pro Leu Ala Arg Ala Ala Trp Glu Thr Ala Arg His<br>                        2420                        2425                        2430 | 7296 |
| ACT CCA GTT AAC TCC TGG CTA GGC AAC ATT ATT ATG TAT GCG CCC ACT<br>Thr Pro Val Asn Ser Trp Leu Gly Asn Ile Ile Met Tyr Ala Pro Thr<br>2435                        2440                        2445 | 7344 |

-continued

```
TTG TGG GCA AGG ATG ATT CTG ATG ACT CAC TTC TTC TCC ATC CTT CTA      7392
Leu Trp Ala Arg Met Ile Leu Met Thr His Phe Phe Ser Ile Leu Leu
    2450                2455                2460

GCG CAG GAG CAA CTT GAA AAA GCC CTG GAC TGC CAG ATC TAC GGG GCC      7440
Ala Gln Glu Gln Leu Glu Lys Ala Leu Asp Cys Gln Ile Tyr Gly Ala
2465                2470                2475                2480

TGT TAC TCC ATT GAG CCA CTT GAC CTA CCT CAG ATC ATT GAA CGA CTC      7488
Cys Tyr Ser Ile Glu Pro Leu Asp Leu Pro Gln Ile Ile Glu Arg Leu
                2485                2490                2495

CAT GGC CTT AGC GCA TTT TCA CTC CAT AGT TAC TCT CCA GGT GAG ATC      7536
His Gly Leu Ser Ala Phe Ser Leu His Ser Tyr Ser Pro Gly Glu Ile
            2500                2505                2510

AAT AGG GTG GCT TCA TGC CTC AGG AAA CTT GGG GTA CCA CCC TTG CGA      7584
Asn Arg Val Ala Ser Cys Leu Arg Lys Leu Gly Val Pro Pro Leu Arg
        2515                2520                2525

GTC TGG AGA CAT CGG GCC AGG AGC GTC CGC GCT AGG CTA CTG TCC CAG      7632
Val Trp Arg His Arg Ala Arg Ser Val Arg Ala Arg Leu Leu Ser Gln
    2530                2535                2540

GGA GGG AGG GCC GCC ACT TGT GGC AAA TAC CTC TTC AAC TGG GCA GTA      7680
Gly Gly Arg Ala Ala Thr Cys Gly Lys Tyr Leu Phe Asn Trp Ala Val
2545                2550                2555                2560

AAA ACC AAA CTT AAA CTC ACT CCA ATC CCG GCT GCG TCC CGG CTG GAC      7728
Lys Thr Lys Leu Lys Leu Thr Pro Ile Pro Ala Ala Ser Arg Leu Asp
                2565                2570                2575

TTG TCC GGC TGG TTC GTT GCT GGT TAC AGC GGG GGA GAC ATA TAT CAC      7776
Leu Ser Gly Trp Phe Val Ala Gly Tyr Ser Gly Gly Asp Ile Tyr His
            2580                2585                2590

AGC CTG TCT CGT GCC CGA CCC CGT TGG TTC ATG CTG TGC CTA CTC CTA      7824
Ser Leu Ser Arg Ala Arg Pro Arg Trp Phe Met Leu Cys Leu Leu Leu
        2595                2600                2605

CTT TCT GTA GGG GTA GGC ATC TAC CTG CTC CCC AAC CG ATGAACGGGG        7872
Leu Ser Val Gly Val Gly Ile Tyr Leu Leu Pro Asn
2610                2615                262

AGATAAACAC TCCAGGCCAA TAGGCCATCC CCCTTTTTTT TTTTT                    7917

(2) INFORMATION FOR SEQ ID NO:32:

(i) SEQUENCE CHARACTERISTICS:
        (A) LENGTH: 2620 amino acids
        (B) TYPE: amino acid
        (D) TOPOLOGY: linear (ii) MOLECULE TYPE: protein (xi) SEQUENCE DESCRIPTION: SEQ ID NO:32:

Gly Ala Gln Ala Lys Thr Thr Asn Arg Leu Val Ser Met Phe Ala Ser
1               5                   10                  15

Gly Pro Ser Gln Lys Ile Gln Leu Ile Asn Thr Asn Gly Ser Trp His
            20                  25                  30

Ile Asn Arg Thr Ala Leu Asn Cys Asn Asp Ser Leu Gln Thr Gly Phe
        35                  40                  45

Leu Ala Ala Leu Phe Tyr Thr His Ser Phe Asn Ser Ser Gly Cys Pro
    50                  55                  60

Glu Arg Met Ala Gln Cys Arg Thr Ile Asp Lys Phe Asp Gln Gly Trp
65                  70                  75                  80

Gly Pro Ile Thr Tyr Ala Glu Ser Ser Arg Ser Asp Gln Arg Pro Tyr
                85                  90                  95

Cys Trp His Tyr Pro Pro Gln Cys Thr Ile Val Pro Ala Ser Glu
            100                 105                 110

Val Cys Gly Pro Val Tyr Cys Phe Thr Pro Ser Pro Val Val Val Gly
```

-continued

```
                115                 120                 125
Thr Thr Asp Arg Phe Gly Val Pro Thr Tyr Arg Trp Gly Glu Asn Glu
        130                 135                 140
Thr Asp Val Leu Leu Leu Asn Asn Thr Arg Pro Pro Gln Gly Asn Trp
145                 150                 155                 160
Phe Gly Cys Thr Trp Met Asn Ser Thr Gly Phe Thr Lys Thr Cys Gly
                165                 170                 175
Gly Pro Pro Cys Asn Ile Gly Gly Val Gly Asn Asn Thr Leu Thr Cys
                180                 185                 190
Pro Thr Asp Cys Phe Arg Lys His Pro Glu Ala Thr Tyr Thr Lys Cys
                195                 200                 205
Gly Ser Gly Pro Trp Leu Thr Pro Arg Cys Met Val Asp Tyr Pro Tyr
210                 215                 220
Arg Leu Trp His Tyr Pro Cys Thr Val Asn Phe Thr Ile Phe Lys Val
225                 230                 235                 240
Arg Met Tyr Val Gly Gly Val Glu His Arg Leu Asn Ala Ala Cys Asn
                245                 250                 255
Trp Thr Arg Gly Glu Arg Cys Asp Leu Glu Asp Arg Asp Arg Pro Glu
                260                 265                 270
Leu Ser Pro Leu Leu Leu Ser Thr Thr Glu Trp Gln Val Leu Pro Cys
                275                 280                 285
Ser Phe Thr Thr Leu Pro Ala Leu Ser Thr Gly Leu Ile His Leu His
                290                 295                 300
Gln Asn Ile Val Asp Val Gln Tyr Leu Tyr Gly Ile Gly Ser Ala Val
305                 310                 315                 320
Val Ser Phe Ala Ile Lys Trp Glu Tyr Val Leu Leu Leu Phe Leu Leu
                325                 330                 335
Leu Ala Asp Ala Arg Val Cys Ala Cys Leu Trp Met Met Leu Leu Ile
                340                 345                 350
Ala Gln Ala Glu Ala Ala Leu Glu Asn Leu Val Val Leu Asn Ser Ala
                355                 360                 365
Ser Val Ala Gly Ala His Gly Ile Leu Ser Phe Leu Val Phe Phe Cys
                370                 375                 380
Ala Ala Trp Tyr Ile Lys Gly Arg Leu Val Pro Gly Ala Thr Tyr Ala
385                 390                 395                 400
Leu Tyr Gly Val Trp Pro Leu Leu Leu Leu Leu Ala Leu Pro Pro
                405                 410                 415
Arg Ala Tyr Ala Met Asp Arg Glu Met Ala Ala Ser Cys Gly Gly Ala
                420                 425                 430
Val Phe Val Gly Leu Val Leu Leu Thr Leu Ser Pro Tyr Tyr Lys Val
                435                 440                 445
Phe Leu Ala Arg Leu Ile Trp Trp Leu Gln Tyr Phe Thr Thr Arg Ala
450                 455                 460
Glu Ala Asp Leu His Val Trp Ile Pro Pro Leu Asn Ala Arg Gly Gly
465                 470                 475                 480
Arg Asp Ala Ile Ile Leu Leu Met Cys Ala Val His Pro Glu Leu Ile
                485                 490                 495
Phe Asp Ile Thr Lys Leu Leu Ile Ala Ile Leu Gly Pro Leu Met Val
                500                 505                 510
Leu Gln Ala Gly Ile Thr Arg Val Pro Tyr Phe Val Arg Ala Gln Gly
                515                 520                 525
Leu Ile His Ala Cys Met Leu Val Arg Lys Val Ala Gly Gly His Tyr
                530                 535                 540
```

-continued

```
Val Gln Met Ala Phe Met Lys Leu Gly Ala Leu Thr Gly Thr Tyr Ile
545                 550                 555                 560

Tyr Asn His Leu Thr Pro Leu Arg Asp Trp Pro Arg Ala Gly Leu Arg
                565                 570                 575

Asp Leu Ala Val Ala Val Glu Pro Val Phe Ser Asp Met Glu Thr
                580                 585                 590

Lys Ile Ile Thr Trp Gly Ala Asp Thr Ala Ala Cys Gly Asp Ile Ile
            595                 600                 605

Leu Gly Leu Pro Val Ser Ala Arg Arg Gly Lys Glu Ile Leu Leu Gly
            610                 615                 620

Pro Ala Asp Ser Leu Glu Gly Arg Gly Leu Arg Leu Leu Ala Pro Ile
625                 630                 635                 640

Thr Ala Tyr Ser Gln Gln Thr Arg Gly Leu Leu Gly Cys Ile Ile Thr
                645                 650                 655

Ser Leu Thr Gly Arg Asp Lys Asn Gln Val Glu Gly Glu Val Gln Val
                660                 665                 670

Val Ser Thr Ala Thr Gln Ser Phe Leu Ala Thr Cys Val Asn Gly Val
                675                 680                 685

Cys Trp Thr Val Tyr His Gly Ala Gly Ser Lys Thr Leu Ala Ala Pro
                690                 695                 700

Lys Gly Pro Ile Thr Gln Met Tyr Thr Asn Val Asp Gln Asp Leu Val
705                 710                 715                 720

Gly Trp Pro Lys Pro Pro Gly Ala Arg Ser Leu Thr Pro Cys Thr Cys
                725                 730                 735

Gly Ser Ser Asp Leu Tyr Leu Val Thr Arg His Ala Asp Val Ile Pro
                740                 745                 750

Val Arg Arg Arg Gly Asp Ser Arg Gly Ser Leu Leu Ser Pro Arg Pro
                755                 760                 765

Val Ser Tyr Leu Lys Gly Ser Ser Gly Gly Pro Leu Leu Cys Pro Phe
770                 775                 780

Gly His Ala Val Gly Ile Phe Arg Ala Ala Val Cys Thr Arg Gly Val
785                 790                 795                 800

Ala Lys Ala Val Asp Phe Val Pro Val Glu Ser Met Glu Thr Thr Met
                805                 810                 815

Arg Ser Pro Val Phe Thr Asp Asn Ser Ser Pro Pro Ala Val Pro Gln
                820                 825                 830

Ser Phe Gln Val Ala His Leu His Ala Pro Thr Gly Ser Gly Lys Ser
                835                 840                 845

Thr Lys Val Pro Ala Ala Tyr Ala Ala Gln Gly Tyr Lys Val Leu Val
850                 855                 860

Leu Asn Pro Ser Val Ala Ala Thr Leu Gly Phe Gly Ala Tyr Met Ser
865                 870                 875                 880

Lys Ala His Gly Ile Asp Pro Asn Ile Arg Thr Gly Val Arg Thr Ile
                885                 890                 895

Thr Thr Gly Ala Pro Val Thr Tyr Ser Thr Tyr Gly Lys Phe Leu Ala
                900                 905                 910

Asp Gly Gly Cys Ser Gly Gly Ala Tyr Asp Ile Ile Cys Asp Glu
                915                 920                 925

Cys His Ser Thr Asp Ser Thr Thr Ile Leu Gly Ile Gly Thr Val Leu
                930                 935                 940

Asp Gln Ala Glu Thr Ala Gly Ala Arg Leu Val Val Leu Ala Thr Ala
945                 950                 955                 960

Thr Pro Pro Gly Ser Val Thr Val Pro His Pro Asn Ile Glu Glu Val
                965                 970                 975
```

```
Ala Leu Ser Asn Thr Gly Glu Ile Pro Phe Tyr Gly Lys Ala Ile Pro
            980                 985                 990

Ile Glu Ala Ile Arg Gly Gly Arg His Leu Ile Phe Cys His Ser Lys
            995                1000                1005

Lys Lys Cys Asp Glu Leu Ala Ala Lys Leu Ser Gly Leu Gly Ile Asn
           1010                1015                1020

Ala Val Ala Tyr Tyr Arg Gly Leu Asp Val Ser Val Ile Pro Thr Ile
1025                1030                1035                1040

Gly Asp Val Val Val Ala Thr Asp Ala Leu Met Thr Gly Tyr Thr
                   1045                1050                1055

Gly Asp Phe Asp Ser Val Ile Asp Cys Asn Thr Cys Val Thr Gln Thr
                   1060                1065                1070

Val Asp Phe Ser Leu Asp Pro Thr Phe Thr Ile Glu Thr Thr Thr Val
               1075                1080                1085

Pro Gln Asp Ala Val Ser Arg Ser Gln Arg Arg Gly Arg Thr Gly Arg
           1090                1095                1100

Gly Arg Arg Gly Ile Tyr Arg Phe Val Thr Pro Gly Glu Arg Pro Ser
1105                1110                1115                1120

Gly Met Phe Asp Ser Ser Val Leu Cys Glu Cys Tyr Asp Ala Gly Cys
                   1125                1130                1135

Ala Trp Tyr Glu Leu Thr Pro Ala Glu Thr Ser Val Arg Leu Arg Ala
                   1140                1145                1150

Tyr Leu Asn Thr Pro Gly Leu Pro Val Cys Gln Asp His Leu Glu Phe
           1155                1160                1165

Trp Glu Ser Val Phe Thr Gly Leu Thr His Ile Asp Ala His Phe Leu
           1170                1175                1180

Ser Gln Thr Lys Gln Ala Gly Asp Asn Phe Pro Tyr Leu Val Ala Tyr
1185                1190                1195                1200

Gln Ala Thr Val Cys Ala Arg Ala Gln Ala Pro Pro Pro Ser Trp Asp
                   1205                1210                1215

Gln Met Trp Lys Cys Leu Ile Arg Leu Lys Pro Thr Leu His Gly Pro
                   1220                1225                1230

Thr Pro Leu Leu Tyr Arg Leu Gly Ala Val Gln Asn Glu Val Thr Leu
                   1235                1240                1245

Thr His Pro Ile Thr Lys Tyr Ile Met Ala Cys Met Ser Ala Asp Leu
           1250                1255                1260

Glu Val Val Thr Ser Thr Trp Val Leu Val Gly Gly Val Leu Ala Ala
1265                1270                1275                1280

Leu Ala Ala Tyr Cys Leu Thr Thr Gly Ser Val Val Ile Val Gly Arg
                   1285                1290                1295

Ile Ile Leu Ser Gly Arg Pro Ala Ile Val Pro Asp Arg Glu Leu Leu
           1300                1305                1310

Tyr Gln Glu Phe Asp Glu Met Glu Glu Cys Ala Ser His Leu Pro Tyr
           1315                1320                1325

Ile Glu Gln Gly Met Gln Leu Ala Glu Gln Phe Lys Gln Lys Ala Leu
           1330                1335                1340

Gly Leu Leu Gln Thr Ala Thr Lys Gln Ala Glu Ala Ala Ala Pro Val
1345                1350                1355                1360

Val Glu Ser Lys Trp Arg Ala Leu Glu Thr Phe Trp Ala Lys His Met
                   1365                1370                1375

Trp Asn Phe Ile Ser Gly Ile Gln Tyr Leu Ala Gly Leu Ser Thr Leu
                   1380                1385                1390

Pro Gly Asn Pro Ala Ile Ala Ser Leu Met Ala Phe Thr Ala Ser Ile
```

-continued

```
           1395              1400              1405
Thr Ser Pro Leu Thr Thr Gln Ser Thr Leu Leu Phe Asn Ile Leu Gly
    1410              1415              1420

Gly Trp Val Ala Ala Gln Leu Ala Pro Pro Ser Ala Ala Ser Ala Phe
1425              1430              1435              1440

Val Gly Ala Gly Ile Ala Gly Ala Ala Val Gly Ser Ile Gly Leu Gly
                1445              1450              1455

Lys Val Leu Val Asp Ile Leu Ala Gly Tyr Gly Ala Gly Val Ala Gly
                1460              1465              1470

Ala Leu Val Ala Phe Lys Val Met Ser Gly Glu Met Pro Ser Thr Glu
        1475              1480              1485

Asp Leu Val Asn Leu Leu Pro Ala Ile Leu Ser Pro Gly Ala Leu Val
        1490              1495              1500

Val Gly Val Val Cys Ala Ala Ile Leu Arg Arg His Val Gly Pro Gly
1505              1510              1515              1520

Glu Gly Ala Val Gln Trp Met Asn Arg Leu Ile Ala Phe Ala Ser Arg
                1525              1530              1535

Gly Asn His Val Ser Pro Thr His Tyr Val Pro Glu Ser Asp Ala Ala
                1540              1545              1550

Ala Arg Val Thr Gln Ile Leu Ser Ser Leu Thr Ile Thr Gln Leu Leu
        1555              1560              1565

Lys Arg Leu His Gln Trp Ile Asn Glu Asp Cys Ser Thr Pro Cys Ser
        1570              1575              1580

Gly Ser Trp Leu Arg Asp Val Trp Asp Trp Ile Cys Thr Val Leu Thr
1585              1590              1595              1600

Asp Phe Lys Thr Trp Leu Gln Ser Lys Leu Leu Pro Gln Leu Pro Gly
                1605              1610              1615

Val Pro Phe Phe Ser Cys Gln Arg Gly Tyr Lys Gly Val Trp Arg Gly
                1620              1625              1630

Asp Gly Ile Met Gln Thr Thr Cys Pro Cys Gly Ala Gln Ile Thr Gly
        1635              1640              1645

His Val Lys Asn Gly Ser Met Arg Ile Val Gly Pro Lys Thr Cys Ser
        1650              1655              1660

Asn Thr Trp His Gly Thr Phe Pro Ile Asn Ala Tyr Thr Thr Gly Pro
1665              1670              1675              1680

Cys Thr Pro Ser Pro Ala Pro Asn Tyr Ser Arg Ala Leu Trp Arg Val
                1685              1690              1695

Ala Ala Glu Glu Tyr Val Glu Val Thr Arg Val Gly Asp Phe His Tyr
                1700              1705              1710

Val Thr Gly Met Thr Thr Asp Asn Val Lys Cys Pro Cys Gln Val Pro
        1715              1720              1725

Ala Pro Glu Phe Phe Ser Glu Val Asp Gly Val Arg Leu His Arg Tyr
        1730              1735              1740

Ala Pro Ala Cys Arg Pro Leu Leu Arg Glu Glu Val Thr Phe Gln Val
1745              1750              1755              1760

Gly Leu Asn Gln Tyr Leu Val Gly Ser Gln Leu Pro Cys Glu Pro Glu
                1765              1770              1775

Pro Asp Val Ala Val Leu Thr Ser Met Leu Thr Asp Pro Ser His Ile
        1780              1785              1790

Thr Ala Glu Thr Ala Lys Arg Arg Leu Ala Arg Gly Ser Pro Pro Ser
        1795              1800              1805

Leu Ala Ser Ser Ser Ala Ser Gln Leu Ser Ala Pro Ser Leu Lys Ala
        1810              1815              1820
```

-continued

Thr Cys Thr Thr His His Val Ser Pro Asp Ala Asp Leu Ile Glu Ala
1825                1830                1835                1840

Asn Leu Leu Trp Arg Gln Glu Met Gly Gly Asn Ile Thr Arg Val Glu
            1845                1850                1855

Ser Glu Asn Lys Val Val Val Leu Asp Ser Phe Asp Pro Leu Arg Ala
        1860                1865                1870

Glu Glu Asp Glu Arg Glu Val Ser Val Pro Ala Glu Ile Leu Arg Lys
    1875                1880                1885

Ser Lys Lys Phe Pro Ala Ala Met Pro Ile Trp Ala Arg Pro Asp Tyr
1890                1895                1900

Asn Pro Pro Leu Leu Glu Ser Trp Lys Asp Pro Asp Tyr Val Pro Pro
1905                1910                1915                1920

Val Val His Gly Cys Pro Leu Pro Pro Ile Lys Ala Pro Pro Ile Pro
            1925                1930                1935

Pro Pro Arg Arg Lys Arg Thr Val Val Leu Thr Glu Ser Ser Val Ser
            1940                1945                1950

Ser Ala Leu Ala Glu Leu Ala Thr Lys Thr Phe Gly Ser Ser Glu Ser
            1955                1960                1965

Ser Ala Val Asp Ser Gly Thr Ala Thr Ala Leu Pro Asp Gln Ala Ser
        1970                1975                1980

Asp Asp Gly Asp Lys Gly Ser Asp Val Glu Ser Tyr Ser Ser Met Pro
1985                1990                1995                2000

Pro Leu Glu Gly Glu Pro Gly Asp Pro Asp Leu Ser Asp Gly Ser Trp
            2005                2010                2015

Ser Thr Val Ser Glu Glu Ala Ser Glu Asp Val Val Cys Cys Ser Met
            2020                2025                2030

Ser Tyr Thr Trp Thr Gly Ala Leu Ile Thr Pro Cys Ala Ala Glu Glu
            2035                2040                2045

Ser Lys Leu Pro Ile Asn Ala Leu Ser Asn Ser Leu Leu Arg His His
            2050                2055                2060

Asn Met Val Tyr Ala Thr Thr Ser Arg Ser Ala Gly Leu Arg Gln Lys
2065                2070                2075                2080

Lys Val Thr Phe Asp Arg Leu Gln Val Leu Asp Asp His Tyr Arg Asp
            2085                2090                2095

Val Leu Lys Glu Met Lys Ala Lys Ala Ser Thr Val Lys Ala Lys Leu
            2100                2105                2110

Leu Ser Val Glu Glu Ala Cys Lys Leu Thr Pro Pro His Ser Ala Lys
            2115                2120                2125

Ser Lys Phe Gly Tyr Gly Ala Lys Asp Val Arg Asn Leu Ser Ser Lys
            2130                2135                2140

Ala Val Asn His Ile His Ser Val Trp Lys Asp Leu Leu Glu Asp Thr
2145                2150                2155                2160

Val Thr Pro Ile Asp Thr Thr Ile Met Ala Lys Asn Glu Val Phe Cys
            2165                2170                2175

Val Gln Pro Glu Lys Gly Gly Arg Lys Pro Ala Arg Leu Ile Val Phe
            2180                2185                2190

Pro Asp Leu Gly Val Arg Val Cys Glu Lys Met Ala Leu Tyr Asp Val
            2195                2200                2205

Val Ser Thr Leu Pro Gln Val Val Met Gly Ser Ser Tyr Gly Phe Gln
            2210                2215                2220

Tyr Ser Pro Gly Gln Arg Val Glu Phe Leu Val Asn Thr Trp Lys Ser
2225                2230                2235                2240

Lys Lys Asn Pro Met Gly Phe Ser Tyr Asp Thr Arg Cys Phe Asp Ser
            2245                2250                2255

```
Thr Val Thr Glu Asn Asp Ile Arg Val Glu Glu Ser Ile Tyr Gln Cys
        2260                2265                2270

Cys Asp Leu Ala Pro Glu Ala Arg Gln Ala Ile Lys Ser Leu Thr Glu
        2275                2280                2285

Arg Leu Tyr Ile Gly Gly Pro Leu Thr Asn Ser Lys Gly Gln Asn Cys
        2290                2295                2300

Gly Tyr Arg Arg Cys Arg Ala Ser Gly Val Leu Thr Thr Ser Cys Gly
2305                2310                2315                2320

Asn Thr Leu Thr Cys Tyr Leu Lys Ala Ser Ala Ala Cys Arg Ala Ala
        2325                2330                2335

Lys Leu Gln Asp Cys Thr Met Leu Val Asn Gly Asp Asp Leu Val Val
        2340                2345                2350

Ile Cys Glu Ser Ala Gly Thr Gln Glu Asp Ala Ala Ser Leu Arg Val
        2355                2360                2365

Phe Thr Glu Ala Met Thr Arg Tyr Ser Ala Pro Pro Gly Asp Pro Pro
        2370                2375                2380

Gln Pro Glu Tyr Asp Leu Glu Leu Ile Thr Ser Cys Ser Ser Asn Val
2385                2390                2395                2400

Ser Val Ala His Asp Ala Ser Gly Lys Arg Val Tyr Tyr Leu Thr Arg
        2405                2410                2415

Asp Pro Thr Thr Pro Leu Ala Arg Ala Ala Trp Glu Thr Ala Arg His
        2420                2425                2430

Thr Pro Val Asn Ser Trp Leu Gly Asn Ile Ile Met Tyr Ala Pro Thr
        2435                2440                2445

Leu Trp Ala Arg Met Ile Leu Met Thr His Phe Phe Ser Ile Leu Leu
        2450                2455                2460

Ala Gln Glu Gln Leu Glu Lys Ala Leu Asp Cys Gln Ile Tyr Gly Ala
2465                2470                2475                2480

Cys Tyr Ser Ile Glu Pro Leu Asp Leu Pro Gln Ile Ile Glu Arg Leu
        2485                2490                2495

His Gly Leu Ser Ala Phe Ser Leu His Ser Tyr Ser Pro Gly Glu Ile
        2500                2505                2510

Asn Arg Val Ala Ser Cys Leu Arg Lys Leu Gly Val Pro Pro Leu Arg
        2515                2520                2525

Val Trp Arg His Arg Ala Arg Ser Val Arg Ala Arg Leu Leu Ser Gln
        2530                2535                2540

Gly Gly Arg Ala Ala Thr Cys Gly Lys Tyr Leu Phe Asn Trp Ala Val
2545                2550                2555                2560

Lys Thr Lys Leu Lys Leu Thr Pro Ile Pro Ala Ala Ser Arg Leu Asp
        2565                2570                2575

Leu Ser Gly Trp Phe Val Ala Gly Tyr Ser Gly Gly Asp Ile Tyr His
        2580                2585                2590

Ser Leu Ser Arg Ala Arg Pro Arg Trp Phe Met Leu Cys Leu Leu Leu
        2595                2600                2605

Leu Ser Val Gly Val Gly Ile Tyr Leu Leu Pro Asn
        2610                2615                2620

(2) INFORMATION FOR SEQ ID NO:33:

(i) SEQUENCE CHARACTERISTICS:
        (A) LENGTH: 1020 base pairs
        (B) TYPE: nucleic acid
        (C) STRANDEDNESS: single
        (D) TOPOLOGY: linear (ii) MOLECULE TYPE: cDNA from genomic RNA
```

(ix) FEATURE:
    (A) NAME/KEY: misc_feature
    (B) LOCATION: 1..1020
    (D) OTHER INFORMATION: /note: "sequence = 1500 - 2519 of
        SEQ ID NO: 1"

(ix) FEATURE:
    (A) NAME/KEY: CDS
    (B) LOCATION: 1..1020

(xi) SEQUENCE DESCRIPTION: SEQ ID NO:33:

| | | | | | | | | | | | | | | | | |
|---|---|---|---|---|---|---|---|---|---|---|---|---|---|---|---|---|
| GGG | GCG | CAA | GCC | AAA | ACC | ACC | AAC | AGG | CTC | GTG | TCC | ATG | TTC | GCA | AGT | 48 |
| Gly | Ala | Gln | Ala | Lys | Thr | Thr | Asn | Arg | Leu | Val | Ser | Met | Phe | Ala | Ser | |
| 1 | | | | 5 | | | | | 10 | | | | | 15 | | |
| GGG | CCG | TCT | CAG | AAA | ATC | CAG | CTT | ATA | AAC | ACC | AAT | GGG | AGT | TGG | CAC | 96 |
| Gly | Pro | Ser | Gln | Lys | Ile | Gln | Leu | Ile | Asn | Thr | Asn | Gly | Ser | Trp | His | |
| | | | 20 | | | | | 25 | | | | | 30 | | | |
| ATC | AAC | AGG | ACT | GCC | CTG | AAC | TGC | AAT | GAC | TCT | CTC | CAG | ACT | GGG | TTT | 144 |
| Ile | Asn | Arg | Thr | Ala | Leu | Asn | Cys | Asn | Asp | Ser | Leu | Gln | Thr | Gly | Phe | |
| | | 35 | | | | | 40 | | | | | 45 | | | | |
| CTT | GCC | GCG | CTG | TTC | TAC | ACA | CAT | AGT | TTC | AAC | TCG | TCC | GGG | TGC | CCA | 192 |
| Leu | Ala | Ala | Leu | Phe | Tyr | Thr | His | Ser | Phe | Asn | Ser | Ser | Gly | Cys | Pro | |
| 50 | | | | | 55 | | | | | 60 | | | | | | |
| GAG | CGC | ATG | GCC | CAG | TGC | CGC | ACC | ATT | GAC | AAG | TTC | GAC | CAG | GGA | TGG | 240 |
| Glu | Arg | Met | Ala | Gln | Cys | Arg | Thr | Ile | Asp | Lys | Phe | Asp | Gln | Gly | Trp | |
| 65 | | | | 70 | | | | | 75 | | | | | 80 | | |
| GGT | CCC | ATT | ACT | TAT | GCT | GAG | TCT | AGC | AGA | TCA | GAC | CAG | AGG | CCA | TAT | 288 |
| Gly | Pro | Ile | Thr | Tyr | Ala | Glu | Ser | Ser | Arg | Ser | Asp | Gln | Arg | Pro | Tyr | |
| | | | 85 | | | | | 90 | | | | | 95 | | | |
| TGC | TGG | CAC | TAC | CCA | CCT | CCA | CAA | TGT | ACC | ATC | GTA | CCT | GCG | TCG | GAG | 336 |
| Cys | Trp | His | Tyr | Pro | Pro | Pro | Gln | Cys | Thr | Ile | Val | Pro | Ala | Ser | Glu | |
| | | | 100 | | | | | 105 | | | | | 110 | | | |
| GTG | TGC | GGC | CCA | GTG | TAC | TGC | TTC | ACC | CCA | AGC | CCT | GTC | GTC | GTG | GGG | 384 |
| Val | Cys | Gly | Pro | Val | Tyr | Cys | Phe | Thr | Pro | Ser | Pro | Val | Val | Val | Gly | |
| | | 115 | | | | | 120 | | | | | 125 | | | | |
| ACG | ACC | GAT | CGT | TTC | GGT | GTC | CCT | ACG | TAT | AGA | TGG | GGG | GAG | AAC | GAG | 432 |
| Thr | Thr | Asp | Arg | Phe | Gly | Val | Pro | Thr | Tyr | Arg | Trp | Gly | Glu | Asn | Glu | |
| | 130 | | | | | 135 | | | | | 140 | | | | | |
| ACT | GAC | GTG | CTG | CTG | CTC | AAC | AAC | ACG | CGG | CCG | CCG | CAA | GGC | AAC | TGG | 480 |
| Thr | Asp | Val | Leu | Leu | Leu | Asn | Asn | Thr | Arg | Pro | Pro | Gln | Gly | Asn | Trp | |
| 145 | | | | | 150 | | | | | 155 | | | | | 160 | |
| TTC | GGC | TGC | ACA | TGG | ATG | AAT | AGC | ACC | GGG | TTC | ACC | AAG | ACA | TGT | GGG | 528 |
| Phe | Gly | Cys | Thr | Trp | Met | Asn | Ser | Thr | Gly | Phe | Thr | Lys | Thr | Cys | Gly | |
| | | | 165 | | | | | 170 | | | | | 175 | | | |
| GGG | CCC | CCG | TGT | AAC | ATC | GGG | GGG | GTC | GGC | AAC | AAC | ACC | CTG | ACC | TGC | 576 |
| Gly | Pro | Pro | Cys | Asn | Ile | Gly | Gly | Val | Gly | Asn | Asn | Thr | Leu | Thr | Cys | |
| | | | 180 | | | | | 185 | | | | | 190 | | | |
| CCC | ACG | GAC | TGC | TTC | CGG | AAG | CAC | CCC | GAG | GCT | ACC | TAC | ACA | AAA | TGT | 624 |
| Pro | Thr | Asp | Cys | Phe | Arg | Lys | His | Pro | Glu | Ala | Thr | Tyr | Thr | Lys | Cys | |
| | | 195 | | | | | 200 | | | | | 205 | | | | |
| GGT | TCG | GGG | CCT | TGG | CTG | ACA | CCT | AGG | TGC | ATG | GTT | GAC | TAT | CCA | TAC | 672 |
| Gly | Ser | Gly | Pro | Trp | Leu | Thr | Pro | Arg | Cys | Met | Val | Asp | Tyr | Pro | Tyr | |
| | 210 | | | | | 215 | | | | | 220 | | | | | |
| AGG | CTC | TGG | CAT | TAC | CCC | TGC | ACT | GTT | AAC | TTT | ACC | ATC | TTC | AAG | GTT | 720 |
| Arg | Leu | Trp | His | Tyr | Pro | Cys | Thr | Val | Asn | Phe | Thr | Ile | Phe | Lys | Val | |
| 225 | | | | | 230 | | | | | 235 | | | | | 240 | |
| AGG | ATG | TAT | GTG | GGG | GGG | GTG | GAG | CAC | AGG | CTC | AAT | GCT | GCA | TGC | AAT | 768 |
| Arg | Met | Tyr | Val | Gly | Gly | Val | Glu | His | Arg | Leu | Asn | Ala | Ala | Cys | Asn | |
| | | | 245 | | | | | 250 | | | | | 255 | | | |
| TGG | ACC | CGA | GGA | GAG | CGT | TGT | GAC | TTG | GAG | GAC | AGG | GAT | AGG | CCG | GAG | 816 |
| Trp | Thr | Arg | Gly | Glu | Arg | Cys | Asp | Leu | Glu | Asp | Arg | Asp | Arg | Pro | Glu | |
| | | | 260 | | | | | 265 | | | | | 270 | | | |

```
CTC AGC CCG CTG CTG CTG TCT ACA ACA GAG TGG CAG GTA CTG CCC TGT                864
Leu Ser Pro Leu Leu Leu Ser Thr Thr Glu Trp Gln Val Leu Pro Cys
        275                 280                 285

TCC TTC ACC ACC CTA CCA GCT CTG TCC ACT GGC TTG ATT CAC CTC CAT                912
Ser Phe Thr Thr Leu Pro Ala Leu Ser Thr Gly Leu Ile His Leu His
        290                 295                 300

CAG AAC ATC GTG GAC GTG CAA TAC CTA TAC GGT ATA GGG TCA GCG GTT                960
Gln Asn Ile Val Asp Val Gln Tyr Leu Tyr Gly Ile Gly Ser Ala Val
305                 310                 315                 320

GTC TCC TTT GCA ATC AAA TGG GAG TAT GTC CTG TTG CTT TTC CTT CTC               1008
Val Ser Phe Ala Ile Lys Trp Glu Tyr Val Leu Leu Leu Phe Leu Leu
                325                 330                 335

CTA GCG GAC GCA                                                               1020
Leu Ala Asp Ala
        340
```

(2) INFORMATION FOR SEQ ID NO:34:

(i) SEQUENCE CHARACTERISTICS:
        (A) LENGTH: 340 amino acids
        (B) TYPE: amino acid
        (D) TOPOLOGY: linear (ii) MOLECULE TYPE: protein (xi) SEQUENCE DESCRIPTION: SEQ ID NO:34:

```
Gly Ala Gln Ala Lys Thr Thr Asn Arg Leu Val Ser Met Phe Ala Ser
1               5                   10                  15

Gly Pro Ser Gln Lys Ile Gln Leu Ile Asn Thr Asn Gly Ser Trp His
                20                  25                  30

Ile Asn Arg Thr Ala Leu Asn Cys Asn Asp Ser Leu Gln Thr Gly Phe
            35                  40                  45

Leu Ala Ala Leu Phe Tyr Thr His Ser Phe Asn Ser Ser Gly Cys Pro
    50                  55                  60

Glu Arg Met Ala Gln Cys Arg Thr Ile Asp Lys Phe Asp Gln Gly Trp
65                  70                  75                  80

Gly Pro Ile Thr Tyr Ala Glu Ser Ser Arg Ser Asp Gln Arg Pro Tyr
                85                  90                  95

Cys Trp His Tyr Pro Pro Pro Gln Cys Thr Ile Val Pro Ala Ser Glu
            100                 105                 110

Val Cys Gly Pro Val Tyr Cys Phe Thr Pro Ser Pro Val Val Val Gly
    115                 120                 125

Thr Thr Asp Arg Phe Gly Val Pro Thr Tyr Arg Trp Gly Glu Asn Glu
130                 135                 140

Thr Asp Val Leu Leu Asn Asn Thr Arg Pro Pro Gln Gly Asn Trp
145                 150                 155                 160

Phe Gly Cys Thr Trp Met Asn Ser Thr Gly Phe Thr Lys Thr Cys Gly
                165                 170                 175

Gly Pro Pro Cys Asn Ile Gly Gly Val Gly Asn Asn Thr Leu Thr Cys
            180                 185                 190

Pro Thr Asp Cys Phe Arg Lys His Pro Glu Ala Thr Tyr Thr Lys Cys
    195                 200                 205

Gly Ser Gly Pro Trp Leu Thr Pro Arg Cys Met Val Asp Tyr Pro Tyr
210                 215                 220

Arg Leu Trp His Tyr Pro Cys Thr Val Asn Phe Thr Ile Phe Lys Val
225                 230                 235                 240

Arg Met Tyr Val Gly Gly Val Glu His Arg Leu Asn Ala Ala Cys Asn
                245                 250                 255
```

```
Trp Thr Arg Gly Glu Arg Cys Asp Leu Glu Asp Arg Asp Arg Pro Glu
            260                 265                 270

Leu Ser Pro Leu Leu Leu Ser Thr Thr Glu Trp Gln Val Leu Pro Cys
            275                 280                 285

Ser Phe Thr Thr Leu Pro Ala Leu Ser Thr Gly Leu Ile His Leu His
            290                 295                 300

Gln Asn Ile Val Asp Val Gln Tyr Leu Tyr Gly Ile Gly Ser Ala Val
305                 310                 315                 320

Val Ser Phe Ala Ile Lys Trp Glu Tyr Val Leu Leu Leu Phe Leu Leu
                325                 330                 335

Leu Ala Asp Ala
            340

(2) INFORMATION FOR SEQ ID NO:35:

(i) SEQUENCE CHARACTERISTICS:
        (A) LENGTH: 7863 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: CDS
        (B) LOCATION: 1..7863

(ix) FEATURE:
        (A) NAME/KEY: misc_feature
        (B) LOCATION: 1..7863
        (D) OTHER INFORMATION: /note= "sequence = 1500 - 9362 of
            SEQ ID NO: 1"

(xi) SEQUENCE DESCRIPTION: SEQ ID NO:35:

GGG GCG CAA GCC AAA ACC ACC AAC AGG CTC GTG TCC ATG TTC GCA AGT        48
Gly Ala Gln Ala Lys Thr Thr Asn Arg Leu Val Ser Met Phe Ala Ser
 1               5                  10                  15

GGG CCG TCT CAG AAA ATC CAG CTT ATA AAC ACC AAT GGG AGT TGG CAC        96
Gly Pro Ser Gln Lys Ile Gln Leu Ile Asn Thr Asn Gly Ser Trp His
            20                  25                  30

ATC AAC AGG ACT GCC CTG AAC TGC AAT GAC TCT CTC CAG ACT GGG TTT       144
Ile Asn Arg Thr Ala Leu Asn Cys Asn Asp Ser Leu Gln Thr Gly Phe
        35                  40                  45

CTT GCC GCG CTG TTC TAC ACA CAT AGT TTC AAC TCG TCC GGG TGC CCA       192
Leu Ala Ala Leu Phe Tyr Thr His Ser Phe Asn Ser Ser Gly Cys Pro
    50                  55                  60

GAG CGC ATG GCC CAG TGC CGC ACC ATT GAC AAG TTC GAC CAG GGA TGG       240
Glu Arg Met Ala Gln Cys Arg Thr Ile Asp Lys Phe Asp Gln Gly Trp
65                  70                  75                  80

GGT CCC ATT ACT TAT GCT GAG TCT AGC AGA TCA GAC CAG AGG CCA TAT       288
Gly Pro Ile Thr Tyr Ala Glu Ser Ser Arg Ser Asp Gln Arg Pro Tyr
                85                  90                  95

TGC TGG CAC TAC CCA CCT CCA CAA TGT ACC ATC GTA CCT GCG TCG GAG       336
Cys Trp His Tyr Pro Pro Pro Gln Cys Thr Ile Val Pro Ala Ser Glu
            100                 105                 110

GTG TGC GGC CCA GTG TAC TGC TTC ACC CCA AGC CCT GTC GTC GTG GGG       384
Val Cys Gly Pro Val Tyr Cys Phe Thr Pro Ser Pro Val Val Val Gly
        115                 120                 125

ACG ACC GAT CGT TTC GGT GTC CCT ACG TAT AGA TGG GGG GAG AAC GAG       432
Thr Thr Asp Arg Phe Gly Val Pro Thr Tyr Arg Trp Gly Glu Asn Glu
    130                 135                 140

ACT GAC GTG CTG CTG CTC AAC AAC ACG CGG CCG CCG CAA GGC AAC TGG       480
Thr Asp Val Leu Leu Leu Asn Asn Thr Arg Pro Pro Gln Gly Asn Trp
```

```
                145                 150                 155                 160
TTC GGC TGC ACA TGG ATG AAT AGC ACC GGG TTC ACC AAG ACA TGT GGG        528
Phe Gly Cys Thr Trp Met Asn Ser Thr Gly Phe Thr Lys Thr Cys Gly
                165                 170                 175

GGG CCC CCG TGT AAC ATC GGG GGT GTC GGC AAC AAC ACC CTG ACC TGC        576
Gly Pro Pro Cys Asn Ile Gly Gly Val Gly Asn Asn Thr Leu Thr Cys
                180                 185                 190

CCC ACG GAC TGC TTC CGG AAG CAC CCC GAG GCT ACC TAC ACA AAA TGT        624
Pro Thr Asp Cys Phe Arg Lys His Pro Glu Ala Thr Tyr Thr Lys Cys
                195                 200                 205

GGT TCG GGG CCT TGG CTG ACA CCT AGG TGC ATG GTT GAC TAT CCA TAC        672
Gly Ser Gly Pro Trp Leu Thr Pro Arg Cys Met Val Asp Tyr Pro Tyr
                210                 215                 220

AGG CTC TGG CAT TAC CCC TGC ACT GTT AAC TTT ACC ATC TTC AAG GTT        720
Arg Leu Trp His Tyr Pro Cys Thr Val Asn Phe Thr Ile Phe Lys Val
225                 230                 235                 240

AGG ATG TAT GTG GGG GGG GTG GAG CAC AGG CTC AAT GCT GCA TGC AAT        768
Arg Met Tyr Val Gly Gly Val Glu His Arg Leu Asn Ala Ala Cys Asn
                245                 250                 255

TGG ACC CGA GGA GAG CGT TGT GAC TTG GAG GAC AGG GAT AGG CCG GAG        816
Trp Thr Arg Gly Glu Arg Cys Asp Leu Glu Asp Arg Asp Arg Pro Glu
                260                 265                 270

CTC AGC CCG CTG CTG CTG TCT ACA ACA GAG TGG CAG GTA CTG CCC TGT        864
Leu Ser Pro Leu Leu Leu Ser Thr Thr Glu Trp Gln Val Leu Pro Cys
                275                 280                 285

TCC TTC ACC ACC CTA CCA GCT CTG TCC ACT GGC TTG ATT CAC CTC CAT        912
Ser Phe Thr Thr Leu Pro Ala Leu Ser Thr Gly Leu Ile His Leu His
                290                 295                 300

CAG AAC ATC GTG GAC GTG CAA TAC CTA TAC GGT ATA GGG TCA GCG GTT        960
Gln Asn Ile Val Asp Val Gln Tyr Leu Tyr Gly Ile Gly Ser Ala Val
305                 310                 315                 320

GTC TCC TTT GCA ATC AAA TGG GAG TAT GTC CTG TTG CTT TTC CTT CTC       1008
Val Ser Phe Ala Ile Lys Trp Glu Tyr Val Leu Leu Phe Leu Leu
                325                 330                 335

CTA GCG GAC GCA CGT GTC TGT GCC TGC TTG TGG ATG ATG CTG CTG ATA       1056
Leu Ala Asp Ala Arg Val Cys Ala Cys Leu Trp Met Met Leu Leu Ile
                340                 345                 350

GCC CAG GCC GAG GCC GCC TTG GAG AAC CTG GTG GTC CTC AAT TCG GCG       1104
Ala Gln Ala Glu Ala Ala Leu Glu Asn Leu Val Val Leu Asn Ser Ala
                355                 360                 365

TCT GTG GCC GGC GCA CAT GGC ATC CTC TCC TTC CTT GTG TTC TTC TGT       1152
Ser Val Ala Gly Ala His Gly Ile Leu Ser Phe Leu Val Phe Phe Cys
                370                 375                 380

GCC GCC TGG TAC ATC AAA GGC AGG CTG GTC CCT GGG GCG ACA TAT GCT       1200
Ala Ala Trp Tyr Ile Lys Gly Arg Leu Val Pro Gly Ala Thr Tyr Ala
385                 390                 395                 400

CTT TAT GGC GTG TGG CCG CTG CTC CTG CTC TTG CTG GCA TTA CCA CCG       1248
Leu Tyr Gly Val Trp Pro Leu Leu Leu Leu Leu Leu Ala Leu Pro Pro
                405                 410                 415

CGA GCT TAC GCC ATG GAC CGG GAG ATG GCT GCA TCG TGC GGA GGC GCG       1296
Arg Ala Tyr Ala Met Asp Arg Glu Met Ala Ala Ser Cys Gly Gly Ala
                420                 425                 430

GTT TTT GTG GGT CTG GTA CTC CTG ACT TTG TCA CCA TAC TAC AAG GTG       1344
Val Phe Val Gly Leu Val Leu Leu Thr Leu Ser Pro Tyr Tyr Lys Val
                435                 440                 445

TTC CTC GCT AGG CTC ATA TGG TGG TTA CAA TAT TTT ACC ACC AGA GCC       1392
Phe Leu Ala Arg Leu Ile Trp Trp Leu Gln Tyr Phe Thr Thr Arg Ala
450                 455                 460

GAG GCG GAC TTA CAT GTG TGG ATC CCC CCC CTC AAC GCT CGG GGA GGC       1440
Glu Ala Asp Leu His Val Trp Ile Pro Pro Leu Asn Ala Arg Gly Gly
```

-continued

```
            465                 470                475                480
CGC GAT GCC ATC ATC CTC CTC ATG TGC GCA GTC CAT CCA GAG CTA ATC      1488
Arg Asp Ala Ile Ile Leu Leu Met Cys Ala Val His Pro Glu Leu Ile
                    485                 490                495

TTT GAC ATC ACC AAA CTT CTA ATT GCC ATA CTC GGT CCG CTC ATG GTG      1536
Phe Asp Ile Thr Lys Leu Leu Ile Ala Ile Leu Gly Pro Leu Met Val
                500                 505                 510

CTC CAA GCT GGC ATA ACC AGA GTG CCG TAC TTC GTG CGC GCT CAA GGG      1584
Leu Gln Ala Gly Ile Thr Arg Val Pro Tyr Phe Val Arg Ala Gln Gly
            515                 520                 525

CTC ATT CAT GCA TGC ATG TTA GTG CGG AAG GTC GCT GGG GGT CAT TAT      1632
Leu Ile His Ala Cys Met Leu Val Arg Lys Val Ala Gly Gly His Tyr
        530                 535                 540

GTC CAA ATG GCC TTC ATG AAG CTG GGC GCG CTA ACA GGC ACG TAC ATT      1680
Val Gln Met Ala Phe Met Lys Leu Gly Ala Leu Thr Gly Thr Tyr Ile
545                 550                 555                 560

TAC AAC CAT CTT ACC CCG CTA CGG GAT TGG CCA CGC GCG GGC CTA CGA      1728
Tyr Asn His Leu Thr Pro Leu Arg Asp Trp Pro Arg Ala Gly Leu Arg
                565                 570                 575

GAC CTT GCG GTG GCA GTG GAG CCC GTC GTC TTC TCC GAC ATG GAG ACC      1776
Asp Leu Ala Val Ala Val Glu Pro Val Val Phe Ser Asp Met Glu Thr
            580                 585                 590

AAG ATC ATC ACC TGG GGA GCA GAC ACC GCG GCG TGT GGG GAC ATC ATC      1824
Lys Ile Ile Thr Trp Gly Ala Asp Thr Ala Ala Cys Gly Asp Ile Ile
        595                 600                 605

TTG GGT CTG CCC GTC TCC GCC CGA AGG GGA AAG GAG ATA CTC CTG GGC      1872
Leu Gly Leu Pro Val Ser Ala Arg Arg Gly Lys Glu Ile Leu Leu Gly
    610                 615                 620

CCG GCC GAT AGT CTT GAA GGG CGG GGG TTG CGA CTC CTC GCG CCC ATC      1920
Pro Ala Asp Ser Leu Glu Gly Arg Gly Leu Arg Leu Leu Ala Pro Ile
625                 630                 635                 640

ACG GCC TAC TCC CAA CAG ACG CGG GGC CTA CTT GGT TGC ATC ATC ACT      1968
Thr Ala Tyr Ser Gln Gln Thr Arg Gly Leu Leu Gly Cys Ile Ile Thr
                645                 650                 655

AGC CTT ACA GGC CGG GAC AAG AAC CAG GTC GAG GGA GAG GTT CAG GTG      2016
Ser Leu Thr Gly Arg Asp Lys Asn Gln Val Glu Gly Glu Val Gln Val
            660                 665                 670

GTT TCC ACC GCA ACA CAA TCC TTC CTG GCG ACC TGC GTC AAC GGC GTG      2064
Val Ser Thr Ala Thr Gln Ser Phe Leu Ala Thr Cys Val Asn Gly Val
        675                 680                 685

TGT TGG ACC GTT TAC CAT GGT GCT GGC TCA AAG ACC TTA GCC GCG CCA      2112
Cys Trp Thr Val Tyr His Gly Ala Gly Ser Lys Thr Leu Ala Ala Pro
    690                 695                 700

AAG GGG CCA ATC ACC CAG ATG TAC ACT AAT GTG GAC CAG GAC CTC GTC      2160
Lys Gly Pro Ile Thr Gln Met Tyr Thr Asn Val Asp Gln Asp Leu Val
705                 710                 715                 720

GGC TGG CCC AAG CCC CCC GGG GCG CGT TCC TTG ACA CCA TGC ACC TGT      2208
Gly Trp Pro Lys Pro Pro Gly Ala Arg Ser Leu Thr Pro Cys Thr Cys
                725                 730                 735

GGC AGC TCA GAC CTT TAC TTG GTC ACG AGA CAT GCT GAC GTC ATT CCG      2256
Gly Ser Ser Asp Leu Tyr Leu Val Thr Arg His Ala Asp Val Ile Pro
            740                 745                 750

GTG CGC CGG CGG GGC GAC AGT AGG GGG AGC CTG CTC TCC CCC AGG CCT      2304
Val Arg Arg Arg Gly Asp Ser Arg Gly Ser Leu Leu Ser Pro Arg Pro
        755                 760                 765

GTC TCC TAC TTG AAG GGC TCT TCG GGT GGT CCA CTG CTC TGC CCC TTC      2352
Val Ser Tyr Leu Lys Gly Ser Ser Gly Gly Pro Leu Leu Cys Pro Phe
    770                 775                 780

GGG CAC GCT GTG GGC ATC TTC CGG GCT GCC GTA TGC ACC CGG GGG GTT      2400
Gly His Ala Val Gly Ile Phe Arg Ala Ala Val Cys Thr Arg Gly Val
```

-continued

| | |
|---|---|
| GCG AAG GCG GTG GAC TTT GTG CCC GTA GAG TCC ATG GAA ACT ACT ATG<br>Ala Lys Ala Val Asp Phe Val Pro Val Glu Ser Met Glu Thr Thr Met<br>                  805                        810                  815 | 2448 |
| CGG TCT CCG GTC TTC ACG GAC AAC TCA TCC CCC CCG GCC GTA CCG CAG<br>Arg Ser Pro Val Phe Thr Asp Asn Ser Ser Pro Pro Ala Val Pro Gln<br>                  820                        825                  830 | 2496 |
| TCA TTT CAA GTG GCC CAC CTA CAC GCT CCC ACT GGC AGC GGC AAG AGT<br>Ser Phe Gln Val Ala His Leu His Ala Pro Thr Gly Ser Gly Lys Ser<br>                  835                        840                  845 | 2544 |
| ACT AAA GTG CCG GCT GCA TAT GCA GCC CAA GGG TAC AAG GTG CTC GTC<br>Thr Lys Val Pro Ala Ala Tyr Ala Ala Gln Gly Tyr Lys Val Leu Val<br>         850                        855                       860 | 2592 |
| CTC AAT CCG TCC GTT GCC GCT ACC TTA GGG TTT GGG GCG TAT ATG TCT<br>Leu Asn Pro Ser Val Ala Ala Thr Leu Gly Phe Gly Ala Tyr Met Ser<br>865                      870                        875                       880 | 2640 |
| AAG GCA CAC GGT ATT GAC CCC AAC ATC AGA ACT GGG GTA AGG ACC ATT<br>Lys Ala His Gly Ile Asp Pro Asn Ile Arg Thr Gly Val Arg Thr Ile<br>                  885                        890                  895 | 2688 |
| ACC ACA GGC GCC CCC GTC ACA TAC TCT ACC TAT GGC AAG TTT CTT GCC<br>Thr Thr Gly Ala Pro Val Thr Tyr Ser Thr Tyr Gly Lys Phe Leu Ala<br>         900                        905                       910 | 2736 |
| GAT GGT GGT TGC TCT GGG GGC GCT TAT GAC ATC ATA ATA TGT GAT GAG<br>Asp Gly Gly Cys Ser Gly Gly Ala Tyr Asp Ile Ile Ile Cys Asp Glu<br>                  915                        920                  925 | 2784 |
| TGC CAT TCA ACT GAC TCG ACT ACA ATC TTG GGC ATC GGC ACA GTC CTG<br>Cys His Ser Thr Asp Ser Thr Thr Ile Leu Gly Ile Gly Thr Val Leu<br>         930                        935                       940 | 2832 |
| GAC CAA GCG GAG ACG GCT GGA GCG CGG CTT GTC GTG CTC GCC ACC GCT<br>Asp Gln Ala Glu Thr Ala Gly Ala Arg Leu Val Val Leu Ala Thr Ala<br>945                      950                        955                       960 | 2880 |
| ACG CCT CCG GGA TCG GTC ACC GTG CCA CAC CCA AAC ATC GAG GAG GTG<br>Thr Pro Pro Gly Ser Val Thr Val Pro His Pro Asn Ile Glu Glu Val<br>                  965                        970                  975 | 2928 |
| GCC CTG TCT AAT ACT GGA GAG ATC CCC TTC TAT GGC AAA GCC ATC CCC<br>Ala Leu Ser Asn Thr Gly Glu Ile Pro Phe Tyr Gly Lys Ala Ile Pro<br>         980                        985                       990 | 2976 |
| ATT GAA GCC ATC AGG GGG GGA AGG CAT CTC ATT TTC TGT CAT TCC AAG<br>Ile Glu Ala Ile Arg Gly Gly Arg His Leu Ile Phe Cys His Ser Lys<br>         995                      1000                  1005 | 3024 |
| AAG AAG TGC GAC GAG CTC GCC GCA AAG CTG TCA GGC CTC GGA ATC AAC<br>Lys Lys Cys Asp Glu Leu Ala Ala Lys Leu Ser Gly Leu Gly Ile Asn<br>1010                      1015                      1020 | 3072 |
| GCT GTG GCG TAT TAC CGG GGG CTC GAT GTG TCC GTC ATA CCA ACT ATC<br>Ala Val Ala Tyr Tyr Arg Gly Leu Asp Val Ser Val Ile Pro Thr Ile<br>1025                      1030                      1035                      1040 | 3120 |
| GGA GAC GTC GTT GTC GTG GCA ACA GAC GCT CTG ATG ACG GGC TAT ACG<br>Gly Asp Val Val Val Val Ala Thr Asp Ala Leu Met Thr Gly Tyr Thr<br>                      1045                      1050                  1055 | 3168 |
| GGC GAC TTT GAC TCA GTG ATC GAC TGT AAC ACA TGT GTC ACC CAG ACA<br>Gly Asp Phe Asp Ser Val Ile Asp Cys Asn Thr Cys Val Thr Gln Thr<br>                  1060                      1065                      1070 | 3216 |
| GTC GAC TTC AGC TTG GAT CCC ACC TTC ACC ATT GAG ACG ACG ACC GTG<br>Val Asp Phe Ser Leu Asp Pro Thr Phe Thr Ile Glu Thr Thr Thr Val<br>         1075                        1080                      1085 | 3264 |
| CCT CAA GAC GCA GTG TCG CGC TCG CAG CGG CGG GGT AGG ACT GGC AGG<br>Pro Gln Asp Ala Val Ser Arg Ser Gln Arg Arg Gly Arg Thr Gly Arg<br>         1090                        1095                      1100 | 3312 |
| GGT AGG AGA GGC ATC TAC AGG TTT GTG ACT CCG GGA GAA CGG CCC TCG<br>Gly Arg Arg Gly Ile Tyr Arg Phe Val Thr Pro Gly Glu Arg Pro Ser | 3360 |

-continued

| | | | | |
|---|---|---|---|---|
| 1105 | 1110 | 1115 | 1120 | |
| GGC ATG TTC GAT TCC TCG GTC CTG TGT GAG TGC TAT GAC GCG GGC TGT<br>Gly Met Phe Asp Ser Ser Val Leu Cys Glu Cys Tyr Asp Ala Gly Cys<br>                    1125                            1130                          1135 | 3408 |
| GCT TGG TAC GAG CTC ACC CCG GCC GAG ACC TCG GTT AGG TTG CGG GCC<br>Ala Trp Tyr Glu Leu Thr Pro Ala Glu Thr Ser Val Arg Leu Arg Ala<br>              1140                          1145                          1150 | 3456 |
| TAC CTG AAC ACA CCA GGG TTG CCC GTT TGC CAG GAC CAC CTG GAG TTC<br>Tyr Leu Asn Thr Pro Gly Leu Pro Val Cys Gln Asp His Leu Glu Phe<br>        1155                            1160                          1165 | 3504 |
| TGG GAG AGT GTC TTC ACA GGC CTC ACC CAT ATA GAT GCA CAC TTC TTG<br>Trp Glu Ser Val Phe Thr Gly Leu Thr His Ile Asp Ala His Phe Leu<br>     1170                         1175                          1180 | 3552 |
| TCC CAG ACC AAG CAG GCA GGA GAC AAC TTC CCC TAC CTG GTA GCA TAC<br>Ser Gln Thr Lys Gln Ala Gly Asp Asn Phe Pro Tyr Leu Val Ala Tyr<br>1185                  1190                         1195                        1200 | 3600 |
| CAA GCC ACG GTG TGC GCC AGG GCT CAG GCC CCA CCT CCA TCA TGG GAT<br>Gln Ala Thr Val Cys Ala Arg Ala Gln Ala Pro Pro Pro Ser Trp Asp<br>                    1205                          1210                         1215 | 3648 |
| CAA ATG TGG AAG TGT CTC ATA CGG CTG AAA CCT ACG CTG CAC GGG CCA<br>Gln Met Trp Lys Cys Leu Ile Arg Leu Lys Pro Thr Leu His Gly Pro<br>        1220                            1225                          1230 | 3696 |
| ACA CCC TTG CTG TAC AGG CTG GGA GCC GTC CAG AAT GAG GTC ACC CTC<br>Thr Pro Leu Leu Tyr Arg Leu Gly Ala Val Gln Asn Glu Val Thr Leu<br>     1235                         1240                          1245 | 3744 |
| ACC CAC CCC ATA ACC AAA TAC ATC ATG GCA TGC ATG TCG GCT GAC CTG<br>Thr His Pro Ile Thr Lys Tyr Ile Met Ala Cys Met Ser Ala Asp Leu<br>  1250                         1255                         1260 | 3792 |
| GAG GTC GTC ACT AGC ACC TGG GTG CTG GTG GGC GGA GTC CTT GCA GCT<br>Glu Val Val Thr Ser Thr Trp Val Leu Val Gly Gly Val Leu Ala Ala<br>1265                  1270                         1275                        1280 | 3840 |
| CTG GCC GCG TAT TGC CTG ACA ACA GGC AGT GTG GTC ATT GTG GGT AGG<br>Leu Ala Ala Tyr Cys Leu Thr Thr Gly Ser Val Val Ile Val Gly Arg<br>                    1285                          1290                         1295 | 3888 |
| ATT ATC TTG TCC GGG AGG CCG GCC ATT GTT CCC GAC AGG GAG CTT CTC<br>Ile Ile Leu Ser Gly Arg Pro Ala Ile Val Pro Asp Arg Glu Leu Leu<br>        1300                            1305                          1310 | 3936 |
| TAC CAG GAG TTC GAT GAA ATG GAA GAG TGC GCC TCG CAC CTC CCT TAC<br>Tyr Gln Glu Phe Asp Glu Met Glu Glu Cys Ala Ser His Leu Pro Tyr<br>     1315                         1320                          1325 | 3984 |
| ATC GAG CAG GGA ATG CAG CTC GCC GAG CAA TTC AAG CAG AAA GCG CTC<br>Ile Glu Gln Gly Met Gln Leu Ala Glu Gln Phe Lys Gln Lys Ala Leu<br>  1330                         1335                         1340 | 4032 |
| GGG TTA CTG CAA ACA GCC ACC AAA CAA GCG GAG GCT GCT GCT CCC GTG<br>Gly Leu Leu Gln Thr Ala Thr Lys Gln Ala Glu Ala Ala Ala Pro Val<br>1345                  1350                         1355                        1360 | 4080 |
| GTG GAG TCC AAG TGG CGA GCC CTT GAG ACA TTC TGG GCG AAG CAC ATG<br>Val Glu Ser Lys Trp Arg Ala Leu Glu Thr Phe Trp Ala Lys His Met<br>                    1365                          1370                         1375 | 4128 |
| TGG AAT TTC ATC AGC GGG ATA CAG TAC TTA GCA GGC TTA TCC ACT CTG<br>Trp Asn Phe Ile Ser Gly Ile Gln Tyr Leu Ala Gly Leu Ser Thr Leu<br>        1380                            1385                          1390 | 4176 |
| CCT GGG AAC CCC GCA ATA GCA TCA TTG ATG GCA TTC ACA GCC TCT ATC<br>Pro Gly Asn Pro Ala Ile Ala Ser Leu Met Ala Phe Thr Ala Ser Ile<br>     1395                         1400                          1405 | 4224 |
| ACC AGC CCG CTC ACC ACC CAA AGT ACC CTC CTG TTT AAC ATC TTG GGG<br>Thr Ser Pro Leu Thr Thr Gln Ser Thr Leu Leu Phe Asn Ile Leu Gly<br>  1410                         1415                         1420 | 4272 |
| GGG TGG GTG GCT GCC CAA CTC GCC CCC CCC AGC GCC GCT TCG GCT TTC<br>Gly Trp Val Ala Ala Gln Leu Ala Pro Pro Ser Ala Ala Ser Ala Phe | 4320 |

-continued

| 1425 | 1430 | 1435 | 1440 | |
|---|---|---|---|---|
| GTG GGC GCC GGC ATC GCC GGT GCG GCT GTT GGC AGC ATA GGC CTT GGG | | | | 4368 |
| Val Gly Ala Gly Ile Ala Gly Ala Ala Val Gly Ser Ile Gly Leu Gly | | | | |
| 1445 | | 1450 | 1455 | |
| AAG GTG CTT GTG GAC ATT CTG GCG GGT TAT GGA GCA GGA GTG GCC GGC | | | | 4416 |
| Lys Val Leu Val Asp Ile Leu Ala Gly Tyr Gly Ala Gly Val Ala Gly | | | | |
| 1460 | | 1465 | 1470 | |
| GCG CTC GTG GCC TTT AAG GTC ATG AGC GGC GAG ATG CCC TCC ACC GAG | | | | 4464 |
| Ala Leu Val Ala Phe Lys Val Met Ser Gly Glu Met Pro Ser Thr Glu | | | | |
| 1475 | | 1480 | 1485 | |
| GAC CTG GTC AAT CTA CTT CCT GCC ATC CTC TCT CCT GGC GCC CTG GTC | | | | 4512 |
| Asp Leu Val Asn Leu Leu Pro Ala Ile Leu Ser Pro Gly Ala Leu Val | | | | |
| 1490 | | 1495 | 1500 | |
| GTC GGG GTC GTG TGT GCA GCA ATA CTG CGT CGA CAC GTG GGT CCG GGA | | | | 4560 |
| Val Gly Val Val Cys Ala Ala Ile Leu Arg Arg His Val Gly Pro Gly | | | | |
| 1505 | | 1510 | 1515 | 1520 |
| GAG GGG GCT GTG CAG TGG ATG AAC CGG CTG ATA GCG TTC GCC TCG CGG | | | | 4608 |
| Glu Gly Ala Val Gln Trp Met Asn Arg Leu Ile Ala Phe Ala Ser Arg | | | | |
| 1525 | | 1530 | 1535 | |
| GGT AAT CAT GTT TCC CCC ACG CAC TAT GTG CCT GAG AGC GAC GCC GCA | | | | 4656 |
| Gly Asn His Val Ser Pro Thr His Tyr Val Pro Glu Ser Asp Ala Ala | | | | |
| 1540 | | 1545 | 1550 | |
| GCG CGT GTT ACT CAG ATC CTC TCC AGC CTT ACC ATC ACT CAG CTG CTG | | | | 4704 |
| Ala Arg Val Thr Gln Ile Leu Ser Ser Leu Thr Ile Thr Gln Leu Leu | | | | |
| 1555 | | 1560 | 1565 | |
| AAA AGG CTC CAC CAG TGG ATT AAT GAA GAC TGC TCC ACA CCG TGT TCC | | | | 4752 |
| Lys Arg Leu His Gln Trp Ile Asn Glu Asp Cys Ser Thr Pro Cys Ser | | | | |
| 1570 | | 1575 | 1580 | |
| GGC TCG TGG CTA AGG GAT GTT TGG GAC TGG ATA TGC ACG GTG TTG ACT | | | | 4800 |
| Gly Ser Trp Leu Arg Asp Val Trp Asp Trp Ile Cys Thr Val Leu Thr | | | | |
| 1585 | 1590 | 1595 | 1600 | |
| GAC TTC AAG ACC TGG CTC CAG TCC AAG CTC CTG CCG CAG CTA CCT GGA | | | | 4848 |
| Asp Phe Lys Thr Trp Leu Gln Ser Lys Leu Leu Pro Gln Leu Pro Gly | | | | |
| 1605 | | 1610 | 1615 | |
| GTC CCT TTT TTC TCG TGC CAA CGC GGG TAC AAG GGA GTC TGG CGG GGA | | | | 4896 |
| Val Pro Phe Phe Ser Cys Gln Arg Gly Tyr Lys Gly Val Trp Arg Gly | | | | |
| 1620 | | 1625 | 1630 | |
| GAC GGC ATC ATG CAA ACC ACC TGC CCA TGT GGA GCA CAG ATC ACC GGA | | | | 4944 |
| Asp Gly Ile Met Gln Thr Thr Cys Pro Cys Gly Ala Gln Ile Thr Gly | | | | |
| 1635 | | 1640 | 1645 | |
| CAT GTC AAA AAC GGT TCC ATG AGG ATC GTC GGG CCT AAG ACC TGC AGC | | | | 4992 |
| His Val Lys Asn Gly Ser Met Arg Ile Val Gly Pro Lys Thr Cys Ser | | | | |
| 1650 | | 1655 | 1660 | |
| AAC ACG TGG CAT GGA ACA TTC CCC ATC AAC GCA TAC ACC ACG GGC CCC | | | | 5040 |
| Asn Thr Trp His Gly Thr Phe Pro Ile Asn Ala Tyr Thr Thr Gly Pro | | | | |
| 1665 | | 1670 | 1675 | 1680 |
| TGC ACA CCC TCT CCA GCG CCA AAC TAT TCT AGG GCG CTG TGG CGG GTG | | | | 5088 |
| Cys Thr Pro Ser Pro Ala Pro Asn Tyr Ser Arg Ala Leu Trp Arg Val | | | | |
| 1685 | | 1690 | 1695 | |
| GCC GCT GAG GAG TAC GTG GAG GTC ACG CGG GTG GGG GAT TTC CAC TAC | | | | 5136 |
| Ala Ala Glu Glu Tyr Val Glu Val Thr Arg Val Gly Asp Phe His Tyr | | | | |
| 1700 | | 1705 | 1710 | |
| GTG ACG GGC ATG ACC ACT GAC AAC GTA AAG TGC CCA TGC CAG GTT CCG | | | | 5184 |
| Val Thr Gly Met Thr Thr Asp Asn Val Lys Cys Pro Cys Gln Val Pro | | | | |
| 1715 | | 1720 | 1725 | |
| GCT CCT GAA TTC TTC TCG GAG GTG GAC GGA GTG CGG TTG CAC AGG TAC | | | | 5232 |
| Ala Pro Glu Phe Phe Ser Glu Val Asp Gly Val Arg Leu His Arg Tyr | | | | |
| 1730 | | 1735 | 1740 | |
| GCT CCG GCG TGC AGG CCT CTC CTA CGG GAG GAG GTT ACA TTC CAG GTC | | | | 5280 |
| Ala Pro Ala Cys Arg Pro Leu Leu Arg Glu Glu Val Thr Phe Gln Val | | | | |

-continued

```
      1745                1750                1755                1760

GGG CTC AAC CAA TAC CTG GTT GGG TCA CAG CTA CCA TGC GAG CCC GAA                5328
Gly Leu Asn Gln Tyr Leu Val Gly Ser Gln Leu Pro Cys Glu Pro Glu
            1765                1770                1775

CCG GAT GTA GCA GTG CTC ACT TCC ATG CTC ACC GAC CCC TCC CAC ATC                5376
Pro Asp Val Ala Val Leu Thr Ser Met Leu Thr Asp Pro Ser His Ile
            1780                1785                1790

ACA GCA GAA ACG GCT AAG CGT AGG TTG GCC AGG GGG TCT CCC CCC TCC                5424
Thr Ala Glu Thr Ala Lys Arg Arg Leu Ala Arg Gly Ser Pro Pro Ser
            1795                1800                1805

TTG GCC AGC TCT TCA GCT AGC CAG TTG TCT GCG CCT TCC TTG AAG GCG                5472
Leu Ala Ser Ser Ser Ala Ser Gln Leu Ser Ala Pro Ser Leu Lys Ala
            1810                1815                1820

ACA TGC ACT ACC CAC CAT GTC TCT CCG GAC GCT GAC CTC ATC GAG GCC                5520
Thr Cys Thr Thr His His Val Ser Pro Asp Ala Asp Leu Ile Glu Ala
1825                1830                1835                1840

AAC CTC CTG TGG CGG CAG GAG ATG GGC GGG AAC ATC ACC CGC GTG GAG                5568
Asn Leu Leu Trp Arg Gln Glu Met Gly Gly Asn Ile Thr Arg Val Glu
            1845                1850                1855

TCG GAG AAC AAG GTG GTA GTC CTG GAC TCT TTC GAC CCG CTT CGA GCG                5616
Ser Glu Asn Lys Val Val Val Leu Asp Ser Phe Asp Pro Leu Arg Ala
            1860                1865                1870

GAG GAG GAT GAG AGG GAA GTA TCC GTT CCG GCG GAG ATC CTG CGG AAA                5664
Glu Glu Asp Glu Arg Glu Val Ser Val Pro Ala Glu Ile Leu Arg Lys
            1875                1880                1885

TCC AAG AAG TTC CCC GCA GCG ATG CCC ATC TGG GCG CGC CCG GAT TAC                5712
Ser Lys Lys Phe Pro Ala Ala Met Pro Ile Trp Ala Arg Pro Asp Tyr
            1890                1895                1900

AAC CCT CCA CTG TTA GAG TCC TGG AAG GAC CCG GAC TAC GTC CCT CCG                5760
Asn Pro Pro Leu Leu Glu Ser Trp Lys Asp Pro Asp Tyr Val Pro Pro
1905                1910                1915                1920

GTG GTG CAC GGG TGC CCG TTG CCA CCT ATC AAG GCC CCT CCA ATA CCA                5808
Val Val His Gly Cys Pro Leu Pro Pro Ile Lys Ala Pro Pro Ile Pro
            1925                1930                1935

CCT CCA CGG AGA AAG AGG ACG GTT GTC CTA ACA GAG TCC TCC GTG TCT                5856
Pro Pro Arg Arg Lys Arg Thr Val Val Leu Thr Glu Ser Ser Val Ser
            1940                1945                1950

TCT GCC TTA GCG GAG CTC GCT ACT AAG ACC TTC GGC AGC TCC GAA TCA                5904
Ser Ala Leu Ala Glu Leu Ala Thr Lys Thr Phe Gly Ser Ser Glu Ser
            1955                1960                1965

TCG GCC GTC GAC AGC GGC ACG GCG ACC GCC CTT CCT GAC CAG GCC TCC                5952
Ser Ala Val Asp Ser Gly Thr Ala Thr Ala Leu Pro Asp Gln Ala Ser
            1970                1975                1980

GAC GAC GGT GAC AAA GGA TCC GAC GTT GAG TCG TAC TCC TCC ATG CCC                6000
Asp Asp Gly Asp Lys Gly Ser Asp Val Glu Ser Tyr Ser Ser Met Pro
1985                1990                1995                2000

CCC CTT GAG GGG GAA CCG GGG GAC CCC GAT CTC AGT GAC GGG TCT TGG                6048
Pro Leu Glu Gly Glu Pro Gly Asp Pro Asp Leu Ser Asp Gly Ser Trp
            2005                2010                2015

TCT ACC GTG AGC GAG GAA GCT AGT GAG GAT GTC GTC TGC TGC TCA ATG                6096
Ser Thr Val Ser Glu Glu Ala Ser Glu Asp Val Val Cys Cys Ser Met
            2020                2025                2030

TCC TAC ACA TGG ACA GGC GCC TTG ATC ACG CCA TGC GCT GCG GAG GAA                6144
Ser Tyr Thr Trp Thr Gly Ala Leu Ile Thr Pro Cys Ala Ala Glu Glu
            2035                2040                2045

AGC AAG CTG CCC ATC AAC GCG TTG AGC AAC TCT TTG CTG CGC CAC CAT                6192
Ser Lys Leu Pro Ile Asn Ala Leu Ser Asn Ser Leu Leu Arg His His
            2050                2055                2060

AAC ATG GTT TAT GCC ACA ACA TCT CGC AGC GCA GGC CTG CGG CAG AAG                6240
Asn Met Val Tyr Ala Thr Thr Ser Arg Ser Ala Gly Leu Arg Gln Lys
```

```
                2065                2070                2075                2080
AAG GTC ACC TTT GAC AGA CTG CAA GTC CTG GAC GAC CAC TAC CGG GAC              6288
Lys Val Thr Phe Asp Arg Leu Gln Val Leu Asp Asp His Tyr Arg Asp
            2085                2090                2095

GTG CTC AAG GAG ATG AAG GCG AAG GCG TCC ACA GTT AAG GCT AAA CTC              6336
Val Leu Lys Glu Met Lys Ala Lys Ala Ser Thr Val Lys Ala Lys Leu
            2100                2105                2110

CTA TCC GTA GAG GAA GCC TGC AAG CTG ACG CCC CCA CAT TCG GCC AAA              6384
Leu Ser Val Glu Glu Ala Cys Lys Leu Thr Pro Pro His Ser Ala Lys
            2115                2120                2125

TCC AAG TTT GGC TAT GGG GCA AAG GAC GTC CGG AAC CTA TCC AGC AAG              6432
Ser Lys Phe Gly Tyr Gly Ala Lys Asp Val Arg Asn Leu Ser Ser Lys
            2130                2135                2140

GCC GTT AAC CAC ATC CAC TCC GTG TGG AAG GAC TTG CTG GAA GAC ACT              6480
Ala Val Asn His Ile His Ser Val Trp Lys Asp Leu Leu Glu Asp Thr
2145                2150                2155                2160

GTG ACA CCA ATT GAC ACC ACC ATC ATG GCA AAA AAT GAG GTT TTC TGT              6528
Val Thr Pro Ile Asp Thr Thr Ile Met Ala Lys Asn Glu Val Phe Cys
            2165                2170                2175

GTC CAA CCA GAG AAA GGA GGC CGT AAG CCA GCC CGC CTT ATC GTA TTC              6576
Val Gln Pro Glu Lys Gly Gly Arg Lys Pro Ala Arg Leu Ile Val Phe
            2180                2185                2190

CCA GAT CTG GGA GTC CGT GTA TGC GAG AAG ATG GCC CTC TAT GAT GTG              6624
Pro Asp Leu Gly Val Arg Val Cys Glu Lys Met Ala Leu Tyr Asp Val
            2195                2200                2205

GTC TCC ACC CTT CCT CAG GTC GTG ATG GGC TCC TCA TAC GGA TTC CAG              6672
Val Ser Thr Leu Pro Gln Val Val Met Gly Ser Ser Tyr Gly Phe Gln
            2210                2215                2220

TAC TCT CCT GGG CAG CGA GTC GAG TTC CTG GTG AAT ACC TGG AAA TCA              6720
Tyr Ser Pro Gly Gln Arg Val Glu Phe Leu Val Asn Thr Trp Lys Ser
2225                2230                2235                2240

AAG AAA AAC CCC ATG GGC TTT TCA TAT GAC ACT CGC TGT TTC GAC TCA              6768
Lys Lys Asn Pro Met Gly Phe Ser Tyr Asp Thr Arg Cys Phe Asp Ser
            2245                2250                2255

ACG GTC ACC GAG AAC GAC ATC CGT GTT GAG GAG TCA ATT TAC CAA TGT              6816
Thr Val Thr Glu Asn Asp Ile Arg Val Glu Glu Ser Ile Tyr Gln Cys
            2260                2265                2270

TGT GAC TTG GCC CCC GAA GCC AGA CAG GCC ATA AAA TCG CTC ACA GAG              6864
Cys Asp Leu Ala Pro Glu Ala Arg Gln Ala Ile Lys Ser Leu Thr Glu
            2275                2280                2285

CGG CTT TAT ATC GGG GGT CCT CTG ACT AAT TCA AAA GGG CAG AAC TGC              6912
Arg Leu Tyr Ile Gly Gly Pro Leu Thr Asn Ser Lys Gly Gln Asn Cys
            2290                2295                2300

GGT TAT CGC CGG TGC CGC GCG AGC GGC GTG CTG ACG ACT AGC TGC GGT              6960
Gly Tyr Arg Arg Cys Arg Ala Ser Gly Val Leu Thr Thr Ser Cys Gly
2305                2310                2315                2320

AAC ACC CTC ACA TGT TAC TTG AAG GCC TCT GCA GCC TGT CGA GCT GCG              7008
Asn Thr Leu Thr Cys Tyr Leu Lys Ala Ser Ala Ala Cys Arg Ala Ala
            2325                2330                2335

AAG CTC CAG GAC TGC ACG ATG CTC GTG AAC GGA GAC GAC CTC GTC GTT              7056
Lys Leu Gln Asp Cys Thr Met Leu Val Asn Gly Asp Asp Leu Val Val
            2340                2345                2350

ATC TGT GAA AGC GCG GGA ACC CAA GAG GAC GCG GCG AGC CTA CGA GTC              7104
Ile Cys Glu Ser Ala Gly Thr Gln Glu Asp Ala Ala Ser Leu Arg Val
            2355                2360                2365

TTC ACG GAG GCT ATG ACT AGG TAC TCC GCC CCC CCC GGG GAC CCG CCC              7152
Phe Thr Glu Ala Met Thr Arg Tyr Ser Ala Pro Pro Gly Asp Pro Pro
            2370                2375                2380

CAA CCA GAA TAC GAC TTG GAG CTG ATA ACA TCA TGT TCC TCC AAT GTG              7200
Gln Pro Glu Tyr Asp Leu Glu Leu Ile Thr Ser Cys Ser Ser Asn Val
```

-continued

```
               2385                2390                2395                2400
TCG GTC GCC CAC GAT GCA TCA GGC AAA AGG GTG TAC TAC CTC ACC CGT            7248
Ser Val Ala His Asp Ala Ser Gly Lys Arg Val Tyr Tyr Leu Thr Arg
                    2405                2410                2415

GAT CCC ACC ACC CCC CTA GCA CGG GCT GCG TGG GAG ACA GCT AGA CAC            7296
Asp Pro Thr Thr Pro Leu Ala Arg Ala Ala Trp Glu Thr Ala Arg His
        2420                2425                2430

ACT CCA GTT AAC TCC TGG CTA GGC AAC ATT ATT ATG TAT GCG CCC ACT            7344
Thr Pro Val Asn Ser Trp Leu Gly Asn Ile Ile Met Tyr Ala Pro Thr
            2435                2440                2445

TTG TGG GCA AGG ATG ATT CTG ATG ACT CAC TTC TTC TCC ATC CTT CTA            7392
Leu Trp Ala Arg Met Ile Leu Met Thr His Phe Phe Ser Ile Leu Leu
        2450                2455                2460

GCG CAG GAG CAA CTT GAA AAA GCC CTG GAC TGC CAG ATC TAC GGG GCC            7440
Ala Gln Glu Gln Leu Glu Lys Ala Leu Asp Cys Gln Ile Tyr Gly Ala
2465                2470                2475                2480

TGT TAC TCC ATT GAG CCA CTT GAC CTA CCT CAG ATC ATT GAA CGA CTC            7488
Cys Tyr Ser Ile Glu Pro Leu Asp Leu Pro Gln Ile Ile Glu Arg Leu
                2485                2490                2495

CAT GGC CTT AGC GCA TTT TCA CTC CAT AGT TAC TCT CCA GGT GAG ATC            7536
His Gly Leu Ser Ala Phe Ser Leu His Ser Tyr Ser Pro Gly Glu Ile
            2500                2505                2510

AAT AGG GTG GCT TCA TGC CTC AGG AAA CTT GGG GTA CCA CCC TTG CGA            7584
Asn Arg Val Ala Ser Cys Leu Arg Lys Leu Gly Val Pro Pro Leu Arg
        2515                2520                2525

GTC TGG AGA CAT CGG GCC AGG AGC GTC CGC GCT AGG CTA CTG TCC CAG            7632
Val Trp Arg His Arg Ala Arg Ser Val Arg Ala Arg Leu Leu Ser Gln
    2530                2535                2540

GGA GGG AGG GCC GCC ACT TGT GGC AAA TAC CTC TTC AAC TGG GCA GTA            7680
Gly Gly Arg Ala Ala Thr Cys Gly Lys Tyr Leu Phe Asn Trp Ala Val
2545                2550                2555                2560

AAA ACC AAA CTT AAA CTC ACT CCA ATC CCG GCT GCG TCC CGG CTG GAC            7728
Lys Thr Lys Leu Lys Leu Thr Pro Ile Pro Ala Ala Ser Arg Leu Asp
                2565                2570                2575

TTG TCC GGC TGG TTC GTT GCT GGT TAC AGC GGG GGA GAC ATA TAT CAC            7776
Leu Ser Gly Trp Phe Val Ala Gly Tyr Ser Gly Gly Asp Ile Tyr His
            2580                2585                2590

AGC CTG TCT CGT GCC CGA CCC CGT TGG TTC ATG CTG TGC CTA CTC CTA            7824
Ser Leu Ser Arg Ala Arg Pro Arg Trp Phe Met Leu Cys Leu Leu Leu
        2595                2600                2605

CTT TCT GTA GGG GTA GGC ATC TAC CTG CTC CCC AAC CGA                        7863
Leu Ser Val Gly Val Gly Ile Tyr Leu Leu Pro Asn Arg
    2610                2615                2620
```

(2) INFORMATION FOR SEQ ID NO:36:

(i) SEQUENCE CHARACTERISTICS:
        (A) LENGTH: 2621 amino acids
        (B) TYPE: amino acid
        (D) TOPOLOGY: linear (ii) MOLECULE TYPE: protein (xi) SEQUENCE DESCRIPTION: SEQ ID NO:36:

```
Gly Ala Gln Ala Lys Thr Thr Asn Arg Leu Val Ser Met Phe Ala Ser
 1               5                  10                  15

Gly Pro Ser Gln Lys Ile Gln Leu Ile Asn Thr Asn Gly Ser Trp His
            20                  25                  30

Ile Asn Arg Thr Ala Leu Asn Cys Asn Asp Ser Leu Gln Thr Gly Phe
        35                  40                  45

Leu Ala Ala Leu Phe Tyr Thr His Ser Phe Asn Ser Ser Gly Cys Pro
```

```
            50                  55                  60
Glu Arg Met Ala Gln Cys Arg Thr Ile Asp Lys Phe Asp Gln Gly Trp
 65                  70                  75                  80

Gly Pro Ile Thr Tyr Ala Glu Ser Ser Arg Ser Asp Gln Arg Pro Tyr
                 85                  90                  95

Cys Trp His Tyr Pro Pro Gln Cys Thr Ile Val Pro Ala Ser Glu
                100                 105                 110

Val Cys Gly Pro Val Tyr Cys Phe Thr Pro Ser Pro Val Val Gly
                115                 120                 125

Thr Thr Asp Arg Phe Gly Val Pro Thr Tyr Arg Trp Gly Glu Asn Glu
130                 135                 140

Thr Asp Val Leu Leu Leu Asn Asn Thr Arg Pro Pro Gln Gly Asn Trp
145                 150                 155                 160

Phe Gly Cys Thr Trp Met Asn Ser Thr Gly Phe Thr Lys Thr Cys Gly
                165                 170                 175

Gly Pro Pro Cys Asn Ile Gly Gly Val Gly Asn Asn Thr Leu Thr Cys
                180                 185                 190

Pro Thr Asp Cys Phe Arg Lys His Pro Glu Ala Thr Tyr Thr Lys Cys
                195                 200                 205

Gly Ser Gly Pro Trp Leu Thr Pro Arg Cys Met Val Asp Tyr Pro Tyr
210                 215                 220

Arg Leu Trp His Tyr Pro Cys Thr Val Asn Phe Thr Ile Phe Lys Val
225                 230                 235                 240

Arg Met Tyr Val Gly Gly Val Glu His Arg Leu Asn Ala Ala Cys Asn
                245                 250                 255

Trp Thr Arg Gly Glu Arg Cys Asp Leu Glu Asp Arg Asp Arg Pro Glu
                260                 265                 270

Leu Ser Pro Leu Leu Leu Ser Thr Thr Glu Trp Gln Val Leu Pro Cys
                275                 280                 285

Ser Phe Thr Thr Leu Pro Ala Leu Ser Thr Gly Leu Ile His Leu His
                290                 295                 300

Gln Asn Ile Val Asp Val Gln Tyr Leu Tyr Gly Ile Gly Ser Ala Val
305                 310                 315                 320

Val Ser Phe Ala Ile Lys Trp Glu Tyr Val Leu Leu Leu Phe Leu Leu
                325                 330                 335

Leu Ala Asp Ala Arg Val Cys Ala Cys Leu Trp Met Met Leu Leu Ile
                340                 345                 350

Ala Gln Ala Glu Ala Ala Leu Glu Asn Leu Val Val Leu Asn Ser Ala
                355                 360                 365

Ser Val Ala Gly Ala His Gly Ile Leu Ser Phe Leu Val Phe Phe Cys
370                 375                 380

Ala Ala Trp Tyr Ile Lys Gly Arg Leu Val Pro Gly Ala Thr Tyr Ala
385                 390                 395                 400

Leu Tyr Gly Val Trp Pro Leu Leu Leu Leu Leu Ala Leu Pro Pro
                405                 410                 415

Arg Ala Tyr Ala Met Asp Arg Glu Met Ala Ala Ser Cys Gly Gly Ala
                420                 425                 430

Val Phe Val Gly Leu Val Leu Leu Thr Leu Ser Pro Tyr Tyr Lys Val
                435                 440                 445

Phe Leu Ala Arg Leu Ile Trp Trp Leu Gln Tyr Phe Thr Thr Arg Ala
                450                 455                 460

Glu Ala Asp Leu His Val Trp Ile Pro Pro Leu Asn Ala Arg Gly Gly
465                 470                 475                 480
```

-continued

```
Arg Asp Ala Ile Ile Leu Leu Met Cys Ala Val His Pro Glu Leu Ile
                485                 490                 495

Phe Asp Ile Thr Lys Leu Leu Ile Ala Ile Leu Gly Pro Leu Met Val
            500                 505                 510

Leu Gln Ala Gly Ile Thr Arg Val Pro Tyr Phe Val Arg Ala Gln Gly
        515                 520                 525

Leu Ile His Ala Cys Met Leu Val Arg Lys Val Ala Gly Gly His Tyr
    530                 535                 540

Val Gln Met Ala Phe Met Lys Leu Gly Ala Leu Thr Gly Thr Tyr Ile
545                 550                 555                 560

Tyr Asn His Leu Thr Pro Leu Arg Asp Trp Pro Arg Ala Gly Leu Arg
                565                 570                 575

Asp Leu Ala Val Ala Val Glu Pro Val Val Phe Ser Asp Met Glu Thr
            580                 585                 590

Lys Ile Ile Thr Trp Gly Ala Asp Thr Ala Ala Cys Gly Asp Ile Ile
        595                 600                 605

Leu Gly Leu Pro Val Ser Ala Arg Gly Lys Glu Ile Leu Leu Gly
    610                 615                 620

Pro Ala Asp Ser Leu Glu Gly Arg Gly Leu Arg Leu Leu Ala Pro Ile
625                 630                 635                 640

Thr Ala Tyr Ser Gln Gln Thr Arg Gly Leu Leu Gly Cys Ile Ile Thr
                645                 650                 655

Ser Leu Thr Gly Arg Asp Lys Asn Gln Val Glu Gly Glu Val Gln Val
            660                 665                 670

Val Ser Thr Ala Thr Gln Ser Phe Leu Ala Thr Cys Val Asn Gly Val
        675                 680                 685

Cys Trp Thr Val Tyr His Gly Ala Gly Ser Lys Thr Leu Ala Ala Pro
    690                 695                 700

Lys Gly Pro Ile Thr Gln Met Tyr Thr Asn Val Asp Gln Asp Leu Val
705                 710                 715                 720

Gly Trp Pro Lys Pro Pro Gly Ala Arg Ser Leu Thr Pro Cys Thr Cys
                725                 730                 735

Gly Ser Ser Asp Leu Tyr Leu Val Thr Arg His Ala Asp Val Ile Pro
            740                 745                 750

Val Arg Arg Arg Gly Asp Ser Arg Gly Ser Leu Leu Ser Pro Arg Pro
        755                 760                 765

Val Ser Tyr Leu Lys Gly Ser Ser Gly Gly Pro Leu Leu Cys Pro Phe
    770                 775                 780

Gly His Ala Val Gly Ile Phe Arg Ala Ala Val Cys Thr Arg Gly Val
785                 790                 795                 800

Ala Lys Ala Val Asp Phe Val Pro Val Glu Ser Met Glu Thr Thr Met
                805                 810                 815

Arg Ser Pro Val Phe Thr Asp Asn Ser Ser Pro Pro Ala Val Pro Gln
            820                 825                 830

Ser Phe Gln Val Ala His Leu His Ala Pro Thr Gly Ser Gly Lys Ser
        835                 840                 845

Thr Lys Val Pro Ala Ala Tyr Ala Ala Gln Gly Tyr Lys Val Leu Val
    850                 855                 860

Leu Asn Pro Ser Val Ala Ala Thr Leu Gly Phe Gly Ala Tyr Met Ser
865                 870                 875                 880

Lys Ala His Gly Ile Asp Pro Asn Ile Arg Thr Gly Val Arg Thr Ile
                885                 890                 895

Thr Thr Gly Ala Pro Val Thr Tyr Ser Thr Tyr Gly Lys Phe Leu Ala
            900                 905                 910
```

```
Asp Gly Gly Cys Ser Gly Gly Ala Tyr Asp Ile Ile Ile Cys Asp Glu
        915                 920                 925

Cys His Ser Thr Asp Ser Thr Thr Ile Leu Gly Ile Gly Thr Val Leu
        930                 935                 940

Asp Gln Ala Glu Thr Ala Gly Ala Arg Leu Val Val Leu Ala Thr Ala
945                 950                 955                 960

Thr Pro Pro Gly Ser Val Thr Val Pro His Pro Asn Ile Glu Glu Val
                965                 970                 975

Ala Leu Ser Asn Thr Gly Glu Ile Pro Phe Tyr Gly Lys Ala Ile Pro
            980                 985                 990

Ile Glu Ala Ile Arg Gly Gly Arg His Leu Ile Phe Cys His Ser Lys
            995                 1000                1005

Lys Lys Cys Asp Glu Leu Ala Ala Lys Leu Ser Gly Leu Gly Ile Asn
        1010                1015                1020

Ala Val Ala Tyr Tyr Arg Gly Leu Asp Val Ser Val Ile Pro Thr Ile
1025                1030                1035                1040

Gly Asp Val Val Val Ala Thr Asp Ala Leu Met Thr Gly Tyr Thr
                1045                1050                1055

Gly Asp Phe Asp Ser Val Ile Asp Cys Asn Thr Cys Val Thr Gln Thr
                1060                1065                1070

Val Asp Phe Ser Leu Asp Pro Thr Phe Thr Ile Glu Thr Thr Thr Val
            1075                1080                1085

Pro Gln Asp Ala Val Ser Arg Ser Gln Arg Arg Gly Arg Thr Gly Arg
            1090                1095                1100

Gly Arg Arg Gly Ile Tyr Arg Phe Val Thr Pro Gly Glu Arg Pro Ser
1105                1110                1115                1120

Gly Met Phe Asp Ser Ser Val Leu Cys Glu Cys Tyr Asp Ala Gly Cys
                1125                1130                1135

Ala Trp Tyr Glu Leu Thr Pro Ala Glu Thr Ser Val Arg Leu Arg Ala
                1140                1145                1150

Tyr Leu Asn Thr Pro Gly Leu Pro Val Cys Gln Asp His Leu Glu Phe
            1155                1160                1165

Trp Glu Ser Val Phe Thr Gly Leu Thr His Ile Asp Ala His Phe Leu
        1170                1175                1180

Ser Gln Thr Lys Gln Ala Gly Asp Asn Phe Pro Tyr Leu Val Ala Tyr
1185                1190                1195                1200

Gln Ala Thr Val Cys Ala Arg Ala Gln Ala Pro Pro Pro Ser Trp Asp
                1205                1210                1215

Gln Met Trp Lys Cys Leu Ile Arg Leu Lys Pro Thr Leu His Gly Pro
                1220                1225                1230

Thr Pro Leu Leu Tyr Arg Leu Gly Ala Val Gln Asn Glu Val Thr Leu
            1235                1240                1245

Thr His Pro Ile Thr Lys Tyr Ile Met Ala Cys Met Ser Ala Asp Leu
        1250                1255                1260

Glu Val Val Thr Ser Thr Trp Val Leu Val Gly Gly Val Leu Ala Ala
1265                1270                1275                1280

Leu Ala Ala Tyr Cys Leu Thr Thr Gly Ser Val Val Ile Val Gly Arg
                1285                1290                1295

Ile Ile Leu Ser Gly Arg Pro Ala Ile Val Pro Asp Arg Glu Leu Leu
                1300                1305                1310

Tyr Gln Glu Phe Asp Glu Met Glu Glu Cys Ala Ser His Leu Pro Tyr
            1315                1320                1325

Ile Glu Gln Gly Met Gln Leu Ala Glu Gln Phe Lys Gln Lys Ala Leu
```

-continued

```
             1330                1335                1340
Gly Leu Leu Gln Thr Ala Thr Lys Gln Ala Glu Ala Ala Pro Val
1345                1350                1355                1360
Val Glu Ser Lys Trp Arg Ala Leu Glu Thr Phe Trp Ala Lys His Met
                1365                1370                1375
Trp Asn Phe Ile Ser Gly Ile Gln Tyr Leu Ala Gly Leu Ser Thr Leu
                1380                1385                1390
Pro Gly Asn Pro Ala Ile Ala Ser Leu Met Ala Phe Thr Ala Ser Ile
                1395                1400                1405
Thr Ser Pro Leu Thr Thr Gln Ser Thr Leu Leu Phe Asn Ile Leu Gly
                1410                1415                1420
Gly Trp Val Ala Ala Gln Leu Ala Pro Pro Ser Ala Ala Ser Ala Phe
1425                1430                1435                1440
Val Gly Ala Gly Ile Ala Gly Ala Ala Val Gly Ser Ile Gly Leu Gly
                1445                1450                1455
Lys Val Leu Val Asp Ile Leu Ala Gly Tyr Gly Ala Gly Val Ala Gly
                1460                1465                1470
Ala Leu Val Ala Phe Lys Val Met Ser Gly Glu Met Pro Ser Thr Glu
                1475                1480                1485
Asp Leu Val Asn Leu Leu Pro Ala Ile Leu Ser Pro Gly Ala Leu Val
                1490                1495                1500
Val Gly Val Val Cys Ala Ala Ile Leu Arg Arg His Val Gly Pro Gly
1505                1510                1515                1520
Glu Gly Ala Val Gln Trp Met Asn Arg Leu Ile Ala Phe Ala Ser Arg
                1525                1530                1535
Gly Asn His Val Ser Pro Thr His Tyr Val Pro Glu Ser Asp Ala Ala
                1540                1545                1550
Ala Arg Val Thr Gln Ile Leu Ser Ser Leu Thr Ile Thr Gln Leu Leu
                1555                1560                1565
Lys Arg Leu His Gln Trp Ile Asn Glu Asp Cys Ser Thr Pro Cys Ser
                1570                1575                1580
Gly Ser Trp Leu Arg Asp Val Trp Asp Trp Ile Cys Thr Val Leu Thr
1585                1590                1595                1600
Asp Phe Lys Thr Trp Leu Gln Ser Lys Leu Leu Pro Gln Leu Pro Gly
                1605                1610                1615
Val Pro Phe Phe Ser Cys Gln Arg Gly Tyr Lys Gly Val Trp Arg Gly
                1620                1625                1630
Asp Gly Ile Met Gln Thr Thr Cys Pro Cys Gly Ala Gln Ile Thr Gly
                1635                1640                1645
His Val Lys Asn Gly Ser Met Arg Ile Val Gly Pro Lys Thr Cys Ser
                1650                1655                1660
Asn Thr Trp His Gly Thr Phe Pro Ile Asn Ala Tyr Thr Thr Gly Pro
1665                1670                1675                1680
Cys Thr Pro Ser Pro Ala Pro Asn Tyr Ser Arg Ala Leu Trp Arg Val
                1685                1690                1695
Ala Ala Glu Glu Tyr Val Glu Val Thr Arg Val Gly Asp Phe His Tyr
                1700                1705                1710
Val Thr Gly Met Thr Thr Asp Asn Val Lys Cys Pro Cys Gln Val Pro
                1715                1720                1725
Ala Pro Glu Phe Phe Ser Glu Val Asp Gly Val Arg Leu His Arg Tyr
                1730                1735                1740
Ala Pro Ala Cys Arg Pro Leu Leu Arg Glu Glu Val Thr Phe Gln Val
1745                1750                1755                1760
```

-continued

```
Gly Leu Asn Gln Tyr Leu Val Gly Ser Gln Leu Pro Cys Glu Pro Glu
            1765                1770                1775

Pro Asp Val Ala Val Leu Thr Ser Met Leu Thr Asp Pro Ser His Ile
            1780                1785                1790

Thr Ala Glu Thr Ala Lys Arg Arg Leu Ala Arg Gly Ser Pro Pro Ser
            1795                1800                1805

Leu Ala Ser Ser Ser Ala Ser Gln Leu Ser Ala Pro Ser Leu Lys Ala
            1810                1815                1820

Thr Cys Thr Thr His His Val Ser Pro Asp Ala Asp Leu Ile Glu Ala
1825                1830                1835                1840

Asn Leu Leu Trp Arg Gln Glu Met Gly Gly Asn Ile Thr Arg Val Glu
            1845                1850                1855

Ser Glu Asn Lys Val Val Val Leu Asp Ser Phe Asp Pro Leu Arg Ala
            1860                1865                1870

Glu Glu Asp Glu Arg Glu Val Ser Val Pro Ala Glu Ile Leu Arg Lys
            1875                1880                1885

Ser Lys Lys Phe Pro Ala Ala Met Pro Ile Trp Ala Arg Pro Asp Tyr
            1890                1895                1900

Asn Pro Pro Leu Leu Glu Ser Trp Lys Asp Pro Asp Tyr Val Pro Pro
1905                1910                1915                1920

Val Val His Gly Cys Pro Leu Pro Pro Ile Lys Ala Pro Pro Ile Pro
            1925                1930                1935

Pro Pro Arg Arg Lys Arg Thr Val Val Leu Thr Glu Ser Ser Val Ser
            1940                1945                1950

Ser Ala Leu Ala Glu Leu Ala Thr Lys Thr Phe Gly Ser Ser Glu Ser
            1955                1960                1965

Ser Ala Val Asp Ser Gly Thr Ala Thr Ala Leu Pro Asp Gln Ala Ser
            1970                1975                1980

Asp Asp Gly Asp Lys Gly Ser Asp Val Glu Ser Tyr Ser Ser Met Pro
1985                1990                1995                2000

Pro Leu Glu Gly Glu Pro Gly Asp Pro Asp Leu Ser Asp Gly Ser Trp
            2005                2010                2015

Ser Thr Val Ser Glu Glu Ala Ser Glu Asp Val Val Cys Cys Ser Met
            2020                2025                2030

Ser Tyr Thr Trp Thr Gly Ala Leu Ile Thr Pro Cys Ala Ala Glu Glu
            2035                2040                2045

Ser Lys Leu Pro Ile Asn Ala Leu Ser Asn Ser Leu Leu Arg His His
            2050                2055                2060

Asn Met Val Tyr Ala Thr Thr Ser Arg Ser Ala Gly Leu Arg Gln Lys
2065                2070                2075                2080

Lys Val Thr Phe Asp Arg Leu Gln Val Leu Asp Asp His Tyr Arg Asp
            2085                2090                2095

Val Leu Lys Glu Met Lys Ala Lys Ala Ser Thr Val Lys Ala Lys Leu
            2100                2105                2110

Leu Ser Val Glu Glu Ala Cys Lys Leu Thr Pro Pro His Ser Ala Lys
            2115                2120                2125

Ser Lys Phe Gly Tyr Gly Ala Lys Asp Val Arg Asn Leu Ser Ser Lys
            2130                2135                2140

Ala Val Asn His Ile His Ser Val Trp Lys Asp Leu Leu Glu Asp Thr
2145                2150                2155                2160

Val Thr Pro Ile Asp Thr Thr Ile Met Ala Lys Asn Glu Val Phe Cys
            2165                2170                2175

Val Gln Pro Glu Lys Gly Gly Arg Lys Pro Ala Arg Leu Ile Val Phe
            2180                2185                2190
```

```
Pro Asp Leu Gly Val Arg Val Cys Glu Lys Met Ala Leu Tyr Asp Val
    2195                2200                2205

Val Ser Thr Leu Pro Gln Val Val Met Gly Ser Ser Tyr Gly Phe Gln
        2210                2215                2220

Tyr Ser Pro Gly Gln Arg Val Glu Phe Leu Val Asn Thr Trp Lys Ser
2225                2230                2235                2240

Lys Lys Asn Pro Met Gly Phe Ser Tyr Asp Thr Arg Cys Phe Asp Ser
            2245                2250                2255

Thr Val Thr Glu Asn Asp Ile Arg Val Glu Glu Ser Ile Tyr Gln Cys
                2260                2265                2270

Cys Asp Leu Ala Pro Glu Ala Arg Gln Ala Ile Lys Ser Leu Thr Glu
            2275                2280                2285

Arg Leu Tyr Ile Gly Gly Pro Leu Thr Asn Ser Lys Gly Gln Asn Cys
        2290                2295                2300

Gly Tyr Arg Arg Cys Arg Ala Ser Gly Val Leu Thr Thr Ser Cys Gly
2305                2310                2315                2320

Asn Thr Leu Thr Cys Tyr Leu Lys Ala Ser Ala Ala Cys Arg Ala Ala
            2325                2330                2335

Lys Leu Gln Asp Cys Thr Met Leu Val Asn Gly Asp Asp Leu Val Val
                2340                2345                2350

Ile Cys Glu Ser Ala Gly Thr Gln Glu Asp Ala Ala Ser Leu Arg Val
            2355                2360                2365

Phe Thr Glu Ala Met Thr Arg Tyr Ser Ala Pro Pro Gly Asp Pro Pro
        2370                2375                2380

Gln Pro Glu Tyr Asp Leu Glu Leu Ile Thr Ser Cys Ser Ser Asn Val
2385                2390                2395                2400

Ser Val Ala His Asp Ala Ser Gly Lys Arg Val Tyr Tyr Leu Thr Arg
            2405                2410                2415

Asp Pro Thr Thr Pro Leu Ala Arg Ala Ala Trp Glu Thr Ala Arg His
            2420                2425                2430

Thr Pro Val Asn Ser Trp Leu Gly Asn Ile Ile Met Tyr Ala Pro Thr
        2435                2440                2445

Leu Trp Ala Arg Met Ile Leu Met Thr His Phe Phe Ser Ile Leu Leu
    2450                2455                2460

Ala Gln Glu Gln Leu Glu Lys Ala Leu Asp Cys Gln Ile Tyr Gly Ala
2465                2470                2475                2480

Cys Tyr Ser Ile Glu Pro Leu Asp Leu Pro Gln Ile Ile Glu Arg Leu
            2485                2490                2495

His Gly Leu Ser Ala Phe Ser Leu His Ser Tyr Ser Pro Gly Glu Ile
        2500                2505                2510

Asn Arg Val Ala Ser Cys Leu Arg Lys Leu Gly Val Pro Pro Leu Arg
    2515                2520                2525

Val Trp Arg His Arg Ala Arg Ser Val Arg Ala Arg Leu Leu Ser Gln
    2530                2535                2540

Gly Gly Arg Ala Ala Thr Cys Gly Lys Tyr Leu Phe Asn Trp Ala Val
2545                2550                2555                2560

Lys Thr Lys Leu Lys Leu Thr Pro Ile Pro Ala Ala Ser Arg Leu Asp
            2565                2570                2575

Leu Ser Gly Trp Phe Val Ala Gly Tyr Ser Gly Gly Asp Ile Tyr His
        2580                2585                2590

Ser Leu Ser Arg Ala Arg Pro Arg Trp Phe Met Leu Cys Leu Leu Leu
        2595                2600                2605

Leu Ser Val Gly Val Gly Ile Tyr Leu Leu Pro Asn Arg
```

(2) INFORMATION FOR SEQ ID NO:37:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..831
        (D) OTHER INFORMATION: /note: "sequence = 2520 - 3350 of
            SEQ ID NO: 1"

(ix) FEATURE:
        (A) NAME/KEY: CDS
        (B) LOCATION: 1..831

(xi) SEQUENCE DESCRIPTION: SEQ ID NO:37:

```
CGT GTC TGT GCC TGC TTG TGG ATG ATG CTG CTG ATA GCC CAG GCC GAG        48
Arg Val Cys Ala Cys Leu Trp Met Met Leu Leu Ile Ala Gln Ala Glu
 1               5                  10                  15

GCC GCC TTG GAG AAC CTG GTG GTC CTC AAT TCG GCG TCT GTG GCC GGC        96
Ala Ala Leu Glu Asn Leu Val Val Leu Asn Ser Ala Ser Val Ala Gly
             20                  25                  30

GCA CAT GGC ATC CTC TCC TTC CTT GTG TTC TTC TGT GCC GCC TGG TAC       144
Ala His Gly Ile Leu Ser Phe Leu Val Phe Phe Cys Ala Ala Trp Tyr
         35                  40                  45

ATC AAA GGC AGG CTG GTC CCT GGG GCG ACA TAT GCT CTT TAT GGC GTG       192
Ile Lys Gly Arg Leu Val Pro Gly Ala Thr Tyr Ala Leu Tyr Gly Val
     50                  55                  60

TGG CCG CTG CTC CTG CTC TTG CTG GCA TTA CCA CCG CGA GCT TAC GCC       240
Trp Pro Leu Leu Leu Leu Leu Leu Ala Leu Pro Pro Arg Ala Tyr Ala
 65                  70                  75                  80

ATG GAC CGG GAG ATG GCT GCA TCG TGC GGA GGC GCG GTT TTT GTG GGT       288
Met Asp Arg Glu Met Ala Ala Ser Cys Gly Gly Ala Val Phe Val Gly
                 85                  90                  95

CTG GTA CTC CTG ACT TTG TCA CCA TAC TAC AAG GTG TTC CTC GCT AGG       336
Leu Val Leu Leu Thr Leu Ser Pro Tyr Tyr Lys Val Phe Leu Ala Arg
            100                 105                 110

CTC ATA TGG TGG TTA CAA TAT TTT ACC ACC AGA GCC GAG GCG GAC TTA       384
Leu Ile Trp Trp Leu Gln Tyr Phe Thr Thr Arg Ala Glu Ala Asp Leu
        115                 120                 125

CAT GTG TGG ATC CCC CCC CTC AAC GCT CGG GGA GGC CGC GAT GCC ATC       432
His Val Trp Ile Pro Pro Leu Asn Ala Arg Gly Gly Arg Asp Ala Ile
    130                 135                 140

ATC CTC CTC ATG TGC GCA GTC CAT CCA GAG CTA ATC TTT GAC ATC ACC       480
Ile Leu Leu Met Cys Ala Val His Pro Glu Leu Ile Phe Asp Ile Thr
145                 150                 155                 160

AAA CTT CTA ATT GCC ATA CTC GGT CCG CTC ATG GTG CTC CAA GCT GGC       528
Lys Leu Leu Ile Ala Ile Leu Gly Pro Leu Met Val Leu Gln Ala Gly
                165                 170                 175

ATA ACC AGA GTG CCG TAC TTC GTG CGC GCT CAA GGG CTC ATT CAT GCA       576
Ile Thr Arg Val Pro Tyr Phe Val Arg Ala Gln Gly Leu Ile His Ala
            180                 185                 190

TGC ATG TTA GTG CGG AAG GTC GCT GGG GGT CAT TAT GTC CAA ATG GCC       624
Cys Met Leu Val Arg Lys Val Ala Gly Gly His Tyr Val Gln Met Ala
        195                 200                 205

TTC ATG AAG CTG GGC GCG CTG ACA GGC ACG TAC ATT TAC AAC CAT CTT       672
Phe Met Lys Leu Gly Ala Leu Thr Gly Thr Tyr Ile Tyr Asn His Leu
    210                 215                 220
```

```
ACC CCG CTA CGG GAT TGG CCA CGC GCG GGC CTA CGA GAC CTT GCG GTG        720
Thr Pro Leu Arg Asp Trp Pro Arg Ala Gly Leu Arg Asp Leu Ala Val
225                 230                 235                 240

GCA GTG GAG CCC GTC GTC TTC TCC GAC ATG GAG ACC AAG ATC ATC ACC        768
Ala Val Glu Pro Val Val Phe Ser Asp Met Glu Thr Lys Ile Ile Thr
                245                 250                 255

TGG GGA GCA GAC ACC GCG GCG TGT GGG GAC ATC ATC TTG GGT CTG CCC        816
Trp Gly Ala Asp Thr Ala Ala Cys Gly Asp Ile Ile Leu Gly Leu Pro
            260                 265                 270

GTC TCC GCC CGA AGG                                                    831
Val Ser Ala Arg Arg
            275
```

(2) INFORMATION FOR SEQ ID NO:38:

(i) SEQUENCE CHARACTERISTICS:
        (A) LENGTH: 277 amino acids
        (B) TYPE: amino acid
        (D) TOPOLOGY: linear (ii) MOLECULE TYPE: protein (xi) SEQUENCE DESCRIPTION: SEQ ID NO:38:

```
Arg Val Cys Ala Cys Leu Trp Met Met Leu Leu Ile Ala Gln Ala Glu
 1               5                  10                  15

Ala Ala Leu Glu Asn Leu Val Val Leu Asn Ser Ala Ser Val Ala Gly
                20                  25                  30

Ala His Gly Ile Leu Ser Phe Leu Val Phe Phe Cys Ala Ala Trp Tyr
            35                  40                  45

Ile Lys Gly Arg Leu Val Pro Gly Ala Thr Tyr Ala Leu Tyr Gly Val
        50                  55                  60

Trp Pro Leu Leu Leu Leu Leu Ala Leu Pro Pro Arg Ala Tyr Ala
 65                  70                  75                  80

Met Asp Arg Glu Met Ala Ala Ser Cys Gly Ala Val Phe Val Gly
                85                  90                  95

Leu Val Leu Leu Thr Leu Ser Pro Tyr Tyr Lys Val Phe Leu Ala Arg
                100                 105                 110

Leu Ile Trp Trp Leu Gln Tyr Phe Thr Thr Arg Ala Glu Ala Asp Leu
            115                 120                 125

His Val Trp Ile Pro Pro Leu Asn Ala Arg Gly Gly Arg Asp Ala Ile
        130                 135                 140

Ile Leu Leu Met Cys Ala Val His Pro Glu Leu Ile Phe Asp Ile Thr
145                 150                 155                 160

Lys Leu Leu Ile Ala Ile Leu Gly Pro Leu Met Val Leu Gln Ala Gly
                165                 170                 175

Ile Thr Arg Val Pro Tyr Phe Val Arg Ala Gln Gly Leu Ile His Ala
            180                 185                 190

Cys Met Leu Val Arg Lys Val Ala Gly Gly His Tyr Val Gln Met Ala
        195                 200                 205

Phe Met Lys Leu Gly Ala Leu Thr Gly Thr Tyr Ile Tyr Asn His Leu
    210                 215                 220

Thr Pro Leu Arg Asp Trp Pro Arg Ala Gly Leu Arg Asp Leu Ala Val
225                 230                 235                 240

Ala Val Glu Pro Val Val Phe Ser Asp Met Glu Thr Lys Ile Ile Thr
                245                 250                 255

Trp Gly Ala Asp Thr Ala Ala Cys Gly Asp Ile Ile Leu Gly Leu Pro
            260                 265                 270
```

```
Val Ser Ala Arg Arg
        275
```

(2) INFORMATION FOR SEQ ID NO:39:

(i) SEQUENCE CHARACTERISTICS:
        (A) LENGTH: 1827 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..1827
        (D) OTHER INFORMATION: /note: "sequence = 3351 - 5177 of
            SEQ ID NO: 1"

(ix) FEATURE:
        (A) NAME/KEY: CDS
        (B) LOCATION: 1..1827

(xi) SEQUENCE DESCRIPTION: SEQ ID NO:39:

```
GGA AAG GAG ATA CTC CTG GGC CCG GCC GAT AGT CTT GAA GGG CGG GGG        48
Gly Lys Glu Ile Leu Leu Gly Pro Ala Asp Ser Leu Glu Gly Arg Gly
 1               5                  10                  15

TTG CGA CTC CTC GCG CCC ATC ACG GCC TAC TCC CAA CAG ACG CGG GGC        96
Leu Arg Leu Leu Ala Pro Ile Thr Ala Tyr Ser Gln Gln Thr Arg Gly
             20                  25                  30

CTA CTT GGT TGC ATC ATC ACT AGC CTT ACA GGC CGG GAC AAG AAC CAG       144
Leu Leu Gly Cys Ile Ile Thr Ser Leu Thr Gly Arg Asp Lys Asn Gln
         35                  40                  45

GTC GAG GGA GAG GTT CAG GTG GTT TCC ACC GCA ACA CAA TCC TTC CTG       192
Val Glu Gly Glu Val Gln Val Val Ser Thr Ala Thr Gln Ser Phe Leu
 50                  55                  60

GCG ACC TGC GTC AAC GGC GTG TGT TGG ACC GTT TAC CAT GGT GCT GGC       240
Ala Thr Cys Val Asn Gly Val Cys Trp Thr Val Tyr His Gly Ala Gly
 65                  70                  75                  80

TCA AAG ACC TTA GCC GCG CCA AAG GGG CCA ATC ACC CAG ATG TAC ACT       288
Ser Lys Thr Leu Ala Ala Pro Lys Gly Pro Ile Thr Gln Met Tyr Thr
                 85                  90                  95

AAT GTG GAC CAG GAC CTC GTC GGC TGG CCC AAG CCC CCG GGC GCG CGT       336
Asn Val Asp Gln Asp Leu Val Gly Trp Pro Lys Pro Pro Gly Ala Arg
            100                 105                 110

TCC TTG ACA CCA TGC ACC TGT GGC AGC TCA GAC CTT TAC TTG GTC ACG       384
Ser Leu Thr Pro Cys Thr Cys Gly Ser Ser Asp Leu Tyr Leu Val Thr
        115                 120                 125

AGA CAT GCT GAC GTC ATT CCG GTG CGC CGG CGG GGC GAC AGT AGG GGG       432
Arg His Ala Asp Val Ile Pro Val Arg Arg Arg Gly Asp Ser Arg Gly
    130                 135                 140

AGC CTG CTC TCC CCC AGG CCT GTC TCC TAC TTG AAG GGC TCT TCG GGT       480
Ser Leu Leu Ser Pro Arg Pro Val Ser Tyr Leu Lys Gly Ser Ser Gly
145                 150                 155                 160

GGT CCA CTG CTC TGC CCC TTC GGG CAC GCT GTG GGC ATC TTC CGG GCT       528
Gly Pro Leu Leu Cys Pro Phe Gly His Ala Val Gly Ile Phe Arg Ala
                165                 170                 175

GCC GTA TGC ACC CGG GGG GTT GCG AAG GCG GTG GAC TTT GTG CCC GTA       576
Ala Val Cys Thr Arg Gly Val Ala Lys Ala Val Asp Phe Val Pro Val
            180                 185                 190

GAG TCC ATG GAA ACT ACT ATG CGG TCT CCG GTC TTC ACG GAC AAC TCA       624
Glu Ser Met Glu Thr Thr Met Arg Ser Pro Val Phe Thr Asp Asn Ser
        195                 200                 205

TCC CCC CCG GCC GTA CCG CAG TCA TTT CAA GTG GCC CAC CTA CAC GCT       672
Ser Pro Pro Ala Val Pro Gln Ser Phe Gln Val Ala His Leu His Ala
```

```
          210                 215                 220
CCC ACT GGC AGC GGC AAG AGT ACT AAA GTG CCG GCT GCA TAT GCA GCC      720
Pro Thr Gly Ser Gly Lys Ser Thr Lys Val Pro Ala Ala Tyr Ala Ala
225                 230                 235                 240

CAA GGG TAC AAG GTG CTC GTC CTC AAT CCG TCC GTT GCC GCT ACC TTA      768
Gln Gly Tyr Lys Val Leu Val Leu Asn Pro Ser Val Ala Ala Thr Leu
                245                 250                 255

GGG TTT GGG GCG TAT ATG TCT AAG GCA CAC GGT ATT GAC CCC AAC ATC      816
Gly Phe Gly Ala Tyr Met Ser Lys Ala His Gly Ile Asp Pro Asn Ile
            260                 265                 270

AGA ACT GGG GTA AGG ACC ATT ACC ACA GGC GCC CCC GTC ACA TAC TCT      864
Arg Thr Gly Val Arg Thr Ile Thr Thr Gly Ala Pro Val Thr Tyr Ser
        275                 280                 285

ACC TAT GGC AAG TTT CTT GCC GAT GGT GGT TGC TCT GGG GGC GCT TAT      912
Thr Tyr Gly Lys Phe Leu Ala Asp Gly Gly Cys Ser Gly Gly Ala Tyr
    290                 295                 300

GAC ATC ATA ATA TGT GAT GAG TGC CAT TCA ACT GAC TCG ACT ACA ATC      960
Asp Ile Ile Ile Cys Asp Glu Cys His Ser Thr Asp Ser Thr Thr Ile
305                 310                 315                 320

TTG GGC ATC GGC ACA GTC CTG GAC CAA GCG GAG ACG GCT GGA GCG CGG     1008
Leu Gly Ile Gly Thr Val Leu Asp Gln Ala Glu Thr Ala Gly Ala Arg
                325                 330                 335

CTT GTC GTG CTC GCC ACC GCT ACG CCT CCG GGA TCG GTC ACC GTG CCA     1056
Leu Val Val Leu Ala Thr Ala Thr Pro Pro Gly Ser Val Thr Val Pro
            340                 345                 350

CAC CCA AAC ATC GAG GAG GTG GCC CTG TCT AAT ACT GGA GAG ATC CCC     1104
His Pro Asn Ile Glu Glu Val Ala Leu Ser Asn Thr Gly Glu Ile Pro
        355                 360                 365

TTC TAT GGC AAA GCC ATC CCC ATT GAA GCC ATC AGG GGG GGA AGG CAT     1152
Phe Tyr Gly Lys Ala Ile Pro Ile Glu Ala Ile Arg Gly Gly Arg His
    370                 375                 380

CTC ATT TTC TGT CAT TCC AAG AAG AAG TGC GAC GAG CTC GCC GCA AAG     1200
Leu Ile Phe Cys His Ser Lys Lys Lys Cys Asp Glu Leu Ala Ala Lys
385                 390                 395                 400

CTG TCA GGC CTC GGA ATC AAC GCT GTG GCG TAT TAC CGG GGG CTC GAT     1248
Leu Ser Gly Leu Gly Ile Asn Ala Val Ala Tyr Tyr Arg Gly Leu Asp
                405                 410                 415

GTG TCC GTC ATA CCA ACT ATC GGA GAC GTC GTT GTC GTG GCA ACA GAC     1296
Val Ser Val Ile Pro Thr Ile Gly Asp Val Val Val Val Ala Thr Asp
            420                 425                 430

GCT CTG ATG ACG GGC TAT ACG GGC GAC TTT GAC TCA GTG ATC GAC TGT     1344
Ala Leu Met Thr Gly Tyr Thr Gly Asp Phe Asp Ser Val Ile Asp Cys
        435                 440                 445

AAC ACA TGT GTC ACC CAG ACA GTC GAC TTC AGC TTG GAT CCC ACC TTC     1392
Asn Thr Cys Val Thr Gln Thr Val Asp Phe Ser Leu Asp Pro Thr Phe
    450                 455                 460

ACC ATT GAG ACG ACG ACC GTG CCT CAA GAC GCA GTG TCG CGC TCG CAG     1440
Thr Ile Glu Thr Thr Thr Val Pro Gln Asp Ala Val Ser Arg Ser Gln
465                 470                 475                 480

CGG CGG GGT AGG ACT GGC AGG GGT AGG AGA GGC ATC TAC AGG TTT GTG     1488
Arg Arg Gly Arg Thr Gly Arg Gly Arg Arg Gly Ile Tyr Arg Phe Val
                485                 490                 495

ACT CCG GGA GAA CGG CCC TCG GGC ATG TTC GAT TCC TCG GTC CTG TGT     1536
Thr Pro Gly Glu Arg Pro Ser Gly Met Phe Asp Ser Ser Val Leu Cys
            500                 505                 510

GAG TGC TAT GAC GCG GGC TGT GCT TGG TAC GAG CTC ACC CCG GCC GAG     1584
Glu Cys Tyr Asp Ala Gly Cys Ala Trp Tyr Glu Leu Thr Pro Ala Glu
        515                 520                 525

ACC TCG GTT AGG TTG CGG GCC TAC CTG AAC ACA CCA GGG TTG CCC GTT     1632
Thr Ser Val Arg Leu Arg Ala Tyr Leu Asn Thr Pro Gly Leu Pro Val
```

```
           530                 535                 540
TGC CAG GAC CAC CTG GAG TTC TGG GAG AGT GTC TTC ACA GGC CTC ACC      1680
Cys Gln Asp His Leu Glu Phe Trp Glu Ser Val Phe Thr Gly Leu Thr
545                 550                 555                 560

CAT ATA GAT GCA CAC TTC TTG TCC CAG ACC AAG CAG GCA GGA GAC AAC      1728
His Ile Asp Ala His Phe Leu Ser Gln Thr Lys Gln Ala Gly Asp Asn
                565                 570                 575

TTC CCC TAC CTG GTA GCA TAC CAA GCC ACG GTG TGC GCC AGG GCT CAG      1776
Phe Pro Tyr Leu Val Ala Tyr Gln Ala Thr Val Cys Ala Arg Ala Gln
            580                 585                 590

GCC CCA CCT CCA TCA TGG GAT CAA ATG TGG AAG TGT CTC ATA CGG CTG      1824
Ala Pro Pro Pro Ser Trp Asp Gln Met Trp Lys Cys Leu Ile Arg Leu
        595                 600                 605

AAA                                                                   1827
Lys
```

(2) INFORMATION FOR SEQ ID NO:40:

(i) SEQUENCE CHARACTERISTICS:
        (A) LENGTH: 609 amino acids
        (B) TYPE: amino acid
        (D) TOPOLOGY: linear (ii) MOLECULE TYPE: protein (xi) SEQUENCE DESCRIPTION: SEQ ID NO:40:

```
Gly Lys Glu Ile Leu Leu Gly Pro Ala Asp Ser Leu Glu Gly Arg Gly
1               5                   10                  15

Leu Arg Leu Leu Ala Pro Ile Thr Ala Tyr Ser Gln Gln Thr Arg Gly
                20                  25                  30

Leu Leu Gly Cys Ile Ile Thr Ser Leu Thr Gly Arg Asp Lys Asn Gln
            35                  40                  45

Val Glu Gly Glu Val Gln Val Val Ser Thr Ala Thr Gln Ser Phe Leu
    50                  55                  60

Ala Thr Cys Val Asn Gly Val Cys Trp Thr Val Tyr His Gly Ala Gly
65                  70                  75                  80

Ser Lys Thr Leu Ala Ala Pro Lys Gly Pro Ile Thr Gln Met Tyr Thr
                85                  90                  95

Asn Val Asp Gln Asp Leu Val Gly Trp Pro Lys Pro Gly Ala Arg
                100                 105                 110

Ser Leu Thr Pro Cys Thr Cys Gly Ser Ser Asp Leu Tyr Leu Val Thr
            115                 120                 125

Arg His Ala Asp Val Ile Pro Val Arg Arg Arg Gly Asp Ser Arg Gly
    130                 135                 140

Ser Leu Leu Ser Pro Arg Pro Val Ser Tyr Leu Lys Gly Ser Ser Gly
145                 150                 155                 160

Gly Pro Leu Leu Cys Pro Phe Gly His Ala Val Gly Ile Phe Arg Ala
                165                 170                 175

Ala Val Cys Thr Arg Gly Val Ala Lys Ala Val Asp Phe Val Pro Val
            180                 185                 190

Glu Ser Met Glu Thr Thr Met Arg Ser Pro Val Phe Thr Asp Asn Ser
    195                 200                 205

Ser Pro Pro Ala Val Pro Gln Ser Phe Gln Val Ala His Leu His Ala
            210                 215                 220

Pro Thr Gly Ser Gly Lys Ser Thr Lys Val Pro Ala Ala Tyr Ala Ala
225                 230                 235                 240

Gln Gly Tyr Lys Val Leu Val Leu Asn Pro Ser Val Ala Ala Thr Leu
                245                 250                 255
```

```
Gly Phe Gly Ala Tyr Met Ser Lys Ala His Gly Ile Asp Pro Asn Ile
            260                 265                 270

Arg Thr Gly Val Arg Thr Ile Thr Thr Gly Ala Pro Val Thr Tyr Ser
        275                 280                 285

Thr Tyr Gly Lys Phe Leu Ala Asp Gly Gly Cys Ser Gly Gly Ala Tyr
        290                 295                 300

Asp Ile Ile Ile Cys Asp Glu Cys His Ser Thr Asp Ser Thr Thr Ile
305                 310                 315                 320

Leu Gly Ile Gly Thr Val Leu Asp Gln Ala Glu Thr Ala Gly Ala Arg
                325                 330                 335

Leu Val Val Leu Ala Thr Ala Thr Pro Pro Gly Ser Val Thr Val Pro
                340                 345                 350

His Pro Asn Ile Glu Glu Val Ala Leu Ser Asn Thr Gly Glu Ile Pro
                355                 360                 365

Phe Tyr Gly Lys Ala Ile Pro Ile Glu Ala Ile Arg Gly Gly Arg His
                370                 375                 380

Leu Ile Phe Cys His Ser Lys Lys Cys Asp Glu Leu Ala Ala Lys
385                 390                 395                 400

Leu Ser Gly Leu Gly Ile Asn Ala Val Ala Tyr Tyr Arg Gly Leu Asp
                405                 410                 415

Val Ser Val Ile Pro Thr Ile Gly Asp Val Val Val Ala Thr Asp
                420                 425                 430

Ala Leu Met Thr Gly Tyr Thr Gly Asp Phe Asp Ser Val Ile Asp Cys
                435                 440                 445

Asn Thr Cys Val Thr Gln Thr Val Asp Phe Ser Leu Asp Pro Thr Phe
450                 455                 460

Thr Ile Glu Thr Thr Thr Val Pro Gln Asp Ala Val Ser Arg Ser Gln
465                 470                 475                 480

Arg Arg Gly Arg Thr Gly Arg Gly Arg Gly Ile Tyr Arg Phe Val
                485                 490                 495

Thr Pro Gly Glu Arg Pro Ser Gly Met Phe Asp Ser Ser Val Leu Cys
                500                 505                 510

Glu Cys Tyr Asp Ala Gly Cys Ala Trp Tyr Glu Leu Thr Pro Ala Glu
                515                 520                 525

Thr Ser Val Arg Leu Arg Ala Tyr Leu Asn Thr Pro Gly Leu Pro Val
                530                 535                 540

Cys Gln Asp His Leu Glu Phe Trp Glu Ser Val Phe Thr Gly Leu Thr
545                 550                 555                 560

His Ile Asp Ala His Phe Leu Ser Gln Thr Lys Gln Ala Gly Asp Asn
                565                 570                 575

Phe Pro Tyr Leu Val Ala Tyr Gln Ala Thr Val Cys Ala Arg Ala Gln
                580                 585                 590

Ala Pro Pro Pro Ser Trp Asp Gln Met Trp Lys Cys Leu Ile Arg Leu
                595                 600                 605

Lys (2) INFORMATION FOR SEQ ID NO:41:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA from genomic RNA
```

```
        (ix) FEATURE:
              (A) NAME/KEY: misc_feature
              (B) LOCATION: 1..90
              (D) OTHER INFORMATION: /note: "sequence = 4485 - 4574 of
                  SEQ ID NO: 1"

(ix) FEATURE:
              (A) NAME/KEY: CDS
              (B) LOCATION: 1..90

(xi) SEQUENCE DESCRIPTION: SEQ ID NO:41:

ATC AGG GGG GGA AGG CAT CTC ATT TTC TGT CAT TCC AAG AAG AAG TGC          48
Ile Arg Gly Gly Arg His Leu Ile Phe Cys His Ser Lys Lys Lys Cys
 1               5                  10                  15

GAC GAG CTC GCC GCA AAG CTG TCA GGC CTC GGA ATC AAC GCT                  90
Asp Glu Leu Ala Ala Lys Leu Ser Gly Leu Gly Ile Asn Ala
                20                  25                  30

(2) INFORMATION FOR SEQ ID NO:42:

(i) SEQUENCE CHARACTERISTICS:
              (A) LENGTH: 30 amino acids
              (B) TYPE: amino acid
              (D) TOPOLOGY: linear (ii) MOLECULE TYPE: protein (xi) SEQUENCE DESCRIPTION: SEQ ID NO:42:

Ile Arg Gly Gly Arg His Leu Ile Phe Cys His Ser Lys Lys Lys Cys
 1               5                  10                  15

Asp Glu Leu Ala Ala Lys Leu Ser Gly Leu Gly Ile Asn Ala
                20                  25                  30

(2) INFORMATION FOR SEQ ID NO:43:

(i) SEQUENCE CHARACTERISTICS:
              (A) LENGTH: 741 base pairs
              (B) TYPE: nucleic acid
              (C) STRANDEDNESS: single
              (D) TOPOLOGY: linear (ii) MOLECULE TYPE: cDNA from genomic RNA (ix) FEATURE:
              (A) NAME/KEY: misc_feature
              (B) LOCATION: 1..741
              (D) OTHER INFORMATION: /note: "sequence = 5178 - 5918 of
                  SEQ ID NO: 1"

(ix) FEATURE:
              (A) NAME/KEY: CDS
              (B) LOCATION: 1..741

(xi) SEQUENCE DESCRIPTION: SEQ ID NO:43:

CCT ACG CTG CAC GGG CCA ACA CCC TTG CTG TAC AGG CTG GGA GCC GTC          48
Pro Thr Leu His Gly Pro Thr Pro Leu Leu Tyr Arg Leu Gly Ala Val
 1               5                  10                  15

CAG AAT GAG GTC ACC CTC ACC CAC CCC ATA ACC AAA TAC ATC ATG GCA          96
Gln Asn Glu Val Thr Leu Thr His Pro Ile Thr Lys Tyr Ile Met Ala
                20                  25                  30

TGC ATG TCG GCT GAC CTG GAG GTC GTC ACT AGC ACC TGG GTG CTG GTG         144
Cys Met Ser Ala Asp Leu Glu Val Val Thr Ser Thr Trp Val Leu Val
             35                  40                  45

GGC GGA GTC CTT GCA GCT CTG GCC GCG TAT TGC CTG ACA ACA GGC AGT         192
Gly Gly Val Leu Ala Ala Leu Ala Ala Tyr Cys Leu Thr Thr Gly Ser
         50                  55                  60

GTG GTC ATT GTG GGT AGG ATT ATC TTG TCC GGG AGG CCG GCC ATT GTT         240
Val Val Ile Val Gly Arg Ile Ile Leu Ser Gly Arg Pro Ala Ile Val
 65                  70                  75                  80
```

```
CCC GAC AGG GAG CTT CTC TAC CAG GAG TTC GAT GAA ATG GAA GAG TGC        288
Pro Asp Arg Glu Leu Leu Tyr Gln Glu Phe Asp Glu Met Glu Glu Cys
                85                  90                  95

GCC TCG CAC CTC CCT TAC ATC GAG CAG GGA ATG CAG CTC GCC GAG CAA        336
Ala Ser His Leu Pro Tyr Ile Glu Gln Gly Met Gln Leu Ala Glu Gln
            100                 105                 110

TTC AAG CAG AAA GCG CTC GGG TTA CTG CAA ACA GCC ACC AAA CAA GCG        384
Phe Lys Gln Lys Ala Leu Gly Leu Leu Gln Thr Ala Thr Lys Gln Ala
        115                 120                 125

GAG GCT GCT GCT CCC GTG GTG GAG TCC AAG TGG CGA GCC CTT GAG ACA        432
Glu Ala Ala Ala Pro Val Val Glu Ser Lys Trp Arg Ala Leu Glu Thr
    130                 135                 140

TTC TGG GCG AAG CAC ATG TGG AAT TTC ATC AGC GGG ATA CAG TAC TTA        480
Phe Trp Ala Lys His Met Trp Asn Phe Ile Ser Gly Ile Gln Tyr Leu
145                 150                 155                 160

GCA GGC TTA TCC ACT CTG CCT GGG AAC CCC GCA ATA GCA TCA TTG ATG        528
Ala Gly Leu Ser Thr Leu Pro Gly Asn Pro Ala Ile Ala Ser Leu Met
                165                 170                 175

GCA TTC ACA GCC TCT ATC ACC AGC CCG CTC ACC ACC CAA AGT ACC CTC        576
Ala Phe Thr Ala Ser Ile Thr Ser Pro Leu Thr Thr Gln Ser Thr Leu
            180                 185                 190

CTG TTT AAC ATC TTG GGG GGT TGG GTG GCT GCC CAA CTC GCC CCC CCC        624
Leu Phe Asn Ile Leu Gly Gly Trp Val Ala Ala Gln Leu Ala Pro Pro
        195                 200                 205

AGC GCC GCT TCG GCT TTC GTG GGC GCC GGC ATC GCC GGT GCG GCT GTT        672
Ser Ala Ala Ser Ala Phe Val Gly Ala Gly Ile Ala Gly Ala Ala Val
    210                 215                 220

GGC AGC ATA GGC CTT GGG AAG GTG CTT GTG GAC ATT CTG GCG GGT TAT        720
Gly Ser Ile Gly Leu Gly Lys Val Leu Val Asp Ile Leu Ala Gly Tyr
225                 230                 235                 240

GGA GCA GGA GTG GCC GGC GCG                                            741
Gly Ala Gly Val Ala Gly Ala
                245
```

(2) INFORMATION FOR SEQ ID NO:44:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO:44:

```
Pro Thr Leu His Gly Pro Thr Pro Leu Leu Tyr Arg Leu Gly Ala Val
1               5                   10                  15

Gln Asn Glu Val Thr Leu Thr His Pro Ile Thr Lys Tyr Ile Met Ala
            20                  25                  30

Cys Met Ser Ala Asp Leu Glu Val Val Thr Ser Thr Trp Val Leu Val
        35                  40                  45

Gly Gly Val Leu Ala Ala Leu Ala Ala Tyr Cys Leu Thr Thr Gly Ser
    50                  55                  60

Val Val Ile Val Gly Arg Ile Ile Leu Ser Gly Arg Pro Ala Ile Val
65                  70                  75                  80

Pro Asp Arg Glu Leu Leu Tyr Gln Glu Phe Asp Glu Met Glu Glu Cys
                85                  90                  95

Ala Ser His Leu Pro Tyr Ile Glu Gln Gly Met Gln Leu Ala Glu Gln
            100                 105                 110

Phe Lys Gln Lys Ala Leu Gly Leu Leu Gln Thr Ala Thr Lys Gln Ala
        115                 120                 125
```

```
Glu Ala Ala Ala Pro Val Val Glu Ser Lys Trp Arg Ala Leu Glu Thr
130                 135                 140

Phe Trp Ala Lys His Met Trp Asn Phe Ile Ser Gly Ile Gln Tyr Leu
145                 150                 155                 160

Ala Gly Leu Ser Thr Leu Pro Gly Asn Pro Ala Ile Ala Ser Leu Met
                165                 170                 175

Ala Phe Thr Ala Ser Ile Thr Ser Pro Leu Thr Thr Gln Ser Thr Leu
                180                 185                 190

Leu Phe Asn Ile Leu Gly Gly Trp Val Ala Ala Gln Leu Ala Pro Pro
            195                 200                 205

Ser Ala Ala Ser Ala Phe Val Gly Ala Gly Ile Ala Gly Ala Ala Val
        210                 215                 220

Gly Ser Ile Gly Leu Gly Lys Val Leu Val Asp Ile Leu Ala Gly Tyr
225                 230                 235                 240

Gly Ala Gly Val Ala Gly Ala
                245
```

(2) INFORMATION FOR SEQ ID NO:45:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..90
        (D) OTHER INFORMATION: /note: "sequence = 5544 - 5633 of
            SEQ ID NO: 1"

(ix) FEATURE:
        (A) NAME/KEY: CDS
        (B) LOCATION: 1..90

(xi) SEQUENCE DESCRIPTION: SEQ ID NO:45:

```
ACA GCC ACC AAA CAA GCG GAG GCT GCT GCT CCC GTG GTG GAG TCC AAG      48
Thr Ala Thr Lys Gln Ala Glu Ala Ala Ala Pro Val Val Glu Ser Lys
 1               5                  10                  15

TGG CGA GCC CTT GAG ACA TTC TGG GCG AAG CAC ATG TGG AAT              90
Trp Arg Ala Leu Glu Thr Phe Trp Ala Lys His Met Trp Asn
             20                  25                  30
```

(2) INFORMATION FOR SEQ ID NO:46:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO:46:

```
Thr Ala Thr Lys Gln Ala Glu Ala Ala Ala Pro Val Val Glu Ser Lys
 1               5                  10                  15

Trp Arg Ala Leu Glu Thr Phe Trp Ala Lys His Met Trp Asn
             20                  25                  30
```

(2) INFORMATION FOR SEQ ID NO:47:

(i) SEQUENCE CHARACTERISTICS:
        (A) LENGTH: 453 base pairs
        (B) TYPE: nucleic acid (C) STRANDEDNESS: single
(D) TOPOLOGY: linear (ii) MOLECULE TYPE: cDNA from genomic RNA (ix) FEATURE:
    (A) NAME/KEY: misc_feature
    (B) LOCATION: 1..453
    (D) OTHER INFORMATION: /note= "sequence = 5919 - 6371 of SEQ ID NO: 1"

(ix) FEATURE:
    (A) NAME/KEY: CDS
    (B) LOCATION: 1..453

(xi) SEQUENCE DESCRIPTION: SEQ ID NO:47:

```
CTC GTG GCC TTT AAG GTC ATG AGC GGC GAG ATG CCC TCC ACC GAG GAC          48
Leu Val Ala Phe Lys Val Met Ser Gly Glu Met Pro Ser Thr Glu Asp
 1               5                  10                  15

CTG GTC AAT CTA CTT CCT GCC ATC CTC TCT CCT GGC GCC CTG GTC GTC          96
Leu Val Asn Leu Leu Pro Ala Ile Leu Ser Pro Gly Ala Leu Val Val
            20                  25                  30

GGG GTC GTG TGT GCA GCA ATA CTG CGT CGA CAC GTG GGT CCG GGA GAG         144
Gly Val Val Cys Ala Ala Ile Leu Arg Arg His Val Gly Pro Gly Glu
        35                  40                  45

GGG GCT GTG CAG TGG ATG AAC CGG CTG ATA GCG TTC GCC TCG CGG GGT         192
Gly Ala Val Gln Trp Met Asn Arg Leu Ile Ala Phe Ala Ser Arg Gly
    50                  55                  60

AAT CAT GTT TCC CCC ACG CAC TAT GTG CCT GAG AGC GAC GCC GCA GCG         240
Asn His Val Ser Pro Thr His Tyr Val Pro Glu Ser Asp Ala Ala Ala
65                  70                  75                  80

CGT GTT ACT CAG ATC CTC TCC AGC CTT ACC ATC ACT CAG CTG CTG AAA         288
Arg Val Thr Gln Ile Leu Ser Ser Leu Thr Ile Thr Gln Leu Leu Lys
                85                  90                  95

AGG CTC CAC CAG TGG ATT AAT GAA GAC TGC TCC ACA CCG TGT TCC GGC         336
Arg Leu His Gln Trp Ile Asn Glu Asp Cys Ser Thr Pro Cys Ser Gly
            100                 105                 110

TCG TGG CTA AGG GAT GTT TGG GAC TGG ATA TGC ACG GTG TTG ACT GAC         384
Ser Trp Leu Arg Asp Val Trp Asp Trp Ile Cys Thr Val Leu Thr Asp
        115                 120                 125

TTC AAG ACC TGG CTC CAG TCC AAG CTC CTG CCG CAG CTA CCT GGA GTC         432
Phe Lys Thr Trp Leu Gln Ser Lys Leu Leu Pro Gln Leu Pro Gly Val
    130                 135                 140

CCT TTT TTC TCG TGC CAA CGC                                             453
Pro Phe Phe Ser Cys Gln Arg
145                 150
```

(2) INFORMATION FOR SEQ ID NO:48:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO:48:

```
Leu Val Ala Phe Lys Val Met Ser Gly Glu Met Pro Ser Thr Glu Asp
 1               5                  10                  15

Leu Val Asn Leu Leu Pro Ala Ile Leu Ser Pro Gly Ala Leu Val Val
            20                  25                  30

Gly Val Val Cys Ala Ala Ile Leu Arg Arg His Val Gly Pro Gly Glu
        35                  40                  45

Gly Ala Val Gln Trp Met Asn Arg Leu Ile Ala Phe Ala Ser Arg Gly
    50                  55                  60
```

```
Asn His Val Ser Pro Thr His Tyr Val Pro Glu Ser Asp Ala Ala Ala
         65                  70                  75                  80

Arg Val Thr Gln Ile Leu Ser Ser Leu Thr Ile Thr Gln Leu Leu Lys
                 85                  90                  95

Arg Leu His Gln Trp Ile Asn Glu Asp Cys Ser Thr Pro Cys Ser Gly
            100                 105                 110

Ser Trp Leu Arg Asp Val Trp Asp Trp Ile Cys Thr Val Leu Thr Asp
        115                 120                 125

Phe Lys Thr Trp Leu Gln Ser Lys Leu Leu Pro Gln Leu Pro Gly Val
    130                 135                 140

Pro Phe Phe Ser Cys Gln Arg
145                 150
```

(2) INFORMATION FOR SEQ ID NO:49:

(i) SEQUENCE CHARACTERISTICS:
        (A) LENGTH: 2991 base pairs
        (B) TYPE: nucleic acid
        (C) STRANDEDNESS: single
        (D) TOPOLOGY: linear (ii) MOLECULE TYPE: cDNA from genomic RNA (ix) FEATURE:
        (A) NAME/KEY: misc_feature
        (B) LOCATION: 1..2991
        (D) OTHER INFORMATION: /note= "sequence = 6372 - 9362 of
            SEQ ID NO: 1"

(ix) FEATURE:
        (A) NAME/KEY: CDS
        (B) LOCATION: 1..2991

(xi) SEQUENCE DESCRIPTION: SEQ ID NO:49:

```
GGG TAC AAG GGA GTC TGG CGG GGA GAC GGC ATC ATG CAA ACC ACC TGC        48
Gly Tyr Lys Gly Val Trp Arg Gly Asp Gly Ile Met Gln Thr Thr Cys
  1               5                  10                  15

CCA TGT GGA GCA CAG ATC ACC GGA CAT GTC AAA AAC GGT TCC ATG AGG        96
Pro Cys Gly Ala Gln Ile Thr Gly His Val Lys Asn Gly Ser Met Arg
             20                  25                  30

ATC GTC GGG CCT AAG ACC TGC AGC AAC ACG TGG CAT GGA ACA TTC CCC       144
Ile Val Gly Pro Lys Thr Cys Ser Asn Thr Trp His Gly Thr Phe Pro
         35                  40                  45

ATC AAC GCA TAC ACC ACG GGC CCC TGC ACA CCC TCT CCA GCG CCA AAC       192
Ile Asn Ala Tyr Thr Thr Gly Pro Cys Thr Pro Ser Pro Ala Pro Asn
     50                  55                  60

TAT TCT AGG GCG CTG TGG CGG GTG GCC GCT GAG GAG TAC GTG GAG GTC       240
Tyr Ser Arg Ala Leu Trp Arg Val Ala Ala Glu Glu Tyr Val Glu Val
 65                  70                  75                  80

ACG CGG GTG GGG GAT TTC CAC TAC GTG ACG GGC ATG ACC ACT GAC AAC       288
Thr Arg Val Gly Asp Phe His Tyr Val Thr Gly Met Thr Thr Asp Asn
                 85                  90                  95

GTA AAG TGC CCA TGC CAG GTT CCG GCT CCT GAA TTC TTC TCG GAG GTG       336
Val Lys Cys Pro Cys Gln Val Pro Ala Pro Glu Phe Phe Ser Glu Val
            100                 105                 110

GAC GGA GTG CGG TTG CAC AGG TAC GCT CCG GCG TGC AGG CCT CTC CTA       384
Asp Gly Val Arg Leu His Arg Tyr Ala Pro Ala Cys Arg Pro Leu Leu
        115                 120                 125

CGG GAG GAG GTT ACA TTC CAG GTC GGG CTC AAC CAA TAC CTG GTT GGG       432
Arg Glu Glu Val Thr Phe Gln Val Gly Leu Asn Gln Tyr Leu Val Gly
    130                 135                 140

TCA CAG CTA CCA TGC GAG CCC GAA CCG GAT GTA GCA GTG CTC ACT TCC       480
Ser Gln Leu Pro Cys Glu Pro Glu Pro Asp Val Ala Val Leu Thr Ser
```

|     |     |     |     |     |     |     |     |     |     |     |     |     |     |     |      |
| --- | --- | --- | --- | --- | --- | --- | --- | --- | --- | --- | --- | --- | --- | --- | ---- |
| 145 |     |     |     |     | 150 |     |     |     |     | 155 |     |     |     |     | 160  |
| ATG | CTC | ACC | GAC | CCC | TCC | CAC | ATC | ACA | GCA | GAA | ACG | GCT | AAG | CGT | AGG  | 528
| Met | Leu | Thr | Asp | Pro | Ser | His | Ile | Thr | Ala | Glu | Thr | Ala | Lys | Arg | Arg  |
|     |     |     |     |     | 165 |     |     |     |     | 170 |     |     |     |     | 175  |
| TTG | GCC | AGG | GGG | TCT | CCC | CCC | TCC | TTG | GCC | AGC | TCT | TCA | GCT | AGC | CAG  | 576
| Leu | Ala | Arg | Gly | Ser | Pro | Pro | Ser | Leu | Ala | Ser | Ser | Ser | Ala | Ser | Gln  |
|     |     |     |     | 180 |     |     |     |     | 185 |     |     |     |     | 190 |      |
| TTG | TCT | GCG | CCT | TCC | TTG | AAG | GCG | ACA | TGC | ACT | ACC | CAC | CAT | GTC | TCT  | 624
| Leu | Ser | Ala | Pro | Ser | Leu | Lys | Ala | Thr | Cys | Thr | Thr | His | His | Val | Ser  |
|     |     |     | 195 |     |     |     |     | 200 |     |     |     |     | 205 |     |      |
| CCG | GAC | GCT | GAC | CTC | ATC | GAG | GCC | AAC | CTC | CTG | TGG | CGG | CAG | GAG | ATG  | 672
| Pro | Asp | Ala | Asp | Leu | Ile | Glu | Ala | Asn | Leu | Leu | Trp | Arg | Gln | Glu | Met  |
|     |     | 210 |     |     |     |     | 215 |     |     |     |     | 220 |     |     |      |
| GGC | GGG | AAC | ATC | ACC | CGC | GTG | GAG | TCG | GAG | AAC | AAG | GTG | GTA | GTC | CTG  | 720
| Gly | Gly | Asn | Ile | Thr | Arg | Val | Glu | Ser | Glu | Asn | Lys | Val | Val | Val | Leu  |
| 225 |     |     |     |     | 230 |     |     |     |     | 235 |     |     |     |     | 240  |
| GAC | TCT | TTC | GAC | CCG | CTT | CGA | GCG | GAG | GAG | GAT | GAG | AGG | GAA | GTA | TCC  | 768
| Asp | Ser | Phe | Asp | Pro | Leu | Arg | Ala | Glu | Glu | Asp | Glu | Arg | Glu | Val | Ser  |
|     |     |     |     | 245 |     |     |     |     | 250 |     |     |     |     | 255 |      |
| GTT | CCG | GCG | GAG | ATC | CTG | CGG | AAA | TCC | AAG | AAG | TTC | CCC | GCA | GCG | ATG  | 816
| Val | Pro | Ala | Glu | Ile | Leu | Arg | Lys | Ser | Lys | Lys | Phe | Pro | Ala | Ala | Met  |
|     |     |     | 260 |     |     |     |     | 265 |     |     |     |     | 270 |     |      |
| CCC | ATC | TGG | GCG | CGC | CCG | GAT | TAC | AAC | CCT | CCA | CTG | TTA | GAG | TCC | TGG  | 864
| Pro | Ile | Trp | Ala | Arg | Pro | Asp | Tyr | Asn | Pro | Pro | Leu | Leu | Glu | Ser | Trp  |
|     |     | 275 |     |     |     |     | 280 |     |     |     |     | 285 |     |     |      |
| AAG | GAC | CCG | GAC | TAC | GTC | CCT | CCG | GTG | GTG | CAC | GGG | TGC | CCG | TTG | CCA  | 912
| Lys | Asp | Pro | Asp | Tyr | Val | Pro | Pro | Val | Val | His | Gly | Cys | Pro | Leu | Pro  |
|     |     | 290 |     |     |     |     | 295 |     |     |     |     | 300 |     |     |      |
| CCT | ATC | AAG | GCC | CCT | CCA | ATA | CCA | CCT | CCA | CGG | AGA | AAG | AGG | ACG | GTT  | 960
| Pro | Ile | Lys | Ala | Pro | Pro | Ile | Pro | Pro | Pro | Arg | Arg | Lys | Arg | Thr | Val  |
| 305 |     |     |     |     | 310 |     |     |     |     | 315 |     |     |     |     | 320  |
| GTC | CTA | ACA | GAG | TCC | TCC | GTG | TCT | TCT | GCC | TTA | GCG | GAG | CTC | GCT | ACT  | 1008
| Val | Leu | Thr | Glu | Ser | Ser | Val | Ser | Ser | Ala | Leu | Ala | Glu | Leu | Ala | Thr  |
|     |     |     |     | 325 |     |     |     |     | 330 |     |     |     |     | 335 |      |
| AAG | ACC | TTC | GGC | AGC | TCC | GAA | TCA | TCG | GCC | GTC | GAC | AGC | GGC | ACG | GCG  | 1056
| Lys | Thr | Phe | Gly | Ser | Ser | Glu | Ser | Ser | Ala | Val | Asp | Ser | Gly | Thr | Ala  |
|     |     |     | 340 |     |     |     |     | 345 |     |     |     |     | 350 |     |      |
| ACC | GCC | CTT | CCT | GAC | CAG | GCC | TCC | GAC | GAC | GGT | GAC | AAA | GGA | TCC | GAC  | 1104
| Thr | Ala | Leu | Pro | Asp | Gln | Ala | Ser | Asp | Asp | Gly | Asp | Lys | Gly | Ser | Asp  |
|     |     | 355 |     |     |     |     | 360 |     |     |     |     | 365 |     |     |      |
| GTT | GAG | TCG | TAC | TCC | TCC | ATG | CCC | CCC | CTT | GAG | GGG | GAA | CCG | GGG | GAC  | 1152
| Val | Glu | Ser | Tyr | Ser | Ser | Met | Pro | Pro | Leu | Glu | Gly | Glu | Pro | Gly | Asp  |
|     | 370 |     |     |     |     | 375 |     |     |     |     | 380 |     |     |     |      |
| CCC | GAT | CTC | AGT | GAC | GGG | TCT | TGG | TCT | ACC | GTG | AGC | GAG | GAA | GCT | AGT  | 1200
| Pro | Asp | Leu | Ser | Asp | Gly | Ser | Trp | Ser | Thr | Val | Ser | Glu | Glu | Ala | Ser  |
| 385 |     |     |     |     | 390 |     |     |     |     | 395 |     |     |     |     | 400  |
| GAG | GAT | GTC | GTC | TGC | TGC | TCA | ATG | TCC | TAC | ACA | TGG | ACA | GGC | GCC | TTG  | 1248
| Glu | Asp | Val | Val | Cys | Cys | Ser | Met | Ser | Tyr | Thr | Trp | Thr | Gly | Ala | Leu  |
|     |     |     |     | 405 |     |     |     |     | 410 |     |     |     |     | 415 |      |
| ATC | ACG | CCA | TGC | GCT | GCG | GAG | GAA | AGC | AAG | CTG | CCC | ATC | AAC | GCG | TTG  | 1296
| Ile | Thr | Pro | Cys | Ala | Ala | Glu | Glu | Ser | Lys | Leu | Pro | Ile | Asn | Ala | Leu  |
|     |     || 420 |     |     |     |     | 425 |     |     |     |     | 430 |     |     |      |
| AGC | AAC | TCT | TTG | CTG | CGC | CAC | CAT | AAC | ATG | GTT | TAT | GCC | ACA | ACA | TCT  | 1344
| Ser | Asn | Ser | Leu | Leu | Arg | His | His | Asn | Met | Val | Tyr | Ala | Thr | Thr | Ser  |
|     |     |     | 435 |     |     |     |     | 440 |     |     |     |     | 445 |     |      |
| CGC | AGC | GCA | GGC | CTG | CGG | CAG | AAG | AAG | GTC | ACC | TTT | GAC | AGA | CTG | CAA  | 1392
| Arg | Ser | Ala | Gly | Leu | Arg | Gln | Lys | Lys | Val | Thr | Phe | Asp | Arg | Leu | Gln  |
|     | 450 |     |     |     |     | 455 |     |     |     |     | 460 |     |     |     |      |
| GTC | CTG | GAC | GAC | CAC | TAC | CGG | GAC | GTG | CTC | AAG | GAG | ATG | AAG | GCG | AAG  | 1440
| Val | Leu | Asp | Asp | His | Tyr | Arg | Asp | Val | Leu | Lys | Glu | Met | Lys | Ala | Lys  |

-continued

| | | | | |
|---|---|---|---|---|
| 465 | 470 | 475 | 480 | |
| GCG TCC ACA GTT AAG GCT AAA CTC CTA TCC GTA GAG GAA GCC TGC AAG<br>Ala Ser Thr Val Lys Ala Lys Leu Leu Ser Val Glu Glu Ala Cys Lys<br>485 490 495 | | | | 1488 |
| CTG ACG CCC CCA CAT TCG GCC AAA TCC AAG TTT GGC TAT GGG GCA AAG<br>Leu Thr Pro Pro His Ser Ala Lys Ser Lys Phe Gly Tyr Gly Ala Lys<br>500 505 510 | | | | 1536 |
| GAC GTC CGG AAC CTA TCC AGC AAG GCC GTT AAC CAC ATC CAC TCC GTG<br>Asp Val Arg Asn Leu Ser Ser Lys Ala Val Asn His Ile His Ser Val<br>515 520 525 | | | | 1584 |
| TGG AAG GAC TTG CTG GAA GAC ACT GTG ACA CCA ATT GAC ACC ACC ATC<br>Trp Lys Asp Leu Leu Glu Asp Thr Val Thr Pro Ile Asp Thr Thr Ile<br>530 535 540 | | | | 1632 |
| ATG GCA AAA AAT GAG GTT TTC TGT GTC CAA CCA GAG AAA GGA GGC CGT<br>Met Ala Lys Asn Glu Val Phe Cys Val Gln Pro Glu Lys Gly Gly Arg<br>545 550 555 560 | | | | 1680 |
| AAG CCA GCC CGC CTT ATC GTA TTC CCA GAT CTG GGA GTC CGT GTA TGC<br>Lys Pro Ala Arg Leu Ile Val Phe Pro Asp Leu Gly Val Arg Val Cys<br>565 570 575 | | | | 1728 |
| GAG AAG ATG GCC CTC TAT GAT GTG GTC TCC ACC CTT CCT CAG GTC GTG<br>Glu Lys Met Ala Leu Tyr Asp Val Val Ser Thr Leu Pro Gln Val Val<br>580 585 590 | | | | 1776 |
| ATG GGC TCC TCA TAC GGA TTC CAG TAC TCT CCT GGG CAG CGA GTC GAG<br>Met Gly Ser Ser Tyr Gly Phe Gln Tyr Ser Pro Gly Gln Arg Val Glu<br>595 600 605 | | | | 1824 |
| TTC CTG GTG AAT ACC TGG AAA TCA AAG AAA AAC CCC ATG GGC TTT TCA<br>Phe Leu Val Asn Thr Trp Lys Ser Lys Lys Asn Pro Met Gly Phe Ser<br>610 615 620 | | | | 1872 |
| TAT GAC ACT CGC TGT TTC GAC TCA ACG GTC ACC GAG AAC GAC ATC CGT<br>Tyr Asp Thr Arg Cys Phe Asp Ser Thr Val Thr Glu Asn Asp Ile Arg<br>625 630 635 640 | | | | 1920 |
| GTT GAG GAG TCA ATT TAC CAA TGT TGT GAC TTG GCC CCC GAA GCC AGA<br>Val Glu Glu Ser Ile Tyr Gln Cys Cys Asp Leu Ala Pro Glu Ala Arg<br>645 650 655 | | | | 1968 |
| CAG GCC ATA AAA TCG CTC ACA GAG CGG CTT TAT ATC GGG GGT CCT CTG<br>Gln Ala Ile Lys Ser Leu Thr Glu Arg Leu Tyr Ile Gly Gly Pro Leu<br>660 665 670 | | | | 2016 |
| ACT AAT TCA AAA GGG CAG AAC TGC GGT TAT CGC CGG TGC CGC GCG AGC<br>Thr Asn Ser Lys Gly Gln Asn Cys Gly Tyr Arg Arg Cys Arg Ala Ser<br>675 680 685 | | | | 2064 |
| GGC GTG CTG ACG ACT AGC TGC GGT AAC ACC CTC ACA TGT TAC TTG AAG<br>Gly Val Leu Thr Thr Ser Cys Gly Asn Thr Leu Thr Cys Tyr Leu Lys<br>690 695 700 | | | | 2112 |
| GCC TCT GCA GCC TGT CGA GCT GCG AAG CTC CAG GAC TGC ACG ATG CTC<br>Ala Ser Ala Ala Cys Arg Ala Ala Lys Leu Gln Asp Cys Thr Met Leu<br>705 710 715 720 | | | | 2160 |
| GTG AAC GGA GAC GAC CTC GTC GTT ATC TGT GAA AGC GCG GGA ACC CAA<br>Val Asn Gly Asp Asp Leu Val Val Ile Cys Glu Ser Ala Gly Thr Gln<br>725 730 735 | | | | 2208 |
| GAG GAC GCG GCG AGC CTA CGA GTC TTC ACG GAG GCT ATG ACT AGG TAC<br>Glu Asp Ala Ala Ser Leu Arg Val Phe Thr Glu Ala Met Thr Arg Tyr<br>740 745 750 | | | | 2256 |
| TCC GCC CCC CCC GGG GAC CCG CCC CAA CCA GAA TAC GAC TTG GAG CTG<br>Ser Ala Pro Pro Gly Asp Pro Pro Gln Pro Glu Tyr Asp Leu Glu Leu<br>755 760 765 | | | | 2304 |
| ATA ACA TCA TGT TCC TCC AAT GTG TCG GTC GCC CAC GAT GCA TCA GGC<br>Ile Thr Ser Cys Ser Ser Asn Val Ser Val Ala His Asp Ala Ser Gly<br>770 775 780 | | | | 2352 |
| AAA AGG GTG TAC TAC CTC ACC CGT GAT CCC ACC ACC CCC CTA GCA CGG<br>Lys Arg Val Tyr Tyr Leu Thr Arg Asp Pro Thr Thr Pro Leu Ala Arg | | | | 2400 |

-continued

```
785                 790                 795                 800
GCT GCG TGG GAG ACA GCT AGA CAC ACT CCA GTT AAC TCC TGG CTA GGC         2448
Ala Ala Trp Glu Thr Ala Arg His Thr Pro Val Asn Ser Trp Leu Gly
                    805                 810                 815

AAC ATT ATT ATG TAT GCG CCC ACT TTG TGG GCA AGG ATG ATT CTG ATG         2496
Asn Ile Ile Met Tyr Ala Pro Thr Leu Trp Ala Arg Met Ile Leu Met
                820                 825                 830

ACT CAC TTC TTC TCC ATC CTT CTA GCG CAG GAG CAA CTT GAA AAA GCC         2544
Thr His Phe Phe Ser Ile Leu Leu Ala Gln Glu Gln Leu Glu Lys Ala
            835                 840                 845

CTG GAC TGC CAG ATC TAC GGG GCC TGT TAC TCC ATT GAG CCA CTT GAC         2592
Leu Asp Cys Gln Ile Tyr Gly Ala Cys Tyr Ser Ile Glu Pro Leu Asp
        850                 855                 860

CTA CCT CAG ATC ATT GAA CGA CTC CAT GGC CTT AGC GCA TTT TCA CTC         2640
Leu Pro Gln Ile Ile Glu Arg Leu His Gly Leu Ser Ala Phe Ser Leu
865                 870                 875                 880

CAT AGT TAC TCT CCA GGT GAG ATC AAT AGG GTG GCT TCA TGC CTC AGG         2688
His Ser Tyr Ser Pro Gly Glu Ile Asn Arg Val Ala Ser Cys Leu Arg
                    885                 890                 895

AAA CTT GGG GTA CCA CCC TTG CGA GTC TGG AGA CAT CGG GCC AGG AGC         2736
Lys Leu Gly Val Pro Pro Leu Arg Val Trp Arg His Arg Ala Arg Ser
                900                 905                 910

GTC CGC GCT AGG CTA CTG TCC CAG GGA GGG AGG GCC GCC ACT TGT GGC         2784
Val Arg Ala Arg Leu Leu Ser Gln Gly Gly Arg Ala Ala Thr Cys Gly
            915                 920                 925

AAA TAC CTC TTC AAC TGG GCA GTA AAA ACC AAA CTT AAA CTC ACT CCA         2832
Lys Tyr Leu Phe Asn Trp Ala Val Lys Thr Lys Leu Lys Leu Thr Pro
        930                 935                 940

ATC CCG GCT GCG TCC CGG CTG GAC TTG TCC GGC TGG TTC GTT GCT GGT         2880
Ile Pro Ala Ala Ser Arg Leu Asp Leu Ser Gly Trp Phe Val Ala Gly
945                 950                 955                 960

TAC AGC GGG GGA GAC ATA TAT CAC AGC CTG TCT CGT GCC CGA CCC CGT         2928
Tyr Ser Gly Gly Asp Ile Tyr His Ser Leu Ser Arg Ala Arg Pro Arg
                    965                 970                 975

TGG TTC ATG CTG TGC CTA CTC CTA CTT TCT GTA GGG GTA GGC ATC TAC         2976
Trp Phe Met Leu Cys Leu Leu Leu Ser Val Gly Val Gly Ile Tyr
                980                 985                 990

CTG CTC CCC AAC CGA                                                     2991
Leu Leu Pro Asn Arg
            995

(2) INFORMATION FOR SEQ ID NO:50:

(i) SEQUENCE CHARACTERISTICS:
        (A) LENGTH: 997 amino acids
        (B) TYPE: amino acid
        (D) TOPOLOGY: linear (ii) MOLECULE TYPE: protein (xi) SEQUENCE DESCRIPTION: SEQ ID NO:50:

Gly Tyr Lys Gly Val Trp Arg Gly Asp Gly Ile Met Gln Thr Thr Cys
1               5                   10                  15

Pro Cys Gly Ala Gln Ile Thr Gly His Val Lys Asn Gly Ser Met Arg
                20                  25                  30

Ile Val Gly Pro Lys Thr Cys Ser Asn Thr Trp His Gly Thr Phe Pro
            35                  40                  45

Ile Asn Ala Tyr Thr Thr Gly Pro Cys Thr Pro Ser Pro Ala Pro Asn
        50                  55                  60

Tyr Ser Arg Ala Leu Trp Arg Val Ala Ala Glu Glu Tyr Val Glu Val
65                  70                  75                  80
```

```
Thr Arg Val Gly Asp Phe His Tyr Val Thr Gly Met Thr Thr Asp Asn
                85                  90                  95
Val Lys Cys Pro Cys Gln Val Pro Ala Pro Glu Phe Phe Ser Glu Val
            100                 105                 110
Asp Gly Val Arg Leu His Arg Tyr Ala Pro Ala Cys Arg Pro Leu Leu
        115                 120                 125
Arg Glu Glu Val Thr Phe Gln Val Gly Leu Asn Gln Tyr Leu Val Gly
    130                 135                 140
Ser Gln Leu Pro Cys Glu Pro Glu Pro Asp Val Ala Val Leu Thr Ser
145                 150                 155                 160
Met Leu Thr Asp Pro Ser His Ile Thr Ala Glu Thr Ala Lys Arg Arg
                165                 170                 175
Leu Ala Arg Gly Ser Pro Pro Ser Leu Ala Ser Ser Ser Ala Ser Gln
            180                 185                 190
Leu Ser Ala Pro Ser Leu Lys Ala Thr Cys Thr Thr His His Val Ser
        195                 200                 205
Pro Asp Ala Asp Leu Ile Glu Ala Asn Leu Leu Trp Arg Gln Glu Met
    210                 215                 220
Gly Gly Asn Ile Thr Arg Val Glu Ser Glu Asn Lys Val Val Val Leu
225                 230                 235                 240
Asp Ser Phe Asp Pro Leu Arg Ala Glu Glu Asp Glu Arg Glu Val Ser
                245                 250                 255
Val Pro Ala Glu Ile Leu Arg Lys Ser Lys Lys Phe Pro Ala Ala Met
            260                 265                 270
Pro Ile Trp Ala Arg Pro Asp Tyr Asn Pro Pro Leu Leu Glu Ser Trp
        275                 280                 285
Lys Asp Pro Asp Tyr Val Pro Pro Val Val His Gly Cys Pro Leu Pro
    290                 295                 300
Pro Ile Lys Ala Pro Pro Ile Pro Pro Pro Arg Arg Lys Arg Thr Val
305                 310                 315                 320
Val Leu Thr Glu Ser Ser Val Ser Ser Ala Leu Ala Glu Leu Ala Thr
                325                 330                 335
Lys Thr Phe Gly Ser Ser Glu Ser Ser Ala Val Asp Ser Gly Thr Ala
            340                 345                 350
Thr Ala Leu Pro Asp Gln Ala Ser Asp Asp Gly Asp Lys Gly Ser Asp
        355                 360                 365
Val Glu Ser Tyr Ser Ser Met Pro Pro Leu Glu Gly Glu Pro Gly Asp
    370                 375                 380
Pro Asp Leu Ser Asp Gly Ser Trp Ser Thr Val Ser Glu Glu Ala Ser
385                 390                 395                 400
Glu Asp Val Val Cys Cys Ser Met Ser Tyr Thr Trp Thr Gly Ala Leu
                405                 410                 415
Ile Thr Pro Cys Ala Ala Glu Glu Ser Lys Leu Pro Ile Asn Ala Leu
            420                 425                 430
Ser Asn Ser Leu Leu Arg His His Asn Met Val Tyr Ala Thr Thr Ser
        435                 440                 445
Arg Ser Ala Gly Leu Arg Gln Lys Lys Val Thr Phe Asp Arg Leu Gln
    450                 455                 460
Val Leu Asp Asp His Tyr Arg Asp Val Leu Lys Glu Met Lys Ala Lys
465                 470                 475                 480
Ala Ser Thr Val Lys Ala Lys Leu Leu Ser Val Glu Glu Ala Cys Lys
                485                 490                 495
Leu Thr Pro Pro His Ser Ala Lys Ser Lys Phe Gly Tyr Gly Ala Lys
```

-continued

```
                500                 505                 510
Asp Val Arg Asn Leu Ser Ser Lys Ala Val Asn His Ile His Ser Val
            515                 520                 525
Trp Lys Asp Leu Leu Glu Asp Thr Val Thr Pro Ile Asp Thr Thr Ile
530                 535                 540
Met Ala Lys Asn Glu Val Phe Cys Val Gln Pro Glu Lys Gly Gly Arg
545                 550                 555                 560
Lys Pro Ala Arg Leu Ile Val Phe Pro Asp Leu Gly Val Arg Val Cys
                565                 570                 575
Glu Lys Met Ala Leu Tyr Asp Val Val Ser Thr Leu Pro Gln Val Val
            580                 585                 590
Met Gly Ser Ser Tyr Gly Phe Gln Tyr Ser Pro Gly Gln Arg Val Glu
        595                 600                 605
Phe Leu Val Asn Thr Trp Lys Ser Lys Lys Asn Pro Met Gly Phe Ser
610                 615                 620
Tyr Asp Thr Arg Cys Phe Asp Ser Thr Val Thr Glu Asn Asp Ile Arg
625                 630                 635                 640
Val Glu Glu Ser Ile Tyr Gln Cys Cys Asp Leu Ala Pro Glu Ala Arg
                645                 650                 655
Gln Ala Ile Lys Ser Leu Thr Glu Arg Leu Tyr Ile Gly Gly Pro Leu
            660                 665                 670
Thr Asn Ser Lys Gly Gln Asn Cys Gly Tyr Arg Arg Cys Arg Ala Ser
        675                 680                 685
Gly Val Leu Thr Thr Ser Cys Gly Asn Thr Leu Thr Cys Tyr Leu Lys
        690                 695                 700
Ala Ser Ala Ala Cys Arg Ala Ala Lys Leu Gln Asp Cys Thr Met Leu
705                 710                 715                 720
Val Asn Gly Asp Asp Leu Val Val Ile Cys Glu Ser Ala Gly Thr Gln
                725                 730                 735
Glu Asp Ala Ala Ser Leu Arg Val Phe Thr Glu Ala Met Thr Arg Tyr
            740                 745                 750
Ser Ala Pro Pro Gly Asp Pro Pro Gln Pro Glu Tyr Asp Leu Glu Leu
        755                 760                 765
Ile Thr Ser Cys Ser Ser Asn Val Ser Val Ala His Asp Ala Ser Gly
770                 775                 780
Lys Arg Val Tyr Tyr Leu Thr Arg Asp Pro Thr Thr Pro Leu Ala Arg
785                 790                 795                 800
Ala Ala Trp Glu Thr Ala Arg His Thr Pro Val Asn Ser Trp Leu Gly
                805                 810                 815
Asn Ile Ile Met Tyr Ala Pro Thr Leu Trp Ala Arg Met Ile Leu Met
            820                 825                 830
Thr His Phe Phe Ser Ile Leu Leu Ala Gln Glu Gln Leu Glu Lys Ala
        835                 840                 845
Leu Asp Cys Gln Ile Tyr Gly Ala Cys Tyr Ser Ile Glu Pro Leu Asp
        850                 855                 860
Leu Pro Gln Ile Ile Glu Arg Leu His Gly Leu Ser Ala Phe Ser Leu
865                 870                 875                 880
His Ser Tyr Ser Pro Gly Glu Ile Asn Arg Val Ala Ser Cys Leu Arg
                885                 890                 895
Lys Leu Gly Val Pro Pro Leu Arg Val Trp Arg His Arg Ala Arg Ser
            900                 905                 910
Val Arg Ala Arg Leu Leu Ser Gln Gly Gly Arg Ala Ala Thr Cys Gly
        915                 920                 925
```

-continued

```
Lys Tyr Leu Phe Asn Trp Ala Val Lys Thr Lys Leu Lys Leu Thr Pro
    930             935             940

Ile Pro Ala Ala Ser Arg Leu Asp Leu Ser Gly Trp Phe Val Ala Gly
945             950             955             960

Tyr Ser Gly Gly Asp Ile Tyr His Ser Leu Ser Arg Ala Arg Pro Arg
            965             970             975

Trp Phe Met Leu Cys Leu Leu Leu Leu Ser Val Gly Val Gly Ile Tyr
        980             985             990

Leu Leu Pro Asn Arg
        995
```